US012703707B2

(12) United States Patent
Takashima et al.

(10) Patent No.: US 12,703,707 B2
(45) Date of Patent: Aug. 11, 2026

(54) HETEROCYCLIC COMPOUNDS

(71) Applicant: PRISM BIOLAB CO., LTD., Kanagawa (JP)

(72) Inventors: Hajime Takashima, Kanagawa (JP); Eiji Honda, Kanagawa (JP); Tomonori Taguri, Kanagawa (JP); Jun Ozawa, Kanagawa (JP); Haruyuki Nishida, Kanagawa (JP); Yoichiro Hirose, Kanagawa (JP); Keisuke Kimura, Kanagawa (JP)

(73) Assignee: PRISM BIOLAB CO., LTD., Kanagawa (JP)

( * ) Notice: Subject to any disclaimer, the term of this patent is extended or adjusted under 35 U.S.C. 154(b) by 858 days.

(21) Appl. No.: 18/014,556

(22) PCT Filed: Jul. 16, 2021

(86) PCT No.: PCT/JP2021/027989

§ 371 (c)(1),
(2) Date: Jan. 5, 2023

(87) PCT Pub. No.: WO2022/014724

PCT Pub. Date: Jan. 20, 2022

(65) Prior Publication Data

US 2023/0265104 A1 Aug. 24, 2023

Related U.S. Application Data

(60) Provisional application No. 63/052,587, filed on Jul. 16, 2020.

(51) Int. Cl.

*C07D 498/04* (2006.01)
*A61P 35/00* (2006.01)
*C07D 487/04* (2006.01)
*C07D 519/00* (2006.01)

(52) U.S. Cl.

CPC ............ *C07D 498/04* (2013.01); *A61P 35/00* (2018.01); *C07D 487/04* (2013.01); *C07D 519/00* (2013.01)

(58) Field of Classification Search

CPC .. C07D 498/04; C07D 487/04; C07D 519/00; A61P 35/00

See application file for complete search history.

(56) References Cited

U.S. PATENT DOCUMENTS

2014/0051706 A1 2/2014 Kouji et al.
2018/0305350 A1 10/2018 Goldstein et al.

FOREIGN PATENT DOCUMENTS

CN 106317057 A 1/2017
WO 2012115286 A1 8/2012

OTHER PUBLICATIONS

International Search Report dated Sep. 28, 2021 issued in PCT/JP2021/027989.

Extended European search report dated Jul. 16, 2024 received in European Patent Application No. 21842594.0.

*Primary Examiner* — Kortney L. Klinkel
*Assistant Examiner* — Grace Ching Hsu
(74) *Attorney, Agent, or Firm* — Scully, Scott, Murphy & Presser, P.C.

(57) ABSTRACT

A compound of the formula (I): wherein each symbol is as defined in the DESCRIPTION, or a pharmaceutically acceptable salt thereof has a superior inhibitory activity on cancer cell proliferation.

(I)

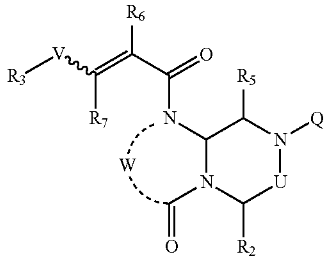

18 Claims, 6 Drawing Sheets

HETEROCYCLIC COMPOUNDS

TECHNICAL FIELD

The present invention relates to a novel heterocyclic compound. More specifically, the present invention relates to a novel heterocyclic compound having inhibitory activities on cancer cell proliferation.

BACKGROUND ART

Cancer is the leading cause of death in animals and humans. Many chemotherapeutic agents effective against cancer and tumor cells have been developed. However, they are not always effective against all types of cancers and tumors, and sometimes show the side effect of destroying normal cells. There is still a need for the development of a pharmaceutical product that shows cancer cell-specific effects and causes fewer side effects.

SUMMARY OF THE INVENTION

Problems to be Solved by the Invention

The present invention aims to provide a compound having inhibitory activities on cancer cell proliferation.

Means of Solving the Problems

The present inventors have conducted intensive studies in an attempt to solve the aforementioned problems and found that a compound having a particular structure shows a superior inhibitory activities on cancer cell proliferation, and completed the present invention.

That is, the present invention relates to the following.

[1] A compound represented by the following formula (I):

(I)

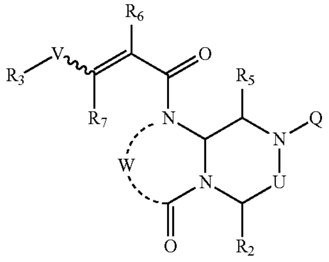

wherein

Q is a hydrogen atom or is represented by any of the following formulas (II-1) to (II-8):

II-1

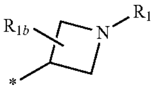

II-2

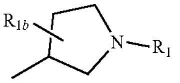

II-3

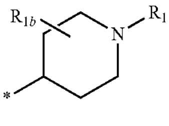

-continued

II-4

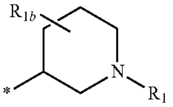

II-5

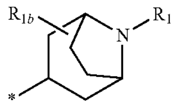

II-6

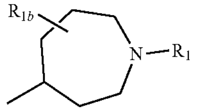

II-7

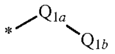

II-8

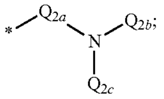

$R_1$ is a hydrogen atom, optionally substituted alkyl, optionally substituted cycloalkyl, optionally substituted heterocycloalkyl, optionally substituted aryl, optionally substituted heteroaryl, optionally substituted arylalkyl, optionally substituted heteroarylalkyl, optionally substituted cycloalkylalkyl, optionally substituted heterocycloalkylalkyl, or —(CO)—$R_{1a}$;

$R_{1a}$ is optionally substituted alkyl, optionally substituted alkoxy, optionally substituted aryl, or optionally substituted heteroaryl;

$R_{1b}$ is a hydrogen atom, or 1 to 3 same or different alkyls;

$Q_{1a}$ is a single bond, or optionally substituted alkylene;

$Q_{1b}$ is a hydrogen atom, hydroxy, halogen, cyano, -$Q_{1c}$, —$COQ_{1c}$, —$CONQ_{1c}Q_{1d}$, $CONQ_{1c}$-$OQ_{1d}$, —$NQ_{1c}Q_{1d}$, or —$OQ_{1c}$;

$Q_{1c}$ is a hydrogen atom, optionally substituted alkyl, optionally substituted cycloalkyl, optionally substituted heterocycloalkyl, optionally substituted aryl, or optionally substituted heteroaryl;

$Q_{1d}$ is a hydrogen atom or optionally substituted alkyl;

$Q_{2a}$ is optionally substituted cycloalkylene;

$Q_{2b}$ and $Q_{2c}$ are the same or different and each is a hydrogen atom or optionally substituted alkyl;

U is —CO— or —$CH_2$—;

$R_2$ is a hydrogen atom, optionally substituted alkyl, optionally substituted alkenyl, optionally substituted alkynyl, optionally substituted arylalkyl, optionally substituted heteroarylalkyl, optionally substituted cycloalkylalkyl, or —X—$N(R_{2a})(R_{2b})$;

X is an alkylene group;

$R_{2a}$ and $R_{2b}$ are the same or different and each is a hydrogen atom, optionally substituted alkyl, optionally substituted cycloalkyl, optionally substituted heterocycloalkyl, optionally substituted aryl, optionally substituted heteroaryl, optionally substituted arylalkyl, optionally substituted heteroarylalkyl, or optionally substituted cycloalkylalkyl;

V is an optionally substituted aryl ring, an optionally substituted heteroaryl ring, an optionally substituted partially saturated heteroaryl ring, or an optionally substituted heterocycloalkyl ring;

$R_3$ is a hydrogen atom, hydroxy, halogen, cyano, optionally substituted alkyl, optionally substituted cycloalkyl, optionally substituted heterocycloalkyl, optionally substituted aryl, optionally substituted heteroaryl, $—C≡C—R_{3a}$ or $—COOR_{3b}$;

$R_{3a}$ is a hydrogen atom, optionally substituted alkyl, optionally substituted cycloalkyl, optionally substituted heterocycloalkyl, or optionally substituted heteroaryl, $R_{3b}$ is a hydrogen atom or optionally substituted alkyl,

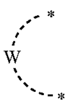

is represented by any of the following formulas (III-1) to (III-4):

(III-1)

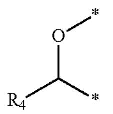

(III-2)

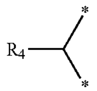

(III-3)

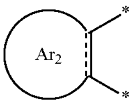

(III-4)

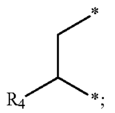

$R_4$ is a hydrogen atom, optionally substituted alkyl, optionally substituted alkenyl, optionally substituted alkynyl, optionally substituted arylalkyl, optionally substituted heteroarylalkyl, optionally substituted cycloalkylalkyl, or optionally substituted heterocycloalkylalkyl, and $Ar_2$ is an optionally substituted aryl ring or an optionally substituted heteroaryl ring; and $R_5$ is a hydrogen atom, or optionally substituted alkyl; and $R_6$ and $R_7$ are the same or different and each is a hydrogen atom or halogen, or a pharmaceutically acceptable salt thereof.

[2] The compound of [1], wherein the compound is represented by the following formula (I-a):

(I-a)

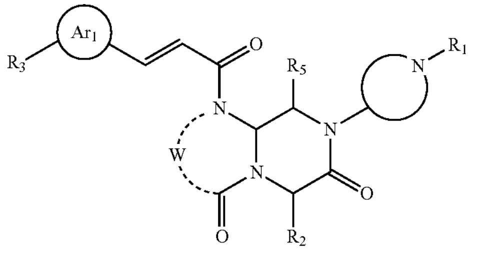

wherein $R_1$ is a hydrogen atom, optionally substituted alkyl, optionally substituted cycloalkyl, optionally substituted heterocycloalkyl, optionally substituted aryl, optionally substituted heteroaryl, optionally substituted arylalkyl, optionally substituted heteroarylalkyl, optionally substituted cycloalkylalkyl, optionally substituted heterocycloalkylalkyl, or $—(CO)—R_{1a}$;

$R_{1a}$ is optionally substituted alkyl, optionally substituted alkoxy, optionally substituted aryl, or optionally substituted heteroaryl;

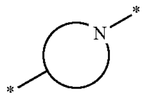

is represented by any of the following formulas (II-1-a) to (II-6-a):

II-1-a

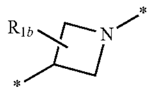

II-2-a

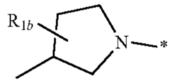

II-3-a

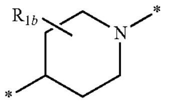

II-4-a

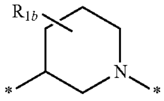

II-5-a

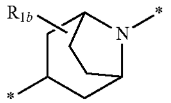

II-6-a

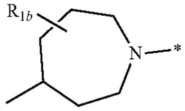

$R_{1b}$ is a hydrogen atom, or 1 to 3 same or different alkyls; $R_2$ is a hydrogen atom, optionally substituted alkyl, optionally substituted alkenyl, optionally substituted alkynyl, optionally substituted arylalkyl, optionally substituted heteroarylalkyl, optionally substituted cycloalkylalkyl, or —X—N($R_{2a}$)($R_{2b}$);

X is an alkylene group;

$R_{2a}$ and $R_{2b}$ are the same or different and each is a hydrogen atom, optionally substituted alkyl, optionally substituted cycloalkyl, optionally substituted heterocycloalkyl, optionally substituted aryl, optionally substituted heteroaryl, optionally substituted arylalkyl, optionally substituted heteroarylalkyl, or optionally substituted cycloalkylalkyl;

$Ar_1$ is an optionally substituted aryl ring or an optionally substituted heteroaryl ring;

$R_3$ is a hydrogen atom, hydroxy, halogen, cyano, optionally substituted alkyl, optionally substituted cycloalkyl, optionally substituted heterocycloalkyl, optionally substituted aryl, optionally substituted heteroaryl, —C≡C—$R_{3a}$ or —COO$R_{3b}$;

$R_{3a}$ is a hydrogen atom, optionally substituted alkyl, optionally substituted cycloalkyl, optionally substituted heterocycloalkyl, or optionally substituted heteroaryl, $R_{3b}$ is a hydrogen atom or optionally substituted alkyl,

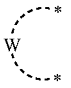

is represented by any of the following formulas (III-1) to (III-3):

(III-1)

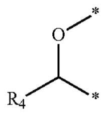

(III-2)

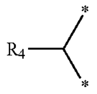

(III-3)

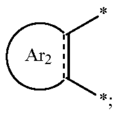

$R_4$ is a hydrogen atom, optionally substituted alkyl, optionally substituted alkenyl, optionally substituted alkynyl, optionally substituted arylalkyl, optionally substituted heteroarylalkyl, optionally substituted cycloalkylalkyl, or optionally substituted heterocycloalkylalkyl, and $Ar_2$ is an optionally substituted aryl ring or an optionally substituted heteroaryl ring; and $R_5$ is a hydrogen atom, or optionally substituted alkyl, or a pharmaceutically acceptable salt thereof.

[3] The compound of [1], wherein the compound is represented by the following formula (IV):

(IV)

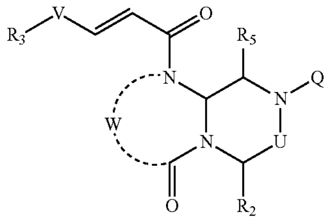

wherein each symbol is as defined in [1], or a pharmaceutically acceptable salt thereof.

[4] The compound of any of [1] to [3], wherein the compound is represented by the following formula (IV-a):

(IV-a)

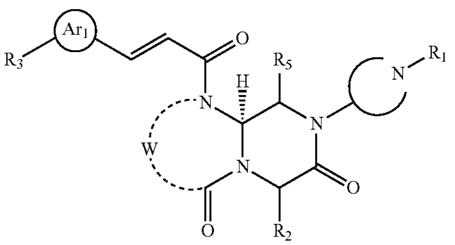

wherein each symbol is as defined in [2], or a pharmaceutically acceptable salt thereof.

[5] The compound of [1] or [3], wherein Q is represented by any of the following formulas (VI-1) to (VI-3):

(VI-1)

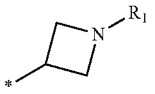

(VI-2)

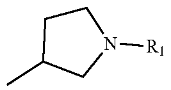

(VI-3)

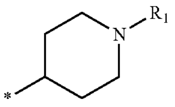

wherein each symbol is as defined in [1], or a pharmaceutically acceptable salt thereof.

[6] The compound of any of [1], [3] and [5], wherein Q is represented by the following formulas (II-7):

II-7

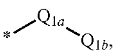

and $Q_{1a}$ is an alkylene and $Q_{1b}$ is —CONH-$Q_{1c}$, -$Q_{1d}$, —CO-$Q_{1d}$, —N($Q_{1c}$)-$Q_{1d}$, wherein $Q_{1c}$ is a hydrogen atom or an alkyl and $Q_{1d}$ is a hydrogen atom or heterocycloalkyl optionally substituted by alkyl, or a pharmaceutically acceptable salt thereof.

[7] The compound of [2] or [4], wherein

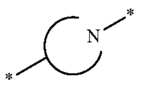

is represented by any of the following formulas (VI-1-a) to (VI-3-a):

(VI-1-a)

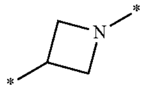

(VI-2-a)

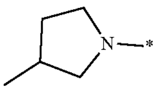

(VI-3-a)

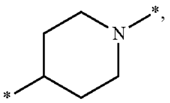

or a pharmaceutically acceptable salt thereof.

[8] The compound of any of [2], [4] and [7], wherein $Ar_1$ is an optionally substituted pyridine ring, an optionally substituted thiazole ring, an optionally substituted benzothiazole ring, or an optionally substituted quinoxaline ring, or a pharmaceutically acceptable salt thereof.

[9] The compound of [8], wherein

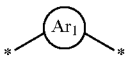

is represented by the following formula (VII-1-a), (VII-2-a), or (VII-3-a):

(VII-1-a)

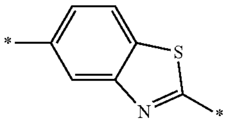

(VII-2-a)

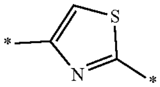

(VII-3-a)

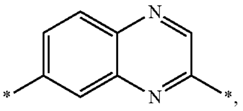

or a pharmaceutically acceptable salt thereof.

[10] The compound of any of [1] to[9], wherein $R_1$ is a hydrogen atom, optionally substituted alkyl, optionally substituted cycloalkyl, optionally substituted heterocycloalkyl, optionally substituted heteroarylalkyl, optionally substituted cycloalkylalkyl, or —(CO)—$R_{1a}$;

$R_{1a}$ is optionally substituted alkyl, optionally substituted alkoxy, optionally substituted aryl, or optionally substituted heteroaryl;

$R_{1b}$ is a hydrogen atom;

$R_2$ is optionally substituted alkyl, or optionally substituted arylalkyl;

$R_{3a}$ is a hydrogen atom, optionally substituted alkyl, optionally substituted cycloalkyl, optionally substituted heterocycloalkyl, or optionally substituted heteroaryl, $R_4$ is optionally substituted alkyl, $Ar_2$ is an optionally substituted aryl ring, and $R_5$ is a hydrogen atom, or a pharmaceutically acceptable salt thereof.

[11] The compound of any of [1] to [10], wherein

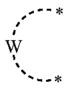

is represented by the following formula (V):

(V)

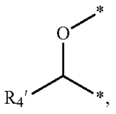

and $R_4$' is optionally substituted alkyl or optionally substituted cycloalkyl, or a pharmaceutically acceptable salt thereof.

[12] The compound of [11], wherein $R_4$' is an alkyl group, or a pharmaceutically acceptable salt thereof.

[13] The compound of [11] or [12], wherein $R_4$' is an isobutyl group, or a pharmaceutically acceptable salt thereof.

[14] The compound of [1] to [13], wherein $R_2$ is alkyl optionally substituted by alkylthio or alkylsulfonyl, or arylalkyl, or a pharmaceutically acceptable salt thereof.

[15] The compound of [14], wherein $R_2$ is isobutyl, neopentyl, sec-butyl, or benzyl, or a pharmaceutically acceptable salt thereof.

[16] The compound of any of [1] to [15], wherein $R_1$ is alkyl or alkyl substituted by 1 or 2 hydroxys, or a pharmaceutically acceptable salt thereof.

[17] The compound of any of [1] to [16], wherein $R_3$ is a hydrogen atom, hydroxy, or —C≡C—$R_{3a}$; and $R_{3a}$ is alkyl substituted by hydroxy, or a pharmaceutically acceptable salt thereof.

[18] A pharmaceutical composition comprising a compound of any of [1] to [17] or a pharmaceutically acceptable salt thereof, and optionally a pharmaceutically acceptable carrier or diluent.

[19] The pharmaceutical composition of [18], wherein the composition comprises an effective amount of the compound.

[20] A method of treating or preventing a cancer, comprising administering to a subject in need thereof a compound of any of [1] to [17] or a pharmaceutically acceptable salt thereof, or a composition of [18] or [19], in an amount effective to treat or prevent the cancer.

[21] An agent for treating or preventing a cancer, comprising a compound of any of [1] to [17] or a pharmaceutically acceptable salt thereof.

[22] A compound of any of [1] to [17] or a pharmaceutically acceptable salt thereof, or a composition of [18] or [19] for the use as a medicament for treating or preventing a cancer.

Effect of the Invention

The compound of the formula (I) of the present invention inhibits cancer cell proliferation and thus can be used for treating various cancers and tumors.

DESCRIPTION OF EMBODIMENTS

Definition

Figure 1:
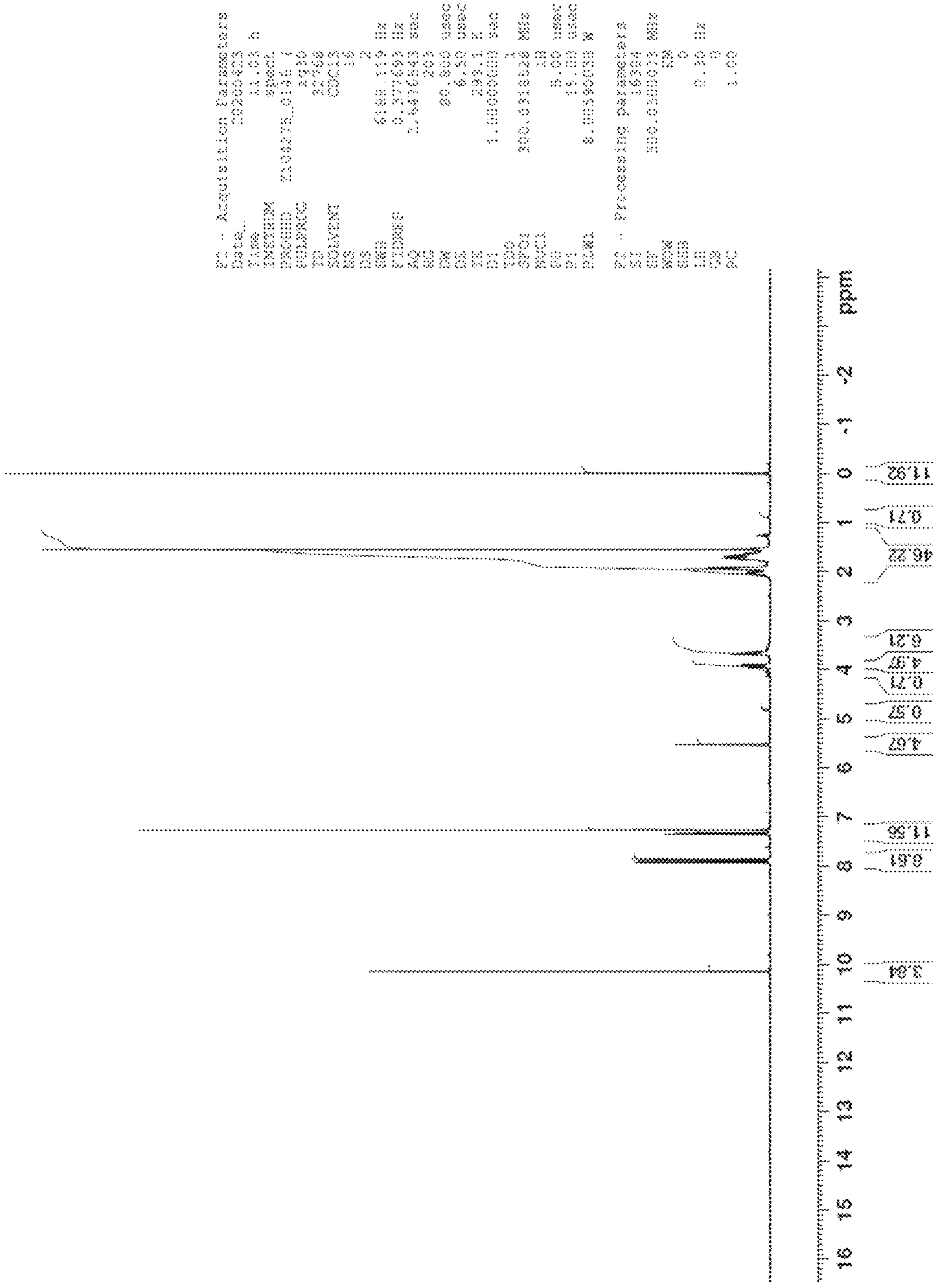
FIG. 1 shows a $^1$H NMR (300 MHz, $CDCl_3$) data of A9-4.

Unless otherwise stated, the following terms used in the specification and claims shall have the following meanings for the purposes of this Application.

"Lower", unless indicated otherwise, means that the number of the carbon atoms constituting the given radicals is between one and six.

"Optionally substituted", unless otherwise stated, means that a given radical may consist of only hydrogen substituents through available valencies or may further comprise one or more non-hydrogen substituents through available valencies. In general, a non-hydrogen substituent may be any substituent that may be bound to an atom of the given radical that is specified to be substituted. Examples of substituents include, but are not limited to, $-R_6$, $-OR_6$, $-COR_6$, $-COOR_6$, $-OCOR_6$, $-CONR_6R_7$, $-NR_6R_7$, $-NR_7COR_6$, $-NR_7COOR_6$, $-SR_6$, $-SO_2R_6$, $-SO_2NR_6R_7$, $-SO_2OR_6$, $-OSO_2R_6$, $-NHC(NHR_6)NR_7$, $-NHC(NH_2)NH$, $-CN$, $-NO_2$, halogen, ethynyl and methylenedioxy, wherein $R^6$ and $R^7$ are independently selected from hydrogen, linear or branched chain, cyclic or noncyclic, substituted or unsubstituted, alkyl, aryl, heteroaryl, arylalkyl and heteroarylalkyl moieties.

"Halogen" means fluorine, chlorine, bromine or iodine. "Halo" means fluoro, chloro, bromo or iodo.

"Alkyl" means a linear or branched, saturated, aliphatic radical having a chain of carbon atoms. $C_{X-Y}$ alkyl is typically used where X and Y indicate the number of carbon atoms in the chain. The number of carbon atoms in the chain is preferably 1 to 10, more preferably 1 to 6, further preferably 1 to 4. Non-exclusive examples of alkyl include methyl, ethyl, propyl, isopropyl, butyl, sec-butyl, isobutyl, tert-butyl, pentyl, isopentyl, neopentyl, tert-pentyl, hexyl, isohexyl, and the like.

"Alkoxy" means an oxygen moiety having a further alkyl substituent. $C_{X-Y}$ alkoxy is typically used where X and Y indicate the number of carbon atoms in the chain. The number of carbon atoms in the chain is preferably 1 to 10, more preferably 1 to 6. Non-exclusive examples of alkoxy include methoxy, ethoy, propoxy, isopropoxy, butoxy, sec-butoxy, isobutoxy, tert-butoxy, pentoxy, isopentoxy, neopentoxy, tert pentoxy, hexyloxy, isohexyloxy, and the like.

"Alkenyl" means a linear or branched, carbon chain that contains at least one carbon-carbon double bond. $C_{X-Y}$ alkenyl is typically used where X and Y indicate the number of carbon atoms in the chain. The number of carbon atoms in the chain is preferably 2 to 10, more preferably 2 to 6. Non-exclusive examples of alkenyl include ethenyl (vinyl), allyl, isopropenyl, 2-methylallyl, 1-pentenyl, hexenyl, heptenyl, 1-propenyl, 2-butenyl, 2-methyl-2-butenyl, and the like.

"Alkynyl" means a linear or branched, carbon chain that contains at least one carbon-carbon triple bond. $C_{X-Y}$ alkynyl is typically used where X and Y indicate the number of carbon atoms in the chain. The number of carbon atoms in the chain is preferably 2 to 10, more preferably 2 to 6. Non-exclusive examples of alkynyl include ethynyl, propargyl, 3-methyl-1-pentynyl, 2-heptynyl and the like.

"Alkylene", unless indicated otherwise, means a linear or branched, saturated, aliphatic, polyvalent carbon chain. $C_{X-Y}$ alkylene is typically used where X and Y indicate the number of carbon atoms in the chain. The number of carbon atoms in the chain is preferably 1 to 10, more preferably 1 to 6. Non-exclusive examples of alkylene include methylene ($-CH_2-$), ethylene ($-CH_2CH_2-$), methylmethylene ($-CH(CH_3)-$), 1,2-propylene ($-CH_2CH(CH_3)-$), 1,3-propylene ($-CH_2CH_2CH_2-$), 1,2-butylene ($-CH_2CH(CH_2CH_3)-$), 1,3-butylene ($-CH_2CH_2CH(CH_3)-$), 1,4-butylene ($-CH_2CH_2CH_2CH_2-$), 2-methyltetramethylene ($-CH_2CH(CH_3)CH_2CH_2-$), pentamethylene ($-CH_2CH_2CH_2CH_2CH_2-$), 1,2,3-propanetriyl, 1,3,3-propanetriyl and the like.

"Heteroatom" refers to an atom that is not a carbon atom and hydrogen atom. Particular examples of heteroatoms include, but are not limited to nitrogen, oxygen, and sulfur.

"Aryl" means a monocyclic or polycyclic radical wherein each ring is aromatic or when fused with one or more rings forms an aromatic ring. $C_{X-Y}$ aryl is typically used where X and Y indicate the number of carbon atoms in the ring assembly. The number of carbon atoms in the ring is preferably 6 to 14, more preferably 6 to 10. Non-exclusive examples of aryl include phenyl, naphthyl, indenyl, azulenyl, biphenyl, fluorenyl, anthracenyl, phenalenyl and the like. "Aryl" may partially be hydrogenated. Non-exclusive examples of partially hydrogenated aryl include tetrahydronaphthyl, indanyl and the like.

"Aryl ring" means a monocyclic or polycyclic ring wherein each ring is aromatic or when fused with one or more rings forms an aromatic ring. $C_{X-Y}$ aryl ring is typically used where X and Y indicate the number of carbon atoms in the ring assembly. The number of carbon atoms in the ring is preferably 6 to 14, more preferably 6 to 10. Non-exclusive examples of aryl ring include benzene, naphthalene, anthracene, phenanthrene, acenaphthylene, indene and the like.

"Partially saturated heteroaryl ring" means a heteroaryl ring of which one or more double bonds are replaced by single bonds.

"Heteroaryl ring" means a monocyclic or polycyclic aromatic ring wherein at least one ring atom is a heteroatom and the remaining ring atoms are carbon. "X-Y membered heteroaryl ring" is typically used where X and Y indicate the number of carbon atoms and heteroatoms in the ring assembly. The number of carbon atoms and heteroatoms in the ring is preferably 5 to 14, more preferably 5 to 10. Monocyclic heteroaryl rings include, but are not limited to, cyclic aromatic rings having five or six ring atoms, wherein at least one ring atom is a heteroatom and the remaining ring atoms are carbon. The nitrogen atoms can be optionally quarternerized and the sulfur atoms can be optionally oxidized. Non-exclusive examples of monocyclic heteroaryl ring of this invention include, but are not limited to, furan, imidazole, isothiazole, isoxazole, oxadiazole, oxazole, 1,2,3-oxadiazole, pyrazine, pyrazole, pyridazine, pyridine, pyrimidine, pyrrole, thiazole, 1,3,4-thiadiazole, triazole and tetrazole. "Heteroaryl ring" also includes, but is not limited to, bicyclic or tricyclic rings, wherein the heteroaryl ring is fused to one or two rings independently selected from the group consisting of an aryl ring, a cycloalkyl ring, and another monocyclic heteroaryl or heterocycloalkyl ring. Non-exclusive examples of bicyclic or tricyclic heteroaryl ring include, but are not limited to, benzofuran (ex. benzo[b]furan), benzothiophene (ex. benzo[b]thiophene), benzimidazole, benzotriazine (ex. benzo[e][1,2,4]triazine, benzo[d][1,2,3]triazine), pyridopyrimidine (ex. pyrido[4,3-d]pyrimidine, pyrido[3,4-d]pyrimidine, pyrido[3,2-d]pyrimidine, pyrido[2,3-d]pyrimidine), pyridopyrazine (ex. pyrido[3,4-b]pyrazine, pyrido[2,3-b]pyrazine), pyridopyridazine (ex. pyrido[2,3-c]pyridazine, pyrido[3,4-c]pyridazine, pyrido[4,3-c]pyridazine, pyrido[3,2-c]pyridazine), pyridotriazine (ex. pyrido[2,3-d][1,2,3]triazine, pyrido[3,4-d][1,2,3]triazine, pyrido[4,3-d][1,2,3]triazine, pyrido[3,2-d][1,2,3]triazine, pyrido[3,4-e][1,2,4]triazine, pyrido[3,2-e][1,2,4]triazine), benzothiadiazole (ex. benzo[c][1,2,5]thiadiazole), furopyridine (ex. furo[3,2-b]pyridine, furo[3,2-c]pyridine, furo[2,3-c]pyridine, furo[2,3-b]pyridine), oxazolopyridine (ex. oxazolo[4,5-b]pyridine, oxazolo[4,5-c]pyridine, oxazolo[5,4-c]pyridine, oxazolo[5,4-b]pyridine), thiazolopyridine (ex. thiazolo[4,5-b]pyridine, thiazolo[4,5-c]pyridine, thiazolo[5,4-c]pyridine, thiazolo[5,4-b]pyridine), imidazopyridine (ex. imidazo[1,2-a]pyridine, imidazo[4,5-c]pyridine, imidazo[1,5-a]pyridine), quinazoline, thienopyridine (ex. thieno[2,3-c]pyridine, thieno[3,2-b]pyridine, thieno[2,3-b]pyridine), indolizine, quinoline, isoquinoline, phthalazine, quinoxaline, cinnoline, naphthyridine, quinolizine, indole, isoindole, indazole, indoline, benzoxazole, benzopyrazole, benzothiazole, pyrazolopyridine (ex. pyrazolo[1,5-a]pyridine), imidazopyrimidine (ex. imidazo[1,2-a]pyrimidine, imidazo[1,2-c]pyrimidine, imidazo[1,5-a]pyrimidine, imidazo[1,5-c]pyrimidine), pyrrolopyridine (ex. pyrrolo[2,3-b]pyridine, pyrrolo[2,3-c]pyridine, pyrrolo[3,2-c]pyridine, pyrrolo[3,2-b]pyridine), pyrrolopyrimidine (ex. pyrrolo[2,3-d]pyrimidine, pyrrolo[3,2-d]pyrimidine, pyrrolo[1,2-c]pyrimidine, pyrrolo[1,2-a]pyrimidine), pyrrolopyrazine (ex. pyrrolo[2,3-b]pyrazine, pyrrolo[1,2-a]pyrazine), pyrrolopyridazine (ex. pyrrolo[1,2-b]pyridazine), triazolopyridine (ex. triazolo[1,5-a]pyridine), pteridine, purine, carbazole, acridine, perimidine, 1,10-phenanthroline, phenoxathiin, phenoxazine, phenothiazine, phenazine and the like. The bicyclic or tricyclic heteroaryl rings can be attached to the parent molecule through either the heteroaryl group itself or the aryl, cycloalkyl, or heterocycloalkyl group to which it is fused.

"Heteroaryl" means a radical derived from the above-mentioned heteroaryl ring.

"Cycloalkyl" means a non-aromatic, saturated or partially unsaturated, monocyclic, fused bicyclic or bridged polycyclic ring radical. $C_{X-Y}$ cycloalkyl is typically used where X and Y indicate the number of carbon atoms in the ring assembly. The number of carbon atoms in the ring is preferably 3 to 10, more preferably 3 to 8. Non-exclusive examples of cycloalkyl include cyclopropyl, cyclobutyl, cyclopentyl, cyclohexyl, cyclohexenyl, 2,5-cyclohexadienyl, bicyclo[2.2.2]octyl, adamantan-1-yl, decahydronaphthyl, bicyclo[2.2.1]hept-1-yl, and the like.

"Heterocycloalkyl" means cycloalkyl, as defined in this Application, provided that one or more of the atoms forming the ring is a heteroatom selected, independently from N, O, or S. $C_{X-Y}$ heterocycloalkyl is typically used where X and Y indicate the number of carbon atoms and heteroatoms in the ring assembly. The number of carbon atoms and heteroatoms in the ring is preferably 3 to 10, more preferably 3 to 8. Non-exclusive examples of heterocycloalkyl include piperidyl, 4-morpholyl, 4-piperazinyl, pyrrolidinyl, perhydropyrrolidinyl, 1,4-diazaperhydroepinyl, 1,3-dioxanyl, 1,4-dioxanyl, and the like.

Moreover, the above-mentioned definitions can apply to groups wherein the above-mentioned substituents are connected. For example, "arylalkyl" means linear or branched alkyl group which is substituted by one or more aryl groups, such as benzyl, 1-phenylethyl, 2-phenylethyl, 3-phenylpropyl, 1-naphthylmethyl, 2-naphthylmethyl and the like. "Heteroarylalkyl" means linear or branched alkyl group which is substituted by one or more heteroaryl groups.

"Cycloalkylalkyl" means linear or branched alkyl group which is substituted by one or more cycloalkyl group (e.g., cyclopropyl, cyclobutyl, cyclopentyl, cyclohexyl, cyclohexenyl, 2,5-cyclohexadienyl, bicyclo[2.2.2]octyl, adamantan-1-yl, decahydronaphthyl, bicyclo[2.2.1]hept-1-yl).

"Heterocycloalkylalkyl" means linear or branched alkyl group which is substituted by one or more heterocycloalkyl groups.

"Alkylthio" means thio radical (—S) substituted with a liner or branched alkyl group. Non-exclusive examples of alkylthio include methylthio, ethylthio, propylthio and the like.

"Alkylsulfonyl" means sulfonyl radical (—$SO_2$—) substituted with a liner or branched alkyl group. Non-exclusive examples of alkylsulfonyl include methylsulfonyl, ethylsulfonyl, propylsulfonyl and the like.

"Monocyclic ring" as used herein refers to a monocyclic, saturated or unsaturated carbocyclic ring or a monocyclic, saturated or unsaturated heterocyclic ring. "X-membered monocyclic ring" is typically used where X indicate the number of carbon atoms and heteroatoms in the ring. The number of carbon atoms and heteroatoms in the ring is preferably 4 to 7, more preferably 5 or 6. "Monocyclic heterocyclic ring" means a monocyclic, aromatic or nonaromatic ring wherein at least one ring atom is a heteroatom (preferably S, N or O) and the remaining ring atoms are carbon. The nitrogen atoms can be optionally quaternerized and the sulfur atoms can be optionally oxidized.

Non-exclusive examples of monocyclic saturated carbocyclic ring include cyclopropane, cyclobutane, cyclopentane, cyclohexane, cycloheptane and the like.

Non-exclusive examples of monocyclic unsaturated carbocyclic ring include cyclopropene, cyclobutene, cyclopentene, cyclohexene, cycloheptene, cyclopentadiene, benzene, and the like.

Non-exclusive examples of monocyclic saturated heterocyclic ring include pyrrolidine, piperidine, morpholine, piperazine, 1,3-dioxane, 1,4-dioxane and the like.

Non-exclusive examples of monocyclic unsaturated heterocyclic ring include pyrazole, dihydro-pyrrole, pyrrole, dihydro-pyrazole, imidazole, thiophene, thiazole, isothiazole, thiadiazole, furan, oxazole, isoxazole, oxadiazole, pyridine, pyridazine, pyrimidine, pyrazine, triazine and the like.

"Protected derivatives" means derivatives of compound in which a reactive site or sites are blocked with protecting groups. A comprehensive list of suitable protecting groups can be found in T. W. Greene, Protecting Groups in Organic Synthesis, 5th edition, John Wiley & Sons, Inc. 2014.

"Leaving group" means an atom or a group of atoms, which is detached from the reaction substrate in substitution reactions, elimination reactions, or the like. As the "leaving group", for example, a halogen atom (e.g., a chlorine atom, a bromine atom, an iodine atom etc.), $C_{1-6}$ alkylsulfonyloxy (e.g., methanesulfonyloxy, ethanesulfonyloxy, trifluoromethanesulfonyloxy etc.), $C_{6-10}$ arylsulfonyloxy (e.g., benzenesulfonyloxy, p-toluenesulfonyloxy etc.), $C_{1-6}$ alkylsulfonyl (e.g., methanesulfonyl, ethanesulfonyl etc.) and the like are used.

"Isomers" mean any compound having identical molecular formulae but differing in the nature or sequence of bonding of their atoms or in the arrangement of their atoms in space. Isomers that differ in the arrangement of their atoms in space are termed "stereoisomers". Stereoisomers that are not mirror images of one another are termed "diastereomers" and stereoisomers that are nonsuperimposable mirror images are termed "enantiomers" or sometimes "optical isomers". A carbon atom bonded to four nonidentical substituents is termed a "chiral center". A compound with one chiral center has two enantiomeric forms of opposite chirality. A mixture of the two enantiomeric forms is termed a "racemic mixture". A compound that has more than one chiral center has $2^{n-1}$ enantiomeric pairs, where n is the number of chiral centers. Compounds with more than one chiral center may exist as either an individual diastereomer or as a mixture of diastereomers, termed a "diastereomeric mixture". When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g., see "Advanced Organic Chemistry", 4th edition, March, Jerry, John Wiley & Sons, New York, 1992). The compounds of the present invention may include these isomers.

"Animal" includes humans, non-human mammals (e.g., mice, rats, dogs, cats, rabbits, cattle, horses, sheep, goats, swine, deer, and the like) and non-mammals (e.g., birds, and the like).

"Disease" specifically includes any unhealthy condition of an animal or part thereof and includes an unhealthy condition that may be caused by, or incident to, medical or veterinary therapy applied to that animal, i.e., the "side effects" of such therapy.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salt" or "salt" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, trifluoroacetic acid, lauryl sulfuric acid, gluconic acid, glutamic acid, hydroxynaphthoic acid, salicylic acid, stearic acid, muconic acid and the like.

Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

"Amount effective to treat" means that amount which, when administered to an animal for treating a disease, is sufficient to effect such treatment for the disease.

"Amount effective to prevent" means that amount which, when administered to an animal for preventing a disease, is sufficient to effect such prophylaxis for the disease.

"Effective amount" equals to "amount effective to treat" and "amount effective to prevent".

"Treatment" or "treat" means any administration of the compound of the present invention and includes:

(1) preventing the disease from occurring in an animal which may be predisposed to the disease but does not yet experience or display the pathology or symptomatology of the disease, (2) inhibiting the disease in an animal that is experiencing or displaying the pathology or symptomatology of the diseased (i.e., arresting further development of the pathology and/or symptomatology), or (3) ameliorating the disease in an animal that is experiencing or displaying the pathology or symptomatology of the diseased (i.e., reversing the pathology and/or symptomatology).

It is noted in regard to all of the definitions provided herein that the definitions should be interpreted as being open ended in the sense that further substituents beyond those specified may be included.

In one aspect of the present invention, a compound represented by the following formula (I):

(I)

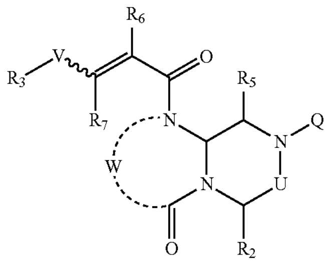

wherein

Q is a hydrogen atom or is represented by any of the following formulas (II-1) to (II-8):

II-1

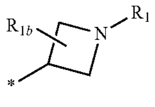

-continued

II-2

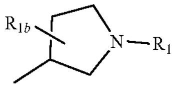

II-3

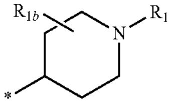

II-4

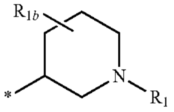

II-5

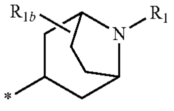

II-6

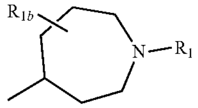

II-7

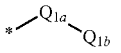

II-8

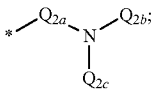

$R_1$ is a hydrogen atom, optionally substituted alkyl, optionally substituted cycloalkyl, optionally substituted heterocycloalkyl, optionally substituted aryl, optionally substituted heteroaryl, optionally substituted arylalkyl, optionally substituted heteroarylalkyl, optionally substituted cycloalkylalkyl, optionally substituted heterocycloalkylalkyl, or —(CO)—$R_{1a}$;

$R_{1a}$ is optionally substituted alkyl, optionally substituted alkoxy, optionally substituted aryl, or optionally substituted heteroaryl;

$R_{1b}$ is a hydrogen atom, or 1 to 3 same or different alkyls;

$Q_{1a}$ is a single bond or optionally substituted alkylene;

$Q_{1b}$ is a hydrogen atom, hydroxy, halogen, cyano, -$Q_{1c}$, —$COQ_{1c}$, —$CONQ_{1c}Q_{1d}$, $CONQ_{1c}$-$OQ_{1d}$, —$NQ_{1c}Q_{1d}$, or —$OQ_{1c}$;

$Q_{1c}$ is a hydrogen atom, optionally substituted alkyl, optionally substituted cycloalkyl, optionally substituted heterocycloalkyl, optionally substituted aryl, or optionally substituted heteroaryl;

$Q_{1a}$ is a hydrogen atom or optionally substituted alkyl;

$Q_{2a}$ is optionally substituted cycloalkyl;

$Q_{2b}$ and $Q_{2c}$ are the same or different and each is a hydrogen atom or optionally substituted alkyl;

U is —CO— or —$CH_2$—;

$R_2$ is a hydrogen atom, optionally substituted alkyl, optionally substituted alkenyl, optionally substituted alkynyl, optionally substituted arylalkyl, optionally substituted heteroarylalkyl, optionally substituted cycloalkylalkyl, or —X—N($R_{2a}$)($R_{2b}$);

X is an alkylene group;

$R_{2a}$ and $R_{2b}$ are the same or different and each is a hydrogen atom, optionally substituted alkyl, optionally substituted cycloalkyl, optionally substituted heterocycloalkyl, optionally substituted aryl, optionally substituted heteroaryl, optionally substituted arylalkyl, optionally substituted heteroarylalkyl, or optionally substituted cycloalkylalkyl;

V is an optionally substituted aryl ring, an optionally substituted heteroaryl ring, an optionally substituted partially saturated heteroaryl ring, or an optionally substituted heterocycloalkyl ring;

$R_3$ is a hydrogen atom, hydroxy, halogen, cyano, optionally substituted alkyl, optionally substituted cycloalkyl, optionally substituted heterocycloalkyl, optionally substituted aryl, optionally substituted heteroaryl, —C≡C—$R_{3a}$ or —$COOR_{3b}$;

$R_{3a}$ is a hydrogen atom, optionally substituted alkyl, optionally substituted cycloalkyl, optionally substituted heterocycloalkyl, or optionally substituted heteroaryl, $R_{3b}$ is a hydrogen atom or optionally substituted alkyl,

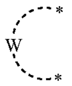

is represented by any of the following formulas (III-1) to (III-4):

(III-1)

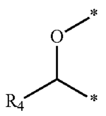

(III-2)

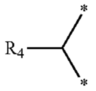

(III-3)

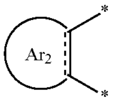

(III-4)

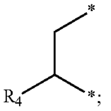

$R_4$ is a hydrogen atom, optionally substituted alkyl, optionally substituted alkenyl, optionally substituted alkynyl, optionally substituted arylalkyl, optionally substituted heteroarylalkyl, optionally substituted cycloalkylalkyl, or optionally substituted heterocycloalkylalkyl, and $Ar_2$ is an optionally substituted aryl ring or an optionally substituted heteroaryl ring; and $R_5$ is a hydrogen atom, or optionally substituted alkyl; and $R_6$ and $R_7$ are the same or different and each is a hydrogen atom or halogen, or a pharmaceutically acceptable salt thereof is disclosed.

In one aspect of the present invention, among the compound represented by the formula (I), a compound represented by the following formula (I-a):

(I-a)

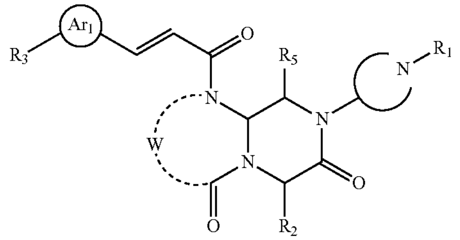

wherein $R_1$ is a hydrogen atom, optionally substituted alkyl, optionally substituted cycloalkyl, optionally substituted heterocycloalkyl, optionally substituted aryl, optionally substituted heteroaryl, optionally substituted arylalkyl, optionally substituted heteroarylalkyl, optionally substituted cycloalkylalkyl, optionally substituted heterocycloalkylalkyl, or —(CO)—$R_{1a}$;

$R_{1a}$ is optionally substituted alkyl, optionally substituted alkoxy, optionally substituted aryl, or optionally substituted heteroaryl;

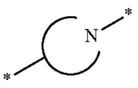

is represented by any of the following formulas (II-1-a) to (II-6-a):

II-1-a

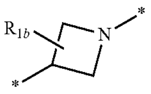

II-2-a

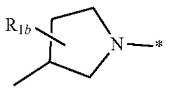

II-3-a

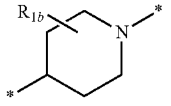

II-4-a

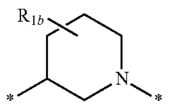

II-5-a

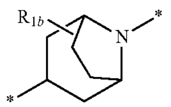

II-6-a

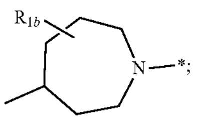

$R_{1b}$ is a hydrogen atom, or 1 to 3 same or different alkyls; $R_2$ is a hydrogen atom, optionally substituted alkyl, optionally substituted alkenyl, optionally substituted alkynyl, optionally substituted arylalkyl, optionally substituted heteroarylalkyl, optionally substituted cycloalkylalkyl, or —X—N($R_{2a}$)($R_{2b}$);

X is an alkylene group;

$R_{2a}$ and $R_{2b}$ are the same or different and each is a hydrogen atom, optionally substituted alkyl, optionally substituted cycloalkyl, optionally substituted heterocycloalkyl, optionally substituted aryl, optionally substituted heteroaryl, optionally substituted arylalkyl, optionally substituted heteroarylalkyl, or optionally substituted cycloalkylalkyl;

$Ar_1$ is an optionally substituted aryl ring or an optionally substituted heteroaryl ring;

$R_3$ is a hydrogen atom, hydroxy, halogen, cyano, optionally substituted alkyl, optionally substituted cycloalkyl, optionally substituted heterocycloalkyl, optionally substituted aryl, optionally substituted heteroaryl, —C≡C—$R_{3a}$ or —COOR$_{3b}$;

$R_{3a}$ is a hydrogen atom, optionally substituted alkyl, optionally substituted cycloalkyl, optionally substituted heterocycloalkyl, or optionally substituted heteroaryl, $R_{3b}$ is a hydrogen atom, or optionally substituted alkyl,

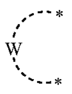

is represented by any of the following formulas (III-1) to (III-3):

(III-1)

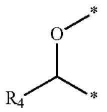

(III-2)

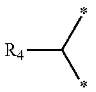

(III-3)

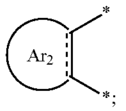

$R_4$ is a hydrogen atom, optionally substituted alkyl, optionally substituted alkenyl, optionally substituted alkynyl, optionally substituted arylalkyl, optionally substituted heteroarylalkyl, optionally substituted cycloalkylalkyl, or optionally substituted heterocycloalkylalkyl, and $Ar_2$ is an optionally substituted aryl ring or an optionally substituted heteroaryl ring; and $R_5$ is a hydrogen atom, or optionally substituted alkyl, or a pharmaceutically acceptable salt thereof is disclosed.

In one embodiment of the formulas (II-1) to (II-6) of Q in the formula (I) or the formula (I-a), $R_1$ is a hydrogen atom, optionally substituted alkyl, optionally substituted cycloalkyl, optionally substituted heterocycloalkyl, optionally substituted aryl, optionally substituted heteroaryl, optionally substituted arylalkyl, optionally substituted heteroarylalkyl, optionally substituted cycloalkylalkyl, or optionally substituted heterocycloalkylalkyl.

Examples of optionally substituted alkyl group include methyl, ethyl, propyl, isopropyl, butyl, isobutyl, sec-butyl, tert-butyl, pentyl, isopentyl, neopentyl, tert-pentyl, aminomethyl, aminoethyl, aminopropyl, aminobutyl, carboxymethyl, carboxyethyl, carboxypropyl, carboxybutyl, carbamoylmethyl, carbamoylethyl, carbamoylpropyl, carbamoylbutyl, methoxymethyl, methoxyethyl, methoxypropyl, methoxybutyl, methylthiomethyl, methylthioethyl, methylthiopropyl, methylthiobutyl, hydroxymethyl, hydroxyethyl, hydroxypropyl, hydroxybutyl, ethoxycarbonylmethyl, ethoxycarbonylethyl, benzyloxymethyl, benzyloxyethyl, benzyloxypropyl, benzyloxybutyl, guanidinomethyl, guanidinoethyl, guanidinopropyl, 4-hydroxy-3-(hydroxymethyl)butyl, hydroxyethoxyethyl, pyrimidinylmethyl and the like.

Examples of optionally substituted cycloalkyl include cyclopropyl, cyclobutyl, cyclopentyl, cyclohexyl, cycloheptyl, adamantyl and the like.

Examples of optionally substituted heterocycloalkyl include piperidinyl, 4-morpholyl, 4-piperazinyl, pyrrolidinyl, perhydropyrrolidinyl, 1,3-dioxanyl, 1,4-dioxanyl, tetrazolyl, isopropylpiperidinyl, acetylpiperidinyl, tetrahydropyranylpiperidinyl, tetrahydropyranyl, cyclohexylpiperidinyl and the like.

Examples of optionally substituted aryl and optionally substituted heteroaryl include biphenyl, phenyl, pyridyl, pyrimidyl, pyridazinyl, pyrazinyl, triazinyl, pyrrolyl, thienyl, furyl, thiazolyl, oxazolyl, imidazolyl, tetrahydronaphthyl, naphthyl, quinolinyl, isoquinolinyl, quinazolinyl, quinoxalinyl, cinnolinyl, naphthyridinyl, benzotriazinyl, indenyl, pyridopyrimidinyl, pyridopyrazinyl, pyridopyridazinyl, pyridotriazinyl, benzofuryl, benzothienyl, indolyl, indazolyl, benzoxazolyl, benzimidazolyl, benzothiazolyl, benzothiadiazolyl, furopyridinyl, thienopyridinyl, pyrropyridinyl, oxazolopyridinyl, thiazolopyridinyl, imidazopyridinyl and the like.

Examples of the optionally substituted arylalkyl group include unsubstituted arylalkyl or arylalkyl having an alkyl group such as benzyl, α-methylbenzyl, phenethyl, α-methylphenethyl, α,α-dimethylbenzyl, α,α-dimethylphenethyl, 4-methylphenethyl, 4-methylbenzyl, 4-isopropylbenzyl and the like; arylalkyl having an aryl group or an arylalkyl group such as 4-benzylbenzyl, 4-phenethylbenzyl, 4-phenylbenzyl and the like; arylalkyl having a substituted oxy group such as 4-methoxybenzyl, 4-n-tetradecyloxybenzyl, 4-n-heptadecyloxybenzyl, 3,4-dimethoxybenzyl, 4-methoxymethylbenzyl, 4-vinyloxymethylbenzyl, 4-benzyloxybenzyl, 4-phenethyloxybenzyl and the like; arylalkyl having a hydroxyl group such as 4-hydroxybenzyl, 4-hydroxy-3-methoxybenzyl and the like; arylalkyl having a halogen atom such as 4-fluorobenzyl, 3-chlorobenzyl, 3,4-dichlorobenzyl and the like; 2-furfuryl, diphenylmethyl, 1-naphthylmethyl, 2-naphthylmethyl and the like.

Examples of the optionally substituted heteroarylalkyl group include 2-pyridylmethyl, 3-pyridylmethyl, 2-pyrimidinylmethyl, 5-pyrimidinylmethyl, 3-pyridazinylmethyl, 2-indolylmethyl, 5-indolylmethyl, 2-benzofuranylmethyl, 5-indolylmethyl, 2-benzothienylmethyl, 5-benzothienylmethyl, 6-fluoro-2-benzofuranylmethyl, 6-chloro-2-benzofuranylmethyl, 6-methoxy-2-benzofuranylmethyl, 6-fluoro-2-benzothienylmethyl, 6-chloro-2-benzothienylmethyl, 6-methoxy-2-benzothienylmethyl and 6-phenyl-3-pyridazinylmethyl and the like.

Examples of the optionally substituted cycloalkylalkyl group include cyclopropylmethyl, fluorocyclopropylmethyl, chlorocyclopropylmethyl, bromocyclopropylmethyl, iodocyclopropylmethyl, methylcyclopropylmethyl, 1,1-dimethylcyclopropylmethyl, 1,2-dimethylcyclopropylmethyl, hydroxycyclopropylmethyl, methoxycyclopropylmethyl, ethoxycyclopropylmethyl, methoxycarbonylcyclopropylmethyl, methylcarbamoylcyclopropylmethyl, cyclopropylethyl, cyclohexylmethyl, cyclopropylhexyl and the like.

Examples of the optionally substituted heterocycloalkylalkyl group include (2-tetrahydrofuryl)methyl, (2-tetrahydrothiofuranyl)methyl and the like.

In one embodiment of the formulas (II-1) to (II-6) of Q in the formula (I) or the formula (I-a), $R_1$ is —(CO)—$R_{1a}$ wherein $R_{1a}$ is optionally substituted alkyl, optionally substituted alkoxy, optionally substituted aryl, or optionally substituted heteroaryl.

Examples of optionally substituted alkyl group include methyl, ethyl, propyl, isopropyl, butyl, isobutyl, sec-butyl, tert-butyl, pentyl, isopentyl, neopentyl, tert-pentyl, aminomethyl, aminoethyl, aminopropyl, aminobutyl, carboxymethyl, carboxyethyl, carboxypropyl, carboxybutyl, carbamoylmethyl, carbamoylethyl, carbamoylpropyl, carbamoylbutyl, methoxymethyl, methoxyethyl, methoxypropyl, methoxybutyl, methylthiomethyl, methylthioethyl, methylthiopropyl, methylthiobutyl, hydroxymethyl, hydroxyethyl, hydroxypropyl, hydroxybutyl, ethoxycarbonylmethyl, ethoxycarbonylethyl, benzyloxymethyl, benzyloxyethyl, benzyloxypropyl, benzyloxybutyl, guanidinomethyl, guanidinoethyl, guanidinopropyl and the like.

Examples of optionally substituted alkoxy group include methoxy, ethoy, propoxy, isopropoxy, butoxy, sec-butoxy, isobutoxy, tert-butoxy, pentoxy, isopentoxy, neopentoxy, tert pentoxy, hexyloxy, isohexyloxy and the like Examples of optionally substituted aryl and optionally substituted heteroaryl include biphenyl, phenyl, pyridyl, pyrimidyl, pyridazinyl, pyrazinyl, triazinyl, pyrrolyl, thienyl, furyl, thiazolyl, oxazolyl, imidazolyl, tetrahydronaphthyl, naphthyl, quinolinyl, isoquinolinyl, quinazolinyl, quinoxalinyl, cinnolinyl, naphthyridinyl, benzotriazinyl, indenyl, pyridopyrimidinyl, pyridopyrazinyl, pyridopyridazinyl, pyridotriazinyl, benzofuryl, benzothienyl, indolyl, indazolyl, benzoxazolyl, benzimidazolyl, benzothiazolyl, benzothiadiazolyl, furopyridinyl, fluoropyrimidinyl, thienopyridinyl, pyrropyridinyl, oxazolopyridinyl, thiazolopyridinyl, imidazopyridinyl and the like.

In another embodiment of the formulas (II-1) to (II-6) of Q in the formula (I) or the formula (I-a), $R_1$ is a hydrogen atom, optionally substituted alkyl (e.g., methyl, isopropyl, hydroxypropyl, hydroxybutyl, 4-hydroxy-3-(hydroxymethyl)butyl, hydroxyethoxyethyl, aminopropyl, carboxypropyl, pyrimidinylmethyl), optionally substituted cycloalkyl (e.g., cyclopropyl, cyclohexyl), optionally substituted heterocycloalkyl (e.g., isopropylpiperidinyl, acetylpiperidinyl, tetrahydropyranylpiperidinyl, tetrahydropyranyl, cyclohexylpiperidinyl), optionally substituted heteroarylalkyl or optionally substituted cycloalkylalkyl.

In another embodiment of the formula (I) or formula (I-a), $R_1$ is —(CO)—$R_{1a}$ wherein $R_{1a}$ is optionally substituted alkyl (e.g., methyl), optionally substituted alkoxy (e.g., tert-butoxy), optionally substituted aryl (e.g., phenyl), or optionally substituted heteroaryl (e.g., fluoropyrimidinyl).

In one embodiment of the formulas (II-7) and (II-8) of Q in the formula (I), $Q_{1a}$ is a single bond or optionally substituted alkylene.

Examples of optionally substituted alkylene group include methylene, ethylene, propylene, butylene, pentylene, aminomethylene, aminoethylene, aminopropylene, aminobutylene, carboxymethylene, carboxyethylene, carboxypropylene, carboxybutylene, carbamoylmethylene, carbamoylethylene, carbamoylpropylene, carbamoylbutylene, methoxymethylene, methoxyethylene, methoxypropylene, methoxybutylene, methylthiomethylene, methylthioethylene, methylthiopropylene, methylthiobutylene, hydroxymethylene, hydroxyethylene, hydroxypropylene, hydroxybutylene, ethoxycarbonylmethylene, ethoxycarbonylethylene, benzyloxymethylene, benzyloxyethylene, benzyloxypropylene, benzyloxybutylene, guanidinomethylene, guanidinoethylene, guanidinopropylene and the like.

In another embodiment of the formulas (II-7) and (II-8) of Q in the formula (I), $Q_{1a}$ is a single bond or optionally substituted alkylene (e.g., methylene, ethylene, propylene).

In one embodiment of the formulas (II-7) and (II-8) of Q in the formula (I), $Q_{1b}$ is a hydrogen atom, hydroxy, halogen, cyano, $-Q_{1c}$, $—COQ_{1c}$, $—CONQ_{1c}Q_{1d}$, $CONQ_{1c}-OQ_{1d}$, $—NQ_{1c}Q_{1d}$, or $—OQ_{1c}$;

$Q_{1c}$ is a hydrogen atom, optionally substituted alkyl, optionally substituted cycloalkyl, optionally substituted heterocycloalkyl, optionally substituted aryl, or optionally substituted heteroaryl;

$Q_{1d}$ is a hydrogen atom or optionally substituted alkyl.

Examples of optionally substituted alkyl group include methyl, ethyl, propyl, isopropyl, butyl, isobutyl, sec-butyl, tert-butyl, pentyl, isopentyl, neopentyl, tert-pentyl, aminomethyl, aminoethyl, aminopropyl, aminobutyl, carboxymethyl, carboxyethyl, carboxypropyl, carboxybutyl, carbamoylmethyl, carbamoylethyl, carbamoylpropyl, carbamoylbutyl, methoxymethyl, methoxyethyl, methoxypropyl, methoxybutyl, methylthiomethyl, methylthioethyl, methylthiopropyl, methylthiobutyl, hydroxymethyl, hydroxyethyl, hydroxypropyl, hydroxybutyl, ethoxycarbonylmethyl, ethoxycarbonylethyl, benzyloxymethyl, benzyloxyethyl, benzyloxypropyl, benzyloxybutyl, guanidinomethyl, guanidinoethyl, guanidinopropyl and the like.

Examples of optionally substituted cycloalkyl include cyclopropyl, cyclobutyl, cyclopentyl, cyclohexyl, cycloheptyl, adamantyl and the like.

Examples of optionally substituted heterocycloalkyl include piperidyl, 4-morpholyl, 4-piperazinyl, pyrrolidinyl, perhydropyrrolidinyl, 1,3-dioxanyl, 1,4-dioxanyl, tetrazolyl, isopropylpiperidinyl, acetylpiperidinyl, tetrahydropyranylpiperidinyl, tetrahydropyranyl, cyclohexylpiperidinyl and the like.

Examples of optionally substituted aryl and optionally substituted heteroaryl include biphenyl, phenyl, pyridyl, pyrimidyl, pyridazinyl, pyrazinyl, triazinyl, pyrrolyl, thienyl, furyl, thiazolyl, oxazolyl, imidazolyl, tetrahydronaphthyl, naphthyl, quinolinyl, isoquinolinyl, quinazolinyl, quinoxalinyl, cinnolinyl, naphthyridinyl, benzotriazinyl, indenyl, pyridopyrimidinyl, pyridopyrazinyl, pyridopyridazinyl, pyridotriazinyl, benzofuryl, benzothienyl, indolyl, indazolyl, benzoxazolyl, benzimidazolyl, benzothiazolyl, benzothiadiazolyl, furopyridinyl, thienopyridinyl, pyrropyridinyl, oxazolopyridinyl, thiazolopyridinyl, imidazopyridinyl and the like.

In another embodiment of the formulas (II-7) and (II-8) of Q in formula (I), $Q_{1b}$ is $—CONH_2$, $—CONHCH_3$, $—NHOCH_3$, methylamino, dimethylamino, piperazinylcarbonyl, thiazolylcarbamoyl, methyl(1-methylpiperidin-4-yl) amino, piperidinyl, or tetrahydropyranyl.

In one embodiment of the formulas (II-7) and (II-8) of Q in formula (I), $Q_{2a}$ is optionally substituted cycloalkylene.

Examples of optionally substituted cycloalkylene include cyclopropylene, cyclobutylene, cyclopentylene, cyclohexylene, cycloheptylene, adamantylene and the like.

In another embodiment of the formulas (II-7) and (II-8) of Q in formula (I), $Q_{2a}$ is optionally substituted cycloalkylene (e.g., cyclohexylene).

In one embodiment of the formulas (II-7) and (II-8) of Q in formula (I), $Q_{2b}$ and $Q_{2c}$ are the same or different and each is a hydrogen atom or optionally substituted alkyl.

Examples of optionally substituted alkyl group include methyl, ethyl, propyl, isopropyl, butyl, isobutyl, sec-butyl, tert-butyl, pentyl, isopentyl, neopentyl, tert-pentyl, aminomethyl, aminoethyl, aminopropyl, aminobutyl, carboxymethyl, carboxyethyl, carboxypropyl, carboxybutyl, carbamoylmethyl, carbamoylethyl, carbamoylpropyl, carbamoylbutyl, methoxymethyl, methoxyethyl, methoxypropyl, methoxybutyl, methylthiomethyl, methylthioethyl, methylthiopropyl, methylthiobutyl, hydroxymethyl, hydroxyethyl, hydroxypropyl, hydroxybutyl, ethoxycarbonylmethyl, ethoxycarbonylethyl, benzyloxymethyl, benzyloxyethyl, benzyloxypropyl, benzyloxybutyl, guanidinomethyl, guanidinoethyl, guanidinopropyl and the like.

In another embodiment of the formulas (II-7) and (II-8) of Q in formula (I), $Q_{2b}$ and $Q_{2c}$ are the same or different and each is a hydrogen atom or optionally substituted alkyl (e.g., methyl).

In one embodiment of the formula (I-a),

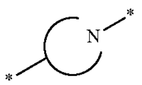

is represented by any of the following formulas (II-1-a) to (II-6-a):

II-1-a

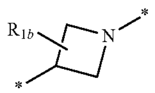

II-2-a

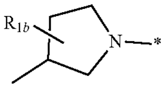

II-3-a

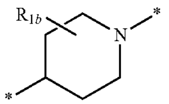

II-4-a

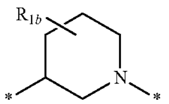

II-5-a

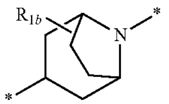

II-6-a

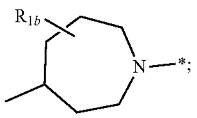

$R_{1b}$ is a hydrogen atom, or 1 to 3 same or different alkyls (wherein * indicates a binding site).

In another embodiment of the formulas (II-1) to (II-6) of Q in the formula (I) or the formula (I-a), $R_{1b}$ is a hydrogen atom.

In one embodiment of the formula (I) or the formula (I-a), $R_2$ is a hydrogen atom, optionally substituted alkyl, optionally substituted alkenyl, optionally substituted alkynyl, optionally substituted arylalkyl, optionally substituted heteroarylalkyl, or optionally substituted cycloalkylalkyl.

Examples of optionally substituted alkyl group include methyl, ethyl, propyl, isopropyl, butyl, isobutyl, sec-butyl, tert-butyl, pentyl, isopentyl, neopentyl, tert-pentyl, aminomethyl, aminoethyl, aminopropyl, aminobutyl, carboxymethyl, carboxyethyl, carboxypropyl, carboxybutyl, carbamoylmethyl, carbamoylethyl, carbamoylpropyl, carbamoylbutyl, methoxymethyl, methoxyethyl, methoxypropyl, methoxybutyl, methylthiomethyl, methylthioethyl, methylthiopropyl, methylthiobutyl, hydroxymethyl, hydroxyethyl, hydroxypropyl, hydroxybutyl, ethoxycarbonylmethyl, ethoxycarbonylethyl, benzyloxymethyl, benzyloxyethyl, benzyloxypropyl, benzyloxybutyl, guanidinomethyl, guanidinoethyl, guanidinopropyl and the like.

Examples of optionally substituted alkenyl group include ethenyl, allyl, 1-propenyl, 2-methylallyl and the like.

Examples of optionally substituted alkynyl group include ethynyl, 1-propynyl, and the like.

Examples of the optionally substituted arylalkyl group include unsubstituted arylalkyl or arylalkyl having an alkyl group such as benzyl, α-methylbenzyl, phenethyl, α-methylphenethyl, α,α-dimethylbenzyl, α,α-dimethylphenethyl, 4-methylphenethyl, 4-methylbenzyl, 4-isopropylbenzyl and the like; arylalkyl having an aryl group or an arylalkyl group such as 4-benzylbenzyl, 4-phenethylbenzyl, 4-phenylbenzyl and the like; arylalkyl having a substituted oxy group such as 4-methoxybenzyl, 4-n-tetradecyloxybenzyl, 4-n-heptadecyloxybenzyl, 3,4-dimethoxybenzyl, 4-methoxymethylbenzyl, 4-vinyloxymethylbenzyl, 4-benzyloxybenzyl, 4-phenethyloxybenzyl and the like; arylalkyl having a hydroxyl group such as 4-hydroxybenzyl, 4-hydroxy-3-methoxybenzyl and the like; arylalkyl having a halogen atom such as 4-fluorobenzyl, 3-chlorobenzyl, 3,4-dichlorobenzyl and the like; 2-furfuryl, diphenylmethyl, 1-naphthylmethyl, 2-naphthylmethyl and the like.

Examples of the optionally substituted heteroarylalkyl group include 2-pyridylmethyl, 3-pyridylmethyl, 2-pyrimidinylmethyl, 5-pyrimidinylmethyl, 3-pyridazinylmethyl, 2-indolylmethyl, 5-indolylmethyl, 2-benzofuranylmethyl, 5-indolylmethyl, 2-benzothienylmethyl, 5-benzothienylmethyl, 6-fluoro-2-benzofuranylmethyl, 6-chloro-2-benzofuranylmethyl, 6-methoxy-2-benzofuranylmethyl, 6-fluoro-2-benzothienylmethyl, 6-chloro-2-benzothienylmethyl, 6-methoxy-2-benzothienylmethyl and 6-phenyl-3-pyridazinylmethyl and the like.

Examples of the optionally substituted cycloalkylalkyl group include cyclopropylmethyl, fluorocyclopropylmethyl, chlorocyclopropylmethyl, bromocyclopropylmethyl, iodocyclopropylmethyl, methylcyclopropylmethyl, 1,1-dimethylcyclopropylmethyl, 1,2-dimethylcyclopropylmethyl, hydroxycyclopropylmethyl, methoxycyclopropylmethyl, ethoxycyclopropylmethyl, methoxycarbonylcyclopropylmethyl, methylcarbamoylcyclopropylmethyl, cyclopropylethyl, cyclohexylmethyl, cyclopropylhexyl and the like.

In one embodiment of the formula (I) or the formula (I-a), $R_2$ is —X—N($R_{2a}$)($R_{2b}$), wherein X is an alkylene group, $R_{2a}$ and $R_{2b}$ are the same or different and each is a hydrogen atom, optionally substituted alkyl, optionally substituted cycloalkyl, optionally substituted heterocycloalkyl, optionally substituted aryl, optionally substituted heteroaryl, optionally substituted arylalkyl, optionally substituted heteroarylalkyl, or optionally substituted cycloalkylalkyl.

Examples of alkylene include methylene ($—CH_2—$), ethylene ($—CH_2CH_2—$), methylmethylene ($—CH(CH_3)—$), 1,2-propylene ($—CH_2CH(CH_3)—$), 1,3-propylene ($—CH_2CH_2CH_2—$), 1,2-butylene ($—CH_2CH(CH_2CH_3)—$), 1,3-butylene ($—CH_2CH_2CH(CH_3)—$), 1,4-butylene ($—CH_2CH_2CH_2CH_2—$), 2-methyltetramethylene ($—CH_2CH(CH_3)CH_2CH_2—$), pentamethylene ($—CH_2CH_2CH_2CH_2CH_2—$), 1,2,3-propanetriyl, 1,3,3-propanetriyl and the like.

Examples of optionally substituted alkyl group include methyl, ethyl, propyl, isopropyl, butyl, isobutyl, sec-butyl, tert-butyl, pentyl, isopentyl, neopentyl, tert-pentyl, aminomethyl, aminoethyl, aminopropyl, aminobutyl, carboxymethyl, carboxyethyl, carboxypropyl, carboxybutyl, carbamoylmethyl, carbamoylethyl, carbamoylpropyl, carbamoylbutyl, methoxymethyl, methoxyethyl, methoxypropyl, methoxybutyl, methylthiomethyl, methylthioethyl, methylthiopropyl, methylthiobutyl, hydroxymethyl, hydroxyethyl, hydroxypropyl, hydroxybutyl, ethoxycarbonylmethyl, ethoxycarbonylethyl, benzyloxymethyl, benzyloxyethyl, benzyloxypropyl, benzyloxybutyl, guanidinomethyl, guanidinoethyl, guanidinopropyl and the like.

Examples of optionally substituted cycloalkyl include cyclopropyl, cyclobutyl, cyclopentyl, cyclohexyl, cycloheptyl, adamantyl and the like.

Examples of optionally substituted heterocycloalkyl include piperidyl, 4-morpholyl, 4-piperazinyl, pyrrolidinyl, perhydropyrrolidinyl, 1,3-dioxanyl, 1,4-dioxanyl, tetrazolyl, and the like.

Examples of optionally substituted aryl and optionally substituted heteroaryl include biphenyl, phenyl, pyridyl, pyrimidyl, pyridazinyl, pyrazinyl, triazinyl, pyrrolyl, thienyl, furyl, thiazolyl, oxazolyl, imidazolyl, tetrahydronaphthyl, naphthyl, quinolinyl, isoquinolinyl, quinazolinyl, quinoxalinyl, cinnolinyl, naphthyridinyl, benzotriazinyl, indenyl, pyridopyrimidinyl, pyridopyrazinyl, pyridopyridazinyl, pyridotriazinyl, benzofuryl, benzothienyl, indolyl, indazolyl, benzoxazolyl, benzimidazolyl, benzothiazolyl, benzothiadiazolyl, furopyridinyl, thienopyridinyl, pyrropyridinyl, oxazolopyridinyl, thiazolopyridinyl, imidazopyridinyl and the like.

Examples of the optionally substituted arylalkyl group include unsubstituted arylalkyl or arylalkyl having an alkyl group such as benzyl, α-methylbenzyl, phenethyl, α-methylphenethyl, α,α-dimethylbenzyl, α,α-dimethylphenethyl, 4-methylphenethyl, 4-methylbenzyl, 4-isopropylbenzyl and the like; arylalkyl having an aryl group or an arylalkyl group such as 4-benzylbenzyl, 4-phenethylbenzyl, 4-phenylbenzyl and the like; arylalkyl having a substituted oxy group such as 4-methoxybenzyl, 4-n-tetradecyloxybenzyl, 4-n-heptadecyloxybenzyl, 3,4-dimethoxybenzyl, 4-methoxymethylbenzyl, 4-vinyloxymethylbenzyl, 4-benzyloxybenzyl, 4-phenethyloxybenzyl and the like; arylalkyl having a hydroxyl group such as 4-hydroxybenzyl, 4-hydroxy-3-methoxybenzyl and the like; arylalkyl having a halogen atom such as 4-fluorobenzyl, 3-chlorobenzyl, 3,4-dichlorobenzyl and the like; 2-furfuryl, diphenylmethyl, 1-naphthylmethyl, 2-naphthylmethyl and the like.

Examples of the optionally substituted heteroarylalkyl group include 2-pyridylmethyl, 3-pyridylmethyl, 2-pyrimidinylmethyl, 5-pyrimidinylmethyl, 3-pyridazinylmethyl, 2-indolylmethyl, 5-indolylmethyl, 2-benzofuranylmethyl, 5-indolylmethyl, 2-benzothienylmethyl, 5-benzothienylmethyl, 6-fluoro-2-benzofuranylmethyl, 6-chloro-2-benzofuranylmethyl, 6-methoxy-2-benzofuranylmethyl, 6-fluoro- 2-benzothienylmethyl, 6-chloro-2-benzothienylmethyl, 6-methoxy-2-benzothienylmethyl and 6-phenyl-3-pyridazinylmethyl and the like.

Examples of the optionally substituted cycloalkylalkyl group include cyclopropylmethyl, fluorocyclopropylmethyl, chlorocyclopropylmethyl, bromocyclopropylmethyl, iodocyclopropylmethyl, methylcyclopropylmethyl, 1,1-dimethylcyclopropylmethyl, 1,2-dimethylcyclopropylmethyl, hydroxycyclopropylmethyl, methoxycyclopropylmethyl, ethoxycyclopropylmethyl, methoxycarbonylcyclopropylmethyl, methylcarbamoylcyclopropylmethyl, cyclopropylethyl, cyclohexylmethyl, cyclopropylhexyl and the like.

In another embodiment of the formula (I) or the formula (I-a), $R_2$ is optionally substituted alkyl (e.g., isobutyl, neopentyl), or optionally substituted arylalkyl.

In another embodiment of the formula (I) or the formula (I-a), $R_2$ is —X—N($R_{2a}$)($R_{2b}$), wherein X is an alkylene group, $R_{2a}$ and $R_{2b}$ are the same or different and each is a hydrogen atom, optionally substituted alkyl, optionally substituted heterocycloalkyl, or optionally substituted arylalkyl.

In one embodiment of the formula (I), V is an optionally substituted aryl ring, an optionally substituted heteroaryl ring, an optionally substituted partially saturated heteroaryl ring, or an optionally substituted heterocycloalkyl ring.

Examples of the optionally substituted aryl ring include, benzene, naphthalene, anthracene, phenanthrene, acenaphthylene, indene and the like.

Examples of the optionally substituted heteroaryl ring include furan, imidazole, isothiazole, isoxazole, oxadiazole, oxazole, 1,2,3-oxadiazole, pyrazine, pyrazole, pyridazine, pyridine, pyrimidine, pyrrole, thiazole, 1,3,4-thiadiazole, triazole, tetrazole, benzofuran, benzothiophene, benzimidazole, benzotriazine, pyridopyrimidine, pyridopyrazine, pyridopyridazine, pyridotriazine, benzothiadiazole, furopyridine, oxazolopyridine, thiazolopyridine, imidazopyridine, quinazoline, thienopyridine, indolizine, quinoline, isoquinoline, phthalazine, quinoxaline, cinnoline, naphthyridine, quinolizine, indole, isoindole, indazole, indoline, benzoxazole, benzopyrazole, benzothiazole, pyrazolopyridine, imidazopyrimidine, pyrrolopyridine, pyrrolopyrimidine, pyrrolopyrazine, pyrrolopyridazine, triazolopyridine, pteridine, purine, carbazole, acridine, perimidine, 1,10-phenanthroline, phenoxathiin, phenoxazine, phenothiazine, phenazine and the like.

Examples of the optionally substituted partially saturated heteroaryl ring include a heteroaryl ring of which one or more double bonds are replaced by single bonds.

Examples of the optionally substituted heterocycloalkyl ring include pyrrolidine, piperidine, morpholine, piperazine, 1,3-dioxane, 1,4-dioxane and the like.

In another embodiment of the formula (I), V is an optionally substituted aryl ring (e.g., benzene, naphthalene), an optionally substituted heteroaryl ring (e.g., pyridine, benzothiazole, thiazole, quinoline, indazole, quinoxaline, thiadiazole, naphthyridine, thiazolopyridin, pyrazole, benzoxazole, pyrimidine, piperidine), an optionally substituted partially saturated heteroaryl ring (e.g., tetrahydrobenzothiazole, dihydropyrazolooxazine), or an optionally substituted heterocycloalkyl ring (e.g., pyrrolidine).

In one embodiment of the formula (I-a), $Ar_1$ is an optionally substituted aryl ring or an optionally substituted heteroaryl ring.

Examples of the optionally substituted aryl ring include benzene, naphthalene, anthracene, phenanthrene, acenaphthylene, indene and the like.

Examples of the optionally substituted heteroaryl ring include furan, imidazole, isothiazole, isoxazole, oxadiazole, oxazole, 1,2,3-oxadiazole, pyrazine, pyrazole, pyridazine, pyridine, pyrimidine, pyrrole, thiazole, 1,3,4-thiadiazole, triazole, tetrazole, benzofuran, benzothiophene, benzimidazole, benzotriazine, pyridopyrimidine, pyridopyrazine, pyridopyridazine, pyridotriazine, benzothiadiazole, furopyridine, oxazolopyridine, thiazolopyridine, imidazopyridine, quinazoline, thienopyridine, indolizine, quinoline, isoquinoline, phthalazine, quinoxaline, cinnoline, naphthyridine, quinolizine, indole, isoindole, indazole, indoline, benzoxazole, benzopyrazole, benzothiazole, pyrazolopyridine, imidazopyrimidine, pyrrolopyridine, pyrrolopyrimidine, pyrrolopyrazine, pyrrolopyridazine, triazolopyridine, pteridine, purine, carbazole, acridine, perimidine, 1,10-phenanthroline, phenoxathiin, phenoxazine, phenothiazine, phenazine and the like.

In another embodiment of the formula (I-a), $Ar_1$ is an optionally substituted aryl ring or an optionally substituted heteroaryl ring (e.g., pyridine, benzothiazole, thiazole, quinoxaline).

In one embodiment of the formula (I) or the formula (I-a), $R_3$ is a hydrogen atom, hydroxy, halogen, cyano, optionally substituted alkyl, optionally substituted cycloalkyl, optionally substituted heterocycloalkyl, optionally substituted aryl, or optionally substituted heteroaryl.

Examples of halogen include fluorine, chlorine, bromine and iodine.

Examples of optionally substituted alkyl group include methyl, ethyl, propyl, isopropyl, butyl, isobutyl, sec-butyl, tert-butyl, pentyl, isopentyl, neopentyl, tert-pentyl, aminomethyl, aminoethyl, aminopropyl, aminobutyl, carboxymethyl, carboxyethyl, carboxypropyl, carboxybutyl, carbamoylmethyl, carbamoylethyl, carbamoylpropyl, carbamoylbutyl, methoxymethyl, methoxyethyl, methoxypropyl, methoxybutyl, methylthiomethyl, methylthioethyl, methylthiopropyl, methylthiobutyl, hydroxymethyl, hydroxyethyl, hydroxypropyl, hydroxybutyl, ethoxycarbonylmethyl, ethoxycarbonylethyl, benzyloxymethyl, benzyloxyethyl, benzyloxypropyl, benzyloxybutyl, guanidinomethyl, guanidinoethyl, guanidinopropyl and the like.

Examples of optionally substituted cycloalkyl include cyclopropyl, cyclobutyl, cyclopentyl, cyclohexyl, cycloheptyl, adamantyl and the like.

Examples of optionally substituted heterocycloalkyl include piperidyl, 4-morpholyl, 4-piperazinyl, pyrrolidinyl, perhydropyrrolidinyl, 1,3-dioxanyl, 1,4-dioxanyl, tetrazolyl, and the like.

Examples of optionally substituted aryl and optionally substituted heteroaryl include biphenyl, phenyl, pyridyl, pyrimidyl, pyridazinyl, pyrazinyl, triazinyl, pyrrolyl, thienyl, furyl, thiazolyl, oxazolyl, imidazolyl, tetrahydronaphthyl, naphthyl, quinolinyl, isoquinolinyl, quinazolinyl, quinoxalinyl, cinnolinyl, naphthyridinyl, benzotriazinyl, indenyl, pyridopyrimidinyl, pyridopyrazinyl, pyridopyridazinyl, pyridotriazinyl, benzofuryl, benzothienyl, indolyl, indazolyl, benzoxazolyl, benzimidazolyl, benzothiazolyl, benzothiadiazolyl, furopyridinyl, thienopyridinyl, pyrropyridinyl, oxazolopyridinyl, thiazolopyridinyl, imidazopyridinyl and the like.

In one embodiment of the formula (I) or the formula (I-a), $R_3$ is —C≡C—$R_{3a}$, wherein $R_{3a}$ is a hydrogen atom, optionally substituted alkyl, optionally substituted cycloalkyl, optionally substituted heterocycloalkyl, or optionally substituted heteroaryl, or $R_3$ is —COOR$_{3b}$, wherein $R_{3b}$ is a hydrogen atom, or optionally substituted alkyl.

Examples of optionally substituted alkyl group include methyl, ethyl, propyl, isopropyl, butyl, isobutyl, sec-butyl, tert-butyl, pentyl, isopentyl, neopentyl, tert-pentyl, aminomethyl, aminoethyl, aminopropyl, aminobutyl, carboxymethyl, carboxyethyl, carboxypropyl, carboxybutyl, carbamoylmethyl, carbamoylethyl, carbamoylpropyl, carbamoylbutyl, methoxymethyl, methoxyethyl, methoxypropyl, methoxybutyl, methylthiomethyl, methylthioethyl, methylthiopropyl, methylthiobutyl, hydroxymethyl, hydroxyethyl, hydroxypropyl, hydroxybutyl, ethoxycarbonylmethyl, ethoxycarbonylethyl, benzyloxymethyl, benzyloxyethyl, benzyloxypropyl, benzyloxybutyl, guanidinomethyl, guanidinoethyl, guanidinopropyl and the like.

Examples of optionally substituted cycloalkyl include cyclopropyl, cyclobutyl, cyclopentyl, cyclohexyl, cycloheptyl, adamantyl and the like.

Examples of optionally substituted heterocycloalkyl include piperidyl, 4-morpholyl, 4-piperazinyl, pyrrolidinyl, perhydropyrrolidinyl, 1,3-dioxanyl, 1,4-dioxanyl, tetrazolyl, and the like.

Examples of optionally substituted heteroaryl include pyridyl, pyrimidyl, pyridazinyl, pyrazinyl, triazinyl, pyrrolyl, thienyl, furyl, thiazolyl, oxazolyl, imidazolyl, tetrahydronaphthyl, naphthyl, quinolinyl, isoquinolinyl, quinazolinyl, quinoxalinyl, cinnolinyl, naphthyridinyl, benzotriazinyl, indenyl, pyridopyrimidinyl, pyridopyrazinyl, pyridopyridazinyl, pyridotriazinyl, benzofuryl, benzothienyl, indolyl, indazolyl, benzoxazolyl, benzimidazolyl, benzothiazolyl, benzothiadiazolyl, furopyridinyl, thienopyridinyl, pyrropyridinyl, oxazolopyridinyl, thiazolopyridinyl, imidazopyridinyl and the like.

In another embodiment of the formula (I) or the formula (I-a), $R_3$ is a hydrogen atom, hydroxy, halogen, cyano, oxo, alkylthio, optionally substituted alkyl, optionally substituted alkoxy, optionally substituted cycloalkyl, optionally substituted heterocycloalkyl, optionally substituted aryl, or optionally substituted heteroaryl.

In another embodiment of the formula (I) or the formula (I-a), $R_3$ is —$COOR_{3b}$, wherein $R_{3b}$ is hydrogen atom or optionally substituted alkyl (e.g., ethyl).

In another embodiment of the formula (I), $R_3$ is —C≡C—$R_{3a}$, wherein $R_{3a}$ is hydrogen atom, optionally substituted alkyl (e.g., hydroxyethyl, hydroxybutyl, hydroxypropyl, hydroxypentyl, hydroxyethoxymethyl, dimethylamino, methylaminocarbonylethyl), optionally substituted cycloalkyl (e.g., aminocyclopropyl), optionally substituted heterocycloalkyl (e.g., tetrahydropyranyl), or optionally substituted heteroaryl.

In one embodiment of the formula (I),

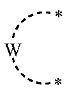

is represented by any of the following formulas (III-1) to (III-4):

(III-1)

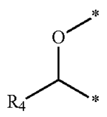

(III-2)

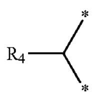

-continued (III-3)

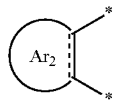

(III-4)

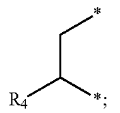

$R_4$ is a hydrogen atom, optionally substituted alkyl, optionally substituted alkenyl, optionally substituted alkynyl, optionally substituted arylalkyl, optionally substituted heteroarylalkyl, optionally substituted cycloalkylalkyl, or optionally substituted heterocycloalkylalkyl, and $Ar_2$ is an optionally substituted aryl ring or an optionally substituted heteroaryl ring.

In one aspect of the present invention, in the case wherein the compound represented by the formula (I) is the compound represented by the formula (I-a), in one embodiment of the formula (I-a),

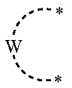

is represented by any of the following formulas (III-1) to (III-3):

(III-1)

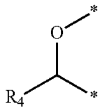

(III-2)

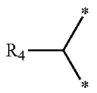

(III-3)

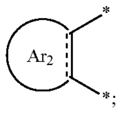

$R_4$ is a hydrogen atom, optionally substituted alkyl, optionally substituted alkenyl, optionally substituted alkynyl, optionally substituted arylalkyl, optionally substituted heteroarylalkyl, optionally substituted cycloalkylalkyl, or optionally substituted heterocycloalkylalkyl, and $Ar_2$ is an optionally substituted aryl ring or an optionally substituted heteroaryl ring (wherein * indicates a binding site).

Examples of optionally substituted alkyl group include methyl, ethyl, propyl, isopropyl, butyl, isobutyl, sec-butyl, tert-butyl, pentyl, isopentyl, neopentyl, tert-pentyl, aminomethyl, aminoethyl, aminopropyl, aminobutyl, carboxymethyl, carboxyethyl, carboxypropyl, carboxybutyl, carbamoylmethyl, carbamoylethyl, carbamoylpropyl, carbamoylbutyl, methoxymethyl, methoxyethyl, methoxypropyl, methoxybutyl, methylthiomethyl, methylthioethyl, methylthiopropyl, methylthiobutyl, hydroxymethyl, hydroxyethyl, hydroxypropyl, hydroxybutyl, ethoxycarbonylmethyl, ethoxycarbonylethyl, benzyloxymethyl, benzyloxyethyl, benzyloxypropyl, benzyloxybutyl, guanidinomethyl, guanidinoethyl, guanidinopropyl and the like.

Examples of optionally substituted alkenyl group including ethenyl, allyl, 1-propenyl, 2-methylallyl and the like.

Examples of optionally substituted alkynyl group include ethynyl, 1-propynyl, and the like.

Examples of the optionally substituted arylalkyl group include unsubstituted arylalkyl or arylalkyl having an alkyl group such as benzyl, α-methylbenzyl, phenethyl, α-methylphenethyl, α,α-dimethylbenzyl, α,α-dimethylphenethyl, 4-methylphenethyl, 4-methylbenzyl, 4-isopropylbenzyl and the like; arylalkyl having an aryl group or an arylalkyl group such as 4-benzylbenzyl, 4-phenethylbenzyl, 4-phenylbenzyl and the like; arylalkyl having a substituted oxy group such as 4-methoxybenzyl, 4-n-tetradecyloxybenzyl, 4-n-heptadecyloxybenzyl, 3,4-dimethoxybenzyl, 4-methoxymethylbenzyl, 4-vinyloxymethylbenzyl, 4-benzyloxybenzyl, 4-phenethyloxybenzyl and the like; arylalkyl having a hydroxyl group such as 4-hydroxybenzyl, 4-hydroxy-3-methoxybenzyl and the like; arylalkyl having a halogen atom such as 4-fluorobenzyl, 3-chlorobenzyl, 3,4-dichlorobenzyl and the like; 2-furfuryl, diphenylmethyl, 1-naphthylmethyl, 2-naphthylmethyl and the like.

Examples of the optionally substituted heteroarylalkyl group include 2-pyridylmethyl, 3-pyridylmethyl, 2-pyrimidinylmethyl, 5-pyrimidinylmethyl, 3-pyridazinylmethyl, 2-indolylmethyl, 5-indolylmethyl, 2-benzofuranylmethyl, 5-indolylmethyl, 2-benzothienylmethyl, 5-benzothienylmethyl, 6-fluoro-2-benzofuranylmethyl, 6-chloro-2-benzofuranylmethyl, 6-methoxy-2-benzofuranylmethyl, 6-fluoro-2-benzothienylmethyl, 6-chloro-2-benzothienylmethyl, 6-methoxy-2-benzothienylmethyl and 6-phenyl-3-pyridazinylmethyl and the like.

Examples of the optionally substituted cycloalkylalkyl group include cyclopropylmethyl, fluorocyclopropylmethyl, chlorocyclopropylmethyl, bromocyclopropylmethyl, iodocyclopropylmethyl, methylcyclopropylmethyl, 1,1-dimethylcyclopropylmethyl, 1,2-dimethylcyclopropylmethyl, hydroxycyclopropylmethyl, methoxycyclopropylmethyl, ethoxycyclopropylmethyl, methoxycarbonylcyclopropylmethyl, methylcarbamoylcyclopropylmethyl, cyclopropylethyl, cyclohexylmethyl, cyclopropylhexyl and the like.

Examples of the optionally substituted heterocycloalkylalkyl group include (2-tetrahydrofuryl)methyl, (2-tetrahydrothiofuranyl)methyl and the like.

Examples of the optionally substituted aryl ring include benzen, benzene, naphthalene, anthracene, phenanthrene, acenaphthylene, indene and the like.

Examples of the optionally substituted heteroaryl ring include furan, imidazole, isothiazole, isoxazole, oxadiazole, oxazole, 1,2,3-oxadiazole, pyrazine, pyrazole, pyridazine, pyridine, pyrimidine, pyrrole, thiazole, 1,3,4-thiadiazole, triazole, tetrazole, benzofuran, benzothiophene, benzimidazole, benzotriazine, pyridopyrimidine, pyridopyrazine, pyridopyridazine, pyridotriazine, benzothiadiazole, furopyridine, oxazolopyridine, thiazolopyridine, imidazopyridine, quinazoline, thienopyridine, indolizine, quinoline, isoquinoline, phthalazine, quinoxaline, cinnoline, naphthyridine, quinolizine, indole, isoindole, indazole, indoline, benzoxazole, benzopyrazole, benzothiazole, pyrazolopyridine, imidazopyrimidine, pyrrolopyridine, pyrrolopyrimidine, pyrrolopyrazine, pyrrolopyridazine, triazolopyridine, pteridine, purine, carbazole, acridine, perimidine, 1,10-phenanthroline, phenoxathiin, phenoxazine, phenothiazine, phenazine and the like.

In another embodiment of the formula (I),

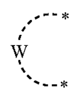

is represented by any of the following formulas (III-1) to (111-4):

(III-1)

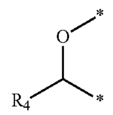

(III-2)

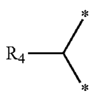

(III-3)

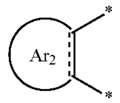

(III-4)

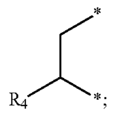

$R_4$ is optionally substituted alkyl (e.g., isobutyl), optionally substituted cycloalkylalkyl (e.g., cyclopropylmethyl), and $Ar_2$ is an optionally substituted aryl ring (e.g., benzene, fluorobenzene).

In another embodiment of the formula (I-a),

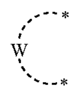

is represented by any of the following formulas (III-1) to (III-3):

(III-1)

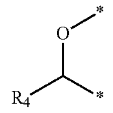

(III-2)

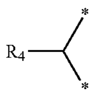

-continued (III-3)

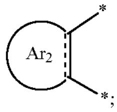

$R_4$ is optionally substituted alkyl (e.g., isobutyl), $Ar_2$ is an optionally substituted aryl ring.

In one embodiment of the formula (I) or the formula (I-a), $R_5$ is a hydrogen atom, or optionally substituted alkyl.

Examples of optionally substituted alkyl group include methyl, ethyl, propyl, isopropyl, butyl, isobutyl, sec-butyl, tert-butyl, pentyl, isopentyl, neopentyl, tert-pentyl, aminomethyl, aminoethyl, aminopropyl, aminobutyl, carboxymethyl, carboxyethyl, carboxypropyl, carboxybutyl, carbamoylmethyl, carbamoylethyl, carbamoylpropyl, carbamoylbutyl, methoxymethyl, methoxyethyl, methoxypropyl, methoxybutyl, methylthiomethyl, methylthioethyl, methylthiopropyl, methylthiobutyl, hydroxymethyl, hydroxyethyl, hydroxypropyl, hydroxybutyl, ethoxycarbonylmethyl, ethoxycarbonylethyl, benzyloxymethyl, benzyloxyethyl, benzyloxypropyl, benzyloxybutyl, guanidinomethyl, guanidinoethyl, guanidinopropyl and the like.

In another embodiment of the formula (I) or the formula (I-a), $R_5$ is a hydrogen atom.

A preferred embodiment of the formula (I) is the following formula (IV):

(IV)

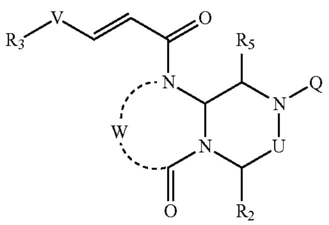

wherein each symbol is as defined above.

A preferred embodiment of the formula (I-a) is the following formula (IV-a):

(IV-a)

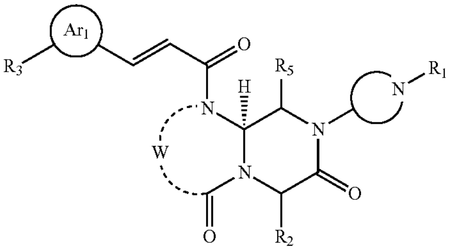

wherein each symbol is as defined above.

In a preferred embodiment of the formula (I) or formula (IV),

Q is represented by any of the following formulas (VI-1) to (VI-3):

(VI-1)

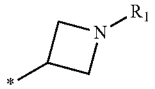

(VI-2)

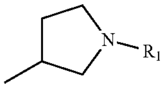

(VI-3)

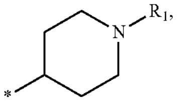

wherein each symbol is as defined above.

In a preferred embodiment of the formula (I) or the formula (IV),

Q is represented by the following formulas (II-7):

II-7

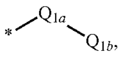

and $Q_{1a}$ is an alkylene and $Q_{1b}$ is —CONH-$Q_1$c, -$Q_{1d}$, —CO-$Q_{1d}$, —N($Q_{1c}$)-$Q_{1d}$, wherein $Q_{1c}$ is a hydrogen atom or an alkyl and $Q_{1d}$ is a hydrogen atom or heterocycloalkyl optionally substituted by alkyl.

In a preferred embodiment of the formula (I-a) or formula (IV-a), $R_1$ is a hydrogen atom, optionally substituted alkyl (e.g., methyl, isopropyl, hydroxybutyl, pyridylmethyl), optionally substituted cycloalkyl, optionally substituted heterocycloalkyl, optionally substituted heteroarylalkyl, optionally substituted cycloalkylalkyl, or —(CO)—$R_{1a}$;

$R_{1a}$ is optionally substituted alkyl, optionally substituted alkoxy, optionally substituted aryl, or optionally substituted heteroaryl;

$R_{1b}$ is a hydrogen atom;

$R_2$ is optionally substituted alkyl (e.g., isobutyl, neopentyl), or optionally substituted arylalkyl;

$R_{3a}$ is a hydrogen atom, optionally substituted alkyl (e.g., hydroxybutyl, hydroxypropyl, hydroxypentyl), optionally substituted cycloalkyl, optionally substituted heterocycloalkyl, or optionally substituted heteroaryl, $R_4$ is optionally substituted alkyl (e.g., isobutyl, 2-ethylbutyl) or optionally substituted cycloalkyl (e.g., cyclohexyl), and $Ar_2$ is an optionally substituted aryl ring.

In a preferred embodiment of the formula (I-a) or formula (IV-a),

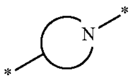

is represented by any of the following formulas (VI-1-a) to (VI-3-a):

(VI-1-a)

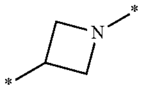

(VI-2-a)

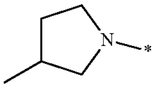

(VI-3-a)

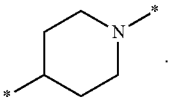

In a preferred embodiment of the formula (I-a) or formula (IV-a), $Ar_1$ is an optionally substituted pyridine ring, an optionally substituted thiazole ring, an optionally substituted benzothiazole ring, or an optionally substituted quinoxaline ring.

In a preferred embodiment of the formula (I-a) or formula (IV-a),

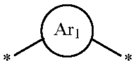

is represented by the following formula (VII-1-a), (VII-2-a), or (VII-3-a):

(VII-1-a)

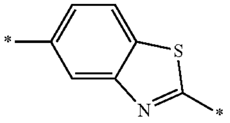

(VII-2-a)

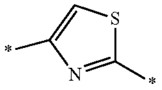

(VII-3-a)

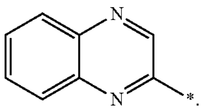

In a preferred embodiment of the formula (I), the formula (I-a), the formula (IV) or the formula (IV-a),

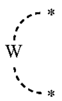

is represented by the following formula (V):

(V)

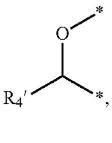

and $R_4'$ is an optionally substituted alkyl or optionally substituted cycloalkyl. Example of the alkyl group for $R_4'$ is preferably isobutyl or 2-ethylbutyl. Example of the cycloalkyl group for $R_4'$ is preferably cyclohexyl.

In a preferred embodiment of the formula (I) or formula (IV), or the formula (I-a) or formula (IV-a), $R_2$ is alkyl optionally substituted by alkylthio or alkylsulfonyl, or arylalkyl.

In another preferred embodiment of the formula (I) or formula (IV), or the formula (I-a) or formula (IV-a), $R_2$ is isobutyl, neopentyl, sec-butyl, or benzyl.

In a preferred embodiment of the formula (I-a) or formula (IV-a), $R_1$ is alkyl (e.g., methyl) or alkyl substituted by 1 or 2 hydroxys.

In a preferred embodiment of the formula (I-a) or formula (IV-a), $R_3$ is a hydrogen atom, hydroxy, or —C≡C—$R_{3a}$ wherein $R_{3a}$ is alkyl substituted by hydroxy (e.g., hydroxybutyl, hydroxypropyl, hydroxypentyl).

In the following, a compound having the formula (I) including a compound having the formula (IV), or the formula (I-a) including a compound having the formula (IV-a) is to be also referred to as "the compound of the present invention".

The general synthesis of the compound of the present invention is described in the following "Production Method".

Abbreviations used in the Production Method and Examples are as follows.

AcOEt (EtOAc): ethyl acetate
AcOH: acetic acid
$AcONH_4$: ammonium acetate
t-BuOH: tert-butanol
$(Boc)_2O$: di-tert-butyl dicarbonate
Cbz: benzyloxycarbonyl
CIP: 2-chloro-1,3-dimethylimidazolinium hexafluorophosphate
DBU: 1,8-diazabicyclo[5.4.0]undec-7-ene
DCE: dichloroethane
DCM: dichloromethane
DIAD: diisopropyl azodicarboxylate
DIC: N,N'-methanediylidenebis[1-methylethanamine]
DIEA (DIPEA): N,N-diisopropylethylamine
DMF: N,N-dimethylformamide
DMSO: dimethylsulfoxide
DMT-MM: 4-(4,6-dimethoxy-1,3,5-triazin-2-yl)-4-methylmorpholinium chloride
EtOH: ethanol
EtO: ethoxy
Fmoc: 9-fluorenylmethyloxycarbonyl
HATU: 1-[bis(dimethylamino)methylene]-1H-1,2,3-triazolo[4,5-b]pyridinium 3-oxide hexafluorophosphate
HMPA: hexamethylphosphoric triamide
LDA: lithium diisopropylamide
MeCN: acetonitrile
MeOH: methanol
Ms: methanesulfonyl
n-BuLi: n-butyllithium
$NaBH(OAc)_3$: Sodium triacetoxyborohydride
OAc (AcO): acetoxy
OEt (EtO): ethoxy
OMe (MeO): methoxy
OTHP (THPO): (tetrahydro-2H-pyran-2-yl)oxy
p-TsOH: p-toluenesulfonic acid
Pd/C: palladium-carbon
PG: amino-protecting group
Ph: phenyl PPh$_3$: triphenylphosphine rt: room temperature TBS: tert-butyldimethylsilyl tBu: tert-butyl TFA: trifluoroacetic acid THF: tetrahydrofuran Trt: trityl Production Method The synthesis method will be explained using one of the formula (I) compounds, formula (I-a), as an example. Other compounds can be synthesized in the same way.

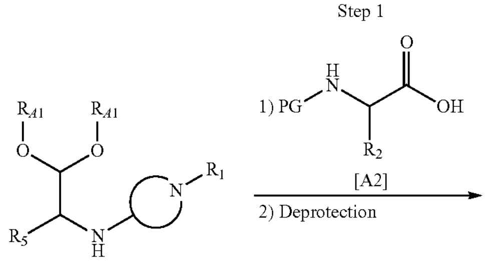

[A1]

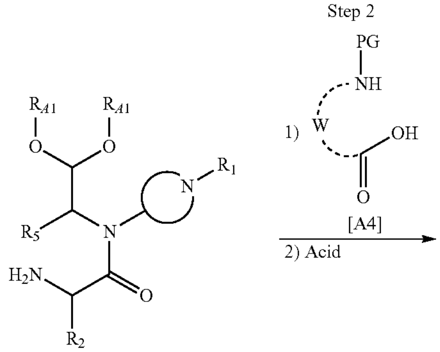

[A3]

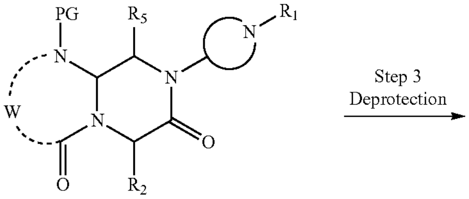

[A5]

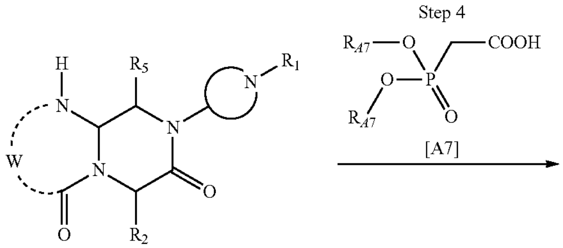

[A6]

-continued

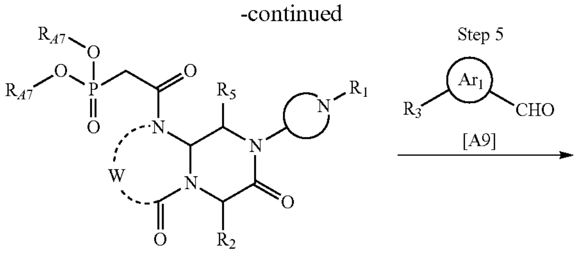

[A8]

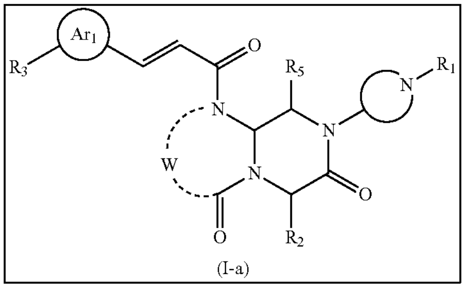

(I-a)

[Step 1] Synthesis of Intermediate [A3]

Intermediate [A3] ($R_{A1}$ is an alkyl group such as methyl and ethyl, and $R_1$, $R_2$ and $R_5$ are as defined above) can be synthesized by an amidation condensation reaction using compound [A1] ($R_{A1}$, $R_1$ and $R_5$ are as defined above) and compound [A2] (PG is an amino-protecting group and $R_2$ is as defined above), followed by an appropriate deprotection reaction of PG. In the amidation condensation reaction, generally known condensing reagents and reaction conditions can be applied. HATU and DMT-MM are preferable as the condensing reagent, DMF, MeOH, THE and the like are preferable as the solvent, and the reaction temperature is preferably from 0° C. to the boiling point of the solvent. Examples of the amino-protecting group include benzyloxycarbonyl (Cbz), tert-butoxycarbonyl (Boc), tert-pentyloxycarbonyl, isobornyloxycarbonyl, 4-methoxybenzyloxycarbonyl, benzyl chloroformate (Cl—Z), benzyl bromoformate (Br—Z), adamantyloxycarbonyl, trifluoroacetyl, phthaloyl, formyl, 2-nitrophenylsulphenyl, diphenylphosphinothioyl, 9-fluorenylmethyloxycarbonyl (Fmoc), trityl (Trt) and the like. In the deprotection reaction, a generally known reaction condition can be applied according as the kind of PG. When PG in the formula is an Fmoc group, a deprotection reaction using piperidine or DBU as a deprotecting reagent in AcOEt, THF or DCM as a solvent is preferable. When PG is a Cbz group, a deprotection reaction using a palladium catalyst such as $Pd(OH)_2$, Pd/C or the like in methanol, ethanol or THE as a solvent under $H_2$ atmosphere is preferable. The reaction temperature is preferably 0° C. to the temperature of the boiling point of the solvent.

[Step 2] Synthesis of Intermediate [A5]

Intermediate [A5] (PG, W, $R_1$, $R_2$ and $R_5$ are as defined above) can be synthesized by an amidation condensation reaction of Intermediate [A3] and Intermediate [A4] (PG and W are as defined above), followed by a ring closure reaction in the presence of an acid. In the amidation condensation reaction, generally known condensing reagents and reaction conditions can be applied. DMT-MM or HATU is preferable as the condensing reagent, DMF, MeOH, THE or the like is preferable as the solvent, and the reaction temperature is preferably 0° C. to the boiling point of the solvent. As the acid to be used for the ring closure reaction, formic acid is preferable and formic acid can also be used as the solvent. The reaction temperature is preferably 0° C. to the boiling point of the solvent.

[Step 3] Synthesis of Intermediate [A6]

Intermediate [A6] (W, $R_1$, $R_2$ and $R_5$ are as defined above) can be synthesized by an appropriate deprotection reaction of PG according as the kind of PG. When PG is a Cbz group, a deprotection reaction using a palladium catalyst such as $Pd(OH)_2$, Pd/C or the like in methanol, ethanol or THE as a solvent under $H_2$ atmosphere is preferable. When PG in the formula is an Fmoc group, a deprotection reaction using piperidine or DBU as a deprotecting reagent in AcOEt, THE or dichloromethane as a solvent is preferable. Both groups can also be deprotected by hydrolysis reaction depending on the kind of W. The reaction temperature is preferably 0° C. to the temperature of the boiling point of the solvent.

[Step 4] Synthesis of Intermediate [A8]

Intermediate [A8] ($R_{A7}$ is an alkyl group such as methyl and ethyl, and W, $R_1$, $R_2$ and $R_5$ are as defined above) can be synthesized by an amidation condensation reaction using intermediate [A6] and compound [A7] ($R_{A7}$ is as defined above). In the amidation condensation reaction, generally known condensing reagents and conditions can be applied. HATU and CIP are preferable as the condensing reagent, DMF, DCM, DCE, THE and the like are preferable as the solvent, and the reaction temperature is preferably from 0° C. to the boiling point of the solvent.

[Step 5] Synthesis of Compound (I-a)

Compound (I-a) (the formulae are as defined above) can be synthesized by Horner-Wadsworth-Emmons (HWE) reaction using Intermediate [A8] and compound [A9] in the presence of a base reagent and in the presence or absence of lithium salt such as lithium bromide and lithium chloride. In this reaction, generally known bases and conditions can be applied. Triethylamine, Hunig's base, DBU, potassium carbonate, sodium methoxide, sodium hydride and LDA are preferable as bases, and THF, chloroform, DCM, DCE, 1,2-dimethoxyethane, methanol, ethanol and DMSO are preferable as solvents. The reaction temperature is preferably −78° C. to the temperature of the boiling point of the solvent.

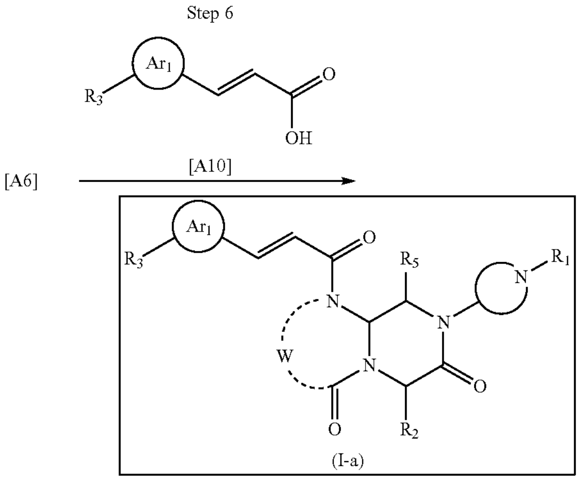

[Step 6] Synthesis of Compound (I-a)

Compound (I) can also be synthesized by an amidation condensation reaction of Intermediate [A6] and Intermediate [A10] ($R_3$ and $Ar_1$ are as defined above). In the amidation condensation reaction, generally known amidation reagents and conditions can be applied. HATU or CIP is preferable as the condensing reagent, DMF, THF, DCM, DCE or the like is preferable as the solvent, and the reaction temperature is preferably 0° C. to the boiling point of the solvent.

When $R_1$ is an optionally substituted alkyl, an optionally substituted cycloalkyl, an optionally substituted heterocycloalkyl, an optionally substituted arylalkyl, an optionally substituted heteroarylalkyl or an optionally substituted cycloalkylalkyl, Intermediate [A5] can also be synthesized as the following scheme.

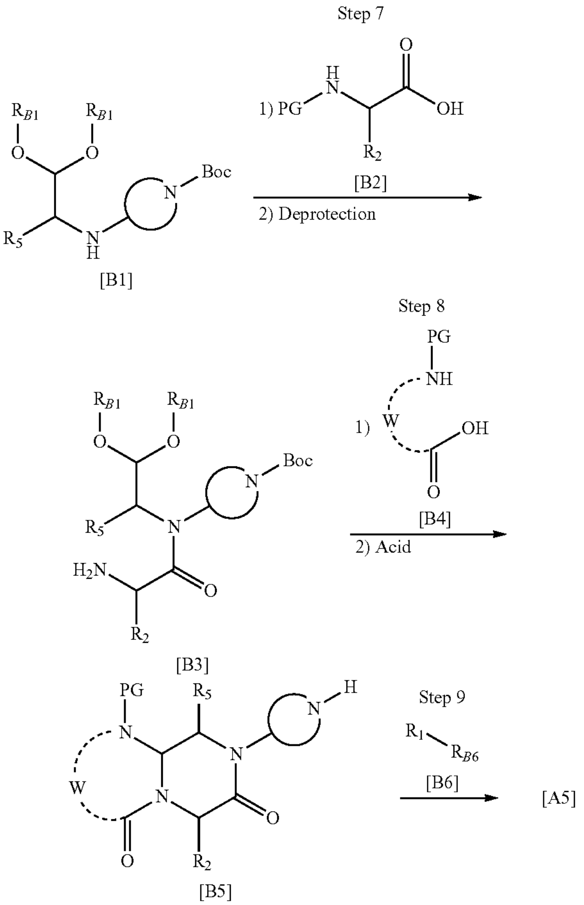

[Step 7] Synthesis of Intermediate [B3]

Intermediate [B3] ($R_{B1}$ is an alkyl group such as methyl and ethyl, and $R_2$ and $R_5$ are as defined above) can be synthesized by an amidation condensation reaction using compound [B1] ($R_{B1}$, and $R_5$ are as defined above) and compound [B2] (PG is an amino-protecting group and $R_2$ is as defined above), followed by an appropriate deprotection reaction of PG according as the kind of PG. In the amidation condensation reaction and deprotection reaction, the same reagents and conditions as Step 1 can be applied.

[Step 8] Synthesis of Intermediate [B5]

Intermediate [B5] (PG, W, $R_1$, $R_2$ and $R_5$ are as defined above) can be synthesized by an amidation condensation reaction of Intermediate [B3] and Intermediate [B4] (PG and W are as defined above), followed by a ring closure reaction in the presence of an acid. The Boc group is deprotected during the ring closure reaction. In the amidation condensation reaction and ring closure reaction, the same reagents and conditions as Step 2 can be applied.

[Step 9] Synthesis of Intermediate [A5]

Intermediate [A5] can be synthesized by the reaction of alkylation reaction using Intermediate [B5] and compound [B6]($R_{B6}$ is a leaving group and $R_1$ is an optionally substituted alkyl, an optionally substituted cycloalkyl, an optionally substituted heterocycloalkyl, an optionally substituted arylalkyl, an optionally substituted heteroarylalkyl or an optionally substituted cycloalkylalkyl) in the presence of base. Triethylamine, Hunig's base, pyridine, DBU, sodium carbonate, potassium carbonate, sodium methoxide and potassium tert-butoxide are preferable as bases. THF, MeCN, chloroform, DCM, DCE, DMF and DMSO are preferable as solvents. The reaction temperature is preferably 0° C. to the temperature of the boiling point of the solvent.

Instead of Intermediate [A5], Intermediates [B8] and [B10] can also be synthesized as the following scheme.

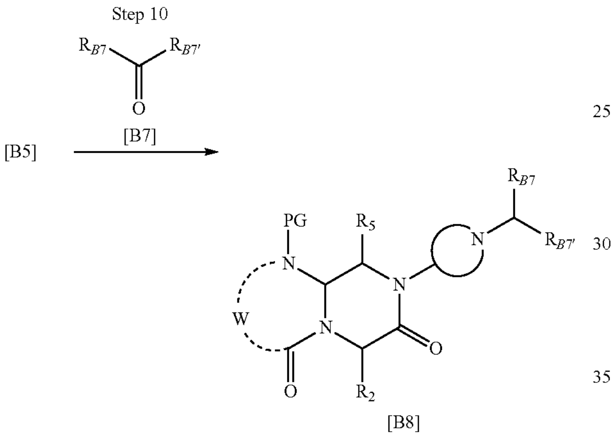

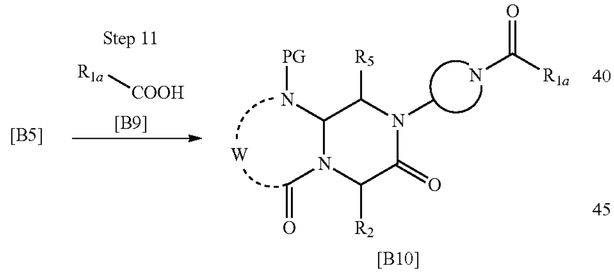

[Step 10] Synthesis of Intermediate [B8]

Intermediate [B8] ($R_{B7}$ and $R_{B7'}$ are independently hydrogen, optionally substituted alkyl, optionally substituted aryl, optionally substituted arylalkyl, optionally substituted heteroaryl, optionally substituted heteroarylalkyl, optionally substituted cycloalkyl or optionally substituted cycloalkylalkyl, and W, PG, $R_2$ and $R_5$ are as defined above) can be synthesized by reductive amination reaction using Intermediate [B5] and compound [B7] ($R_{B7}$ and $R_{B7'}$ are as defined above). In the reductive amination reaction, generally known reducing reagents and conditions can be applied. Sodium triacetoxyborohydride, sodium cyanoborohydride, sodium tetrahydroborate, lithium tetrahydroborate, THF-borane complex, pyridine-borane complex, picoline-borane complex and the like are preferable as the reducing reagent, MeOH, THF, chloroform, DCM, DCE and the like are preferable as solvent, and the reaction temperature is preferably from 0° C. to the boiling point of the solvent.

[Step 11] Synthesis of Intermediate [B10]

Intermediate [B10] (W, PG, $R_{1a}$, $R_2$ and $R_5$ are as defined above) can be synthesized by an amidation condensation reaction using compound [B5] and compound [B9] ($R_{1a}$ is as defined above). In the amidation condensation reaction, generally known amidation reagents and conditions can be applied. HATU, WSC hydrochloride, T3P and DMT-MM are preferable as the condensing reagent, DMF, MeOH, THF and the like are preferable as the solvent, and the reaction temperature is preferably from 0° C. to the boiling point of the solvent.

From Intermediates [B8] and [B10], Compound (I) can be synthesized by the same manners as Steps 3, 4, 5 and 6.

Intermediates [A1] and [B1] can also be synthesized by the following scheme, wherein intermediate [C1] corresponds to intermediate [A1] when $R_{C1'}$ is $R_1$ and corresponds to intermediate [B1] when $R_{C1'}$ is Boc group.

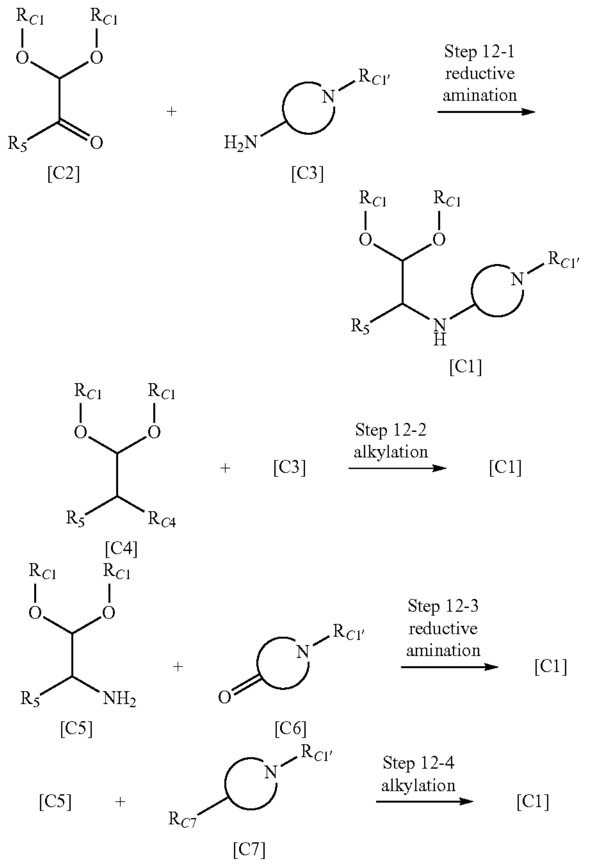

[Step 12-1] Synthesis of Intermediate [C1]

Intermediate [C1] ($R_{C1}$ is an alkyl group such as methyl and ethyl, $R_{C1'}$ is $R_1$ or Boc group, and $R_5$ is as defined above) can be synthesized by reductive amination reaction using Intermediate [C2] ($R_{C1}$ and $R_5$ are as defined above) and compound [C3] ($R_{C1'}$ is as defined above). In the reductive amination reaction, generally known reducing reagents and conditions can be applied such as Step 10.

[Step 12-2] Synthesis of Intermediate [C1]

Intermediate [C1] can also be synthesized by alkylation reaction using Intermediate [C4] ($R_{C1}$ and $R_5$ are as defined above) and compound [C3]. In the reductive amination reaction, generally known reducing reagents and conditions can be applied such as Step 9.

[Step 12-3] Synthesis of Intermediate [C1]

Intermediate [C1] can also be synthesized by reductive amination reaction using Intermediate [C5] ($R_{C1}$ and $R_5$ are as defined above) and compound [C6] ($R_{C1'}$ is as defined above). In the reductive amination reaction, generally known reducing reagents and conditions can be applied such as Step 10.

[Step 12-4] Synthesis of Intermediate [C1]

Intermediate [C1] can also be synthesized by alkylation reaction using Intermediate [C5] and compound [C7] ($R_{C7}$ is a leaving group and $R_{C1'}$ is as defined above). In the reductive amination reaction, generally known reducing reagents and conditions can be applied such as Step 9.

Intermediate [A4] can be synthesized as intermediate [D6] by the following scheme.

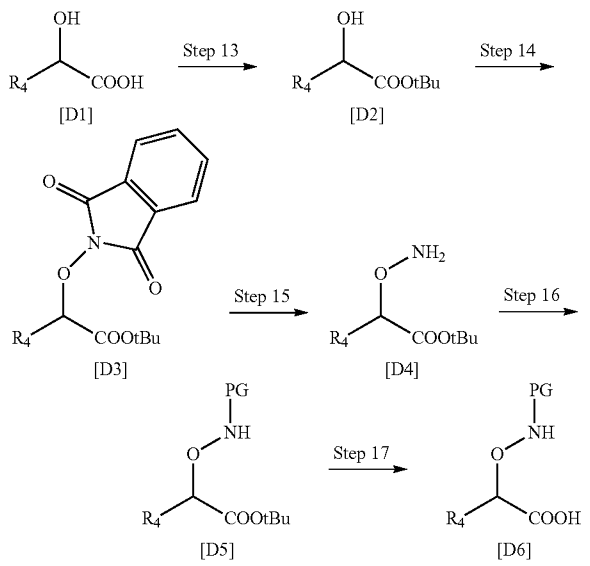

[D1] [D2] [D3] [D4] [D5] [D6]

[Step 13] Synthesis of Intermediate [D2]

Intermediate [D2] ($R_4$ is as defined above) can be synthesized by esterification reaction from compound [D1] ($R_4$ is as defined above). In this reaction, generally known condensation reagents and conditions can be applied. DIC are preferable as the condensing reagent, tert-butanol is used as a reagent and solvent, and the reaction temperature is preferably from 0° C. to the boiling point of the solvent.

[Step 14] Synthesis of Intermediate [D3]

Intermediate [D3] ($R_4$ is as defined above) can be synthesized by Mitsunobu reaction from Intermediate [D2] using N-hydroxyphthalimide, triphenylphosphine and DIAD. In the Mitsunobu amination reaction, generally known reagents and conditions can be applied other than triphenylphosphine and DIAD. The reaction temperature is preferably from 0° C. to the boiling point of the solvent.

[Step 15] Synthesis of Intermediate [D4]

Intermediate [D4] ($R_4$ is as defined above) can be synthesized using hydrazine. Generally known conditions can be applied, and the reaction temperature is preferably from 0° C. to the boiling point of the solvent.

[Step 16] Synthesis of Intermediate [D5]

Intermediate [D5] (PG and $R_4$ are as defined above) can be synthesized by generally known reagents and conditions according as the kind of PG. Preferable amino-protecting groups PG are Cbz and Fmoc groups. Other protecting groups that are not deprotected by acetic condition are also available. The reaction temperature is preferably from 0° C. to the boiling point of the solvent.

[Step 17] Synthesis of Intermediate [D6]

Intermediate [D6] (PG and $R_4$ are as defined above) can be synthesized by acidic condition. In the deprotecting condensation reaction, generally known acidic reagents and conditions can be applied. Formic acid is preferable as the condensing reagent and solvent as well. The reaction temperature is preferably from 0° C. to the boiling point of the solvent.

The protecting group in each step is not limited to the protecting group. When $R_1$, $R_2$, $R_3$, $Ar_1$ or $R_5$ has a protected functional group, deprotection can be performed in any step. The compound synthesized in each step of the reaction may be directly used in the next reaction without isolation. Under the conditions of Steps 2 and 8, the ring closure reaction and the deprotection reaction may proceed simultaneously.

The compound to be obtained in the cyclization reaction can be isolated and purified by a conventional method such as extraction, water-washing, acid washing, alkali washing, crystallization, recrystallization, or silica gel column chromatography.

Furthermore continuing the explanation, the compounds of the present invention, salts thereof and derivatives thereof are excellent in pharmacological action selectivity, safety (various toxicities and safety pharmacology), pharmacokinetic performance, physicochemical property and the like, and therefore the usefulness as active ingredients of medicaments can be confirmed.

Examples of tests concerning pharmacological action selectivity include, but not be limited to, inhibition or activation assays on various pharmacological target receptors, inhibition assays on various pharmacological target enzymes, ion channels or transporters, cell tests to be used for the evaluation for various pharmacological action, and the like.

Examples of tests concerning safety include, but not be limited to, the following list including cytotoxic tests (e.g., tests using HL60 cells, hepatocytes, etc., and the like), genotoxicity tests (e.g., Ames test, mouse lymphoma TK test, chromosomal aberration test, micronucleus test and the like), skin sensitization tests (e.g., Buehler method, GPMT method, APT method, LLNA test and the like), skin photosensitization tests (e.g., Adjuvant and Strip method and the like), eye irritation tests (e.g., single instillation, short-term continuation instillation, repetitive instillation and the like), safety pharmacology tests for the cardiovascular system (e.g., telemetry method, APD method, hERG inhibition assay and the like), safety pharmacology tests for the central nervous system (e.g., FOB method, modified version of Irwin method and the like), safety pharmacology tests for the respiratory system (e.g., measurement method using a respiratory function measuring apparatus, measurement method using a blood gas analyzer and the like), general toxicity tests, and the like.

Examples of tests concerning pharmacokinetic performance include, but not be limited to, the following list including cytochrome P450 enzyme inhibition or induction tests, cell permeability tests (e.g., tests using CaCO-2 cells, MDCK cells etc., and the like), drug transporter ATPase assay, oral absorption tests, blood concentration transition measurement tests, metabolism tests (e.g., stability test, metabolite molecular species test, reactivity test and the like), solubility tests (e.g., solubility test based on turbidity method and the like), and the like.

Examples of tests concerning physicochemical property include, but not be limited to, the following list including chemical stability test (e.g., stability test using HPLC etc., and the like), partition coefficient (e.g., partition test using octanol phase/water phase and the like), ionization constant test, crystallization test, and the like.

In other embodiment, a method for treating cancer by administration of the compound of the present invention is provided. The compound of the present invention has an action of inhibiting proliferation of cancer cells and may be used for treating cancer.

The test compound here is a compound described in the present specification, that is, the compound of the present invention. Typically, test compounds are tested at several different concentrations, and the concentrations are partly selected according to the assay conditions.

The compound of the present invention may be used for suppressing cancer cells, and therefore, is useful for controlling cell proliferation. The compound of the present invention may also be used favorably for inducing apoptosis of cells.

In other aspects, the present invention provides pharmaceutical compositions containing the compound of the present invention. These compositions may be used in various methods (e.g., treatment of cancer) of the present invention as described in detail below.

The pharmaceutical composition of the present invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions (e.g., injection) used for parenteral (particularly, intravenous), intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. In addition, pH may be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, NJ) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound, e.g., the compound of the present invention in the required amount, in an appropriate solvent with one or a combination of ingredients enumerated above, as required, followed by filtered sterilization. Generally, dispersions are prepared by incorporating the active compound into a sterile vehicle that contains a dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules.

Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent I such as peppermint, methyl salicylate, or orange flavoring.

For administration by inhalation, the compounds are delivered in the form of an aerosol spray from pressured container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It can be advantageous to formulate oral or parenteral compositions in dosage unit form for ease of administration and uniformity of dosage. Dosage unit form as used herein refers to physically discrete units suited as unitary dosages for the subject to be treated; each unit containing a 5 predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

For instance, in certain embodiments, a pharmaceutical composition of the present invention is one suitable for oral administration in unit dosage form such as a tablet or capsule that contains from about 1 mg to about 1 g of the compound of this invention. In some other embodiments, a pharmaceutical composition of the present invention is one suitable for intravenous, subcutaneous or intramuscular injection. A patient may receive, for example, an intravenous, subcutaneous or intramuscular dose of about 1 μg/kg to about 1 g/kg of the compound of the present invention. The intravenous, subcutaneous and intramuscular dose may be given by means of a bolus injection or by continuous infusion over a period of time. Alternatively a patient will receive a daily oral dose approximately equivalent to the daily parenteral dose, the composition being administered 1 to 4 times per day.

Preferably, the compound of the present invention can be administered intravenously (particularly preferably, by continuous drip infusion or rapid intravenous administration) to mammals inclusive of human.

In the case, the dose is selected appropriately depending on various factors such as the body weight and/or age of patients, and/or the degree of the symptom and an administration route. For example, the dose of the compound of the formula (I) for intravenous administration is generally in the range of 1 to 10000 mg/day/$m^2$ human body surface area, preferably in the range of 1 to 5000 mg/day/$m^2$ human body surface area, and more preferably 10 to 5000 mg/day/$m^2$ human body surface area.

The pharmaceutical composition containing the compound of present invention can be used for treatment of disease, especially cancer.

In one aspect, the present invention provides methods for inhibiting tumor growth. Such methods comprise the step of administering to a subject (e.g., a mammalian subject) having a tumor a compound with the compound of the present invention in an amount effective to inhibit tumor growth. A compound or composition inhibits tumor growth if the tumor sizes are statistically significantly smaller in subjects with the treatment of the compound or composition than those without the treatment.

The inhibitory effect of a particular compound or composition of the present invention on tumor growth was characterized to the binding inhibition of eIF4E (eukaryotic translation initiation factor 4E) and eIF4G eukaryotic translation initiation factor 4G) by m7GTP pull-down assay and proximity ligation assay. Translation can be inhibited by blocking the binding of eIF4E to eIF4G. The binding of a particular compound to eIF4E was also observed by NMR measurements.

The inhibitory effect of a particular compound or composition of the present invention on tumor growth may be characterized by any appropriate methods known in the art. For instance, the effect of the compound or composition on survivin expression may be measured. Compounds or compositions down-regulate survivin expression are likely to have inhibitory effects on tumor growth. In addition, assays using tumor cell lines (e.g., soft agar assays using SW480 cells) and animal models for tumor growth (e.g., nude mice grafted with tumor cells and Min mouse model) may also be used to evaluate the inhibitory effect on tumor growth of a given compound or composition as described in detail in the examples. Other exemplary animal models or xenografts for tumor growth include those for breast cancer (Guo et al, Cancer Res. 62: 4678-84, 2002; Lu et al, Breast Cancer Res. Treat. 57: 183-92, 1999), pancreatic cancer (Bouvet et al, Cancer Res. 62: 1534-40, 2002), ovarian tumor (Nilsson et al, Cancer Chemother. Pharmacol. 49: 93-100, 2002; Bao et al, Gynecol. Oncol. 78: 373-9, 2000), melanoma (Demidem et al, Cancer Res. 61: 2294-300, 2001), colorectal cancer (Brown et al, Dig. Dis. Sci. 45: 1578-84, 2000; Tsunoda et al, Anticancer Res. 19: 1149-52, 1999; Cao et al, Clin. Cancer Res. 5: 267-74, 1999; Shawler et al, J. Immunother. Emphasis Tumor Immunol. 17: 201-8, 1995; McGregor et al, Dis. Colon. Rectum. 36: 834-9, 1993; Verstijnen et al, Anticancer Res. 8: 1193-200, 1988), hepatocellular cancer (Labonte et al, Hepatol. Res. 18: 72-85, 2000), and gastric cancer (Takahashi et al, Int. J. Cancer 85: 243-7, 2000).

The compound or composition that inhibits tumor growth may be administrated into a subject with a tumor via an appropriate route depending on, for example, the tissue in which the tumor resides. The appropriate dosage may be determined using knowledge and techniques known in the art as described above. The effect of the treatment of the compound or composition on tumor growth may also be monitored using methods known in the art. For instance, various methods may be used for monitoring the progression and/or growth of colorectal cancer, including colonoscopy, sigmoidoscopy, biopsy, computed tomograph, ultrasound, magnetic resonance imaging, and positron emission tomography. Methods for monitoring the progression and/or growth of ovarian cancer include, for example, ultrasound, computed tomography, magnetic resonance imaging, chest X-ray, laparoscopy, and tissue sampling.

In a related aspect, the present invention provides a method for treating or preventing cancer. Such methods comprise the step of administering to a subject in need thereof a compound or composition of the present invention in an amount effective to treat or prevent cancer in the subject. Treating cancer is understood to encompass reducing or eliminating cancer progression, e.g., cancer growth and metastasis. Preventing cancer is understood to encompass preventing or delaying the onset of cancer. Various types of cancer may be treated or prevented by the present invention. They include, but are not limited to, lung cancer, breast cancer, colorectal cancer, stomach cancer, pancreatic cancer, liver cancer, uterus cancer, ovarian cancer, gliomas, melanoma, lymphoma, and leukemia. A subject in need of treatment may be a human or non-human primate or other animal with various types of cancer.

A subject in need of prevention may be a human or non-human primate or other animal that is at risk for developing cancer. Methods for diagnosing cancer and screening for individuals with high risk of cancer are known in the art and may be used in the present invention. For instance, colorectal cancer may be diagnosized by fecal occult blood test, sigmoidoscopy, colonoscopy, barium enema with air contrast, and virtual colonoscopy. An individual with high risk of colorectal cancer may have one or more colorectal cancer risk factors such as a strong family history of colorectal cancer or polyps, a known family history of hereditary colorectal cancer syndromes, a personal history of adenomatous polyps, and a personal history of chronic inflammatory bowel disease.

The compound of the present invention useful in cancer treatment or prevention may be identified by appropriate methods known in the art. Methods that may be used to select compounds for inhibitory effect on tumor (or cancer cells) growth (or proliferation) as described above may also be used. The route of administration, the dosage of a given compound, the effectiveness of the treatment may be determined using knowledge and techniques known in the art. Factors that may be considered in making such a determination include, for example, type and stage of the cancer to be treated.

The compound of the present invention useful in cancer treatment and prevention may be administered in combination with an other anti-neoplastic agent. The anti-neoplastic agent refers to a compound that inhibits tumor growth.

Specific examples of the other anti-neoplastic agent include alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammalI and calicheamicin omegaI1 (see, e.g., Agnew, Chem Intl. Ed. Engl. 33:183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRLAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU), tegafur, raltitrexed; folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Illinois), and TAXOTERE™ doxetaxel (Rhne-Poulenc Rorer, Antony, France); chloranbucil; GEMZAR™ gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; NAVELBINE™ vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids such as retinoic acid; capecitabine; and pharmaceutically acceptable salts, acids or derivatives of any of the above.

In addition, examples of the other anti-neoplastic agent also include anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestane, fadrozole, RIVISOR® vorozole, FEMARA® letrozole, and ARIMIDEX™ anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF expression inhibitor (e.g., ANGIOZYME™ ribozyme) and a HER2 expression inhibitor; vaccines such as gene therapy vaccines, for example, ALLOVECTIN® vaccine, LEUVECTIN™ vaccine, and VAXID™ vaccine; PROLEUKIN™ rIL-2; LURTOTECAN™ topoisomerase 1 inhibitor; ABARELIX™ rmRH; and pharmaceutically acceptable salts, acids or derivatives of any of the above.

Moreover, examples of the other anti-neoplastic agent also include a "growth inhibitory agent" referring to a compound or composition which inhibits growth of a cell in vitro and/or in vivo. Thus, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), TAXOL®, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C.

Furthermore, examples of the other anti-neoplastic agent also include a "molecular target drug" that blocks the proliferation and metastasis of cancer by interfering with specific molecules involved in carcinogenesis (the process by which normal cells become cancer cells), tumor growth, or tumor spread. Specific examples of the "molecular target drug" include kinase inhibitors that inhibit kinase activity on tumors, including, for example, imatinib, erlotinib, gefitinib, sunitinib, sorafenib, dasatinib, nilotinib; antibodies that bind to the cell surface molecule on tumor cells or to the growth factor and the like such as, for example, ibritumomab, cetuximab, trastuzumab, panitumumab, bevacizumab, rituximab; and proteasome inhibitors that inhibit the proteasome which regulates protein expression and function by degradation of ubiquitinylated proteins, such as bortezomib; and pharmaceutically acceptable salts, acids or derivatives of any of above.

Further information can be found in The Molecular Basis of Cancer, Mendelsohn and Israel, eds., Chapter 1, entitled "Cell cycle regulation, oncogenes, and antineoplastic drugs" by Murakami et al. (W B Saunders: Philadelphia, 1995), especially p. 13.

The compound of the present invention administered in combination with an anti-neoplastic agent does not necessarily require that the compound and the anti-neoplastic agent be administered concurrently. The compound and the agent may be administered separately as long as at a time point, they both have effects on same cancer cells.

For example, the administration mode may be exemplified by (1) administration of a single preparation obtained by simultaneously formulating the compound of the present invention and the other anti-neoplastic agent, (2) simultaneous administration through the same administration route of two preparations obtained by separately formulating the compound of the present invention and the other anti-neoplastic agent, (3) administration with a time interval through the same administration route of two preparations obtained by separately formulating the compound of the present invention and the other anti-neoplastic agent, (4) simultaneous administration through different administration routes of two preparations obtained by separately formulating the compound of the present invention and the other anti-neoplastic agent, (5) administration with a time interval through different administration routes of two preparations obtained by separately formulating the compound of the present invention and the other anti-neoplastic agent (e.g., administration in order of the compound of the present invention and then the other anti-neoplastic agent, or administration in the reverse order), or the like. The amount of the other anti-neoplastic agent to be administered can be appropriately selected with reference to the clinically used dosage. The mixing ratio of the compound of the present invention and the other anti-neoplastic agent can be appropriately selected in accordance with the subject of administration, administration route, disease to be treated, symptoms, combination, and the like.

In a further related aspect, the present invention provides methods for promoting apoptosis in cancer cells. Such methods comprise the step of contacting cancer cells with the compound of the present invention in an amount effective to promote apoptosis in these cells. A compound promotes apoptosis if the number of cancer cells undergoing apoptosis is statistically significantly larger in the presence of the compound than that in the absence of the compound. Such compounds may be identified by methods known in the art (e.g., measuring caspase activities and/or cell death) using cultured cancer cell lines, xenografts, or animal cancer models. Preferably, the compound is more active in promoting apoptosis in cancer cells than in normal cells. Cancer cells treatable by the present method may be from various tissue origins.

The following non-limiting examples illustrate the compounds, compositions, and methods of use of this invention.

EXAMPLES

The present invention is explained in more detail in the following by referring to Production Examples, Examples, Reference Examples and Experimental Examples; however, the scope of the present invention is not limited thereto.

In the Examples, $^1H$ NMR was measured using Bruker AVANCE III 300. For the analysis, Topspin (Bruker, trade name) and the like were used.

Mass spectrometric analysis was performed using the following Method A, B, C or D:

(Method A)

System: Shimadzu UFLC/MS System (Shimazu-2020 mass spectrometer)

Column: ODS column for the chromatography column

Eluents: A (water with 0.04% TFA) and B (acetonitrile with 0.04% TFA)

(Method B)

System: Shimadzu UFLC/MS System (Shimazu-2020 mass spectrometer)

Column: ODS column for the chromatography column

Eluents: A (5 mM $AcONH_4$ in water) and B (5 mM $AcONH_4$ in acetonitrile)

(Method C)

System: Water 2795 System

Column: Develosil C30-UG-5, 50×4.6 mm, Nomura Kagaku Co., Ltd.

Eluents: A (water with 0.1% HCOOH) and B (acetonitrile with 0.1% HCOOH).

Flow rate: 1.0 mL/min (Method D)

System: Shimadzu

Column: SunFire C18 50×4.6 mm Sum

Eluents: A (water with 0.1% trifluoroacetic acid and 10% acetonitrile) and B (acetonitrile with 0.1% trifluoroacetic acid and 10% water).

Flow rate: 2.0 mL/min

Biotage Initiator was used for organic microwave synthesis.

Column chromatography was performed using flash purification system of SHOKO Scientific Purif-espoir 2 and Biotage Isolera One using n-hexane-AcOEt and/or AcOEt-MeOH with a gradient as an eluent. One or several columns selected from prepacked cartridge columns listed in below were used for purification depending on the amount and purity of sample: $SiO_2$: CHROMATOREX Q-PACK S130 (SIZE10, SIZE20, SIZE60 and SIZE200), Biotage SNAP KP-Sil (10 g, 25 g and 50 g), Biotage Rening Cartridges (5 g, 10 g, 30 g, 45 g and 80 g) $NHSiO_2$: CHROMATOREX Q-PACK NH60 (SIZE10, SIZE20, SIZE60 and SIZE200), CHROMATOREX Q-PACK DNH600 (SIZE20, SIZE60 and SIZE200)

Preparative HPLC (prep-HPLC) was performed using Waters FractionLynx system.

General Prep-HPLC Condition (AcOH):

Column: C30-UG 25 mmID*150 mmL, 5 um
Mobile phase A: water with 0.10% v/v acetic acid
Mobile phase B: acetonitrile
UV detection wavelength: 220 nm
Flow rate: 25 ml/min
Temperature: room temperature
Gradient time table:
0 min B=x %, A=100−x %
0.01-10.99 min linear gradient
11.00 min B=y %, A=100−y %
11.01-11.20 min B=y %, A=100−y %
11.21-13.00 min B=100%
13.01-15.00 min B=z %, A=100−z %
x, y and z values depend on the kind of compounds.

General Prep-HPLC Condition (TEA):

Column: L-Column2 ODS 20 mmID*150 mmL, 5 um
Mobile phase A: water with 0.10% v/v TEA
Mobile phase B: acetonitrile with 0.10% v/v TEA
UV detection wavelength: 220 nm
Flow rate: 20 ml/min
Temperature: room temperature
Gradient time table:
0 min B=x %, A=100−x %
0.01-6.99 min linear gradient
7.00 min B=y %, A=100−y %
7.01-10.99 min B=100%
11.00-12.00 min B=z %, A=100−z %
x, y and z values depend on the kind of compounds.

Intermediates B1 listed in the Table 1 are known compounds or were synthesized according to a known method or a method below.

List of Intermediate B1

TABLE 1

| Intermediate B1 | Structure |
|---|---|
| B1-1 | 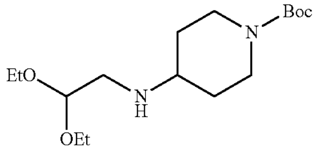 [SMILES: CCOC(CNC1CCN(C(=O)OC(C)(C)C)CC1)OCC] |
| B1-2 | 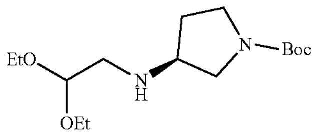 [SMILES: CCOC(CN[C@H]1CCN(C(=O)OC(C)(C)C)C1)OCC] |
| B1-3 | 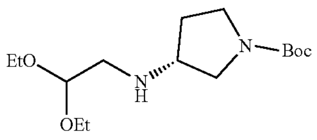 [SMILES: CCOC(CN[C@@H]1CCN(C(=O)OC(C)(C)C)C1)OCC] |

TABLE 1-continued

| Intermediate B1 | Structure |
|---|---|
| B1-4 | 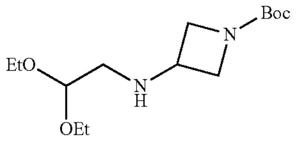 [SMILES: CCOC(CNC1CN(C(=O)OC(C)(C)C)C1)OCC] |
| B1-5 | 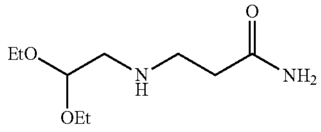 [SMILES: CCOC(CNCCC(N)=O)OCC] |
| B1-6 | 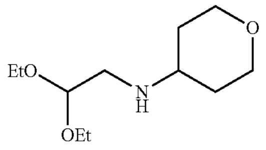 [SMILES: CCOC(CNC1CCOCC1)OCC] |
| B1-7 | 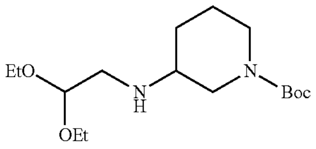 [SMILES: CCOC(CNC1CCCN(C(=O)OC(C)(C)C)C1)OCC] |
| B1-8 | 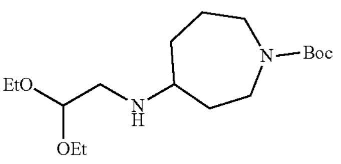 [SMILES: CCOC(CNC1CCCN(C(=O)OC(C)(C)C)CC1)OCC] |
| B1-9 | 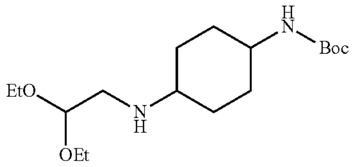 [SMILES: CCOC(CNC1CCC(NC(=O)OC(C)(C)C)CC1)OCC] |
| B1-10 | 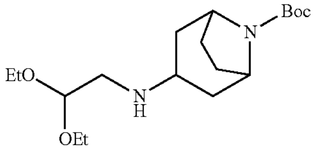 [SMILES: CCOC(CNC1CC2CCC(C1)N2C(=O)OC(C)(C)C)OCC] |
| B1-11 | 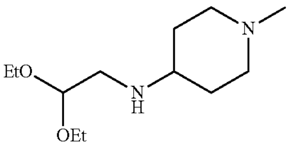 [SMILES: CCOC(CNC1CCN(C)CC1)OCC] |
| B1-12 | 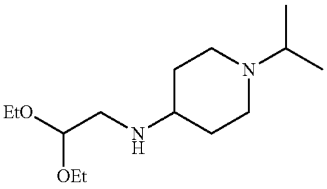 [SMILES: CCOC(CNC1CCN(C(C)C)CC1)OCC] |

TABLE 1-continued

| Intermediate B1 | Structure |
|---|---|
| B1-13 | 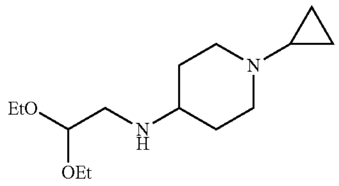 [SMILES: CCOC(CNC1CCN(C2CC2)CC1)OCC] |
| B1-14 | 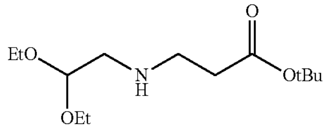 [SMILES: CCOC(CNCCC(=O)OC(C)(C)C)OCC] |
| B1-15 | 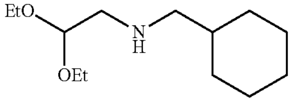 [SMILES: CCOC(CNCC1CCCCC1)OCC] |
| B1-16 | 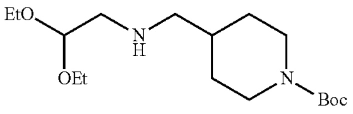 [SMILES: CCOC(CNCC1CCN(C(=O)OC(C)(C)C)CC1)OCC] |

Production Example 1: Synthesis of Intermediate B1-3

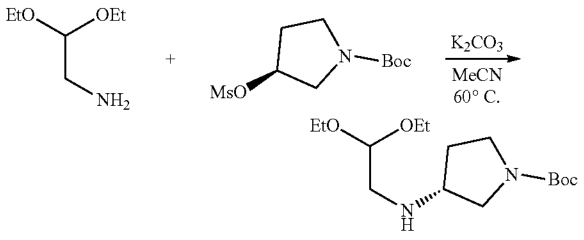

B1-3

To a solution of tert-butyl (S)-3-((methylsulfonyl)oxy) pyrrolidine-1-carboxylate (26 g) in MeCN (0.25 L) was added 2,2-diethoxyethan-1-amine (66 g). After stirring for 3.5 days at 60° C., the reaction mixture was cooled to room temperature and the precipitated solid was filtered out. The obtained filtrate was concentrated in vacuo and purified by column chromatography ($SiO_2$, n-hexane:AcOEt=75:25-0:100 and AcOEt:MeOH=100:0-80:20, gradient) to give B1-3 (18 g) as light yellow syrup.

LCMS (method A): m/z=303.1[M+H]$^+$.

Production Example 2: Synthesis of Intermediate B1-11

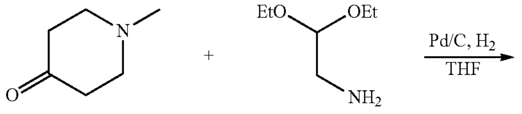

-continued

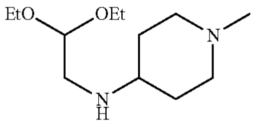

B1-11

To a solution of 1-methylpiperidin-4-one (10 g) and 2,2-diethoxyethan-1-amine (12 g) in THF (100 mL) was added 5% Wt palladium-carbon (1.0 g, 5% Wt). The mixture was stirred overnight under hydrogen atmosphere. The reaction mixture was filtered and the filtrate was concentrated to give B1-11 (19 g) as gray oil.

LCMS (method A): m/z=231.4[M+H]$^+$.

Intermediates B2 listed in the Table 2 are known compounds or were synthesized according to a known method.

List of Intermediate B2

TABLE 2

| Intermediate B2 | Structure |
|---|---|
| B2-1 | 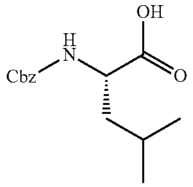 [SMILES: CC(C)C[C@H](NC(=O)OCc1ccccc1)C(=O)O] |
| B2-2 | 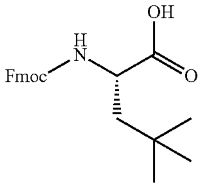 |
| B2-3 | 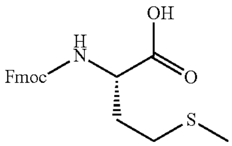 |
| B2-4 | 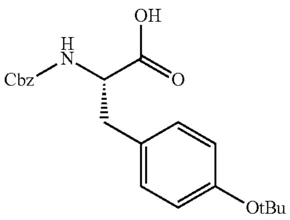 [SMILES: CC(C)(C)Oc1ccc(C[C@H](NC(=O)OCc2ccccc2)C(=O)O)cc1] |
| B2-5 | 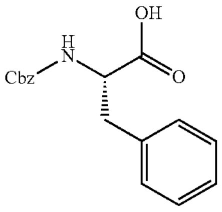 [SMILES: O=C(N[C@@H](Cc1ccccc1)C(=O)O)OCc1ccccc1] |

TABLE 2-continued
| Intermediate B2 | Structure |
|---|---|
| B2-6 | 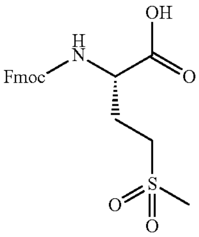 |
| B2-7 | 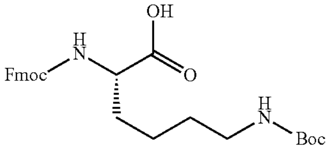 |
Intermediates B4 listed in the Table 3 are known compounds or were synthesized according to a known method or a method below.
List of Intermediate B4
TABLE 3
| Intermediate B4 | Structure |
|---|---|
| B4-1 | 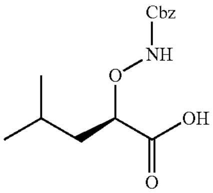 [SMILES: CC(C)C[C@@H](ONC(=O)OCc1ccccc1)C(=O)O] |
| B4-2 | 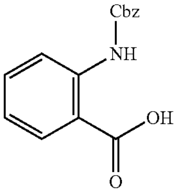 [SMILES: O=C(Nc1ccccc1C(=O)O)OCc1ccccc1] |
| B4-3 | 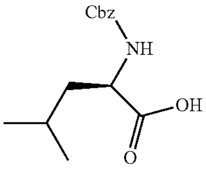 [SMILES: CC(C)C[C@@H](NC(=O)OCc1ccccc1)C(=O)O] |
| B4-4 | 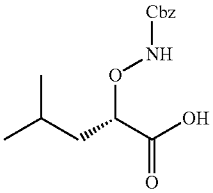 [SMILES: CC(C)C[C@H](ONC(=O)OCc1ccccc1)C(=O)O] |
TABLE 3-continued
| Intermediate B4 | Structure |
|---|---|
| B4-5 | 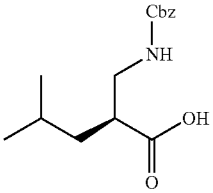 [SMILES: CC(C)C[C@@H](CNC(=O)OCc1ccccc1)C(=O)O] |
| B4-6 | 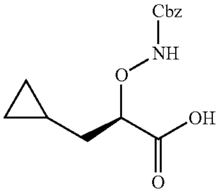 [SMILES: O=C(NO[C@H](CC1CC1)C(=O)O)OCc1ccccc1] |
| B4-7 | 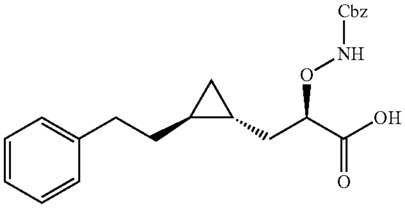 [SMILES: O=C(NO[C@H](C[C@H]1C[C@@H]1CCc1ccccc1)C(=O)O)OCc1ccccc1] |
| B4-8 | 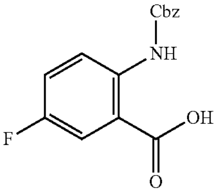 [SMILES: O=C(Nc1ccc(F)cc1C(=O)O)OCc1ccccc1] |
| B4-9 | 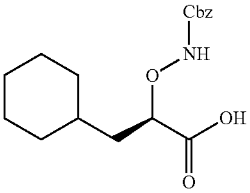 [SMILES: O=C(NO[C@H](CC1CCCCC1)C(=O)O)OCc1ccccc1] |
| B4-10 | 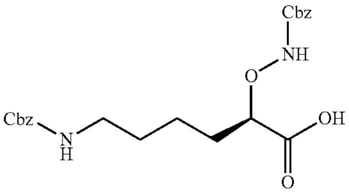 [SMILES: O=C(NCCCC[C@@H](ONC(=O)OCc1ccccc1)C(=O)O)OCc1ccccc1] |
| B4-11 | 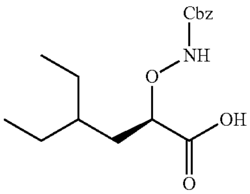 [SMILES: CCC(CC)C[C@@H](ONC(=O)OCc1ccccc1)C(=O)O] |

Production Example 3: Synthesis of Intermediate B4-6

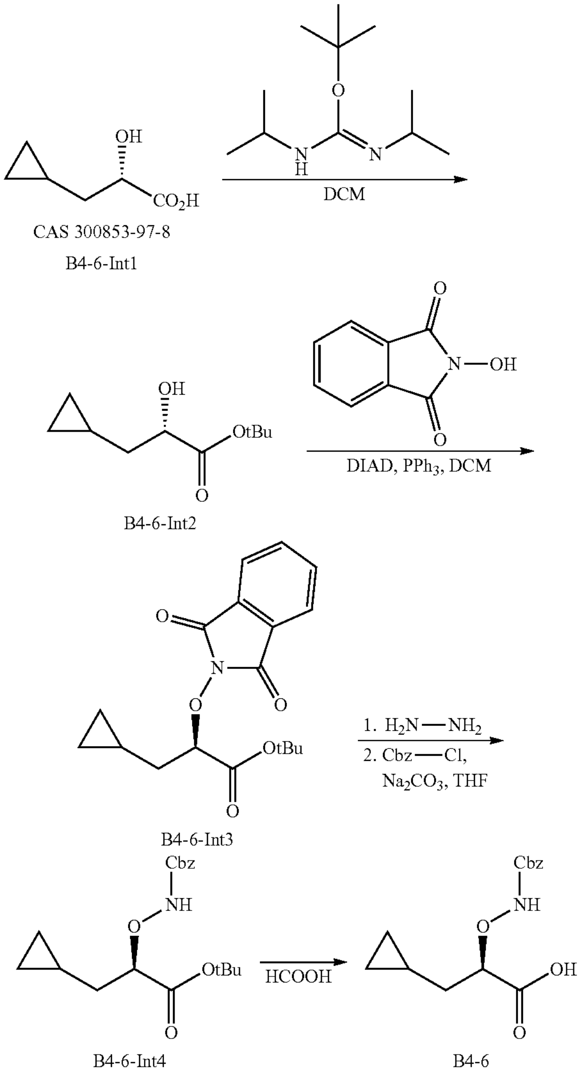

3-1) Synthesis of Intermediate B4-6-Int2

To a stirred solution of (S)-3-cyclopropyl-2-hydroxypropanoic acid (B4-6-Int1, CAS No. 300853-97-8, 1.6 g) in dichloromethane (15 mL) was added tert-butyl (Z)—N,N'-diisopropylcarbamimidate (7.4 g) at room temperature. After stirring for 2 hours at room temperature, urea solid was filtered and removed by Celite pad. The filtrate was concentrated under reduced pressure and purified by column chromatography ($SiO_2$, n-Hexane:AcOEt=100:0-70:30, gradient) to give B4-6-Int2 (1.4 g) as a colorless oil.

Figure 5:
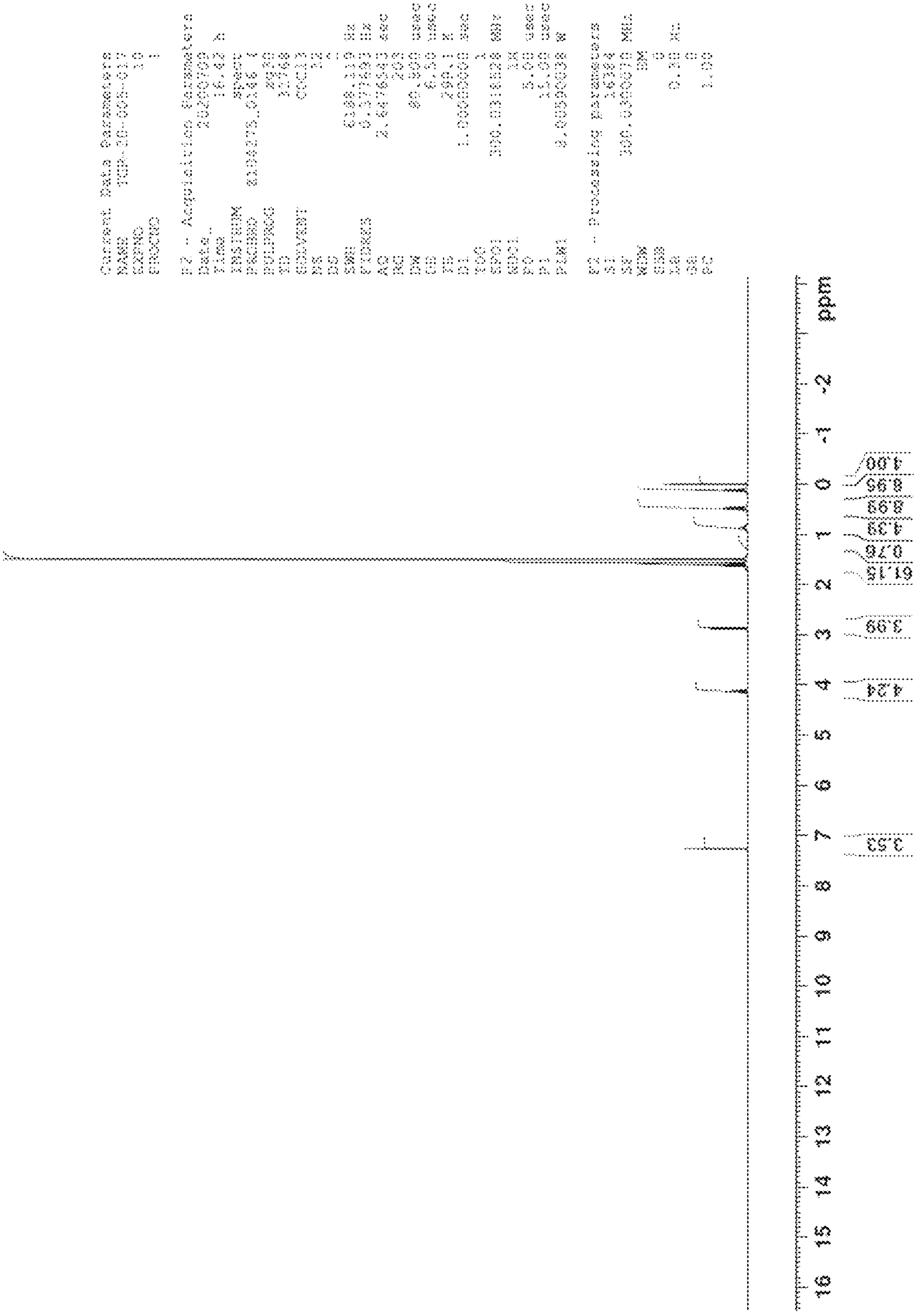
FIG. 5 shows a $^1$H NMR (300 MHz, $CDCl_3$) data of B-4-6-Int2.

$^1H$ NMR (300 MHz, $CDCl_3$) data of B4-6-Int2 is shown in FIG. 5

3-2) Synthesis of Intermediate B4-6-Int3

To a stirred mixture of B4-6-Int2 (1.4 g), 2-hydroxyisoindoline-1,3-dione (1.4 g) and triphenylphosphane (3.9 g) in dichloromethane (20 mL) was added DIAD (4.5 g) at −20° C. After stirring for 1 hour at same temperature, the reaction mixture was gradually warmed to room temperature for 1 hour. The resulting mixture was concentrated in vacuo and purified by column chromatography ($SiO_2$, n-Hexane: AcOEt=100:0-80:20, gradient) to give B4-6-Int3 (2.3 g) as light yellow syrup.

LCMS (method A): m/z=332.1[M+H]$^+$.

3-3) Synthesis of Intermediate B4-6-Int4

To a stirred solution of B4-6-Int3 (2.3 g) in EtOH (5 mL) was added hydrazine monohydrate (0.27 g) at room temperature. After stirring for 2 hours at room temperature, white precipitate was filtered and removed by Celite pad. The filtrate was concentrated under reduced pressure and dissolved in THE (20 mL), which was added sodium bicarbonate (1.0 g), Cbz-Cl (1.2 g) and water (20 mL). The reaction mixture was stirred for 16 hours at room temperature. After stirring, the mixture was added 20 mL of brine and 30 mL of AcOEt. The organic layer was separated, washed with 20 mL of brine, dried over $Na_2SO_4$ and concentrated in vacuo. The crude mixture was purified by column chromatography ($SiO_2$, n-Hexane:AcOEt=100:0-70:30, gradient) to give B4-6-Int4 (1.9 g) as colorless amorphous.

LCMS (method B): m/z=358.1[M+Na]$^+$.

3-4) Synthesis of Intermediate B4-6

A solution tert-butyl B4-6-Int4 (1.9 g) in formic acid (39 g) was stirred for 17 hours at room temperature. The reaction mixture was concentrated in vacuo. The residue was purified by column chromatography ($SiO_2$, n-hexane:AcOEt=100:0-0:100, gradient) to give B4-6 (1.4 g) as a colorless oil.

LCMS (method B): m/z=302.0[M+Na]$^+$.

Production Example 4: Synthesis of Intermediate B4-8

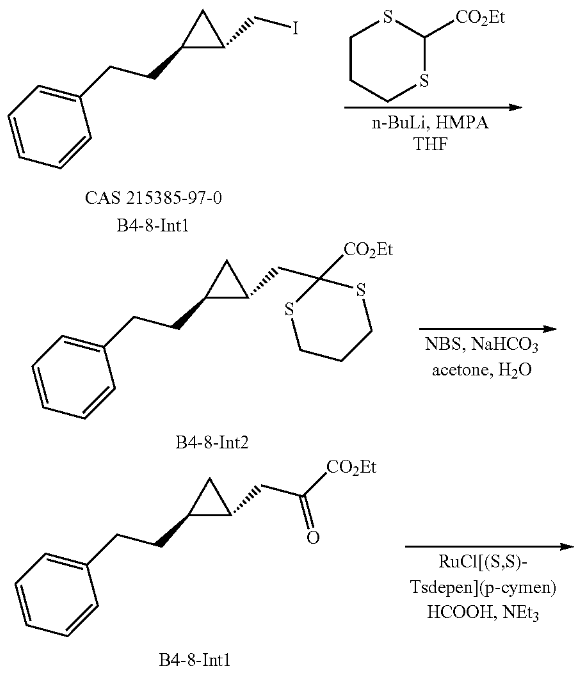

-continued

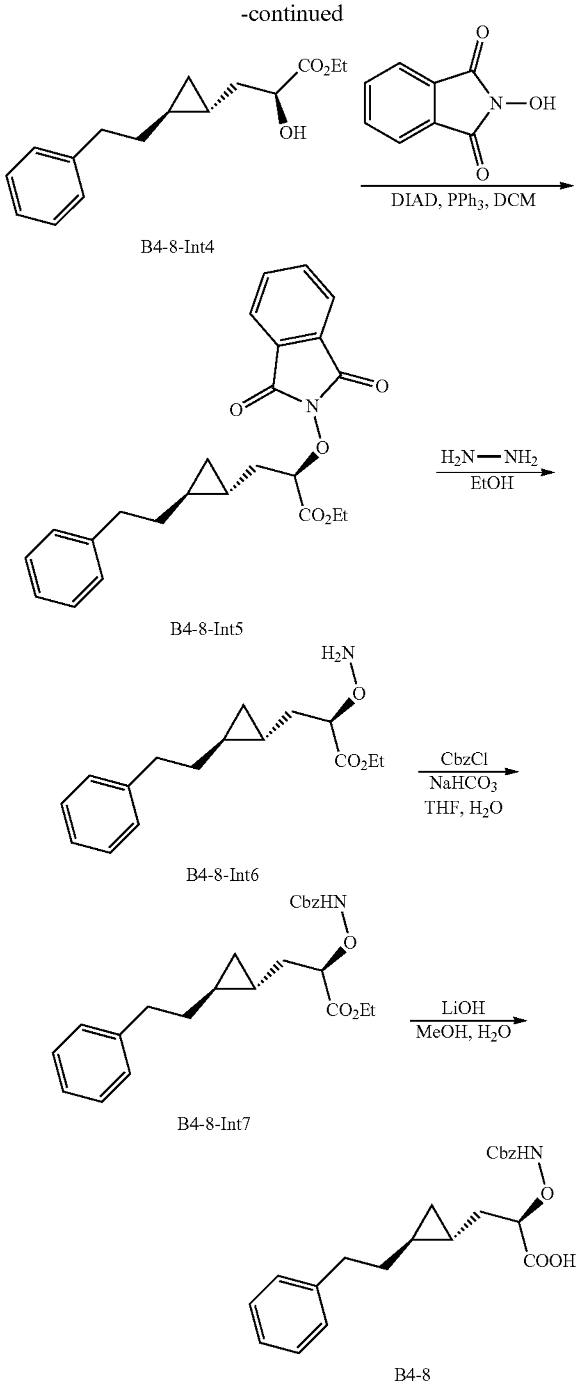

4-1) Synthesis of Intermediate B4-8-Int2

To a stirred solution of ethyl 1,3-dithiane-2-carboxylate (1.7 g) and HMPA (1.6 g) in THE (15 mL) was added n-butyllithium (2.6 mol/L) in hexane (3.3 mL) at −70° C. under nitrogen atmosphere. After stirring for 5 minutes, a solution of B4-8-Int1 (CAS no. 215385-97-0, 2.1 g) in THE (3 mL) was added. The reaction mixture was gradually warmed to room temperature for 2 hours. After the reaction completed, the mixture was quenched with saturated aqueous ammonium chloride solution and extracted with AcOEt twice. The organic layer was washed with brine, dried over $Na_2SO_4$, concentrated in vacuo. The residue was purified by column chromatography ($SiO_2$, n-hexane:AcOEt=100:0-80:20, gradient) to give B4-8-Int2 (2.3 g) as a colorless oil.

LCMS (method A): m/z=351.1[M+H]$^+$.

4-2) Synthesis of Intermediate B4-8-Int3

To a stirred mixture of ethyl B4-8-Int2 (2.3 g) in acetone (97 mL) and water (3 mL) was added sodium bicarbonate (1.7 g) and NBS (7.0 g). After stirring for 2 hours at room temperature, the reaction mixture was concentrated in vacuo. The obtained residue was diluted with AcOEt (20 mL) and washed with water (20 mL) and then brine. The organic phase was dried over $Na_2SO_4$, concentrated in vacuo and purified by column chromatography ($SiO_2$, n-Hexane: AcOEt=100:0-80:20, gradient) to give B4-8-Int3 (1.3 g) as a colorless oil.

LCMS (method A): m/z=261.1[M+H]$^+$.

4-3) Synthesis of Intermediate B4-8-Int4

To a mixture of B4-8-Int4 (1.3 g) and formic acid (0.7 mL) were added triethylamine (1.8 mL) and Chloro[(1S, 2S)—N-(p-toluenesulfonyl)-1,2-diphenyl-1,2-ethanediamine] (p-cymene) ruthenium(II) (32 mg). The mixture was stirred for 14 hours at room temperature. The reaction mixture was diluted with AcOEt and washed with saturated aqueous sodium bicarbonate solution and then brine. The organic phase was dried over $Na_2SO_4$ and concentrated in vacuo. The residue was purified by column chromatography ($SiO_2$, n-Hexane:AcOEt=100:0-80:20, gradient) to give ethyl B4-8-Int4 (1.1 g) as a colorless oil.

LCMS (method A): m/z=263.2[M+H]$^+$.

4-4) Synthesis of Intermediate B4-8-Int5

To a stirred mixture of B4-8-Int4 (1.0 g), 2-hydroxyisoindoline-1,3-dione (0.75 g) and triphenylphosphine (2.0 g) in $CH_2Cl_2$ (20 mL) was added DIAD (2.3 g) at −20° C. After stirring for 1 hour at same temperature, the reaction mixture was gradually warmed to room temperature for 1 hour. The resulting mixture was concentrated in vacuo and purified by column chromatography ($SiO_2$, n-Hexane:AcOEt=100:0-80:20, gradient) to give ethyl B4-8-Int5 (1.5 g) as light yellow syrup.

LCMS (method A): m/z=408.2[M+H]$^+$.

4-5) Synthesis of Intermediate B4-8-Int6

To a stirred solution of B4-8-Int5 (1.5 g) in EtOH (5 mL) was added hydrazine monohydrate (0.19 g) at room temperature. After stirring for 2 hours at room temperature, white precipitate was filtered and removed by Celite pad. The filtrate was concentrated under reduced pressure and purified by column chromatography ($SiO_2$, n-Hexane: AcOEt=100:0-70:30, gradient) to give B4-8-Int6 (1.1 g) as colorless oil.

LCMS (method A): m/z=278.2[M+H]$^+$.

4-6) Synthesis of Intermediate B4-8-Int7

To a stirred solution of B4-8-Int6 (1.0 g) in THE (20 mL) was added sodium bicarbonate (1.1 g), Cbz-Cl (0.77 g) and water (20 mL). The reaction mixture was stirred for 16 hours at room temperature. After stirring, the mixture was added 20 mL of brine and 30 mL of AcOEt. The organic layer was separated, washed with 20 mL of brine, dried over $Na_2SO_4$ and concentrated in vacuo. The crude mixture was purified by column chromatography ($SiO_2$, n-Hexane:AcOEt=100:0-70:30, gradient) to give B4-8-Int7 (1.5 g) as colorless oil.

LCMS (method A): m/z=412.2[M+H]$^+$.

4-7) Synthesis of Intermediate B4-8

To a stirred solution of B4-8-Int7 (1.5 g) in MeOH (10 mL) and water (0.5 mL) was added lithium hydroxide hydrate (0.93 g). After stirring for 3 hours at room temperature, the reaction mixture was concentrated in vacuo. The obtained residue was added water (30 mL), NaCl (4.0 g) and potassium hydrogen sulfate (3.5 g). The solution was extracted with AcOEt (30 mL×2) and washed with water (20 mL) and then brine. The organic phase was dried over $Na_2SO_4$, concentrated in vacuo and purified by column chromatography ($SiO_2$, n-Hexane:AcOEt=80:20-0:100, gradient) to give B4-8 (0.54 g) as colorless oil.

LCMS (method A): m/z=384.2[M+H]$^+$, 406.1[M+Na]$^+$.

Production Example 5: Synthesis of Intermediate B4-12

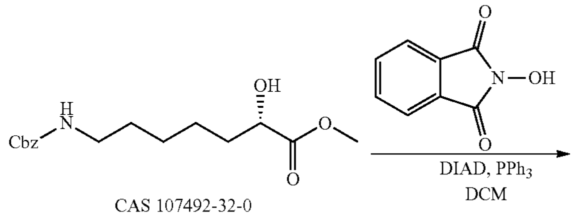

CAS 107492-32-0

B4-12-Intl

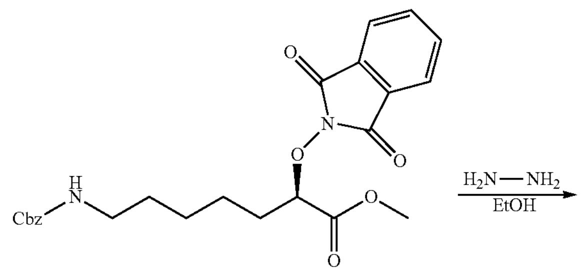

B4-12-Int2

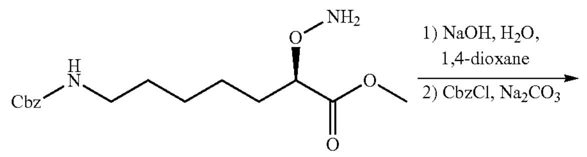

B4-12-Int3

-continued

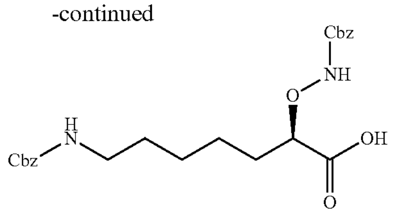

B4-12

5-1) Synthesis of Intermediate B4-12-Int2

B4-12-Intl (CAS No. 107492-32-0, 33 g), $PPh_3$ (38 g) and 2-hydroxyisoindoline-1,3-dione (27 g) was dissolved in DCM (400 mL) were added DIAD (29.5 g, 145 mmol) in −20° C.-−40° C. The mixture was stirred at room temperature for 16 hours. The resulting solid was filtrated. The organic layers were washed with brine (100 mL×2), dried over $Na_2SO_4$, concentrated in vacuum, the residue was purified by silica column (petroleum ether:Ethyl acetate=1:1) to give B4-12-Int2 (45 g) as yellow oil.

LCMS (method D): m/z=441.1[M+H]$^+$.

5-2) Synthesis of Intermediate B4-12-Int3

To a solution of B4-12-Int2 (45 g) in EtOH (400 mL) at room temperature was added hydrazine monohydrate (10 g). The reaction was stirred at room temperature for 16 hours. The mixture was filtered and washed with ethyl acetate. The filtrate was concentrated. The residue was purified by silica column (petroleum ether:Ethyl acetate=1:1) to give B4-12-Int3 (23 g) as a yellow oil.

LCMS (method D): m/z=311.2[M+H]$^+$.

5-3) Synthesis of Intermediate B4-12

B4-12-Int3 (10 g) was dissolved in water (150 mL) and 1,4-dioxane (150 mL). NaOH (2.5 g) was dissolved in water (50 mL) and then slowly added to the stirred solution over 2 hours. The pH was adjusted to about 10.5 by adding of 2 mol/L aqueous $Na_2CO_3$. Benzyl chloroformate (7.0 g) was added while maintaining the pH at about 10-11 by adding at the same time 2 mol/L aqueous $Na_2CO_3$. After completing addition, the reaction mixture was stirred at 20° C. for 1 hour. Then AcOEt (150 mL) was added and pH of the resulting mixture was adjusted to 2-3 with conc. HCl. The organic layer was separated, and the aqueous layer was extracted with AcOEt (200 mL×3). The combined organic layers were washed with brine (200 mL) and dried over $Na_2SO_4$. Filtration and concentration under reduced pressure. The residue was purified by silica column (petroleum ether:Ethyl acetate=1:1) to give B4-12 (10 g) as a white solid.

LCMS (method D): m/z=431.1[M+H]$^+$.

Intermediates B5 listed in the Table 4 were synthesized according to the below method or a known method using Intermediate B1, B2 and B4 as synthetic materials.

List of Intermediate B5 and its Synthetic Materials B1, B2 and B4.
TABLE 4
| Intermediate B5 | Structure | B1 | B2 | B4 |
|---|---|---|---|---|
| B5-1 | 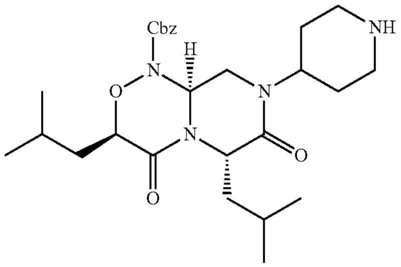 [SMILES: CC(C)C[C@H]1ON(C(=O)OCc2ccccc2)[C@H]2CN(C3CCNCC3)C(=O)[C@H](CC(C)C)N2C1=O] | B1-1 | B2-1 | B4-1 |
| B5-2 | 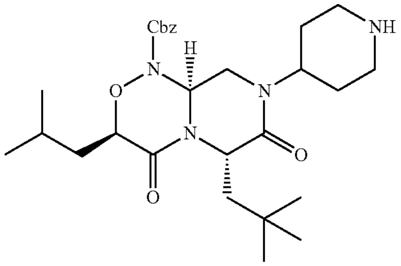 [SMILES: CC(C)C[C@H]1ON(C(=O)OCc2ccccc2)[C@H]2CN(C3CCNCC3)C(=O)[C@H](CC(C)(C)C)N2C1=O] | B1-1 | B2-2 | B4-1 |
| B5-3 | 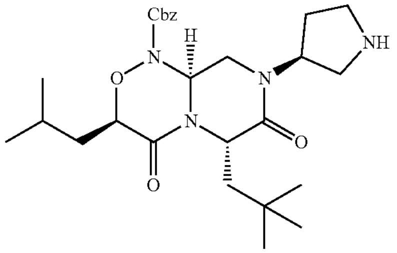 [SMILES: CC(C)C[C@H]1ON(C(=O)OCc2ccccc2)[C@H]2CN([C@H]3CCNC3)C(=O)[C@H](CC(C)(C)C)N2C1=O] | B1-2 | B2-2 | B4-1 |
| B5-4 | 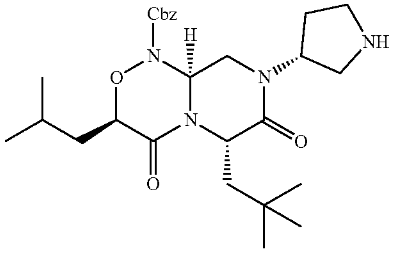 [SMILES: CC(C)C[C@H]1ON(C(=O)OCc2ccccc2)[C@H]2CN([C@@H]3CCNC3)C(=O)[C@H](CC(C)(C)C)N2C1=O] | B1-3 | B2-2 | B4-1 |
| B5-5 | 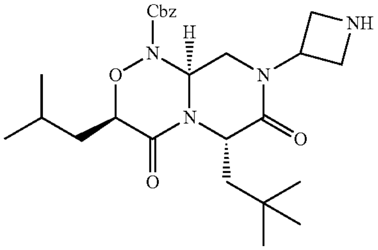 [SMILES: CC(C)C[C@H]1ON(C(=O)OCc2ccccc2)[C@H]2CN(C3CNC3)C(=O)[C@H](CC(C)(C)C)N2C1=O] | B1-4 | B2-2 | B4-1 |

TABLE 4-continued
| Intermediate B5 | Structure | B1 | B2 | B4 |
|---|---|---|---|---|
| B5-6 | 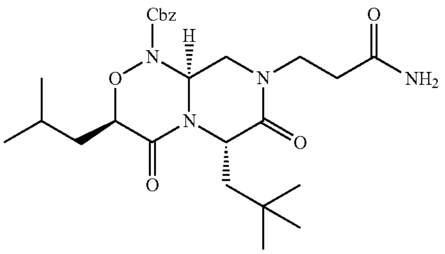 [SMILES: CC(C)C[C@H]1ON(C(=O)OCc2ccccc2)[C@H]2CN(CCC(N)=O)C(=O)[C@H](CC(C)(C)C)N2C1=O] | B1-5 | B2-1 | B4-1 |
| B5-7 | 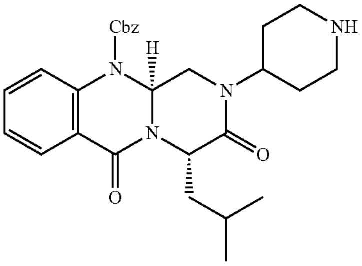 [SMILES: CC(C)C[C@H]1C(=O)N(C2CCNCC2)C[C@@H]2N(C(=O)OCc3ccccc3)c3ccccc3C(=O)N21] | B1-1 | B2-1 | B4-2 |
| B5-8 | 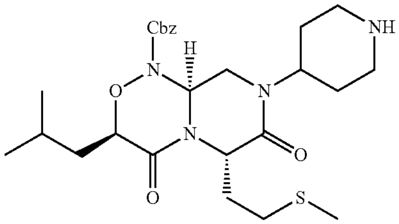 [SMILES: CSCC[C@H]1C(=O)N(C2CCNCC2)C[C@@H]2N(C(=O)OCc3ccccc3)O[C@H](CC(C)C)C(=O)N21] | B1-1 | B2-3 | B4-1 |
| B5-9 | 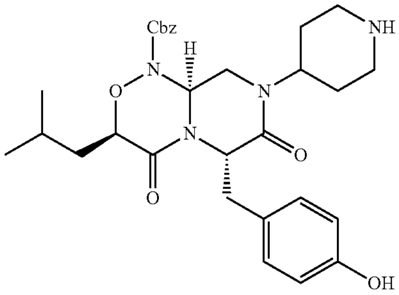 [SMILES: CC(C)C[C@H]1ON(C(=O)OCc2ccccc2)[C@H]2CN(C3CCNCC3)C(=O)[C@H](Cc3ccc(O)cc3)N2C1=O] | B1-1 | B2-4 | B4-1 |
| B5-10 | 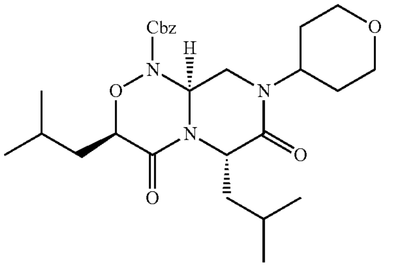 [SMILES: CC(C)C[C@H]1ON(C(=O)OCc2ccccc2)[C@H]2CN(C3CCOCC3)C(=O)[C@H](CC(C)C)N2C1=O] | B1-6 | B2-1 | B4-1 |

TABLE 4-continued
| Intermediate B5 | Structure | B1 | B2 | B4 |
| --- | --- | --- | --- | --- |
| B5-11 | 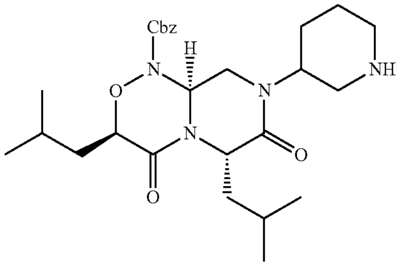 [SMILES: CC(C)C[C@H]1ON(C(=O)OCc2ccccc2)[C@H]2CN(C3CCCNC3)C(=O)[C@H](CC(C)C)N2C1=O] | B1-7 | B2-1 | B4-1 |
| B5-12 | 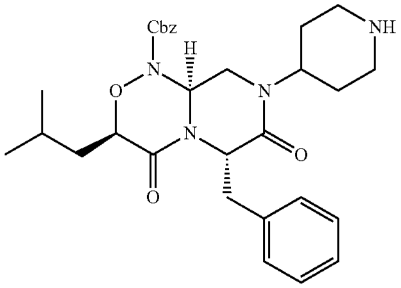 [SMILES: CC(C)C[C@H]1ON(C(=O)OCc2ccccc2)[C@H]2CN(C3CCNCC3)C(=O)[C@H](Cc3ccccc3)N2C1=O] | B1-1 | B2-5 | B4-1 |
| B5-13 | 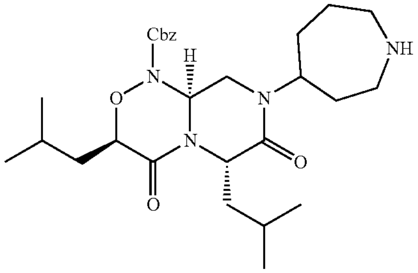 [SMILES: CC(C)C[C@H]1ON(C(=O)OCc2ccccc2)[C@H]2CN(C3CCCNCC3)C(=O)[C@H](CC(C)C)N2C1=O] | B1-8 | B2-1 | B4-1 |
| B5-14 | 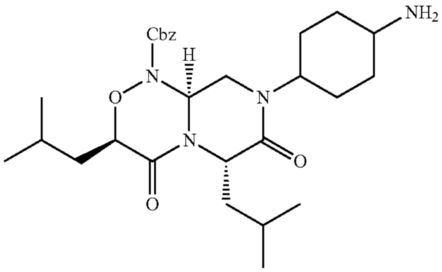 [SMILES: CC(C)C[C@H]1ON(C(=O)OCc2ccccc2)[C@H]2CN(C3CCC(N)CC3)C(=O)[C@H](CC(C)C)N2C1=O] | B1-9 | B2-1 | B4-1 |
| B5-15 | 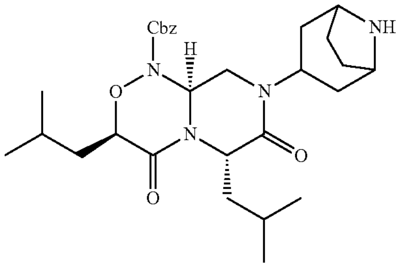 [SMILES: CC(C)C[C@H]1ON(C(=O)OCc2ccccc2)[C@H]2CN(C3CC4CCC(C3)N4)C(=O)[C@H](CC(C)C)N2C1=O] | B1-10 | B2-1 | B4-1 |

TABLE 4-continued
| Intermediate B5 | Structure | B1 | B2 | B4 |
|---|---|---|---|---|
| B5-16 | 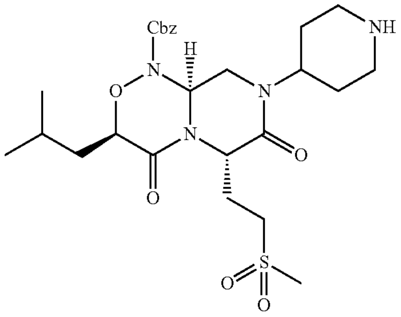 [SMILES: CC(C)C[C@H]1ON(C(=O)OCc2ccccc2)[C@H]2CN(C3CCNCC3)C(=O)[C@H](CCS(C)(=O)=O)N2C1=O] | B1-1 | B2-6 | B4-1 |
| B5-17 | 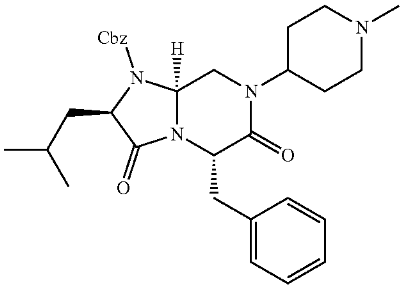 [SMILES: CC(C)C[C@@H]1C(=O)N2[C@H](CN(C3CCN(C)CC3)C(=O)[C@@H]2Cc2ccccc2)N1C(=O)OCc1ccccc1] | B1-11 | B2-5 | B4-3 |
| B5-18 | 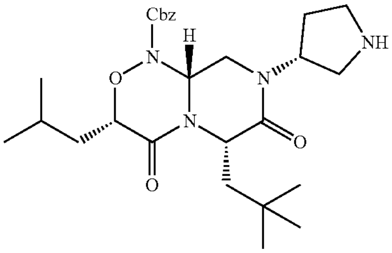 [SMILES: CC(C)C[C@@H]1ON(C(=O)OCc2ccccc2)[C@@H]2CN([C@@H]3CCNC3)C(=O)[C@H](CC(C)(C)C)N2C1=O] | B1-3 | B2-2 | B4-4 |
| B5-19 | 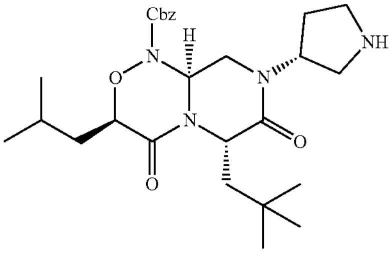 [SMILES: CC(C)C[C@H]1ON(C(=O)OCc2ccccc2)[C@H]2CN([C@@H]3CCNC3)C(=O)[C@H](CC(C)(C)C)N2C1=O] | B1-3 | B2-2 | B4-5 |
| B5-20 | 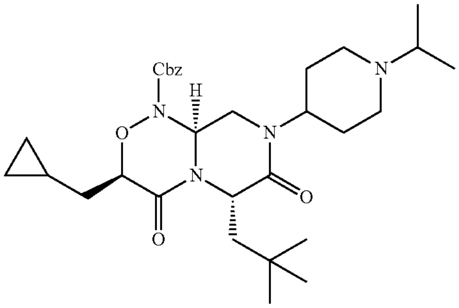 [SMILES: CC(C)N1CCC(N2C[C@@H]3N(C(=O)OCc4ccccc4)O[C@H](CC4CC4)C(=O)N3[C@@H](CC(C)(C)C)C2=O)CC1] | B1-12 | B2-2 | B4-6 |

TABLE 4-continued
| Intermediate B5 | Structure | B1 | B2 | B4 |
|---|---|---|---|---|
| B5-21 | 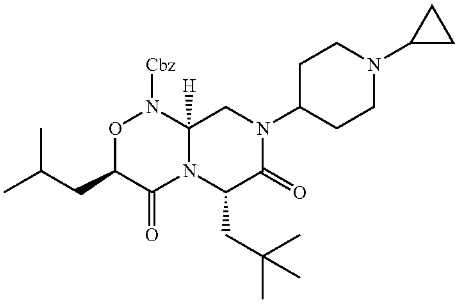 [SMILES: CC(C)C[C@H]1ON(C(=O)OCc2ccccc2)[C@H]2CN(C3CCN(C4CC4)CC3)C(=O)[C@H](CC(C)(C)C)N2C1=O] | B1-13 | B2-2 | B4-1 |
| B5-22 | 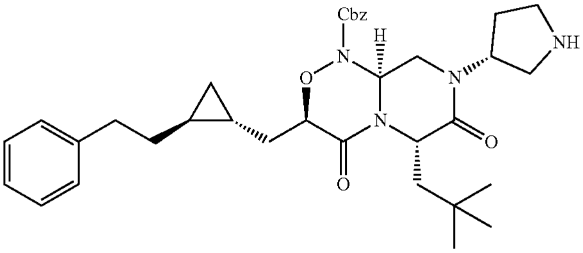 [SMILES: CC(C)(C)C[C@H]1C(=O)N([C@@H]2CCNC2)C[C@@H]2N(C(=O)OCc3ccccc3)O[C@H](C[C@H]3C[C@@H]3CCc3ccccc3)C(=O)N21] | B1-3 | B2-2 | B4-7 |
| B5-23 | 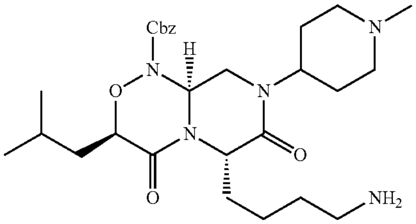 [SMILES: CC(C)C[C@H]1ON(C(=O)OCc2ccccc2)[C@H]2CN(C3CCN(C)CC3)C(=O)[C@H](CCCCN)N2C1=O] | B1-11 | B2-7 | B4-1 |
| B5-24 | 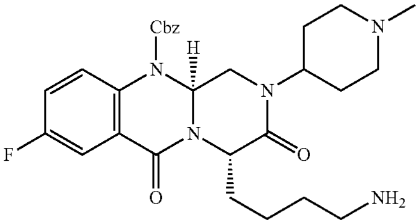 [SMILES: CN1CCC(N2C[C@@H]3N(C(=O)OCc4ccccc4)c4ccc(F)cc4C(=O)N3[C@@H](CCCCN)C2=O)CC1] | B1-11 | B2-7 | B4-8 |
| B5-25 | 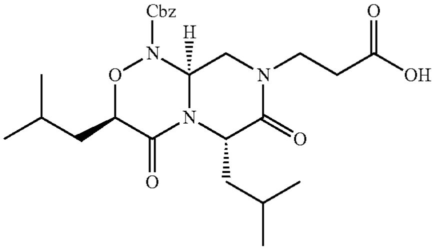 [SMILES: CC(C)C[C@H]1ON(C(=O)OCc2ccccc2)[C@H]2CN(CCC(=O)O)C(=O)[C@H](CC(C)C)N2C1=O] | B1-14 | B2-1 | B4-1 |
| B5-26 | 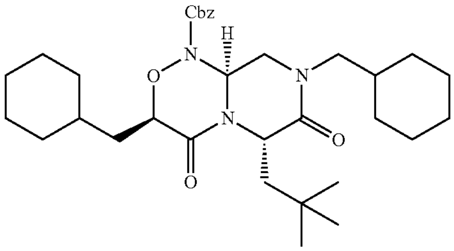 [SMILES: CC(C)(C)C[C@H]1C(=O)N(CC2CCCCC2)C[C@@H]2N(C(=O)OCc3ccccc3)O[C@H](CC3CCCCC3)C(=O)N21] | B1-15 | B2-2 | B4-9 |

TABLE 4-continued
| Intermediate B5 | Structure | B1 | B2 | B4 |
|---|---|---|---|---|
| B5-27 | 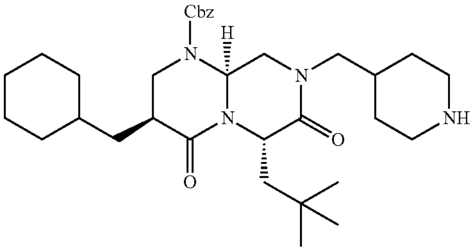 [SMILES: CC(C)(C)C[C@H]1C(=O)N(CC2CCNCC2)C[C@@H]2N(C(=O)OCc3ccccc3)C[C@H](CC3CCCCC3)C(=O)N21] | B1-16 | B2-2 | B4-9 |
| B5-28 | 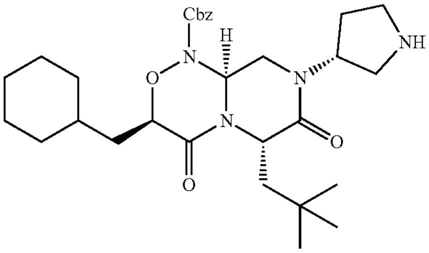 [SMILES: CC(C)(C)C[C@H]1C(=O)N([C@@H]2CCNC2)C[C@@H]2N(C(=O)OCc3ccccc3)O[C@H](CC3CCCCC3)C(=O)N21] | B1-3 | B2-2 | B4-9 |
| B5-29 | 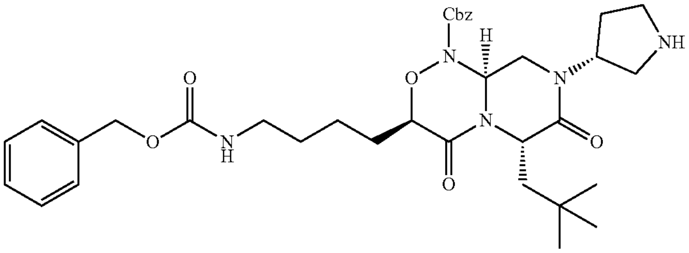 [SMILES: CC(C)(C)C[C@H]1C(=O)N([C@@H]2CCNC2)C[C@@H]2N(C(=O)OCc3ccccc3)O[C@H](CCCCNC(=O)OCc3ccccc3)C(=O)N21] | B1-3 | B2-2 | B4-10 |
| B5-30 | 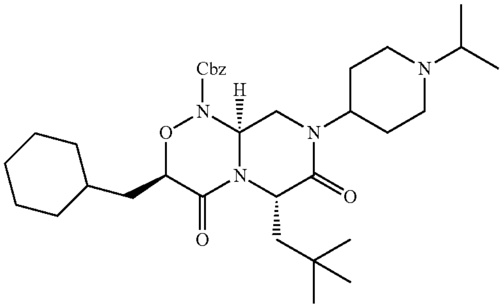 [SMILES: CC(C)N1CCC(N2C[C@@H]3N(C(=O)OCc4ccccc4)O[C@H](CC4CCCCC4)C(=O)N3[C@@H](CC(C)(C)C)C2=O)CC1] | B1-12 | B2-2 | B4-9 |
| B5-31 | 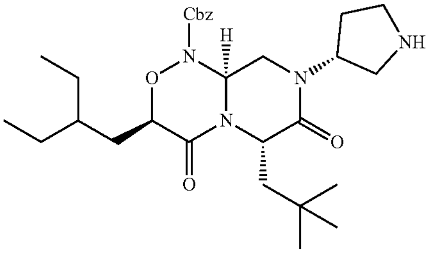 [SMILES: CCC(CC)C[C@H]1ON(C(=O)OCc2ccccc2)[C@H]2CN([C@@H]3CCNC3)C(=O)[C@H](CC(C)(C)C)N2C1=O] | B1-3 | B2-2 | B4-11 |

Production Example 6: Synthesis of Intermediate B5-4

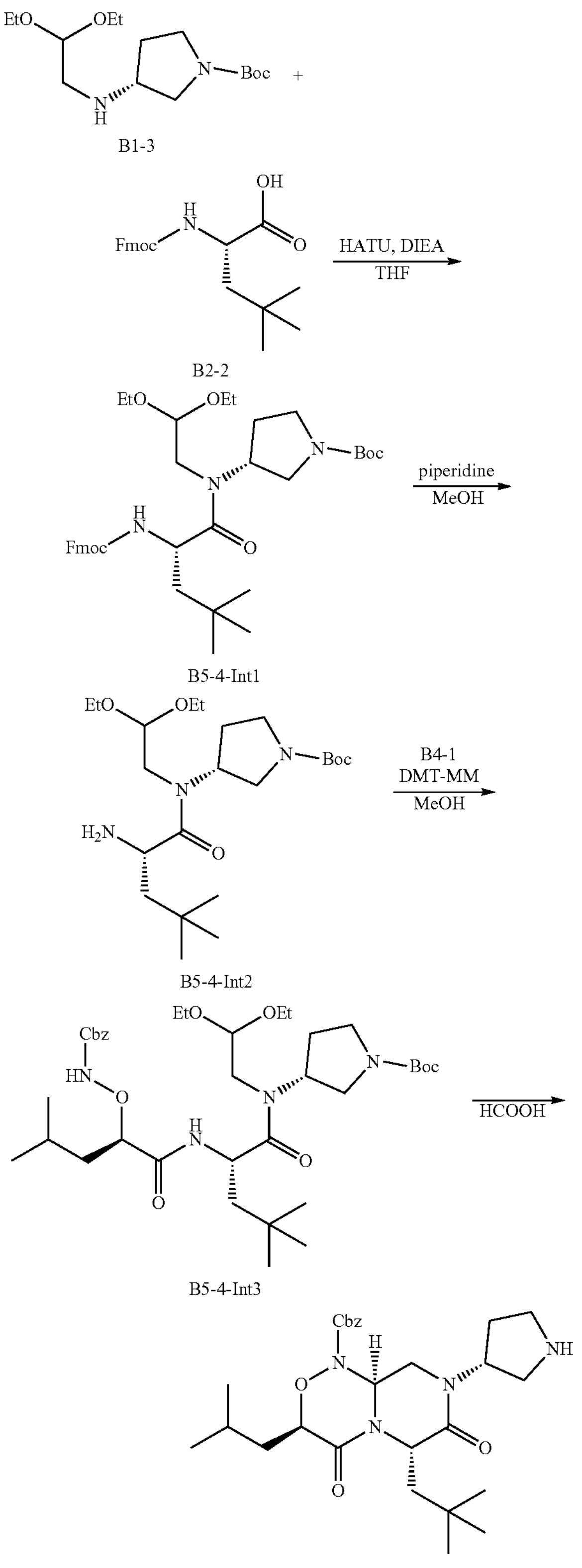

B1-3

B2-2

B5-4-Int1

B5-4-Int2

B5-4-Int3

B5-4

6-1) Synthesis of Intermediate B5-4-Int1

A mixed suspension of B1-3 (14 g), B2-2 (18 g), HATU (22 g) and DIEA (11 mL) in THE (0.20 L) was stirred for 2 hours at room temperature. After addition of B2-2 (1.5 g), HATU (1.7 g) and DIEA (1 mL), the reaction mixture was stirred for another 1 hour. The reaction mixture was poured into a saturated aqueous sodium bicarbonate solution and extracted by AcOEt twice. The organic layer was concentrated in vacuo and purified by column chromatography ($SiO_2$, n-hexane:AcOEt=95:5-50:50, gradient). The obtained material was further purified by column chromatography ($NHSiO_2$, n-hexane:AcOEt=50:50) to give B5-4-Int1 (21 g) as colorless gum.

LCMS (method A): m/z=674.4[M+Na]$^+$.

6-2) Synthesis of Intermediate B5-4-Int2

To a solution of B5-4-Int1 (20 g) in MeOH (0.25 L) was added piperidine (25 mL). After stirring for 4 hours at room temperature, the reaction mixture was concentrated to about a half volume and the obtained precipitates was filtered out. The obtained filtrate was concentrated in vacuo and purified by column chromatography ($SiO_2$, n-hexane:AcOEt=50:50-0:100 and AcOEt:MeOH=100:0-80:20, gradient) to give B5-4-Int2 (8.2 g) as slightly yellow oil.

LCMS (method A): m/z=430.3[M+H]$^+$, 384.3[M-EtOH+H]$^+$.

6-3) Synthesis of Intermediate B5-4-Int3

A mixture solution of B5-4-Int2 (9.5 g), B4-1 (7.4 g) and DMT-MM (7.3 g) in MeOH (0.10 L) was stirred for 1 hour at room temperature. After addition of DMT-MM (1.5 g), the reaction mixture was stirred for another 1 hour. After concentrated to about one third volume, the mixture was poured into saturated aqueous sodium bicarbonate solution and extracted by AcOEt twice. The organic layer was concentrated in vacuo and purified by column chromatography ($SiO_2$, n-hexane:AcOEt=94:6-50:50, gradient) to give B5-4-Int3 (15 g) as colorless syrup.

LCMS (method A): m/z=715.5[M+Na]$^+$, 647.4[M-EtOH+H]$^+$.

6-4) Synthesis of Intermediate B5-4

A solution B5-4-Int3 (15 g) in formic acid (0.10 L) was stirred for 22 hours at 60° C. The reaction mixture was cooled to room temperature and then concentrated in vacuo. The residue was dissolved in AcOEt and washed with a mixture of aqueous sodium bicarbonate solution and aqueous sodium carbonate solution. The organic layer was concentrated in vacuo and purified by column chromatography ($NHSiO_2$, n-hexane:AcOEt=50:50-0:100 and AcOEt:MeOH=100:0-40:60, gradient) to give B5-4 (8.8 g) as light yellow amorphous.

LCMS (method A): m/z=501.3[M+H]$^+$.

Intermediate A6 listed in the Table 5 were synthesized according to the below method or a known method using Intermediate B5 as a synthetic material.

List of Intermediate A6 and its synthetic material B5.

TABLE 5

| Intermediate A6 | Structure | B5 |
|---|---|---|
| A6-1 | 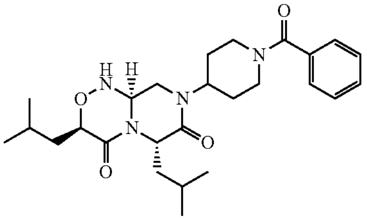 [SMILES: CC(C)C[C@H]1ON[C@H]2CN(C3CCN(C(=O)c4ccccc4)CC3)C(=O)[C@H](CC(C)C)N2C1=O] | B5-1 |
| A6-2 | 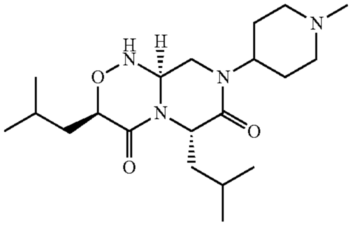 [SMILES: CC(C)C[C@H]1ON[C@H]2CN(C3CCN(C)CC3)C(=O)[C@H](CC(C)C)N2C1=O] | B5-1 |

Production Example 7: Synthesis of Intermediate A6-1

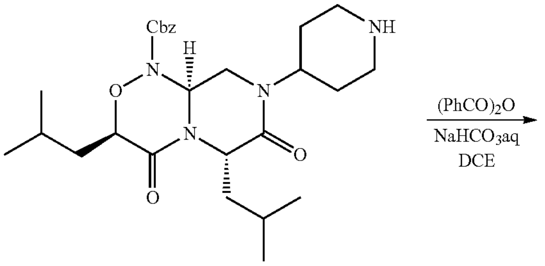

B5-1

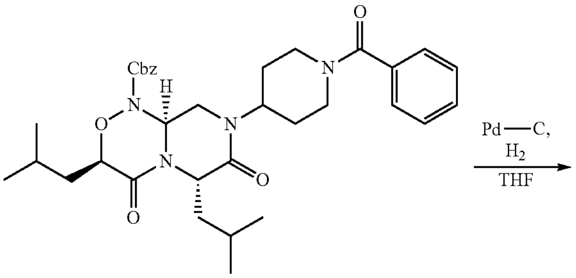

A6-1-Int1

-continued

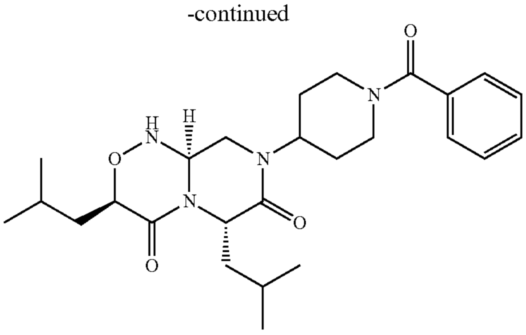

A6-1

7-1) Synthesis of Intermediate A6-1-Int1

To a solution of B5-1 (0.33 g) in DCE (10 mL) were added benzoic anhydride (0.23 g) and aqueous sodium bicarbonate solution (10 mL). After stirring for overnight at room temperature, aqueous 25% ammonia solution was added. The mixture was extracted with chloroform. The organic layer was dried over $Na_2SO_4$ and concentrated in vacuo to give A6-1-Int1 (0.31 g) as a white solid, which was used in the next reaction without any purification.

LCMS (method C): m/z=605.1[M+H]$^+$.

7-2) Synthesis of Intermediate A6-1

A mixture of A6-1-Int1 (0.27 g) and 10% Pd/C (0.10 g) in THF (15 mL) was stirred at room temperature for 2 hours under $H_2$ atmosphere. The mixture was filtered, and the filtrate was concentrated in vacuo to give A6-1 (0.26 g) as gray amorphous, which was used in the next reaction without any purification.

LCMS (method C): m/z=471.1[M+H]$^+$.

Production Example 8: Synthesis of Intermediate A6-2

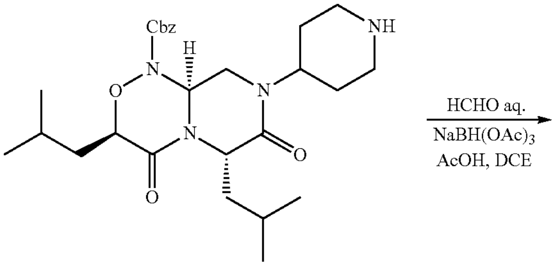

B5-1

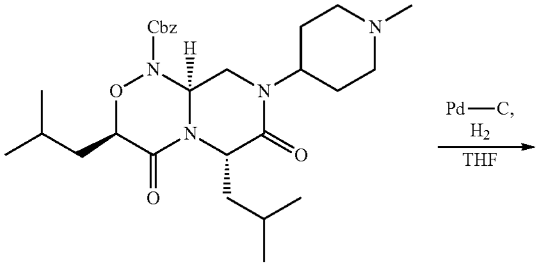

A6-2-Int1

-continued

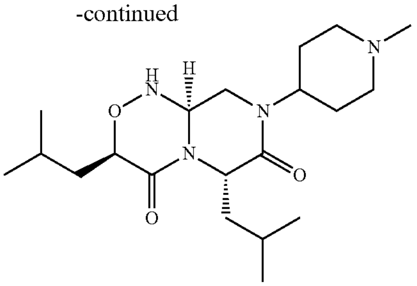

A6-2

8-1) Synthesis of Intermediate A6-2-Int1

To a solution of B5-1 (2.9 g) in DCE (30 mL) were added 37% formaldehyde solution (1.4 g) and acetic acid (0.14 g). After stirring for a while, sodium triacetoxyborohydride (1.9 g) was slowly added to the mixture. After stirring for another 1 hour, 1N NaOH solution (40 mL) and chloroform (50 mL) were added. The organic layer was separated, then washed with 40 mL of water, dried over $Na_2SO_4$, concentrated in vacuo. The crude product was purified by column chromatography ($SiO_2$, AcOEt:MeOH=80:20-50:50, gradient) to give A6-2-Int1 (1.1 g) as colorless oil.

LCMS (method A): m/z=515.5[M+H]$^+$.

8-2) Synthesis of Intermediate A6-2

To a solution of A6-2-Int1 (1.1 g) in THF (20 mL) was added 10% Pd/C (0.22 g) was stirred at room temperature for 3.5 hours under $H_2$ atmosphere. The mixture was filtered, and the filtrate was concentrated in vacuo to give crude A6-2 (0.70 g) as dark brown solid.

LCMS (method A): m/z=381.4[M+H]$^+$.

Intermediates A8 listed in the Table 6 were synthesized according to the below method or a known method using Intermediate B5 as a synthetic material.

List of Intermediate A8 and its Synthetic Material B5.

TABLE 6

| Intermediate A8 | Structure | B5 |
|---|---|---|
| A8-1 | 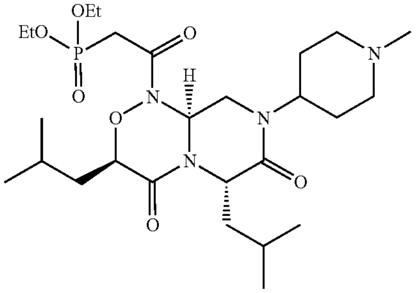 [SMILES: CCOP(=O)(CC(=O)N1O[C@H](CC(C)C)C(=O)N2[C@@H]1CN(C1CCN(C)CC1)C(=O)[C@@H]2CC(C)C)OCC] | B5-1 |
| A8-2 | 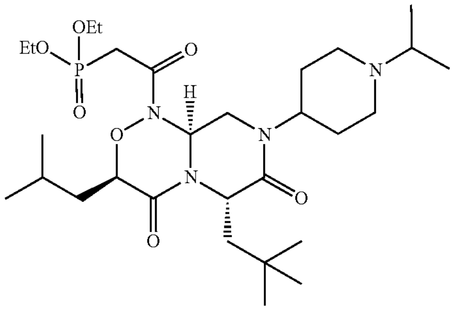 [SMILES: CCOP(=O)(CC(=O)N1O[C@H](CC(C)C)C(=O)N2[C@@H]1CN(C1CCN(C(C)C)CC1)C(=O)[C@@H]2CC(C)(C)C)OCC] | B5-2 |
| A8-3 | 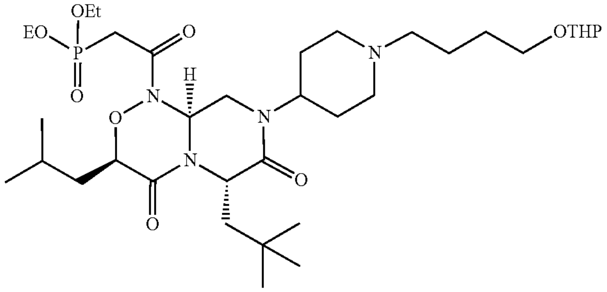 | B5-2 |

TABLE 6-continued
| Intermediate A8 | Structure | B5 |
|---|---|---|
| A8-4 | 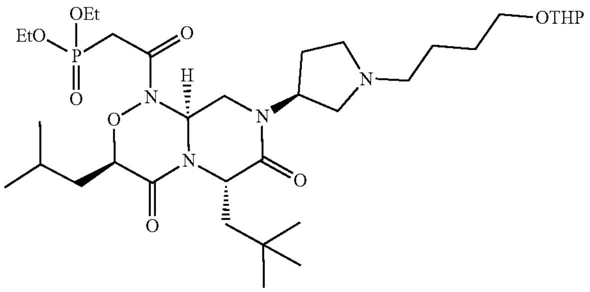 | B5-3 |
| A8-5 | 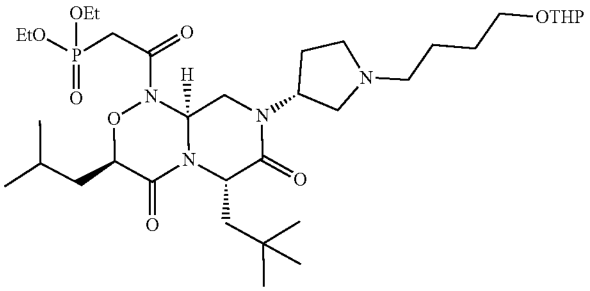 | B5-4 |
| A8-6 | 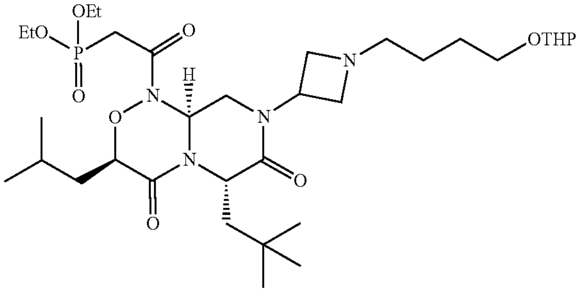 | B5-5 |
| A8-7 | 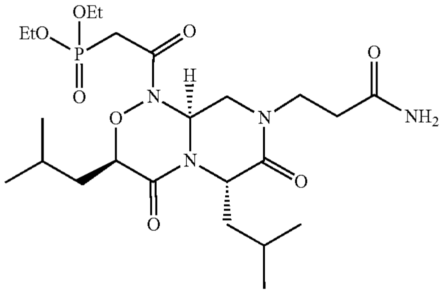 [SMILES: CCOP(=O)(CC(=O)N1O[C@H](CC(C)C)C(=O)N2[C@@H]1CN(CCC(N)=O)C(=O)[C@@H]2CC(C)C)OCC] | B5-6 |
| A8-8 | 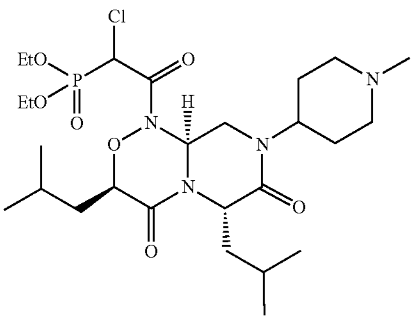 [SMILES: CCOP(=O)(OCC)C(Cl)C(=O)N1O[C@H](CC(C)C)C(=O)N2[C@@H]1CN(C1CCN(C)CC1)C(=O)[C@@H]2CC(C)C] | B5-1 |

TABLE 6-continued
| Intermediate A8 | Structure | B5 |
|---|---|---|
| A8-9 | 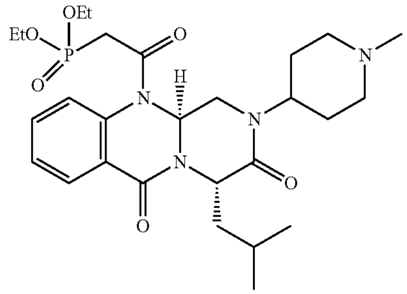 [SMILES: CCOP(=O)(CC(=O)N1c2ccccc2C(=O)N2[C@@H]1CN(C1CCN(C)CC1)C(=O)[C@@H]2CC(C)C)OCC] | B5-7 |
| A8-10 | 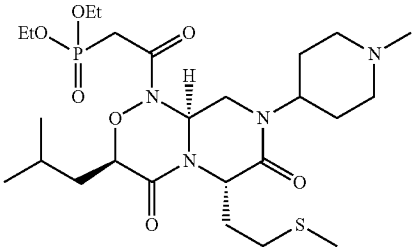 [SMILES: CCOP(=O)(CC(=O)N1O[C@H](CC(C)C)C(=O)N2[C@@H]1CN(C1CCN(C)CC1)C(=O)[C@@H]2CCSC)OCC] | B5-8 |
| A8-11 | 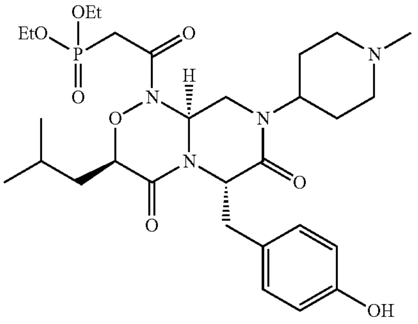 [SMILES: CCOP(=O)(CC(=O)N1O[C@H](CC(C)C)C(=O)N2[C@@H]1CN(C1CCN(C)CC1)C(=O)[C@@H]2Cc1ccc(O)cc1)OCC] | B5-9 |
| A8-12 | 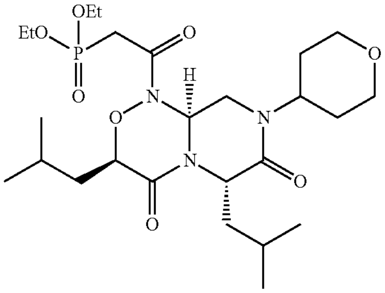 [SMILES: CCOP(=O)(CC(=O)N1O[C@H](CC(C)C)C(=O)N2[C@@H]1CN(C1CCOCC1)C(=O)[C@@H]2CC(C)C)OCC] | B5-10 |
| A8-13 | 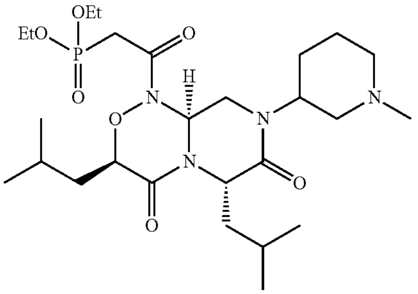 [SMILES: CCOP(=O)(CC(=O)N1O[C@H](CC(C)C)C(=O)N2[C@@H]1CN(C1CCCN(C)C1)C(=O)[C@@H]2CC(C)C)OCC] | B5-11 |

TABLE 6-continued
| Intermediate A8 | Structure | B5 |
| --- | --- | --- |
| A8-14 | 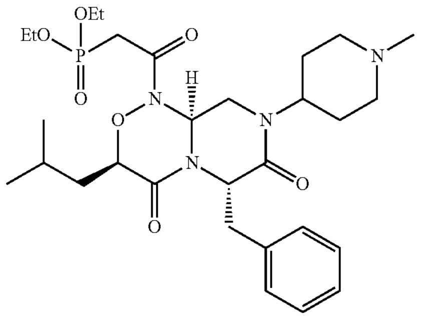 [SMILES: CCOP(=O)(CC(=O)N1O[C@H](CC(C)C)C(=O)N2[C@@H]1CN(C1CCN(C)CC1)C(=O)[C@@H]2Cc1ccccc1)OCC] | B5-12 |
| A8-15 | 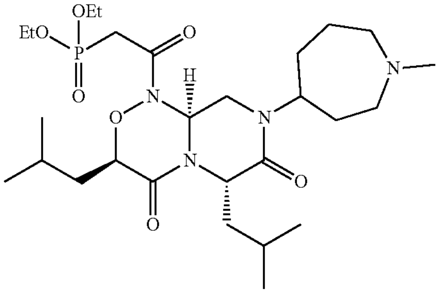 [SMILES: CCOP(=O)(CC(=O)N1O[C@H](CC(C)C)C(=O)N2[C@@H]1CN(C1CCCN(C)CC1)C(=O)[C@@H]2CC(C)C)OCC] | B5-13 |
| A8-16 | 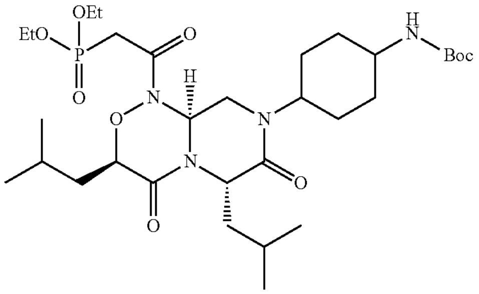 [SMILES: CCOP(=O)(CC(=O)N1O[C@H](CC(C)C)C(=O)N2[C@@H]1CN(C1CCC(NC(=O)OC(C)(C)C)CC1)C(=O)[C@@H]2CC(C)C)OCC] | B5-14 |
| A8-17 | 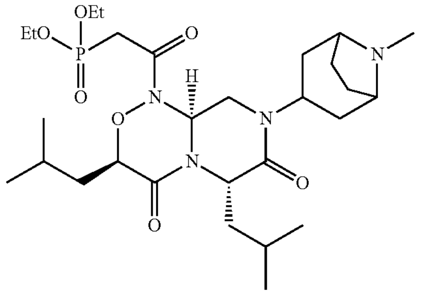 [SMILES: CCOP(=O)(CC(=O)N1O[C@H](CC(C)C)C(=O)N2[C@@H]1CN(C1CC3CCC(C1)N3C)C(=O)[C@@H]2CC(C)C)OCC] | B5-15 |
| A8-18 | 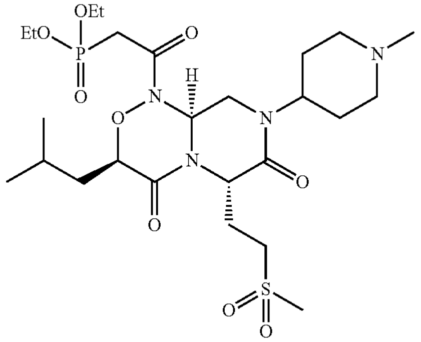 [SMILES: CCOP(=O)(CC(=O)N1O[C@H](CC(C)C)C(=O)N2[C@@H]1CN(C1CCN(C)CC1)C(=O)[C@@H]2CCS(C)(=O)=O)OCC] | B5-16 |

TABLE 6-continued
| Intermediate A8 | Structure | B5 |
|---|---|---|
| A8-19 | 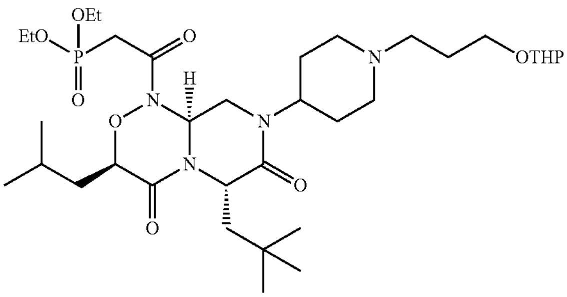 | B5-2 |
| A8-20 | 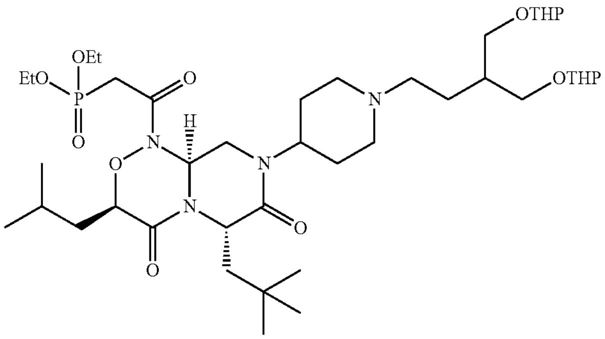 | B5-2 |
| A8-21 | 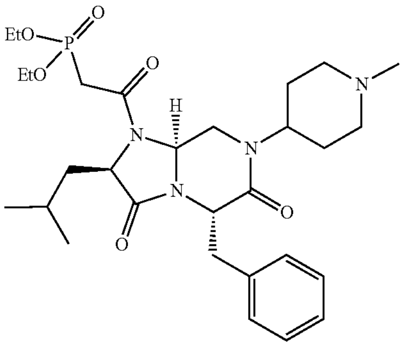 [SMILES: CCOP(=O)(CC(=O)N1[C@H]2CN(C3CCN(C)CC3)C(=O)[C@H](Cc3ccccc3)N2C(=O)[C@H]1CC(C)C)OCC] | B5-17 |
| A8-22 | 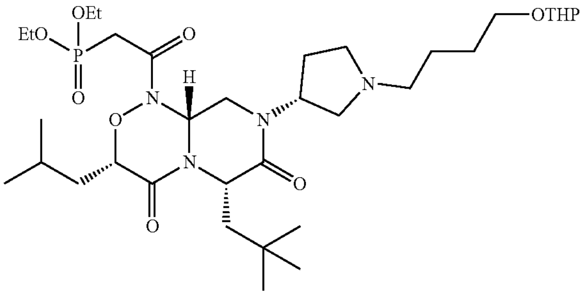 | B5-18 |
| A8-23 | 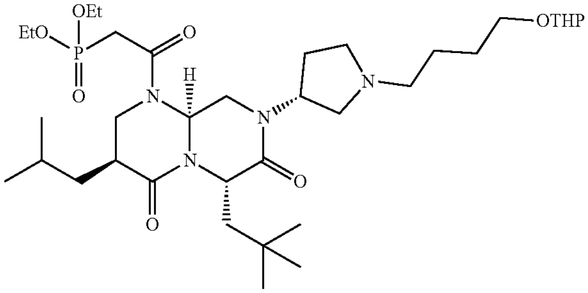 | B5-19 |

TABLE 6-continued
| Intermediate A8 | Structure | B5 |
|---|---|---|
| A8-24 | 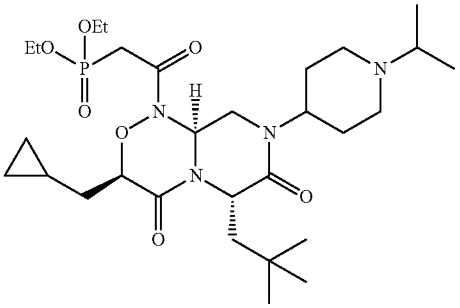 [SMILES: CCOP(=O)(CC(=O)N1O[C@H](CC2CC2)C(=O)N2[C@@H]1CN(C1CCN(C(C)C)CC1)C(=O)[C@@H]2CC(C)(C)C)OCC] | B5-20 |
| A8-25 | 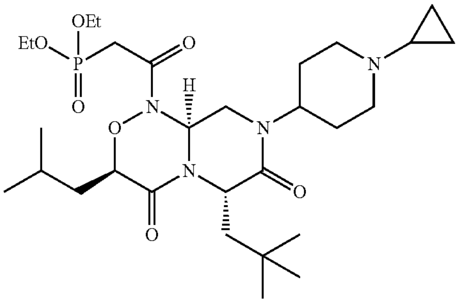 [SMILES: CCOP(=O)(CC(=O)N1O[C@H](CC(C)C)C(=O)N2[C@@H]1CN(C1CCN(C3CC3)CC1)C(=O)[C@@H]2CC(C)(C)C)OCC] | B5-21 |
| A8-26 | 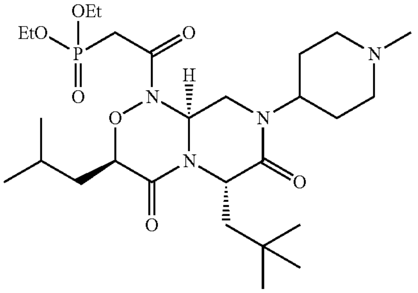 [SMILES: CCOP(=O)(CC(=O)N1O[C@H](CC(C)C)C(=O)N2[C@@H]1CN(C1CCN(C)CC1)C(=O)[C@@H]2CC(C)(C)C)OCC] | B5-2 |
| A8-27 | 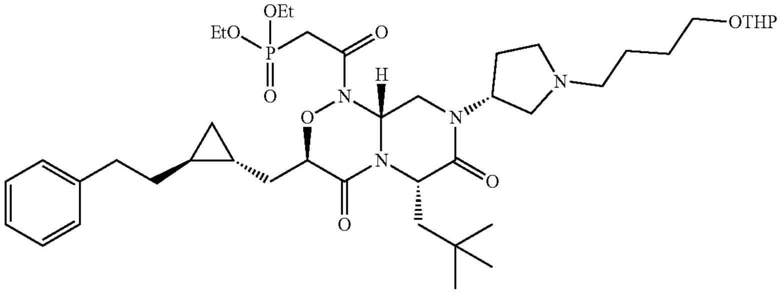 | B5-22 |
| A8-28 | 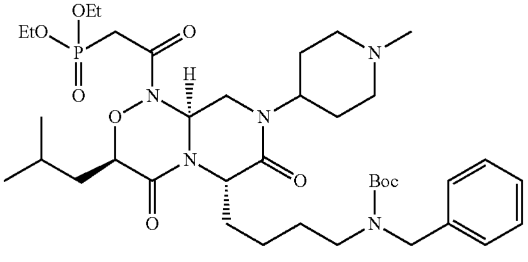 [SMILES: CCOP(=O)(CC(=O)N1O[C@H](CC(C)C)C(=O)N2[C@@H]1CN(C1CCN(C)CC1)C(=O)[C@@H]2CCCCN(Cc1ccccc1)C(=O)OC(C)(C)C)OCC] | B5-23 |

TABLE 6-continued
| Intermediate A8 | Structure | B5 |
| --- | --- | --- |
| A8-29 | 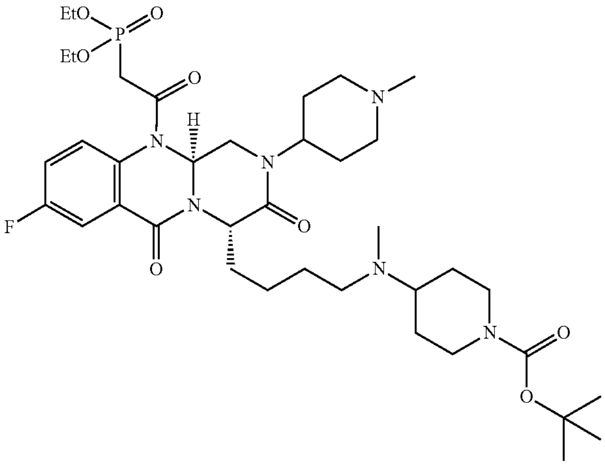 [SMILES: CCOP(=O)(CC(=O)N1c2ccc(F)cc2C(=O)N2[C@@H]1CN(C1CCN(C)CC1)C(=O)[C@@H]2CCCCN(C)C1CCN(C(=O)OC(C)(C)C)CC1)OCC] | B5-24 |
| A8-30 | 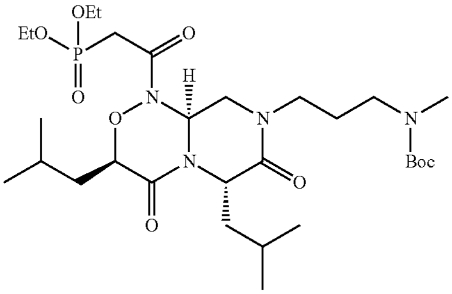 [SMILES: CCOP(=O)(CC(=O)N1O[C@H](CC(C)C)C(=O)N2[C@@H]1CN(CCCN(C)C(=O)OC(C)(C)C)C(=O)[C@@H]2CC(C)C)OCC] | B5-25 |
| A8-31 | 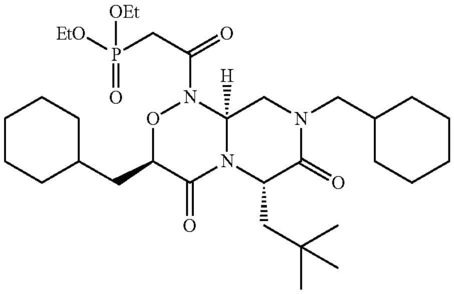 [SMILES: CCOP(=O)(CC(=O)N1O[C@H](CC2CCCCC2)C(=O)N2[C@@H]1CN(CC1CCCCC1)C(=O)[C@@H]2CC(C)(C)C)OCC] | B5-26 |
| A8-32 | 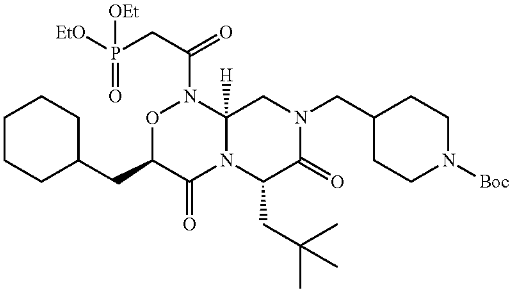 [SMILES: CCOP(=O)(CC(=O)N1O[C@H](CC2CCCCC2)C(=O)N2[C@@H]1CN(CC1CCN(C(=O)OC(C)(C)C)CC1)C(=O)[C@@H]2CC(C)(C)C)OCC] | B5-27 |

TABLE 6-continued
| Intermediate A8 | Structure | B5 |
|---|---|---|
| A8-33 | 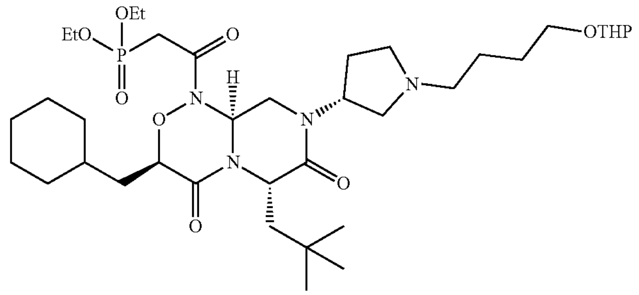 | B5-28 |
| A8-34 | 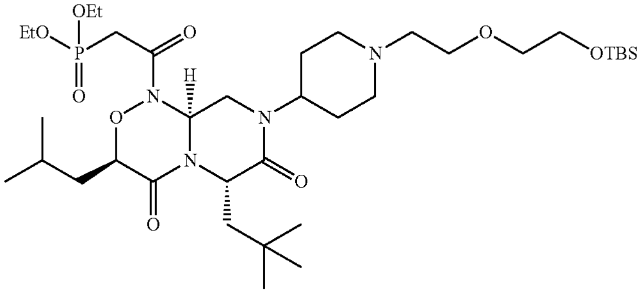 [SMILES: CCOP(=O)(CC(=O)N1O[C@H](CC(C)C)C(=O)N2[C@@H]1CN(C1CCN(CCOCCO[Si](C)(C)C(C)(C)C)CC1)C(=O)[C@@H]2CC(C)(C)C)OCC] | B5-2 |
| A8-35 | 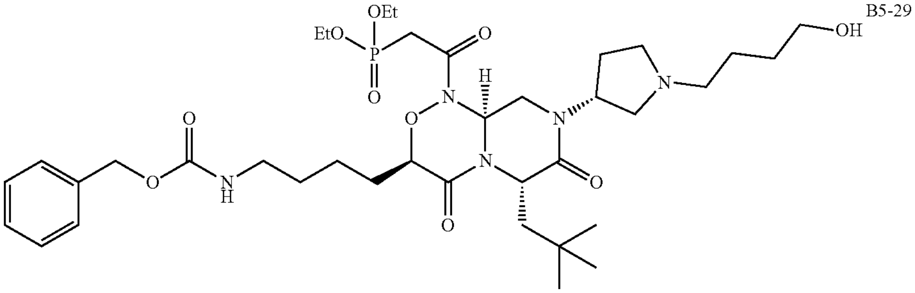 | B5-29 |
| A8-36 | 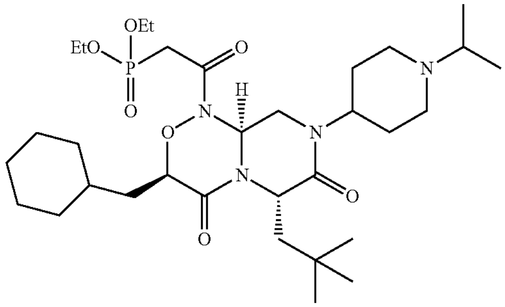 [SMILES: CCOP(=O)(CC(=O)N1O[C@H](CC2CCCCC2)C(=O)N2[C@@H]1CN(C1CCN(C(C)C)CC1)C(=O)[C@@H]2CC(C)(C)C)OCC] | B5-30 |
| A8-37 | 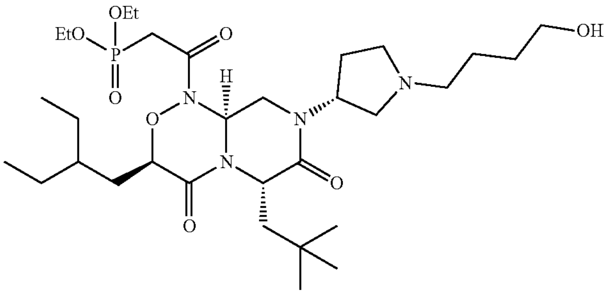 [SMILES: CCOP(=O)(CC(=O)N1O[C@H](CC(CC)CC)C(=O)N2[C@@H]1CN([C@@H]1CCN(CCCCO)C1)C(=O)[C@@H]2CC(C)(C)C)OCC] | B5-31 |

Production Example 9: Synthesis of Intermediate A8-2

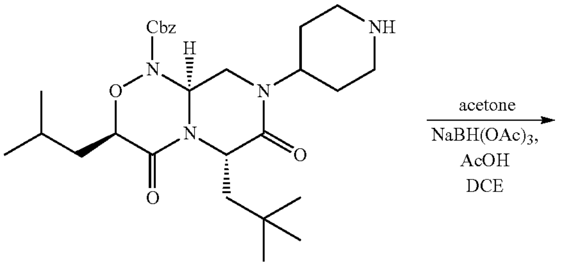

B5-2

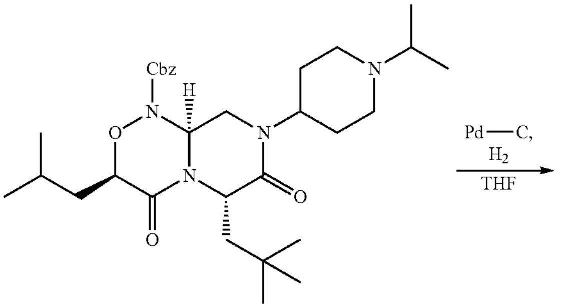

A8-2-Int1

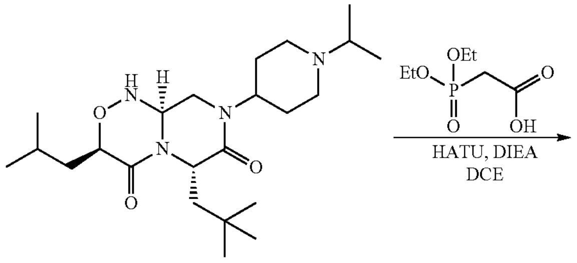

A8-2-Int2

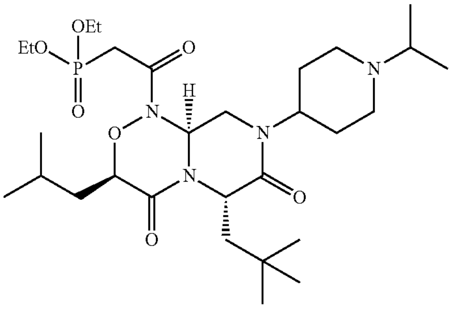

A8-2

9-1) Synthesis of Intermediate A8-2-Int1

To a stirred solution of B5-2 (0.56 g) in DCE (15 mL) were added sodium triacetoxyborohydride (0.35 g), acetone (0.25 g) and AcOH (65 mg) at room temperature. After stirring for 1 hour at 60° C., the mixture was added 20 mL of saturated aqueous sodium bicarbonate solution and 30 mL of DCM. The organic layer was separated, washed with 30 mL of brine, dried over $Na_2SO_4$ and concentrated in vacuo. The crude product was purified by column chromatography ($SiO_2$, AcOEt:MeOH=100:0-80:20, gradient) to give A8-2-Int1 (0.35 g) as a colorless solid.

LCMS (method A): m/z=557.4[M+H]$^+$.

9-2) Synthesis of Intermediate A8-2-Int2

To a stirred solution of A8-2-Int1 (1.7 g) in THE (15 mL) was added 10% palladium-carbon (0.85 g). The resulting mixture was stirred under hydrogen atmosphere (balloon pressure) for 2 hours at room temperature. After the reaction completed, palladium-carbon was filtered and removed by Celite pad. The filtrate was concentrated under reduced pressure to give A8-2-Int2 (1.3 g) as a white solid, which was used in the next reaction without any purification.

LCMS (method A): m/z=423.3[M+H]$^+$.

9-3) Synthesis of Intermediate A8-2

To a stirred solution of A8-2-Int2 (1.3 g) in DCE (15 mL) were added 2-(diethoxyphosphoryl)acetic acid (0.89 g), DIEA (1.3 mL) and HATU (1.8 g). The reaction mixture was stirred for 16 hours at room temperature. After stirring, the mixture was added 30 mL of saturated aqueous sodium bicarbonate solution and 30 mL of DCM. The organic layer was separated, washed with 30 mL of brine, dried over $Na_2SO_4$ and concentrated in vacuo. The crude mixture was purified by column chromatography ($NHSiO_2$, AcOEt: MeOH=100:0-40:60, gradient) to give A8-2 (1.5 g) as colorless amorphous.

LCMS (method B): m/z=601.5 [M+H]$^+$.

A8-1, A8-20, and A8-34 can be synthesized by a similar method to the Production Example 9.

Production Example 10: Synthesis of Intermediate A8-5

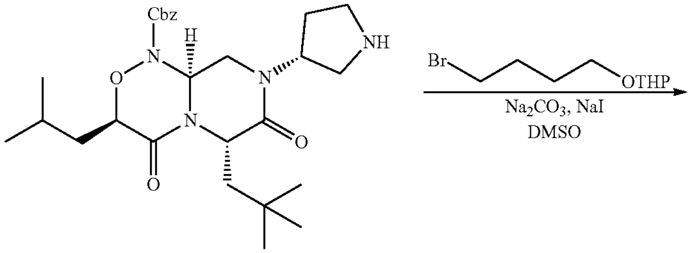

B5-4

-continued

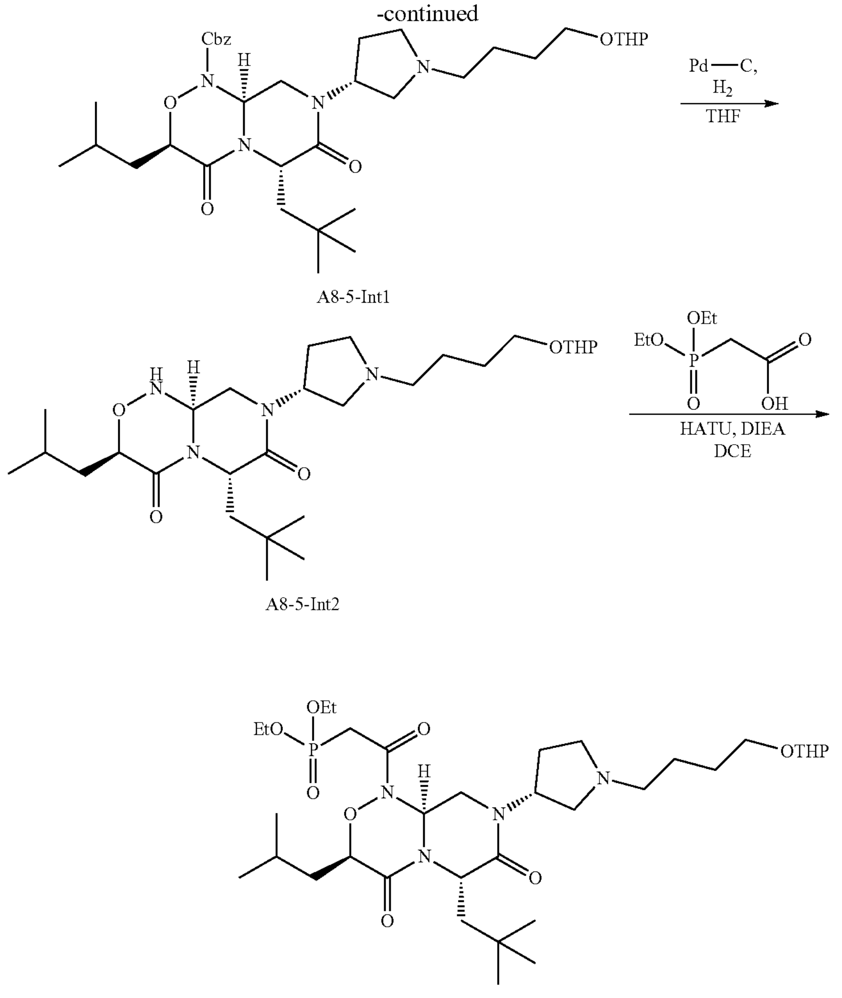

A8-5-Int1

A8-5-Int2

A8-5

10-1) Synthesis of Intermediate A8-5-Int1

A mixture suspension of B5-4 (7.4 g), 2-(4-bromobutoxy) tetrahydro-2H-pyran (3.9 g), sodium carbonate (4.7 g) and sodium iodide (2.2 g) in DMSO (0.10 L) was stirred for 1 hours at 70° C. After addition of 2-(4-bromobutoxy)tetrahydro-2H-pyran (0.36 g), the reaction mixture was stirred for another 30 minutes. After cooled to room temperature, the mixture was poured into saturated aqueous sodium bicarbonate solution and extracted by AcOEt three times. The organic layer was concentrated in vacuo and purified by column chromatography ($SiO_2$, AcOEt:MeOH=100:0-70:30, gradient) followed by further purification by column chromatography ($SiO_2$, AcOEt:MeOH=100:0-85:15, gradient) to give A8-5-Int1 (6.2 g) as light yellow syrup.

LCMS (method A): m/z=657.5[M+H]$^+$.

10-2) Synthesis of Intermediate A8-5-Int2

To a solution of A8-5-Int1 (1.6 g) of THE (20 mL) was added 10% palladium-carbon (0.50 g). The resulting mixture was stirred under hydrogen atmosphere (balloon pressure) for 2 hours at room temperature. After the reaction completed, palladium-carbon was filtrated out and removed through Celite pad. The filtrate was concentrated in vacuo to give A8-5-Int2 (1.3 g) as colorless syrup, which was used in the next reaction without any purification.

LCMS (method A): m/z=523.4[M+H]$^+$.

10-3) Synthesis of Intermediate A8-5

To a solution of A8-5-Int2 (1.3 g) in DCE (20 mL) were added 2-(diethoxyphosphoryl)acetic acid (0.63 g), HATU (1.5 g) and DIEA (0.86 mL). After stirring for 4 hours at room temperature, the mixture was concentrated in vacuo and purified by column chromatography ($NHSiO_2$, n-hexane:AcOEt=75:25-0:100, gradient). The obtained material was dissolved in chloroform and washed with aqueous sodium carbonate solution. The organic layer was concentrated in vacuo to give A8-5 (1.5 g) as light yellow syrup.

LCMS (method A): m/z=701.5[M+H]$^+$.

A8-3, A8-4, A8-6, A8-19, A8-22, A8-23, A8-27, and A8-33 can be synthesized by similar methods to the Production Example 10.

Production Example 11: Synthesis of Intermediate A8-28

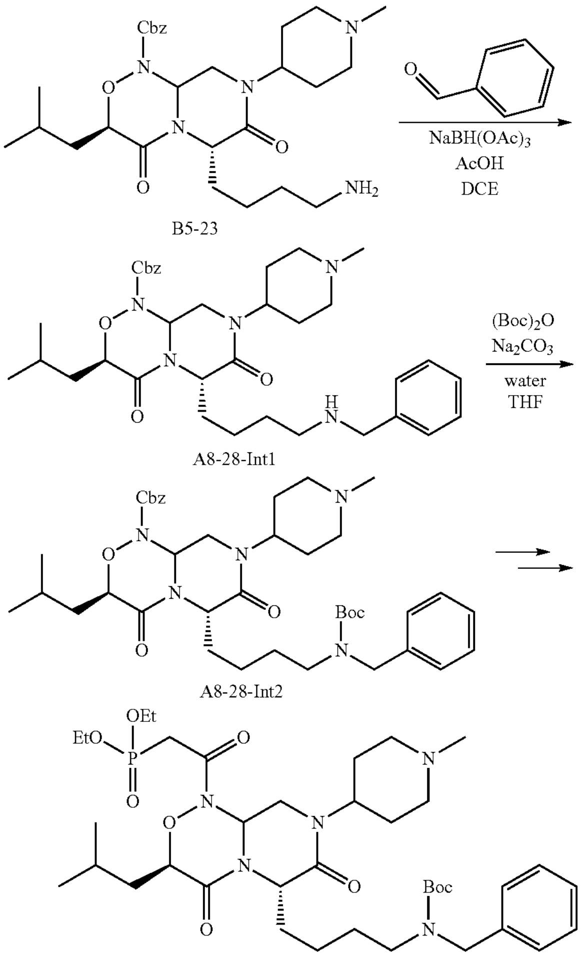

B5-23

A8-28-Int1

A8-28-Int2

A8-28

11-1) Synthesis of Intermediate A8-28-Int1

To a solution of B5-23 (0.50 g) in DCE (50 mL) were added benzaldehyde (0.10 g) and acetic acid (17 mg). After stirring for a while, sodium triacetoxyborohydride (0.24 g) was slowly added to the mixture. After stirring for another 40 minutes, 1 mol/L NaOH solution (20 mL) and chloroform (30 mL) were added. The organic layer was separated, then washed with 20 mL of water, dried over $Na_2SO_4$, concentrated in vacuo. The crude product was purified by column chromatography ($SiO_2$, AcOEt:MeOH=100:0-20:80, gradient) to give A8-28-Int1 (0.28 g) as white amorphous.

LCMS (method B): m/z=620.4[M+H]$^+$.

11-2) Synthesis of Intermediate A8-28-Int2

To a solution of A8-28-Int1 (0.14 g) in 5 mL of THE 5 mL were added sodium carbonate (47 mg) in water (5 mL), and di-tert-butyl dicarbonate (53 mg). After stirred for overnight, the reaction mixture was diluted with 50 ml of ethyl acetate and 20 mL of saturated aqueous sodium bicarbonate solution. The extracted organic layer was separated, dried over $Na_2SO_4$, and concentrated in vacuo. The obtained crude product was purified by column chromatography ($SiO_2$, AcOEt:MeOH=80:20-20:80, gradient) to give A8-28-Int2 (77 mg) as colorless oil.

LCMS (method A): m/z=720.5[M+H]$^+$.

11-3) Synthesis of Intermediate A8-28

From A8-28-Int2, A8-28 were synthesized by similar methods to the procedures 10-2) and 10-3).

LCMS (method A): m/z=678.4[M+H]$^+$.

Production Example 12: Synthesis of Intermediate A8-29

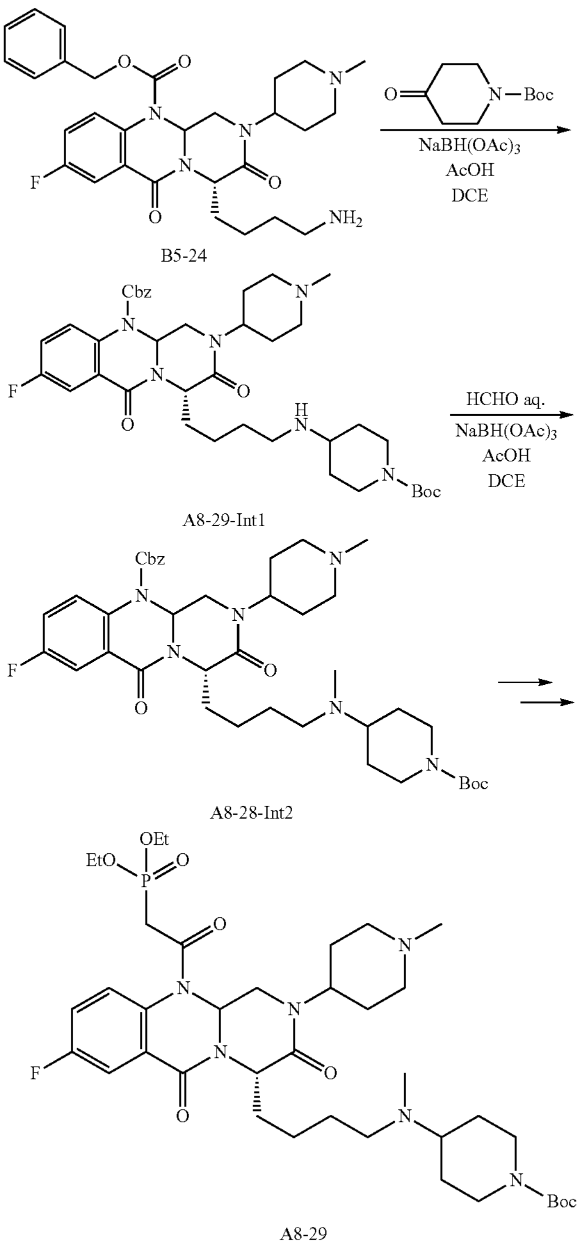

B5-24

A8-29-Int1

A8-28-Int2

A8-29

12-1) Synthesis of Intermediate A8-29-Int1

From 0.54 g of B5-24, 0.31 g of A8-29-Int1 (colorless oil) were synthesized by a similar method to the procedure 10-1).

LCMS (method A): m/z=721.4[M+H]$^+$.

12-2) Synthesis of Intermediate A8-29-Int2

From 0.31 g of A8-29-Int1, 0.33 g of crude A8-29-Int2 (colorless oil) were synthesized by a similar method to the procedure 10-1).

LCMS (method A): m/z=735.5[M+H]$^+$.

12-3) Synthesis of Intermediate A8-29

From A8-28-Int2, unpurified A8-28 (brown oil) were synthesized by similar methods to reaction procedure 10-2) and 10-3).

LCMS (method A): m/z=779.5[M+H]$^+$.

Production Example 13: Synthesis of Intermediate A8-30

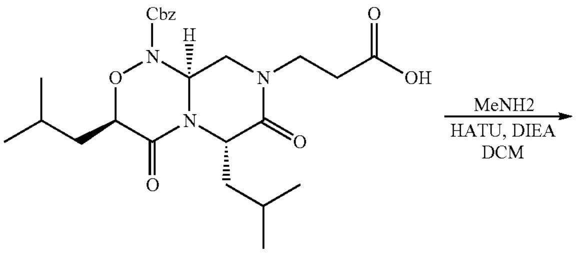

B5-25

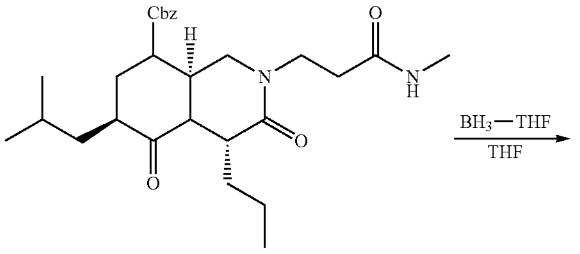

A8-30-Int1

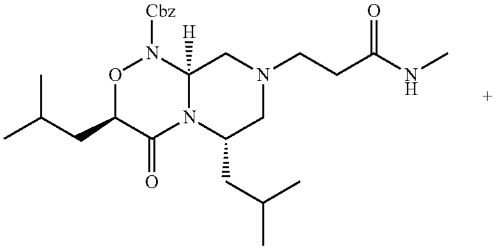

A8-30-Int2a

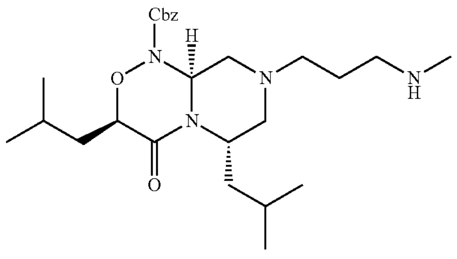

A8-30-Int2b

-continued

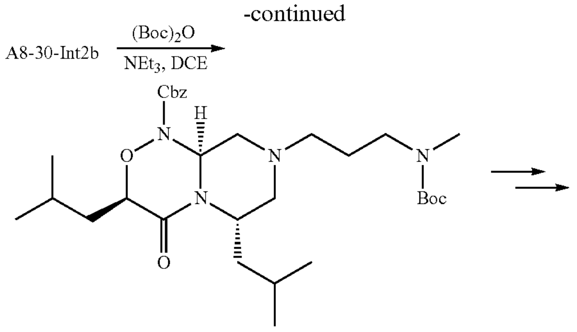

A8-30-Int3

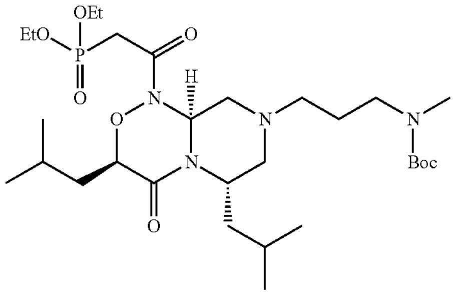

A8-30

13-1) Synthesis of Intermediate A8-30-Int1

To a solution of B5-25 (52 mg) in $CH_2Cl_2$ (2 mL) were added methylamine (2 mol/L in THF, 95 μL), DIEA (65 μL), and HATU (72 mg) at room temperature. After stirring for 1 hour at room temperature, the mixture was diluted with $CHCl_3$ (30 mL), and then washed with 1 mol/L aqueous HCl solution (10 mL), saturated aqueous sodium bicarbonate solution (10 mL), and brine (10 mL). The organic layer was dried over $Na_2SO_4$, concentrated in vacuo, and purified by column chromatography ($SiO_2$, $CHCl_3$:MeOH=100:0-90:10, gradient) to give A8-30-Int1 (48 mg) as white amorphous.

LCMS (method C): m/z=503.0[M+H]$^+$.

13-2) Synthesis of Intermediate A8-30-Int2a and Int2b

To a solution of A8-30-Int1 (0.96 g) in THF (20 mL), cooled by ice/water bath, was added $BH_3$·THF (0.9 M in THF, 7.5 mL). After stirring for 1 hour at 0° C. and 2 hours at room temperature, MeOH (4 mL) was added dropwise. The mixture was concentrated in vacuo and purified by column chromatography (NH $SiO_2$, n-hexane:AcOEt=80:20-0:100, gradient) to give A8-30-Int2a (0.17 g) and A8-30-Int2b (0.27 g) as colorless oil.

LCMS (A8-30-Int2a, method C): m/z=489.1[M+H]$^+$

LCMS (A8-30-Int2b, method C): m/z=475.2[M+H]$^+$ 13-3) Synthesis of Intermediate A8-30-Int3

To a solution of A8-30-Int2b (0.27 g) in DCE (6 mL) were added triethylamine (0.16 mL) and $(Boc)_2O$ (0.25 g). After stirring for 1 hour at room temperature, the mixture was concentrated in vacuo, and purified by column chromatography (NH $SiO_2$, n-hexane:AcOEt=100:0-50:50, gradient) to give A8-30-Int3 (0.30 g) as colorless oil.

LCMS (method C): m/z=575.2[M+H]$^+$.

13-4) Synthesis of Intermediate A8-30

From A8-30-Int3, A8-30 (brown oil) were synthesized by similar methods to reaction procedure 9-2) and 9-3).

LCMS (method C): m/z=619.2[M+H]$^+$.

Production Example 14: Synthesis of Intermediate A8-32

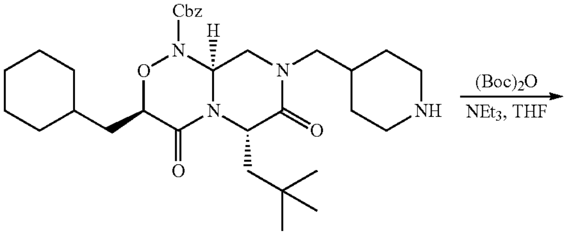

B5-27

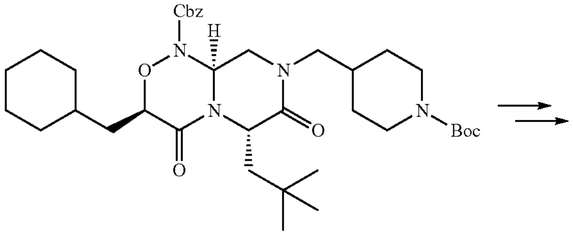

A8-32-Int1

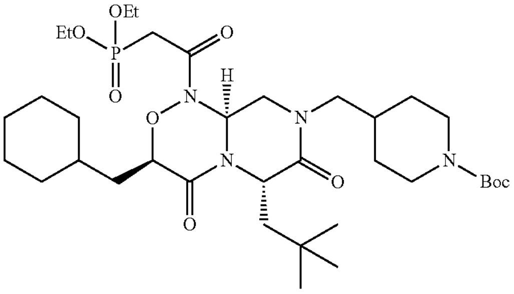

A8-32

14-1) Synthesis of Intermediate A8-32-Int1

A mixture of B5-27 (0.34 g), triethylamine (0.34 mL), and di-tert-butyl dicarbonate (0.26 g) in THF (5 mL) was stirred at room temperature for 1.5 hours. The mixture was concentrated in vacuo. The residue was purified by column chromatography ($SiO_2$, n-hexane:AcOEt=100:0-0:100, gradient) to give A8-32-Int1 (0.38 g) as yellow oil.

LCMS (method A): m/z=569.4[M-Boc+H]$^+$.

14-2) Synthesis of Intermediate A8-32

From A8-32-Int1, A8-32 was synthesized by similar methods to reaction procedures 10-2) and 10-3).

LCMS (method A): m/z=613.4[M-Boc+H]$^+$.

A8-16 can be synthesized by a similar method to the Production Example 14.

Intermediate A9 listed in the Table 7 are known compounds or were synthesized according to a known method or a method below.

List of Intermediate A9

TABLE 7

| Intermediate A9 | Structure |
|---|---|
| A9-1 | 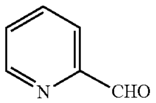 |
| A9-2 | 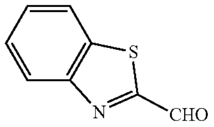 [SMILES: O=Cc1nc2ccccc2s1] |
| A9-3 | 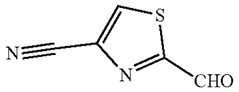 |
| A9-4 | 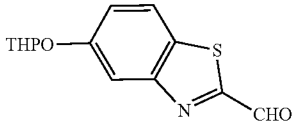 |
| A9-5 | 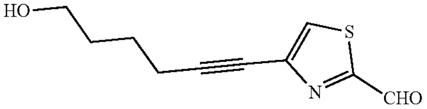 [SMILES: O=Cc1nc(C#CCCCCO)cs1] |
| A9-6 | 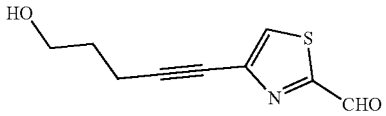 [SMILES: O=Cc1nc(C#CCCCO)cs1] |
| A9-7 | 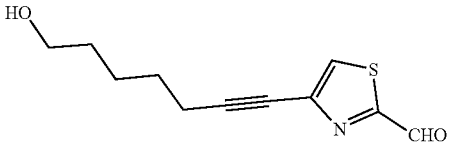 [SMILES: O=Cc1nc(C#CCCCCCO)cs1] |
| A9-8 | 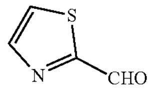 |
| A9-9 | 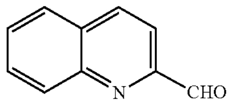 [SMILES: O=Cc1ccc2ccccc2n1] |
| A9-10 | 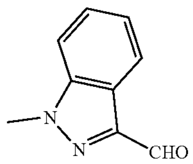 |
| A9-11 | 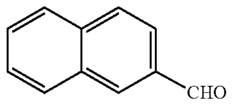 [SMILES: O=Cc1ccc2ccccc2c1] |

TABLE 7-continued
| Intermediate A9 | Structure |
|---|---|
| A9-12 | 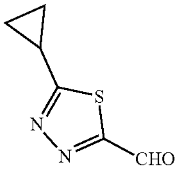 |
| A9-13 | 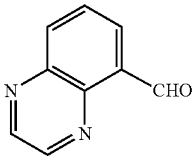 [SMILES: O=Cc1cccc2nccnc12] |
| A9-14 | 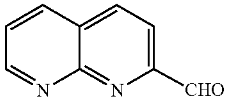 [SMILES: O=Cc1ccc2cccnc2n1] |
| A9-15 | 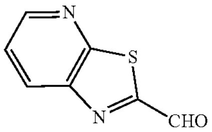 [SMILES: O=Cc1nc2cccnc2s1] |
| A9-16 | 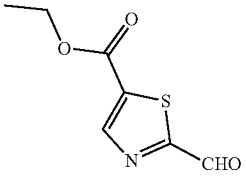 |
| A9-17 | 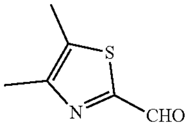 |
| A9-18 | 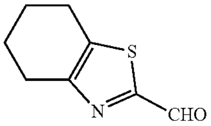 [SMILES: O=Cc1nc2c(s1)CCCC2] |
| A9-19 | 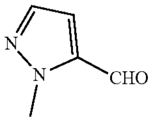 |
| A9-20 | 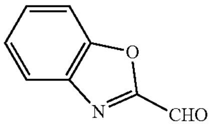 [SMILES: O=Cc1nc2ccccc2o1] |
| A9-21 | 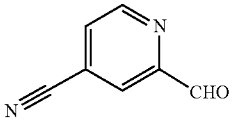 |
TABLE 7-continued
| Intermediate A9 | Structure |
|---|---|
| A9-22 | 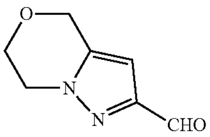 [SMILES: O=Cc1cc2n(n1)CCOC2] |
| A9-23 | 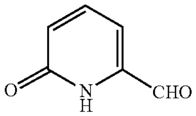 |
| A9-24 | 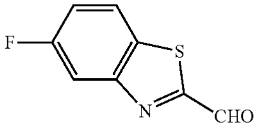 [SMILES: O=Cc1nc2cc(F)ccc2s1] |
| A9-25 | 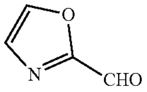 |
| A9-26 | 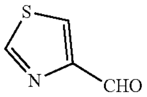 |
| A9-27 | 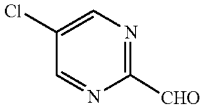 |
| A9-28 | 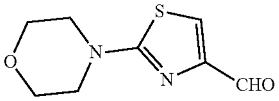 [SMILES: O=Cc1csc(N2CCOCC2)n1] |
| A9-29 | 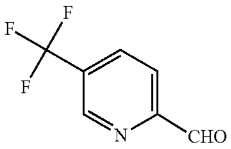 [SMILES: O=Cc1ccc(C(F)(F)F)cn1] |
| A9-30 | 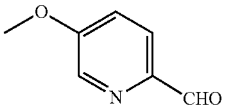 |
| A9-31 | 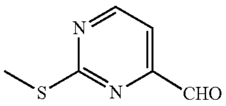 |
| A9-32 | 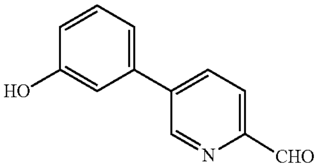 [SMILES: O=Cc1ccc(-c2cccc(O)c2)cn1] |
| A9-33 | 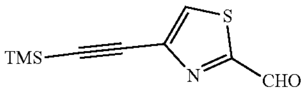 [SMILES: C[Si](C)(C)C#Cc1csc(C=O)n1] |

TABLE 7-continued

| Intermediate A9 | Structure |
|---|---|
| A9-34 | 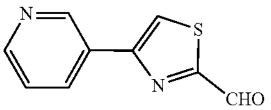 |
| A9-35 | 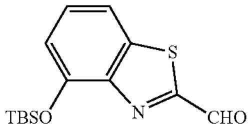 [SMILES: CC(C)(C)[Si](C)(C)Oc1cccc2sc(C=O)nc12] |
| A9-36 | 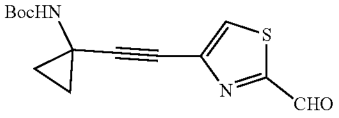 [SMILES: CC(C)(C)OC(=O)NC1(C#Cc2csc(C=O)n2)CC1] |
| A9-37 | 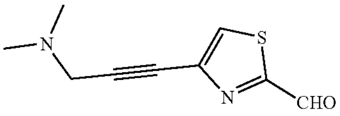 |
| A9-38 | 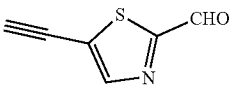 |
| A9-39 | 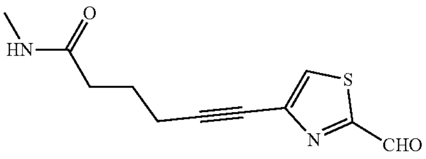 [SMILES: CNC(=O)CCCC#Cc1csc(C=O)n1] |
| A9-40 | 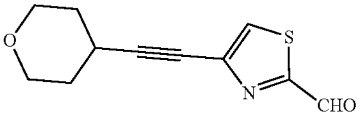 [SMILES: O=Cc1nc(C#CC2CCOCC2)cs1] |
| A9-41 | 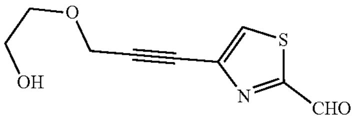 [SMILES: O=Cc1nc(C#CCOCCO)cs1] |
| A9-42 | 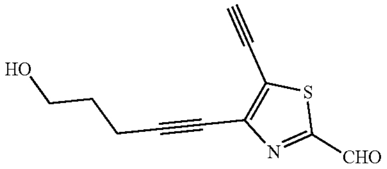 |
| A9-43 | 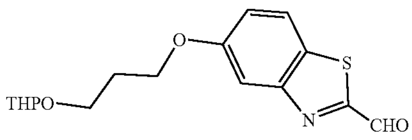 |
| A9-44 | 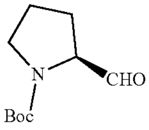 |

TABLE 7-continued

| Intermediate A9 | Structure |
|---|---|
| A9-45 | 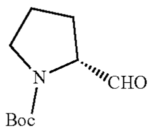 |
| A9-46 | 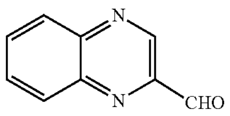 [SMILES: O=Cc1cnc2ccccc2n1] |

Production Example 15: Synthesis of Intermediate A9-4

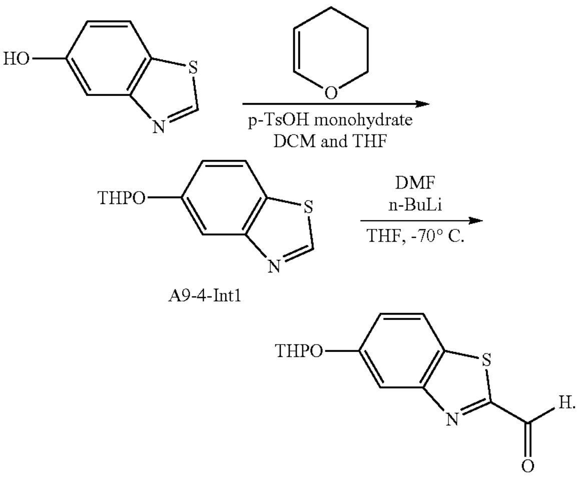

A9-4

15-1) Synthesis of Intermediate A9-4-Intl

To a suspension of benzo[d]thiazol-5-ol (0.50 g) in DCM (20 mL) and THF (5 mL) were added 3,4-dihydro-2H-pyran (0.80 mL) and p-TsOH monohydrate (30 mg). After stirring for 5 hours at room temperature, the mixture was poured into a saturated aqueous sodium bicarbonate solution and extracted with chloroform twice. The organic layer was concentrated in vacuo and purified by column chromatography ($SiO_2$, n-hexane:AcOEt=75:25-30:70, gradient) to give A9-4-Intl (0.73 g) as colorless syrup.

LCMS (method B): m/z=236.1[M+H]$^+$.

15-2) Synthesis of Intermediate A9-4

To a solution of A9-4-Intl (0.73 g) in THF (15 mL) was added n-BuLi (2.8 mol/L) in hexane (1.2 mL) at −70° C. under nitrogen atmosphere. After stirring for 30 minutes, a solution of DMF (0.27 g) in THF (1 mL) was added. After stirring for another 30 minutes at the same temperature, the reaction mixture was quenched with saturated aqueous ammonium chloride solution, warmed to room temperature and extracted with AcOEt twice. The organic layer was concentrated in vacuo and purified by column chromatography ($SiO_2$, n-hexane:AcOEt=94:6-50:50, gradient) to give A9-4 (0.64 g) as a yellow solid.

$^1H$ NMR (300 MHz, $CDCl_3$) data of A9-4 is shown in FIG. 1.

Production Example 16: Synthesis of Intermediate A9-5

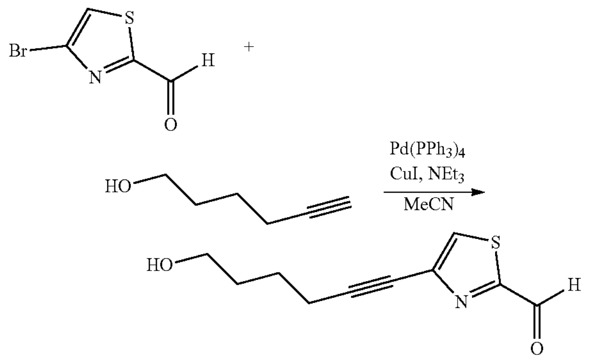

A9-5

To a stirred mixture of 4-bromothiazole-2-carbaldehyde (96 mg) in MeCN (4 mL) was added hex-5-yn-1-ol (98 mg), copper(I) iodide (9.5 mg) triethylamine (0.51 g) and tetrakis (triphenylphosphine)palladium(0) (58 mg). After stirring for 2 hours at 60° C. under microwave irradiation, the reaction mixture was cooled to room temperature. The precipitated solid was filtered out, and the resulting filtrate was concentrated in vacuo and purified by column chromatography ($SiO_2$, n-Hexane:AcOEt=100:0-50:50, gradient) to give A9-5 (46 mg) as light yellow syrup.

LCMS (method A): m/z=210.0 $[M+H]^+$.

A9-6, A9-7, A9-36, A9-37, A9-39, A9-40, and A9-41 can be synthesized by a similar method to the Production Example 16.

Production Example 17: Synthesis of Intermediate A9-32

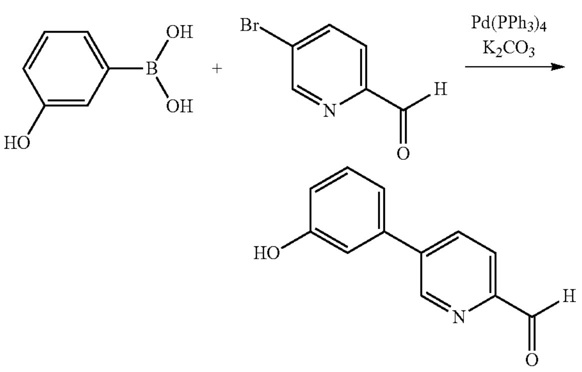

A9-32

17-1) Synthesis of Intermediate A9-32

A mixture of (3-hydroxyphenyl)boronic acid (0.13 g), 5-bromopicolinaldehyde (0.15 g), potassium carbonate (0.33 g) and tetrakis(triphenylphosphine)palladium(0) (0.19 g) in toluene (3 mL) and water (1.5 mL) was stirred at 140° C. for 20 min under microwave irradiation. The toluene phase of the mixture was purified by column chromatography ($SiO_2$, n-hexane:AcOEt=100:0-0:100, gradient) to give A9-32 (35 mg) as a white powder.

LCMS (method B): m/z=200.1$[M+H]^+$.

Production Example 18: Synthesis of Intermediate A9-35

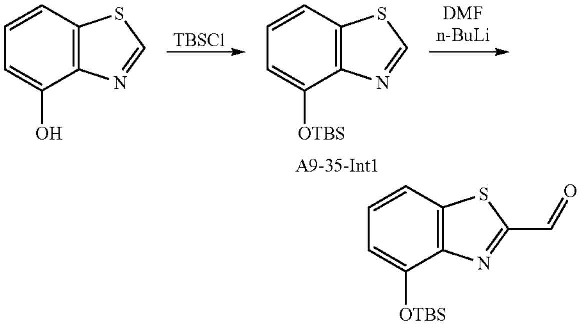

A9-35-Int1

A9-35

18-1) Synthesis of Intermediate A9-35-Int1

To a solution of benzo[d]thiazol-4-ol (0.20 g) in THE (3 mL) cooled with ice/water bath were added imidazole (0.14 g) and TBS-C1 (0.24 g). The cool bath was removed soon after the addition of the reagents. After stirring for 2 hours at room temperature, saturated aqueous ammonium chloride solution (5 mL) and water (2.5 mL) were added. The mixture was extracted by AcOEt (10 mL, twice). The combined organic layer was dried over $Na_2SO_4$, concentrated in vacuo, and purified by column chromatography ($SiO_2$, n-hexane: AcOEt=100:0-80:20, gradient) to give A9-35-Int1 (0.33 g) as light yellow syrup.

LCMS (method A): m/z=266.1$[M+H]^+$.

18-2) Synthesis of Intermediate A9-35

To a solution of A9-35-Int1 (60 mg) in dry THF (0.50 mL) cooled with $CO_2$/acetone bath was added n-BuLi (2.6 M in n-hexane, 130 μL). After stirring for 30 minutes, dry DMF (35 μL) in dry THE (0.50 mL) was added dropwise. After stirring for 2 hours, saturated aqueous ammonium chloride solution (2 mL) and water (1 mL) were added. The mixture was extracted by AcOEt (8 mL) twice. The combined organic layer was dried over $Na_2SO_4$, concentrated in vacuo, and purified by column chromatography ($SiO_2$, n-hexane: AcOEt=100:0-90:10, gradient) to give a mixture of mixture of A9-35-Int1 and A9-35 (ca. 2:1, 34 mg) as yellow syrup, which was used for next step without further purification.

LCMS (method A): m/z=294.1$[M+H]^+$.

Production Example 19: Synthesis of Intermediate A9-42

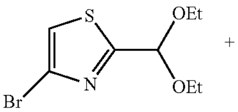

-continued

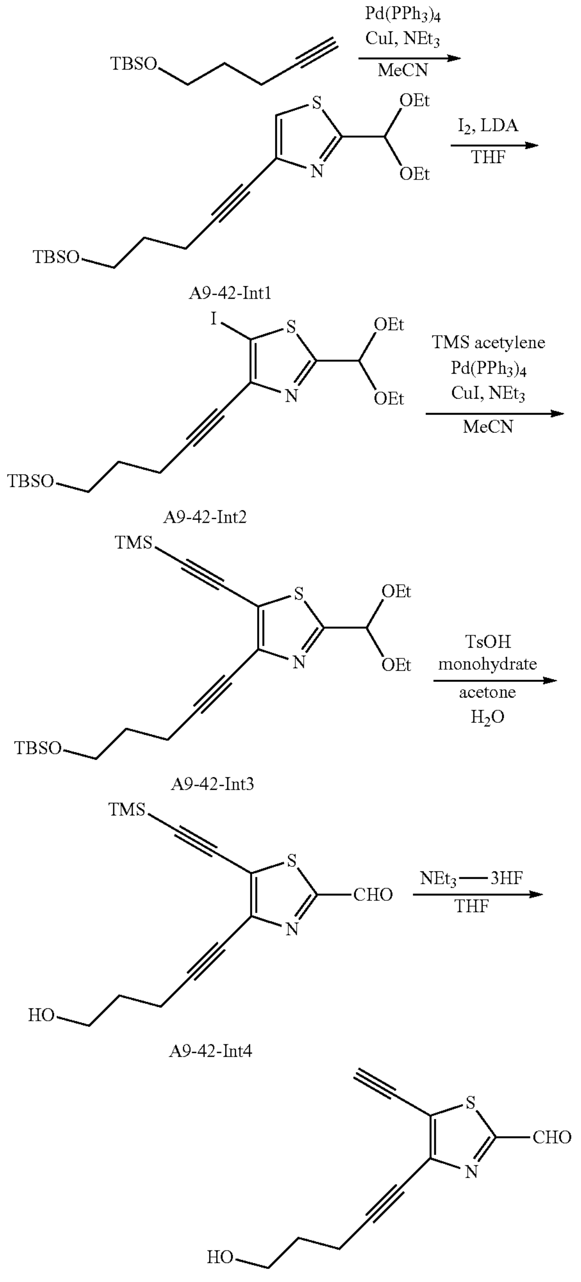

A9-42-Int1

A9-42-Int2

A9-42-Int3

A9-42-Int4

A9-42

19-1) Synthesis of Intermediate A9-42-Int1

To a stirred mixture of 4-bromo-2-(diethoxymethyl)thiazole (2.7 g) in MeCN (15 mL) were added tert-butyldimethyl(pent-4-yn-1-yloxy)silane (2.4 g), copper(I) iodide (0.19 g), triethylamine (10 g) and $Pd(Ph_3)_4$ (1.2 g). After stirring for 2 hours at 60° C. under microwave irradiation, the reaction mixture was cooled to room temperature. The precipitated solid was filtered out, and the resulting filtrate was concentrated in vacuo and purified by column chromatography ($SiO_2$, n-Hexane:AcOEt=100:0-80:20, gradient) to give A9-42-Int1 (2.4 g) as light yellow syrup.

LCMS (method A): m/z=384.2$[M+H]^+$ 19-2) Synthesis of Intermediate A9-42-Int2

To a solution of A9-42-Int1 (0.59 g) in THF (10 mL) was added LDA (1.08 mol/L) in hexane (3.7 mL) at −70° C. under nitrogen atmosphere. After stirring for 10 minutes, a solution of iodine (1.2 g) in THF (3 mL) was added. After stirring for another 5 minutes at the same temperature, the reaction mixture was gradually warmed to room temperature for 1 hour, the reaction mixture was quenched with 10% aqueous sodium thiosulfate solution (20 ml) and extracted with AcOEt twice. The organic layer was concentrated in vacuo and purified by column chromatography ($SiO_2$, n-hexane:AcOEt=100:0-80:20, gradient) to give A9-42-Int2 (0.59 g) as a brown oil.

LCMS (method A): m/z=510.1$[M+H]^+$ 19-3) Synthesis of Intermediate A9-42-Int3

To a stirred mixture of A9-42-Int2 (0.59 g) in MeCN (20 mL) were added ethynyltrimethylsilane (0.23 g), copper(I) iodide (22 mg), triethylamine (1.2 g) and $Pd(Ph_3)_4$ (0.13 g). After stirring for 2 hours at 60° C. under microwave irradiation, the reaction mixture was cooled to room temperature. The precipitated solid was filtered out, and the resulting filtrate was concentrated in vacuo and purified by column chromatography ($SiO_2$, n-Hexane:AcOEt=100:0-80:20, gradient) to give 4 A9-42-Int3 (0.49 g) as light yellow syrup.

LCMS (method A): m/z=480.2$[M+H]^+$ 19-4) Synthesis of Intermediate A9-42-Int4

To a stirred mixture of A9-42-Int3 (0.24 g) in acetone (9 mL) and water (1 mL) was added p-TsOH monohydrate (0.29 g). After stirring for 3 hours at 80° C. under microwave irradiation, the reaction mixture was cooled to room temperature. The solution was concentrated in vacuo and added saturated aqueous sodium bicarbonate solution, extracted with chloroform twice. The organic layer was concentrated in vacuo to give A9-42-Int4 (0.15 g) as a brown syrup, which was used for next step without further purification.

LCMS (method A): m/z=292.2$[M+H]^+$ 19-5) Synthesis of Intermediate A9-42

To a stirred mixture of A9-42-Int4 (0.11 g) in THE (10 mL) was added triethylamine trihydrofluoride (0.18 g). After stirring for 1.5 hours at 60° C. under microwave irradiation, the reaction mixture was cooled to room temperature. The solution was concentrated in vacuo and added saturated aqueous sodium bicarbonate solution, extracted with AcOEt twice. The organic layer was washed with brine, dried over $Na_2SO_4$ and concentrated in vacuo to give A9-42 (71 mg) as a brown syrup, which was used for next step without further purification.

LCMS (method B): m/z=220.0$[M+H]^+$

Production Example 20: Synthesis of Intermediate A9-43

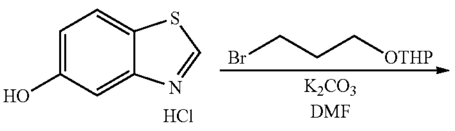

-continued

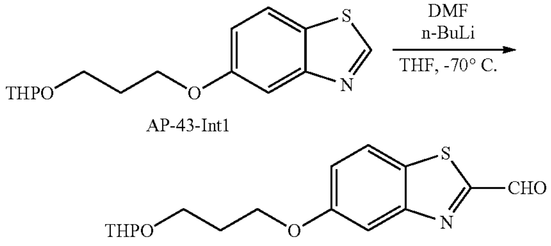

AP-43-Int1

AP-43

20-1) Synthesis of Intermediate A9-43-Int1

A suspension mixture of benzothiazole-5-ol hydrochloride (0.40 g), 2-(3-bromopropoxy)tetrahydro-2H-pyran (0.95 g), and potassium carbonate (0.88 g) in DMF (5 mL) was stirred for 2 hours at room temperature and for 3 hours at 60° C. After cooled to room temperature, the reaction mixture was poured into saturated aqueous sodium bicarbonate solution and extracted by AcOEt. The organic layer was washed by brine, concentrated in vacuo, and purified by column chromatography ($SiO_2$, n-hexane:AcOEt=94:6-30:70, gradient) to give A9-43-Int1 (0.34 g) as colorless syrup.

LCMS (method A): m/z=210.1[M-THP+H]$^+$.

20-2) Synthesis of Intermediate A9-43

From 0.34 g of A8-43-Int1, 0.25 g of A8-32 (yellow syrup) was synthesized by a similar method to the reaction procedure 15-2).

Figure 6:
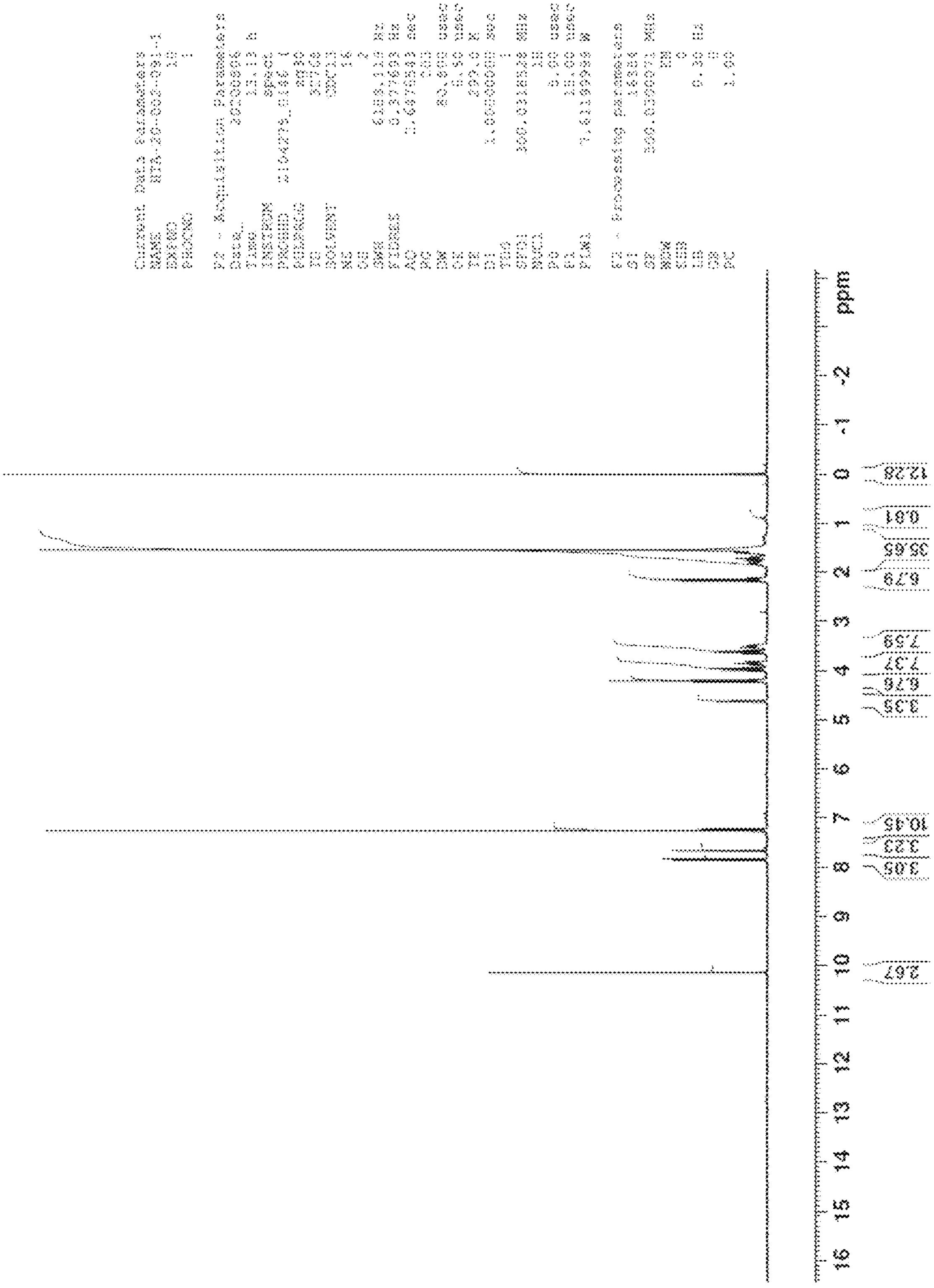
FIG. 6 shows a $^1$H NMR (300 MHz, $CDCl_3$) data of A9-43.

$^1$H NMR (300 MHz, $CDCl_3$) data of A9-43 is shown in FIG. 6.

Intermediate A10 listed in the Table 8 are known compounds or were synthesized according to a known method.

List of Intermediate A10

TABLE 8

| Intermediate A10 | Structure |
|---|---|
| A10-1 | 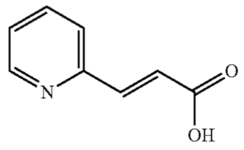 [SMILES: O=C(O)/C=C/c1ccccn1] |
| A10-2 | 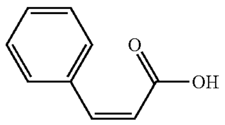 [SMILES: O=C(O)/C=C\c1ccccc1] |
| A10-3 | 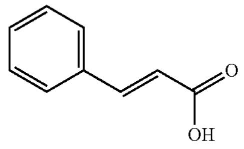 [SMILES: O=C(O)/C=C/c1ccccc1] |

Compounds listed in Table 9 were synthesized according to the below method or a known method using the Intermediates A8 and A9 shown in Table 9.

TABLE 9

| Compound ID | A8 | A9 |
|---|---|---|
| ID-1 | A8-1 | A9-1 |
| ID-2 | A8-1 | A9-2 |
| ID-3 | A8-1 | A9-3 |
| ID-4 | A8-3 | A9-2 |
| ID-5 | A8-4 | A9-2 |
| ID-6 | A8-5 | A9-2 |
| ID-7 | A8-4 | A9-4 |
| ID-8 | A8-6 | A9-4 |
| ID-9 | A8-4 | A9-5 |
| ID-10 | A8-2 | A9-6 |
| ID-11 | A8-5 | A9-5 |
| ID-12 | A8-5 | A9-4 |
| ID-13 | A8-5 | A9-7 |
| ID-14 | A8-7 | A9-1 |
| ID-17 | A8-7 | A9-8 |
| ID-19 | A8-30 | A9-1 |
| ID-20 | A8-7 | A9-9 |
| ID-22 | A8-7 | A9-10 |
| ID-23 | A8-7 | A9-2 |
| ID-24 | A8-7 | A9-11 |
| ID-25 | A8-31 | A9-46 |
| ID-26 | A8-32 | A9-46 |
| ID-29 | A8-7 | A9-12 |
| ID-30 | A8-7 | A9-13 |
| ID-31 | A8-7 | A9-14 |
| ID-32 | A8-7 | A9-15 |
| ID-33 | A8-7 | A9-16 |
| ID-34 | A8-7 | A9-17 |
| ID-37 | A8-7 | A9-18 |
| ID-42 | A8-7 | A9-44 |
| ID-43 | A8-7 | A9-45 |
| ID-44 | A8-1 | A9-19 |
| ID-46 | A8-1 | A9-20 |
| ID-47 | A8-8 | A9-1 |
| ID-48 | A8-1 | A9-21 |
| ID-49 | A8-1 | A9-22 |
| ID-51 | A8-1 | A9-23 |
| ID-52 | A8-1 | A9-24 |
| ID-53 | A8-1 | A9-25 |
| ID-54 | A8-1 | A9-26 |
| ID-55 | A8-1 | A9-27 |
| ID-56 | A8-1 | A9-28 |
| ID-57 | A8-28 | A9-1 |
| ID-58 | A8-9 | A9-2 |
| ID-59 | A8-29 | A9-2 |
| ID-60 | A8-10 | A9-2 |
| ID-61 | A8-11 | A9-1 |
| ID-64 | A8-12 | A9-2 |
| ID-65 | A8-13 | A9-1 |
| ID-66 | A8-14 | A9-1 |
| ID-67 | A8-15 | A9-1 |
| ID-68 | A8-16 | A9-1 |
| ID-70 | A8-17 | A9-1 |
| ID-71 | A8-1 | A9-29 |
| ID-72 | A8-1 | A9-30 |
| ID-73 | A8-2 | A9-2 |
| ID-74 | A8-18 | A9-2 |
| ID-77 | A8-34 | A9-2 |
| ID-78 | A8-4 | A9-31 |
| ID-79 | A8-19 | A9-2 |
| ID-80 | A8-3 | A9-32 |
| ID-81 | A8-4 | A9-33 |
| ID-82 | A8-4 | A9-34 |
| ID-83 | A8-20 | A9-2 |
| ID-84 | A8-6 | A9-2 |
| ID-85 | A8-4 | A9-35 |
| ID-86 | A8-21 | A9-2 |
| ID-87 | A8-4 | A9-36 |
| ID-88 | A8-4 | A9-37 |
| ID-89 | A8-4 | A9-38 |
| ID-90 | A8-33 | A9-46 |
| ID-91 | A8-6 | A9-7 |
| ID-92 | A8-6 | A9-5 |
| ID-93 | A8-4 | A9-39 |
| ID-94 | A8-5 | A9-40 |
| ID-95 | A8-22 | A9-2 |
| ID-96 | A8-23 | A9-2 |
| ID-97 | A8-2 | A9-41 |

TABLE 9-continued

| Compound ID | A8 | A9 |
|---|---|---|
| ID-98 | A8-2 | A9-4 |
| ID-99 | A8-24 | A9-5 |
| ID-100 | A8-2 | A9-42 |
| ID-101 | A8-2 | A9-43 |
| ID-102 | A8-25 | A9-6 |
| ID-103 | A8-26 | A9-42 |
| ID-104 | A8-27 | A9-2 |
| ID-105 | A8-35 | A9-46 |
| ID-106 | A8-36 | A9-46 |
| ID-107 | A8-37 | A9-46 |

Example 1: Synthesis of ID-1

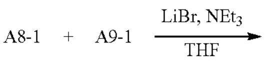

-continued

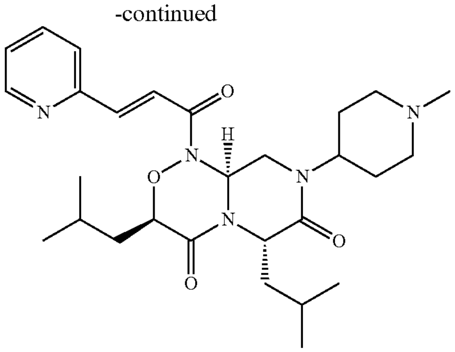

ID-1

To a mixture of A8-1 (1.6 g), A9-1 (1.2 g) and lithium bromide (0.75 g) in THE (50 mL) was added triethylamine (1.2 g) slowly. After stirring for 2 hours at room temperature, the mixture was added 10 mL of water and 0.15 L of ethyl acetate. The organic layer was separated, washed with 30 mL of brine, dried over $Na_2SO_4$ and concentrated in vacuo. The residue was purified by column chromatography (NH-$SiO_2$, n-Hexane:AcOEt=80:20-20:80, gradient) to give ID-1 (1.3 g) as a white solid.

Figure 2:
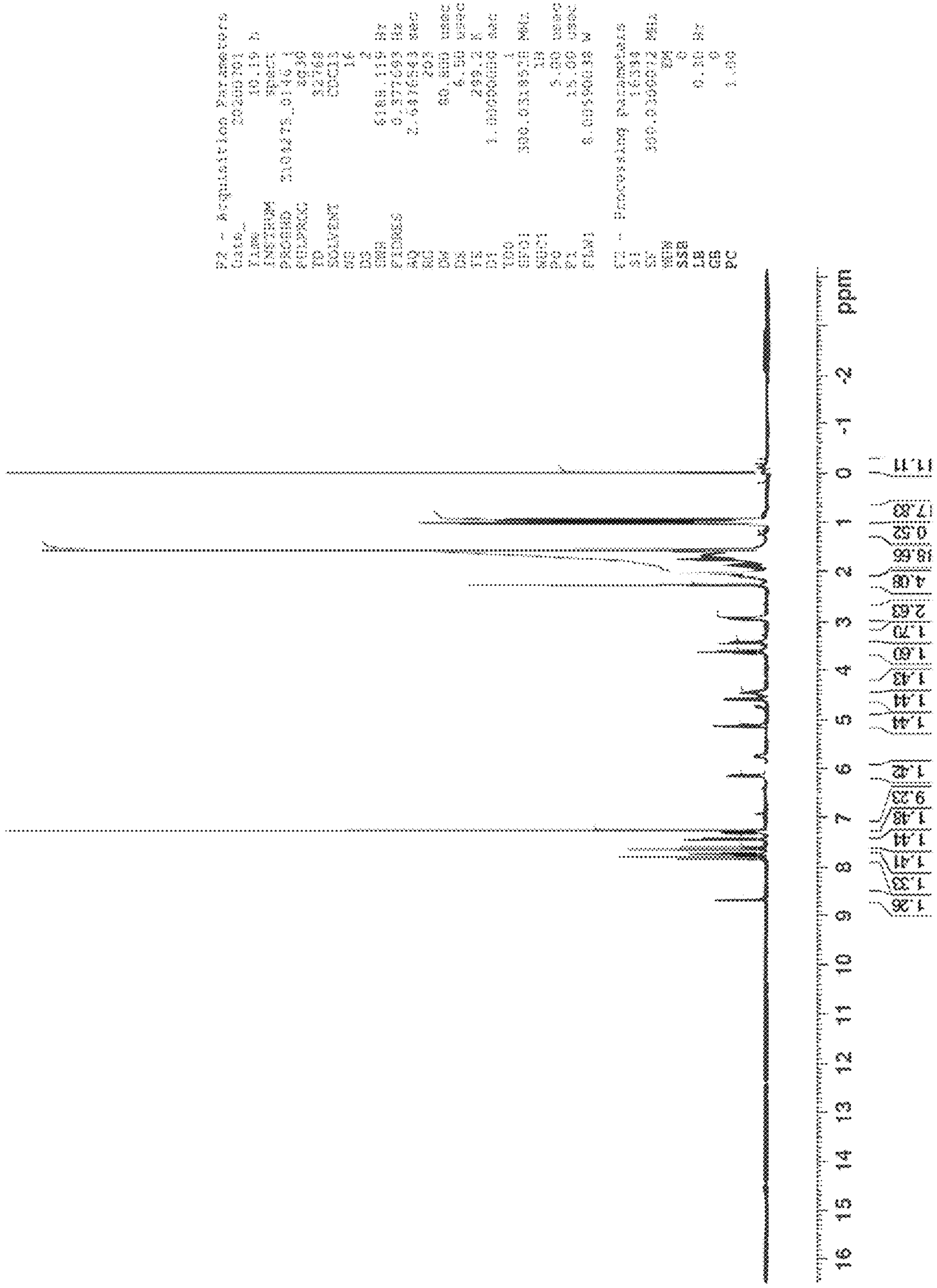
FIG. 2 shows a $^1$H NMR (300 MHz, $CDCl_3$) data of ID-1.

$^1H$ NMR (300 MHz, $CDCl_3$) data of ID-1 is shown in FIG. 2.

Example 2: Synthesis of ID-6

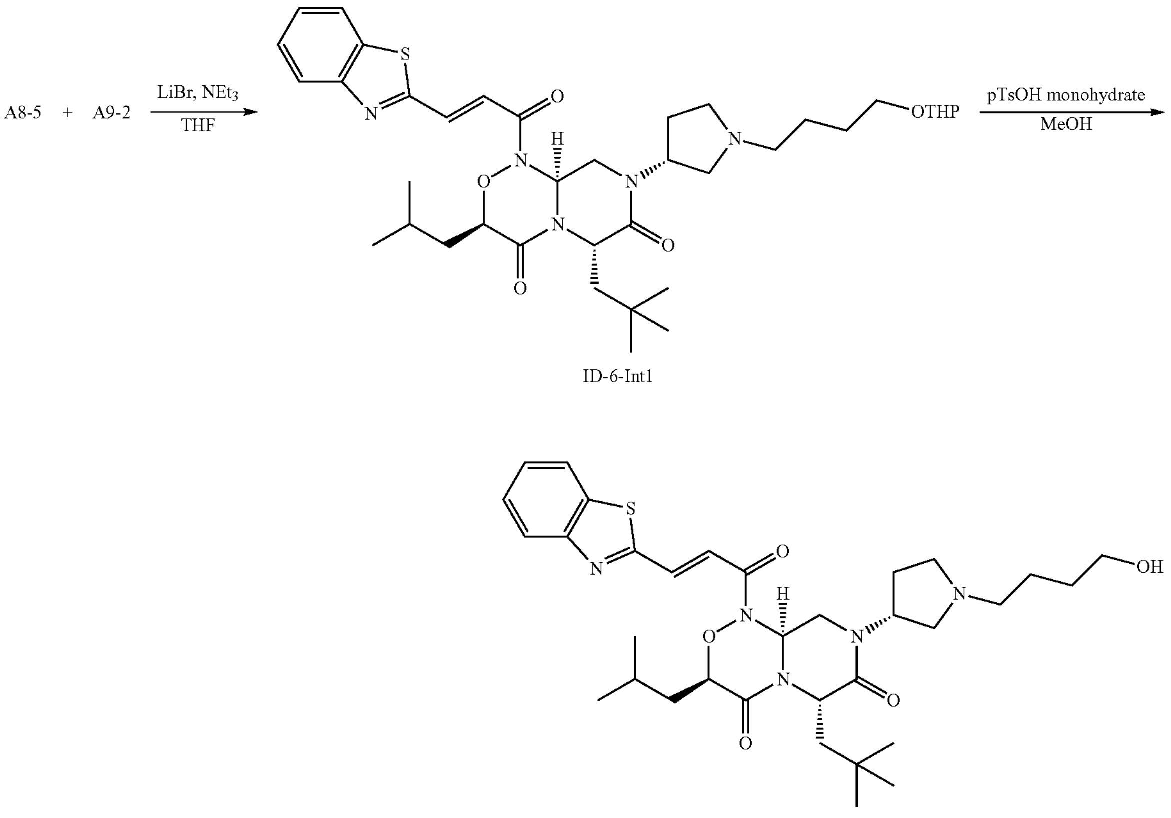

ID-6-Int1

ID-6

Ex2-1) Synthesis of ID-6-Int1

To a mixture of A8-5 (0.50 g), A9-2 (0.14 g) and lithium bromide (0.12 g) in THF (7.0 mL) was added triethylamine (0.14 g). The mixture was stirred for 20 minutes at room temperature. The reaction mixture was diluted with AcOEt and washed with saturated aqueous sodium bicarbonate solution and then brine. The organic phase was dried over $Na_2SO_4$ and concentrated in vacuo. The obtained residue was purified by column chromatography ($NHSiO_2$, n-hexane:AcOEt=50:50-0:100, gradient) to give ID-6-Int1 (0.28 g) as yellow amorphous.

LCMS (method A): m/z=710.4$[M+H]^+$.

Ex2-2) Synthesis of ID-6

A mixture of ID-6-Int1 (0.28 g) and p-TsOH monohydrate (0.15 g) in MeOH (7 mL) was stirred for 45 minutes at room temperature. The reaction mixture was concentrated in vacuo. The obtained residue was diluted with AcOEt and washed with saturated aqueous sodium bicarbonate solution and then brine. The organic phase was dried over $Na_2SO_4$, concentrated in vacuo and purified by prep-HPLC (condition (AcOH): B=30 to 80%). The collected fraction was concentrated in vacuo to give ID-6 (0.19 g) as a pale yellow amorphous powder.

Figure 3:
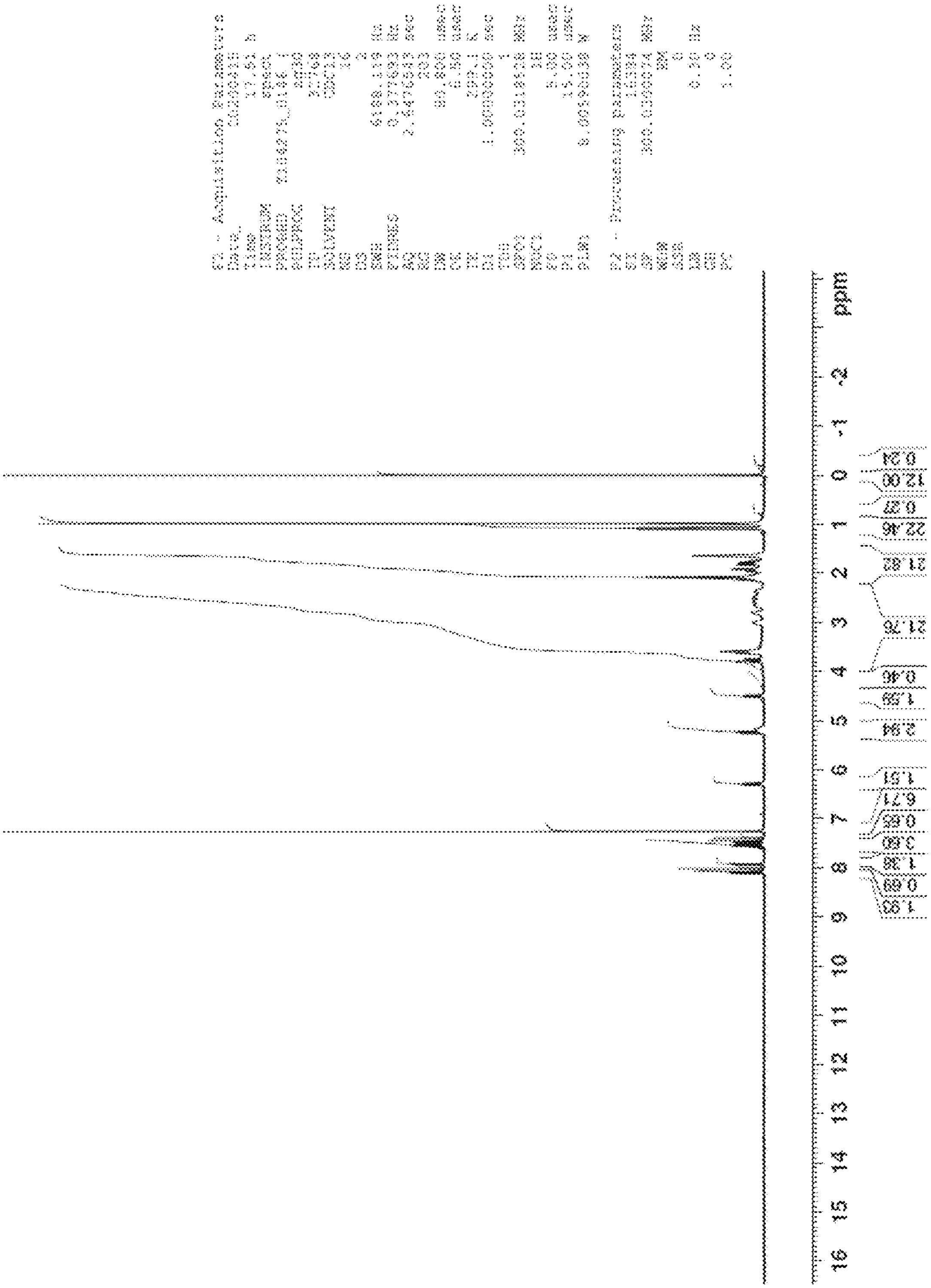
FIG. 3 shows a $^1$H NMR (300 MHz, $CDCl_3$) data of ID-6.

$^1H$ NMR (300 MHz, $CDCl_3$) data of ID-6 is shown in FIG. 3.

Example 3: Synthesis of ID-11

Ex3-1) Synthesis of ID-11-Int1

To a mixture of A8-5 (73 mg), A9-5 (40 mg) and lithium bromide (18 mg) in THE (2 mL) was added triethylamine (21 mg). The mixture was stirred for 30 minutes at room temperature. The reaction mixture was diluted with AcOEt and washed with saturated aqueous sodium bicarbonate solution and then brine. The organic phase was dried over $Na_2SO_4$ and concentrated in vacuo. The residue was purified by column chromatography ($NHSiO_2$, n-Hexane: AcOEt=50:50-0:100, gradient) to give ID-11-Int1 (55 mg) as yellow amorphous.

LCMS (method A): m/z=756.4$[M+H]^+$.

Ex3-2) Synthesis of ID-11 mixture of ID-11-Int1 (55 mg) and p-TsOH monohydrate (28 mg) in MeOH (2 mL) was stirred for 45 minutes at room temperature. The reaction mixture was concentrated in vacuo, diluted with AcOEt and washed with saturated aqueous sodium bicarbonate solution and then brine. The organic phase was dried over $Na_2SO_4$ and concentrated in vacuo. The residue was purified by prep-HPLC (condition (AcOH): B=30 to 80%). The collected fractions were combined and concentrated in vacuo. The aqueous solution was freeze-dried to give ID-11 (30 mg) as a white powder.

Figure 4:
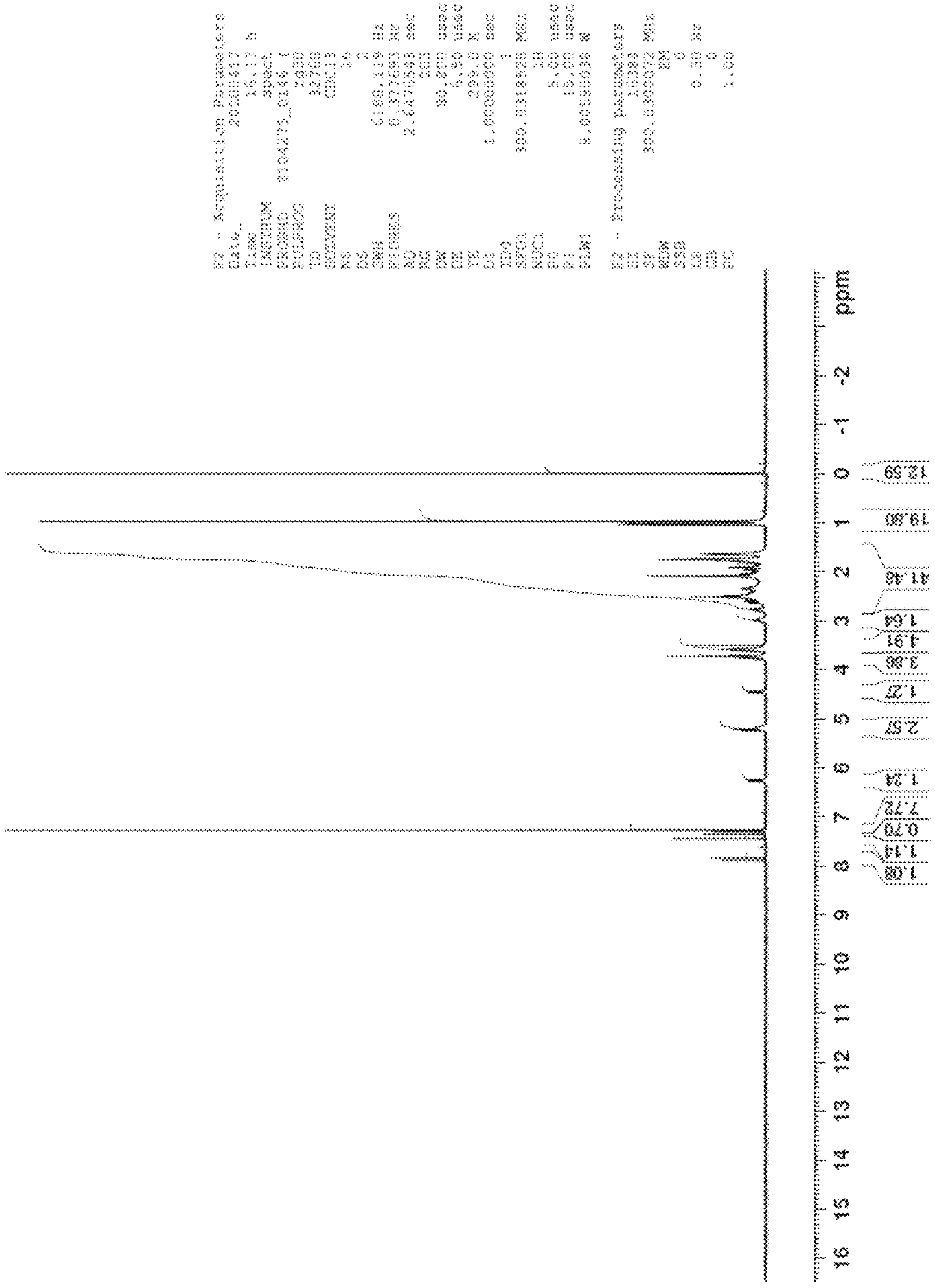
FIG. 4 shows a $^1$H NMR (300 MHz, $CDCl_3$) data of ID-11.

$^1H$ NMR (300 MHz, $CDCl_3$) data of ID-11 is shown in FIG. 4.

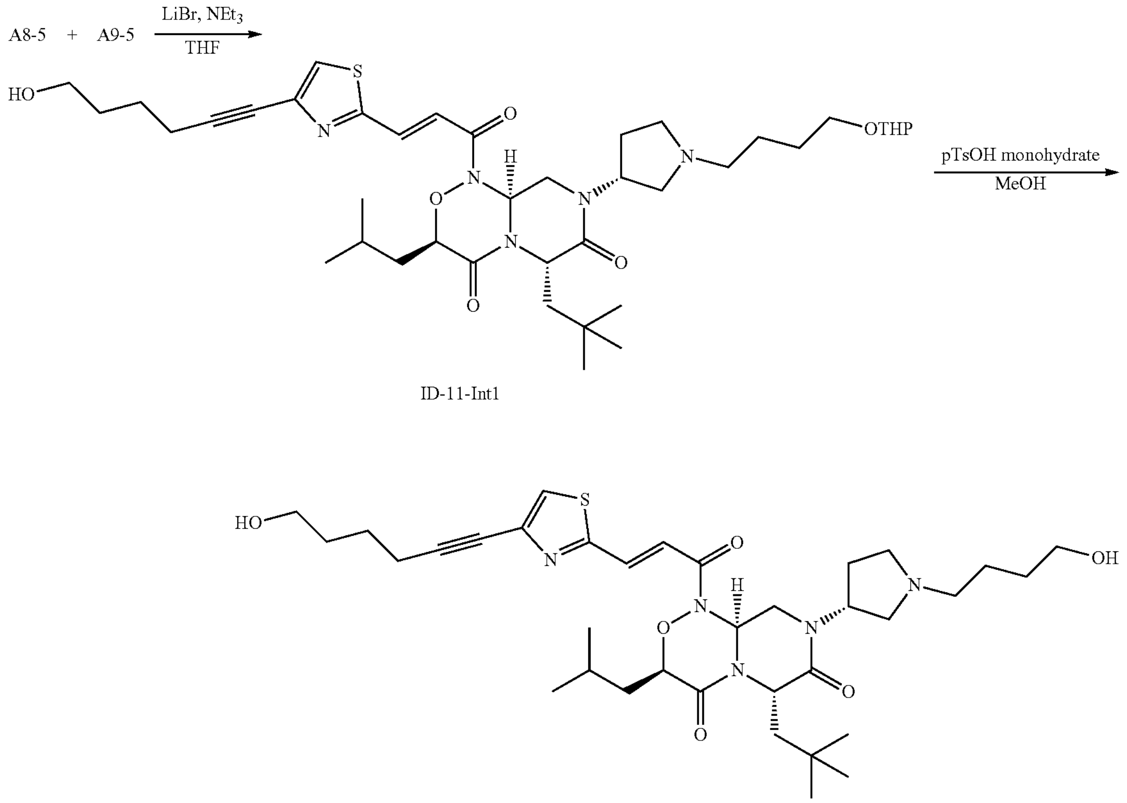

ID-11-Int1

ID-11

Example 4: Synthesis of ID-42

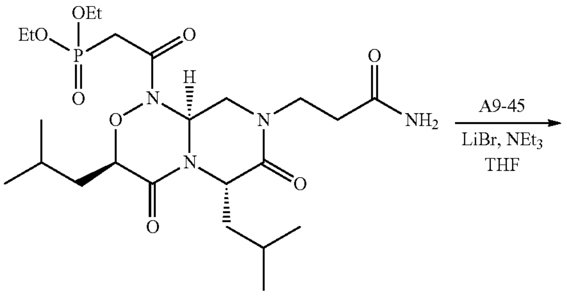

A8-7

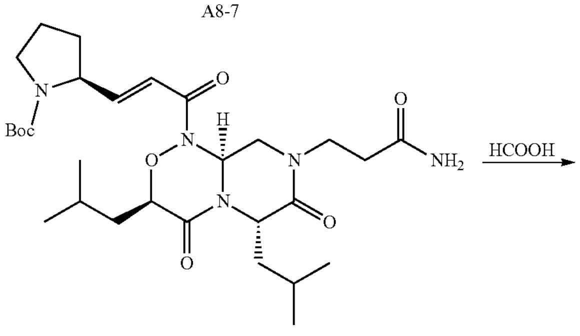

ID-42-Int1

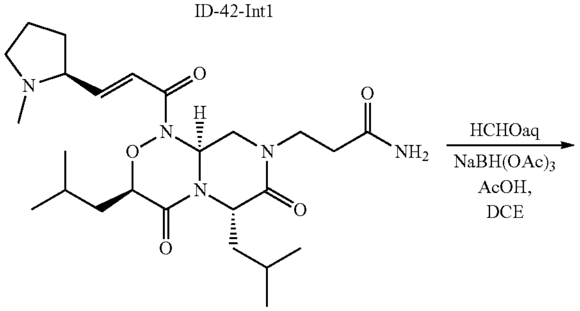

ID-42-Int2

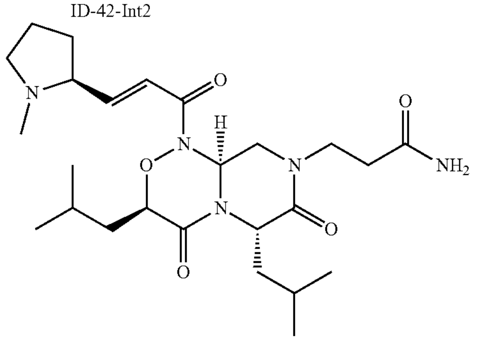

ID-42

Ex4-1) Synthesis of ID-42-Int1

To a solution of A8-7 (80 mg), LiBr (13 mg), and A9-45 (56 μL) in THF (1.5 mL) was added $Et_3N$ (42 μL). After stirring for 18 hours, brine (1.5 mL) and water (3 mL) were added. The mixture was extracted by AcOEt (5 mL) three times. The combined organic layer was washed with brine (3 mL), dried over $Na_2SO_4$, concentrated in vacuo, and purified by column chromatography ($SiO_2$, AcOEt:MeOH=100:0-90:10, gradient) to give ID-42-Int1 (38 mg) as light yellow syrup.

LCMS (method A): m/z=478.4[M-Boc+H]$^+$.

Ex4-2) Synthesis of ID-42-Int2

To a flask charged with ID-42-Int1 (38 mg) was added formic acid (2.0 mL) and the mixture was allowed to stand still. After 3 hours, the mixture was concentrated in vacuo to give ID-42-Int2 as light yellow syrup, which was used for next step without further purification.

LCMS (method A): m/z=478.4[M+H]$^+$.

Ex4-3) Synthesis of ID-42

To a solution of ID-42-Int2 (15 mg), AcOH (20 μL), aqueous HCHO solution (37%, 7.4 μL) in DCE (2.0 mL) was added $NaBH(OAc)_3$ (11 mg). After stirring for 2 hours, 1 mol/L aqueous sodium hydroxide solution (1.0 mL) was added. The mixture was extracted by $CHCl_3$ (2 mL) three times. The combined organic layer was washed with brine (1 mL), dried over $Na_2SO_4$, concentrated in vacuo, and purified by preparative HPLC (Column: C30-UG-5, MeCN/0.1% solution of AcOH=10/90-60/40) to give ID-42 (5.0 mg) as white solid.

LCMS (method A): m/z=492.4[M+H]$^+$.

The Compound ID-43 was synthesized by a synthetic method similar to that of ID-42.

The compounds listed in Table 10 were synthesized according to the below method or a known method using the Intermediates A6 and A10 shown in Table 10

TABLE 10

| Compound ID | A6 | A10 |
|---|---|---|
| ID-15 | A6-1 | A10-1 |
| ID-38 | A6-2 | A10-2 |
| ID-39 | A6-2 | A10-3 |

Example 5: Synthesis of ID-38

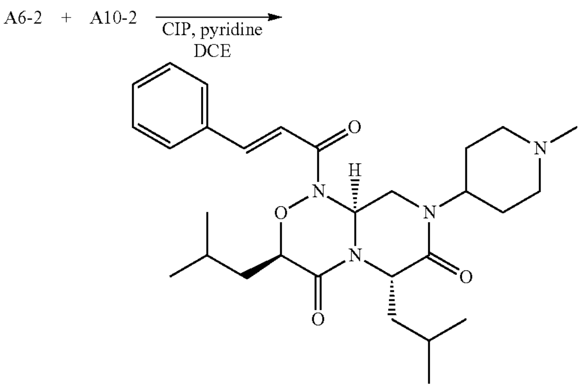

ID-38

Ex5-1) Synthesis of ID-38

To a solution of A6-2 (12 mg), A10-2 (6.8 mg), and pyridine (12 μL) in DCE (1.0 mL) was added CIP (26 mg). After stirring for 2 days, saturated aqueous sodium bicarbonate solution (3 mL) was added. The mixture was extracted by $CHCl_3$ (10 mL) three times. The combined organic layer was washed with brine (2 mL), dried over $Na_2SO_4$, concentrated in vacuo, and purified by preparative HPLC (Column: C30-UG-5, MeCN/0.1% solution of AcOH=20/80-70/30) to give ID-38 (9.8 mg) as white solid.

LCMS (method A): m/z=511.4[M+H]$^+$.

Compound ID-16 was synthesized according to the below methods.

Example 6: Synthesis of ID-16

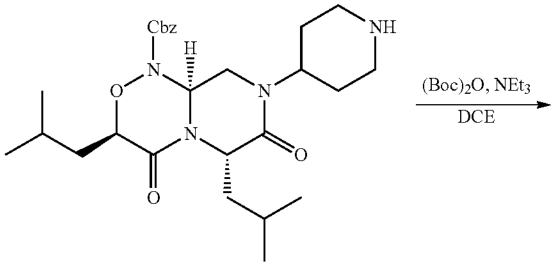

B5-1

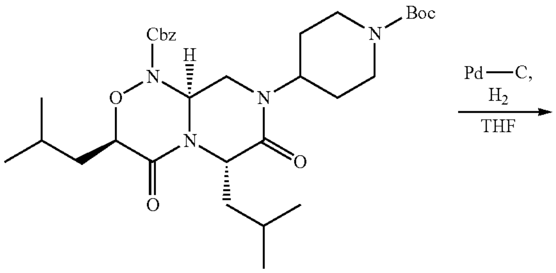

ID-16-Int1

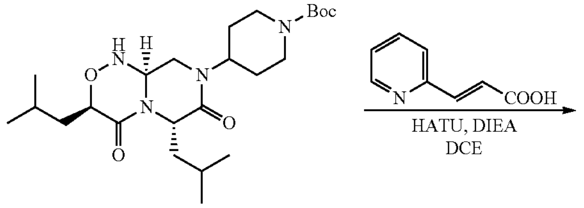

ID-16-Int2

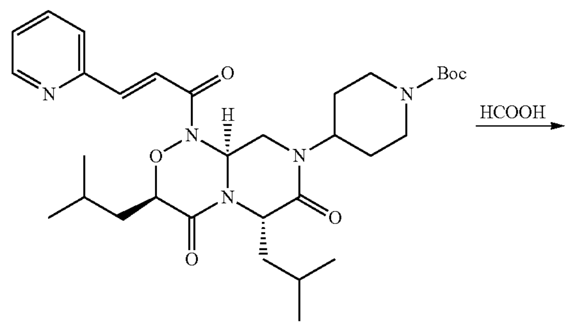

ID-16-Int3

-continued

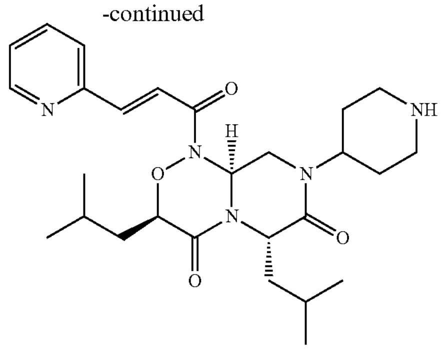

ID-16

Ex6-1) Synthesis of ID-16-Int1

A mixture of B5-1 (0.34 g), TEA (0.18 mL), and $(Boc)_2O$ (0.28 g) in DCE (10 mL) was stirred at room temperature for 16 hours. The mixture was concentrated in vacuo. The residue was purified by column chromatography ($SiO_2$, n-hexane:AcOEt=90:10-40:60, gradient) to give ID-16-Int1 (0.29 g) as colorless oil.

Ex6-2) Synthesis of ID-16-Int2

A mixture of ID-16-Int1 (0.29 g) and 10% Pd/C (0.10 g) in THF (10 mL) was stirred at room temperature for 1 hour under $H_2$ atmosphere. The mixture was filtered, and the filtrate was concentrated in vacuo to give ID-16-Int2 (0.22 g) as a white solid.

LCMS (method C): m/z=467.1[M+H]$^+$.

Ex6-3) Synthesis of ID-16-Int3

A mixture of ID-16-Int2 (0.10 g), (2E)-3-(2-Pyridinyl)-2-propenoic acid (75 mg), DIEA (0.24 mL), and HATU (0.27 g) in DCE (6.0 mL) was stirred at room temperature for 41 hours. The mixture was added DIEA (0.24 mL) and HATU (0.27 g). After stirring for 24 hours, the mixture was added DIEA (0.12 mL), and HATU (0.13 g). After stirring for 3 days, the mixture was added 25% ammonia aqueous solution (0.20 mL) and water (10 mL). The mixture was extracted with $CHCl_3$ (30 mL). The organic phase was washed with sodium bicarbonate aqueous solution (10 mL), then brine (10 mL). The organic phase was dried over $Na_2SO_4$ and concentrated in vacuo. The residue was purified by preparative HPLC (Column: C30-UG-5, MeCN—H2O w/0.1% AcOH=50 to 100%). The collected fractions were combined and concentrated in vacuo. The aqueous solution was freeze-dried to give ID-16-Int3 (82 mg)

Ex6-4) Synthesis of ID-16

A mixture of ID-16-Int3 (25 mg) and formic acid (2.0 mL) was stood at room temperature for 3 hours. The mixture was azeotroped with $CH_2Cl_2$ three times. The residue was purified by preparative HPLC (Column: C30-UG-5, MeCN—$H_2O$ with 0.1% AcOH=20 to 70%). The collected fractions were combined and concentrated in vacuo. The aqueous solution was freeze-dried to give ID-16 (15 mg) as a white solid.

LCMS (method C): m/z=498.1[M+H]$^+$.

Compound ID-18 was synthesized according to the below methods.

Example 7: Synthesis of ID-18

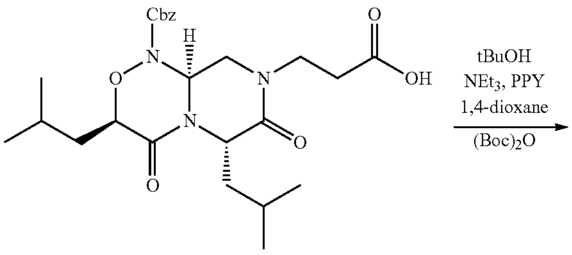

B5-25

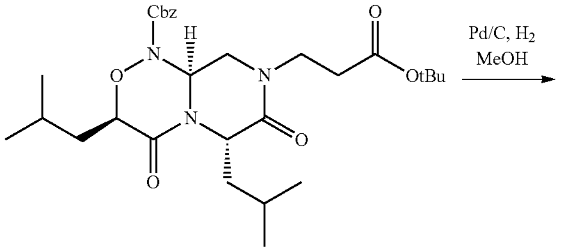

ID-18-Int1

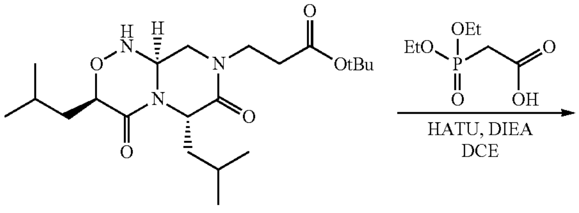

ID-18-Int2

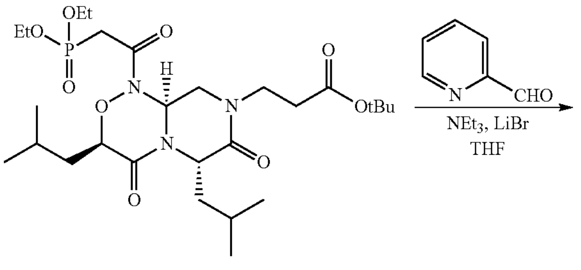

ID-18-Int3

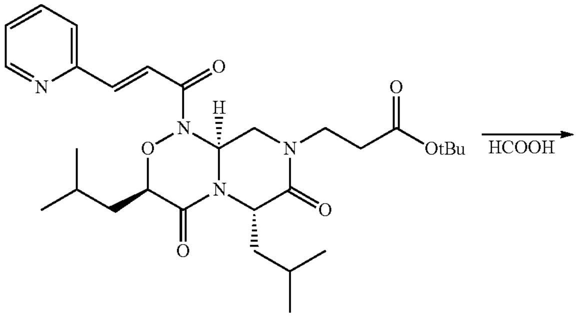

ID-18-Int4

-continued

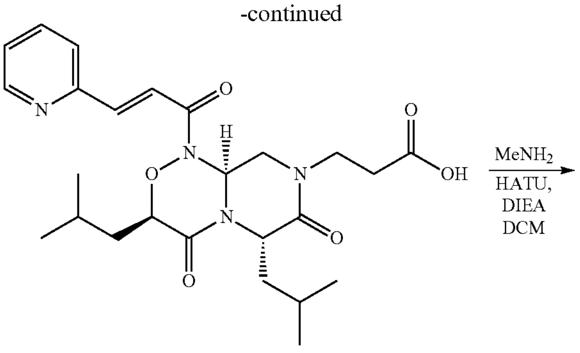

ID-18-Int5

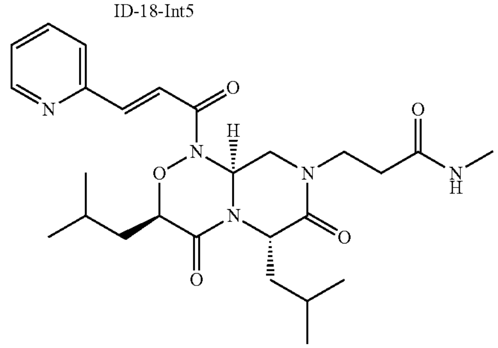

ID-18

Ex7-1) Synthesis of ID-18-Int1

To a solution of B5-25 (16 g) in tert-butanol (160 mL) was added 1,4-dioxane (24 mL), TEA (48 mL) and catalytic amount of 4-Pyrrolidinopyridine (PPY), and stirred the reaction and cooled to −20° C., then 48 mL of molten $(Boc)_2O$ was added to the above mixture. After 10 minutes, the mixture solution was warmed to room temperature and stirred for overnight. The organic layer was washed with 2 mol/L aqueous HCl solution and brine. The organic layer was dried over $Na_2SO_4$, then filtered and concentrated in vacuo and was further purified by silica gel chromatography to give ID-18-Int1 (15 g) as colorless oil.

Ex7-2) Synthesis of ID-18-Int2

To a stirred solution of ID-18-Int1 (13 g) in MeOH (300 mL) was added 20% Pd/C (2.5 g) under $H_2$ atmosphere at room temperature. The mixture was stirred overnight at room temperature, then filtrated and washed with methanol. The filtrate was concentrated in vacuum to give a crude product, which was purified by column chromatography to afford ID-18-Int2 (8.5 g) as white solid.

LCMS (method A): m/z=356.3[M-tBu+H]$^+$.

Ex7-3) Synthesis of ID-18-Int3

To a solution of ID-18-Int2 (0.25 g), diethylphosphonoacetic acid (0.16 mL), and DIEA (0.63 mL) in DCE (10 mL) was added HATU (0.69 g). After stirring for 1 hour, aqueous ammonia solution (25%, 1.0 mL) and water (20 mL) were added. The mixture was diluted with $CHCl_3$ (30 mL), and the organic layer was washed with saturated aqueous sodium bicarbonate solution (20 mL) and brine (20 mL), dried over $Na_2SO_4$, concentrated in vacuo, and purified by column chromatography ($SiO_2$, AcOEt:MeOH=100:0-90:10, gradient) to give ID-18-Int3 (357 mg) as colorless syrup.

LCMS (method C): m/z=590.1[M+H]$^+$.

Ex7-4) Synthesis of ID-18-Int4

To a solution of ID-18-Int3 (96 mg), LiBr (14 mg), and 2-pyridinecarboxaldehyde (17 μL) in THE (3 mL) was added triethylamine (27 μL). After stirring for 1 hour, water (10 mL) was added. The mixture was extracted by AcOEt (10 mL) three times. The combined organic layer was washed with water (10 mL) and brine (10 mL), dried over $Na_2SO_4$, concentrated in vacuo, and purified by column chromatography ($SiO_2$, n-hexane:AcOEt=90:10-40:60, gradient) to give ID-18-Int4 (60 mg) as light yellow syrup.

Ex7-5) Synthesis of ID-18-Int5

To a flask charged with ID-18-Int4 (60 mg) was added formic acid (3 mL) and the mixture was allowed to stand still. After 6 hours, the mixture was concentrated in vacuo to give ID-18-Int5 as light yellow syrup, which was used in the next reaction without any purification.

LCMS (method C): m/z=487.0[M+H]$^+$.

Ex7-6) Synthesis of ID-18

To a solution of ID-18-Int5 (35 mg), methylamine (2 mol/L in THF, 64 μL), and DIEA (44 μL) in $CH_2Cl_2$ (2 mL) was added HATU (48 mg). After stirring for 1 hour, the mixture was diluted with $CHCl_3$ (30 mL), washed with 1 mol/L aqueous HCl solution (10 mL) saturated sodium aqueous sodium bicarbonate solution (10 mL) and brine (10 mL), dried over $Na_2SO_4$, concentrated in vacuo, and purified by preparative HPLC (Column: C30-UG-5, MeCN/0.1% solution of AcOH=30/70-80/20) to give ID-18 (21.0 mg) as white solid.

LCMS (method C): m/z=500.1[M+H]$^+$.

The Compounds ID-21, 27, 28 were synthesized by using the amine reagents listed in Table 11 in the reaction step Ex7-6).

TABLE 11

| ID | Reagents |
|---|---|
| ID-21 | 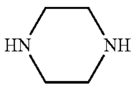 |
| ID-27 | 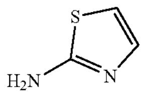 |
| ID-28 | 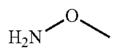 |

Compound ID-35 was synthesized according to the below method.

Example 8: Synthesis of ID-35

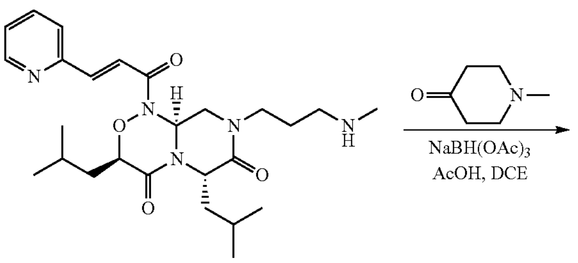

ID-19

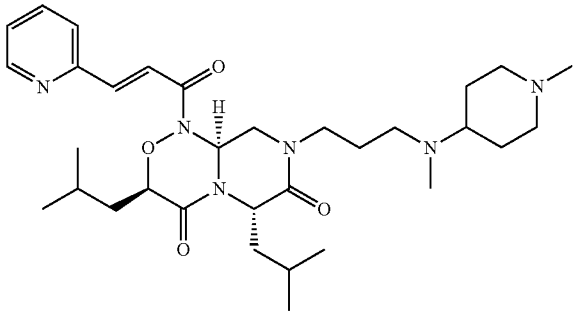

ID-35

Ex8-1) Synthesis of ID-35

To a solution of ID-19 (27 mg), 1-methyl-4-piperidone (26 μL), AcOH (9.4 μL) in DCE (2 mL) was added NaBH$(OAc)_3$ (47 mg). After stirring for 2 hours, saturated aqueous sodium bicarbonate solution (3 mL) was added. The mixture was extracted by $CHCl_3$ (3 mL) twice. The combined organic layer was washed with brine (3 mL), dried over $Na_2SO_4$, concentrated in vacuo, and purified by preparative HPLC (Column: C30-UG-5, MeCN/0.1% solution of AcOH=0/100-50/50) to give ID-35 (17 mg) as white solid.

LCMS (method C): m/z=569.1[M+H]$^+$.

Compound ID-69 was synthesized according to the below method.

Example 9: Synthesis of ID-69

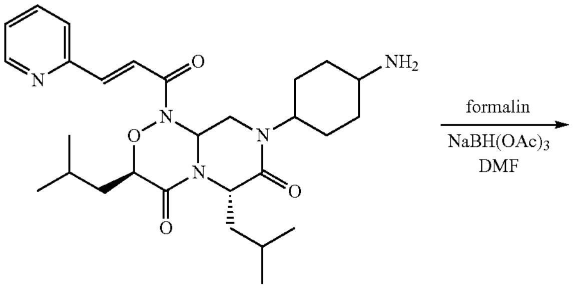

ID-68

-continued

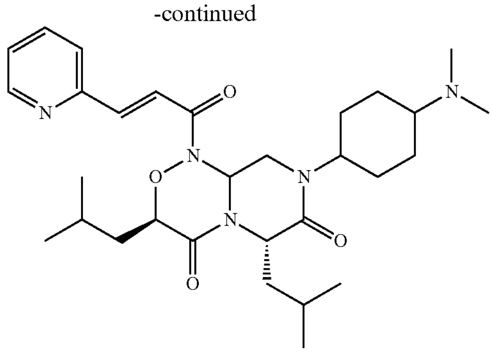

ID-69

Ex9-1) Synthesis of ID-69

To a solution of ID-68 (59 mg) in DMF (4 mL) was added formaldehyde (37%) (34 μL), and sodium triacetoxyborohydride (61 mg). After stirring at room temperature for 1 hour, 1 mol/L aqueous sodium hydroxide solution (10 mL) and brine (5 mL) were added and the mixture was extracted with AcOEt (30 mL). The organic phase was washed with brine (10 mL) twice, dried over $Na_2SO_4$, and concentrated in vacuo. The residue was purified by preparative HPLC (Column: C30-UG-5, MeCN—$H_2O$ with 0.1% AcOH=20 to 70%). The collected fractions were combined and concentrated in vacuo. The aqueous solution was freeze-dried to give ID-69 (32 mg) as a white powder.

LCMS (method A): m/z=540.4 $[M+H]^+$.

Compound ID-36 was synthesized according to the below method.

Example 10: Synthesis of ID-36

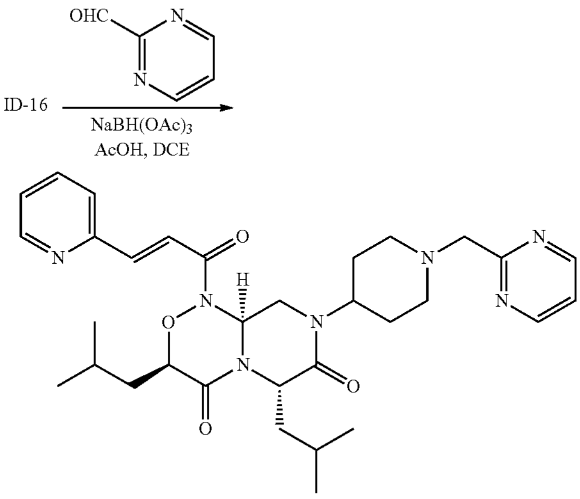

ID-36

Ex10-1) Synthesis of ID-36

To a stirred solution of ID-16 (35 mg) in DCE (2 mL) was added sodium triacetoxyborohydride (30 mg), 2-Pyrimidinecarboxaldehyde (38 mg) and AcOH (20 μL) at room temperature. After stirring for overnight at room temperature, 2 mol/L NaOH solution (10 mL) and chloroform (20 mL) were added. The organic layer was separated, then washed with 10 mL of water, dried over $Na_2SO_4$, concentrated in vacuo. The crude product was purified by prep-HPLC to give ID-36 (19 mg) as white solid.

LCMS (method A): m/z=590.4$[M+H]^+$.

The Compounds ID-40, 41, 62, and 63 were synthesized by using the reagents listed in Table 12 in the reaction step Ex10-1).

TABLE 12

| ID | Reagents |
| --- | --- |
| ID-40 | 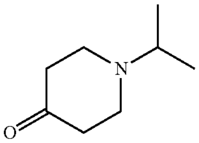 |
| ID-41 | 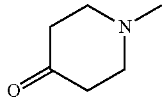 |
| ID-62 | 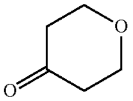 |
| ID-63 | 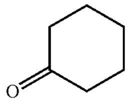 |

Compounds ID-45 and 50 were synthesized according to the below method.

Example 11: Synthesis of ID-45

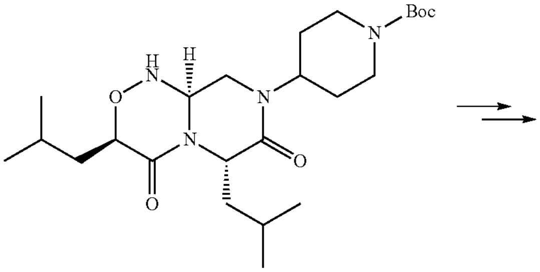

ID-16-Int2

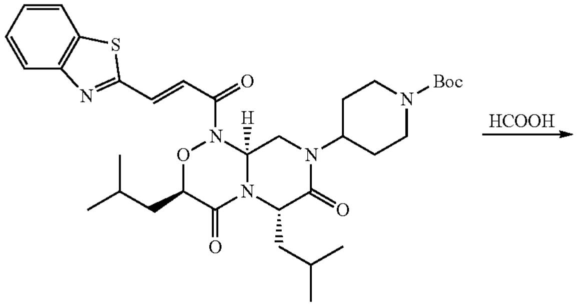

ID-45-Int1

-continued

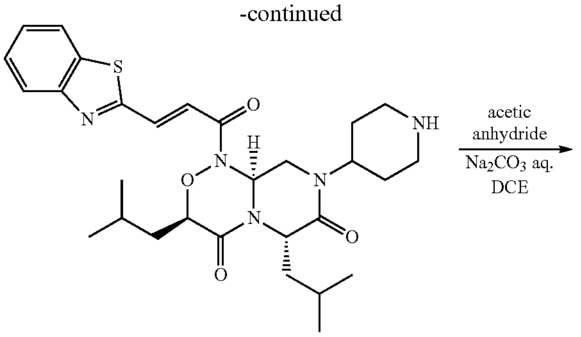

ID-45-Int2

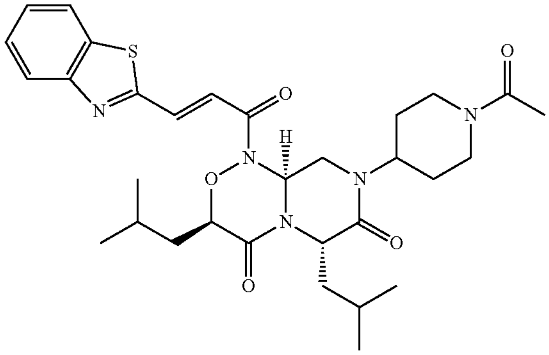

ID-45

Ex11-1) Synthesis of ID-45-Int1

From 0.88 g of ID-16-Int2, 0.13 g of ID-45-Int1 (yellow oil) was synthesized by similar methods to the reaction procedures 9-2) and Ex2-1).

LCMS (method A): m/z=554.4[M-Boc+H]$^+$, 676.4[M+Na]$^+$.

Ex11-2) Synthesis of ID-45-Int2

A mixture of ID-43-Int1 (0.13 g) and formic acid (2 mL) was stood at room temperature for overnight. The mixture was azeotroped with $CHCl_3$ three times to give crude ID-45-Int2 (0.13 g) as yellow oil, which was used in the next reaction without any purification.

LCMS (method A): m/z=554.4[M+H]$^+$.

Ex11-3) Synthesis of ID-45

A mixture of ID-45-Int2 (30 mg) and acetic anhydride (10 μL) in sodium carbonate solution (4 mL) and DCE (2 mL) was stirred at room temperature for 2 hours. After 25% ammonia aqueous solution (5 mL) and chloroform (20 mL) were added, the organic phase was extracted, dried over $Na_2SO_4$, and concentrated in vacuo. The obtained residue was purified by prep-HPLC to give ID-45 (22 mg) as white solid.

LCMS (method A): m/z=596.4[M+H]$^+$.

Example 12: Synthesis of ID-50

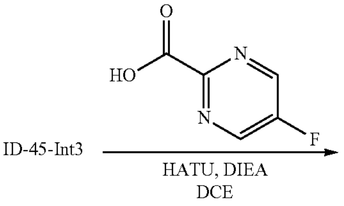

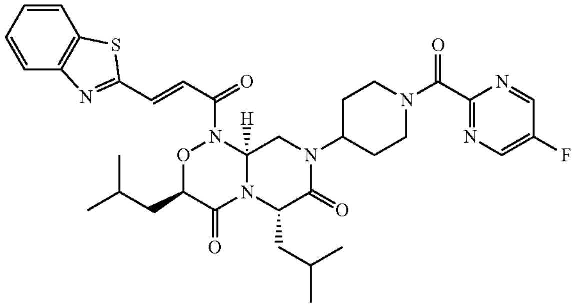

ID-50

Ex12-4) Synthesis of ID-50

To a solution of 5-fluoropyrimidine-2-carboxylic acid (29 mg) in DCE (1 mL) were added HATU (93 mg) and DIEA (32 mg). After stirred for 2 hours at room temperature, ID-45-Int3 (45 mg) in DCE (3 mL) was added, and the mixture was stirred for another 95 minutes. To the mixture were added 10 mL of 1 mol/L aqueous HCl solution and 20 ml of chloroform. The organic layer was separated, washed with 10 mL of sodium bicarbonate solution, dried over $Na_2SO_4$, and concentrated in vacuo. The obtained crude product was purified by prep-HPLC to give ID-50 (7.8 mg) as white solid.

LCMS (method A): m/z=678.3[M+H]$^+$.

Chemical structures and the LCMS measurement method and results of compounds ID-1 to ID-107 are shown in Table 13 (Table 13-1-Table 13-19).

TABLE 13-1
| Compound ID | Structure | MW | Mass | LCMS observed | LCMS method |
|---|---|---|---|---|---|
| ID-1 | 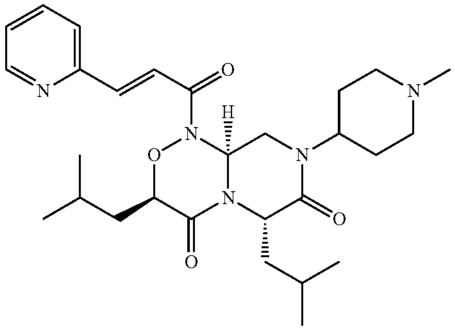 [SMILES: CC(C)C[C@H]1ON(C(=O)/C=C/c2ccccn2)[C@H]2CN(C3CCN(C)CC3)C(=O)[C@H](CC(C)C)N2C1=O] | 511.67 | 511.32 | 512.4 | A |
| ID-2 | 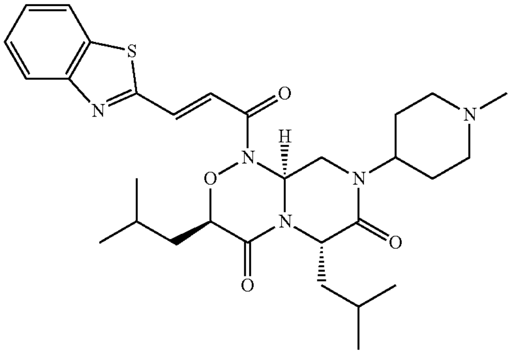 [SMILES: CC(C)C[C@H]1ON(C(=O)/C=C/c2nc3ccccc3s2)[C@H]2CN(C3CCN(C)CC3)C(=O)[C@H](CC(C)C)N2C1=O] | 567.75 | 567.29 | 568.4 | A |
| ID-3 | 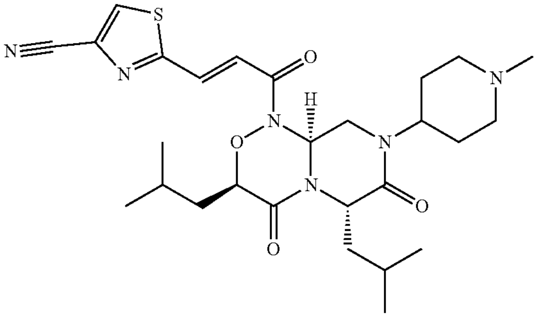 [SMILES: CC(C)C[C@H]1ON(C(=O)/C=C/c2nc(C#N)cs2)[C@H]2CN(C3CCN(C)CC3)C(=O)[C@H](CC(C)C)N2C1=O] | 542.70 | 542.27 | 543.4 | A |
| ID-4 | 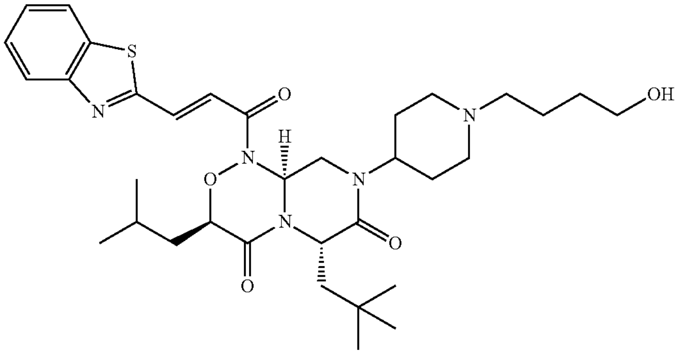 [SMILES: CC(C)C[C@H]1ON(C(=O)/C=C/c2nc3ccccc3s2)[C@H]2CN(C3CCN(CCCCO)CC3)C(=O)[C@H](CC(C)(C)C)N2C1=O] | 639.86 | 639.35 | 640.4 | A |

TABLE 13-1-continued
| Compound ID | Structure | MW | Mass | LCMS observed | LCMS method |
|---|---|---|---|---|---|
| ID-5 | 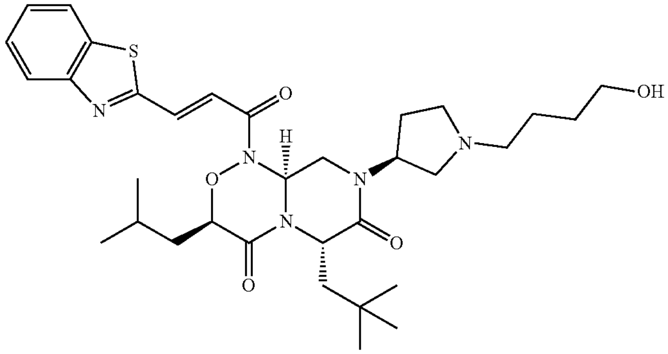 [SMILES: CC(C)C[C@H]1ON(C(=O)/C=C/c2nc3ccccc3s2)[C@H]2CN([C@H]3CCN(CCCCO)C3)C(=O)[C@H](CC(C)(C)C)N2C1=O] | 625.83 | 625.33 | 626.4 | A |
TABLE 13-2
| | | | | | |
|---|---|---|---|---|---|
| ID-6 | 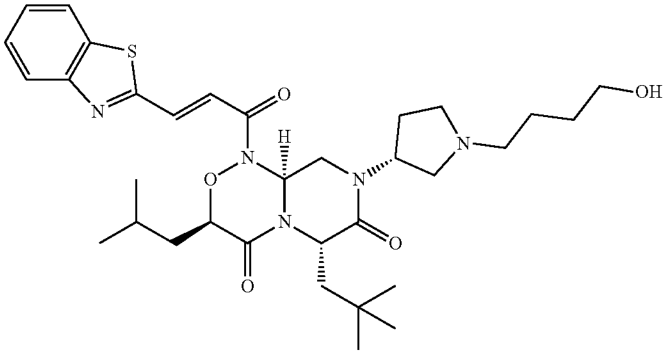 [SMILES: CC(C)C[C@H]1ON(C(=O)/C=C/c2nc3ccccc3s2)[C@H]2CN([C@@H]3CCN(CCCCO)C3)C(=O)[C@H](CC(C)(C)C)N2C1=O] | 625.83 | 625.33 | 626.3 | A |
| ID-7 | 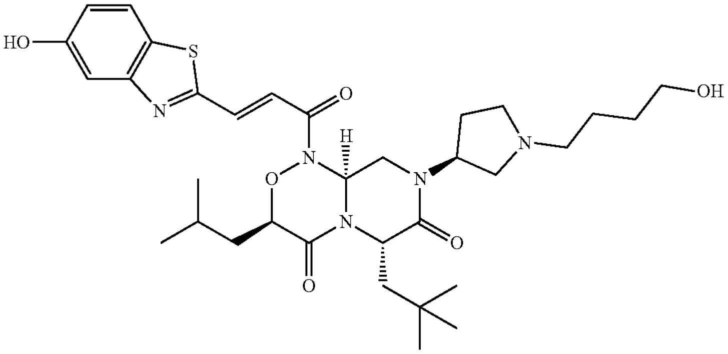 [SMILES: CC(C)C[C@H]1ON(C(=O)/C=C/c2nc3cc(O)ccc3s2)[C@H]2CN([C@H]3CCN(CCCCO)C3)C(=O)[C@H](CC(C)(C)C)N2C1=O] | 641.83 | 641.32 | 642.3 | A |
| ID-8 | 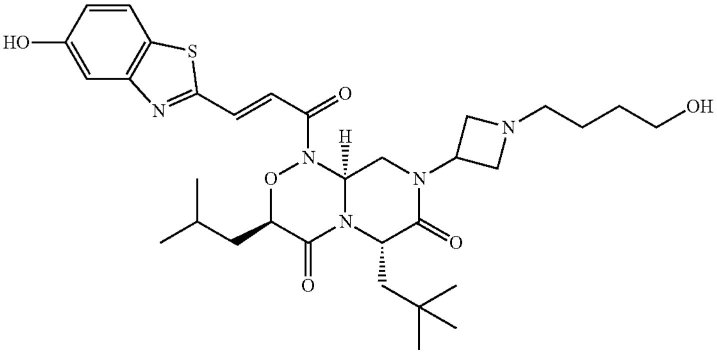 [SMILES: CC(C)C[C@H]1ON(C(=O)/C=C/c2nc3cc(O)ccc3s2)[C@H]2CN(C3CN(CCCCO)C3)C(=O)[C@H](CC(C)(C)C)N2C1=O] | 627.80 | 627.31 | 628.3 | B |

TABLE 13-2-continued
| | | | | | |
|---|---|---|---|---|---|
| ID-9 | 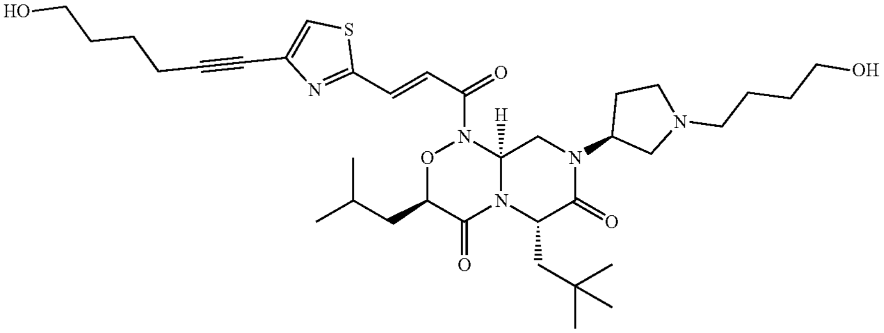 [SMILES: CC(C)C[C@H]1ON(C(=O)/C=C/c2nc(C#CCCCCO)cs2)[C@H]2CN([C@H]3CCN(CCCCO)C3)C(=O)[C@H](CC(C)(C)C)N2C1=O] | 671.90 | 671.37 | 672.3 | A |
| ID-10 | 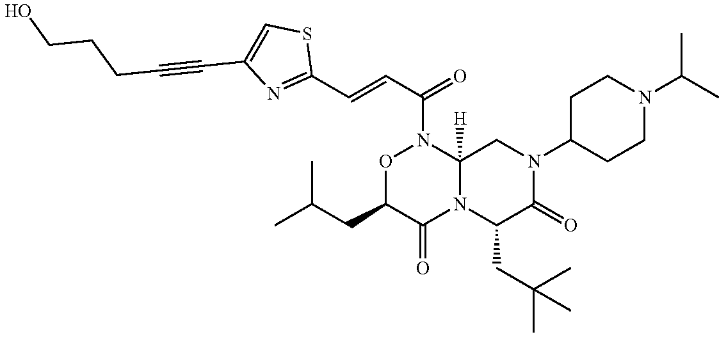 [SMILES: CC(C)C[C@H]1ON(C(=O)/C=C/c2nc(C#CCCCO)cs2)[C@H]2CN(C3CCN(C(C)C)CC3)C(=O)[C@H](CC(C)(C)C)N2C1=O] | 641.87 | 641.36 | 642.4 | A |
| ID-11 | 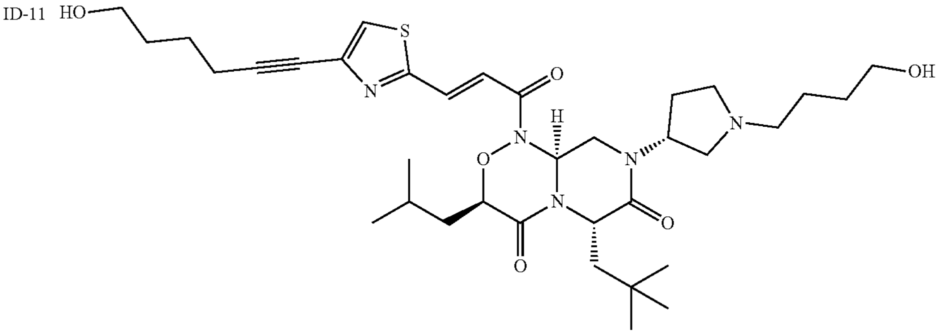 | 671.90 | 671.37 | 672.4 | A |
TABLE 13-3
| | | | | | |
|---|---|---|---|---|---|
| ID-12 | 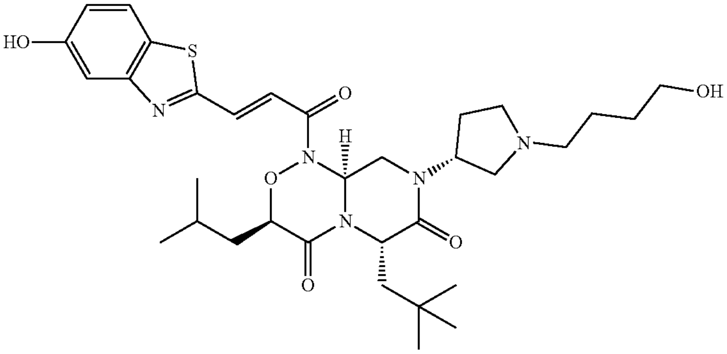 [SMILES: CC(C)C[C@H]1ON(C(=O)/C=C/c2nc3cc(O)ccc3s2)[C@H]2CN([C@@H]3CCN(CCCCO)C3)C(=O)[C@H](CC(C)(C)C)N2C1=O] | 641.83 | 641.32 | 642.3 | A |

TABLE 13-3-continued
| | | | | | |
|---|---|---|---|---|---|
| ID-13 | 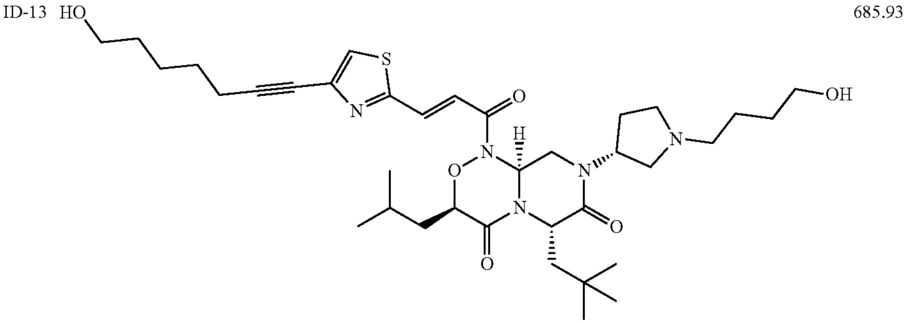 | 685.93 | 685.39 | 685.4 | A |
| ID-14 | 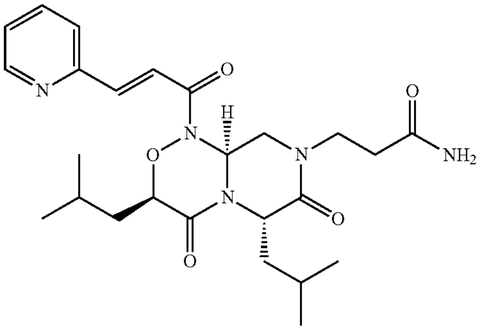 [SMILES: CC(C)C[C@H]1ON(C(=O)/C=C/c2ccccn2)[C@H]2CN(CCC(N)=O)C(=O)[C@H](CC(C)C)N2C1=O] | 485.59 | 485.26 | 486.3 | A |
| ID-15 | 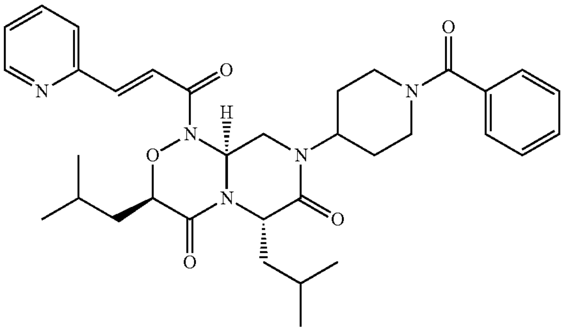 [SMILES: CC(C)C[C@H]1ON(C(=O)/C=C/c2ccccn2)[C@H]2CN(C3CCN(C(=O)c4ccccc4)CC3)C(=O)[C@H](CC(C)C)N2C1=O] | 601.75 | 601.33 | 602.4 | A |
| ID-16 | 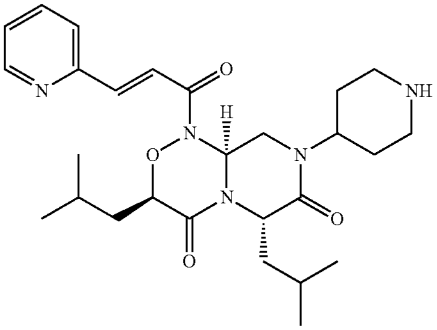 [SMILES: CC(C)C[C@H]1ON(C(=O)/C=C/c2ccccn2)[C@H]2CN(C3CCNCC3)C(=O)[C@H](CC(C)C)N2C1=O] | 497.64 | 497.30 | 498.3 | A |

TABLE 13-3-continued
| | | | | | |
|---|---|---|---|---|---|
| ID-17 | 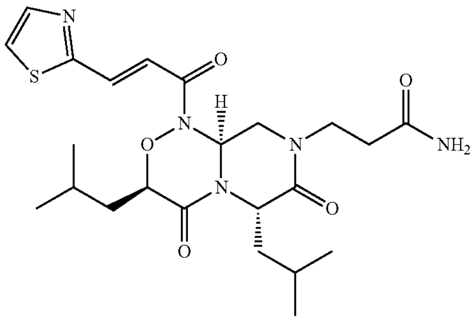 [SMILES: CC(C)C[C@H]1ON(C(=O)/C=C/c2nccs2)[C@H]2CN(CCC(N)=O)C(=O)[C@H](CC(C)C)N2C1=O] | 491.61 | 491.22 | 492.3 | A |
TABLE 13-4
| | | | | | |
|---|---|---|---|---|---|
| ID-18 | 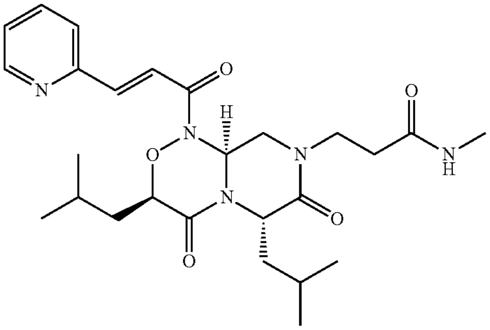 [SMILES: CNC(=O)CCN1C[C@@H]2N(C(=O)/C=C/c3ccccn3)O[C@H](CC(C)C)C(=O)N2[C@@H](CC(C)C)C1=O] | 499.61 | 499.28 | 500.3 | A |
| ID-19 | 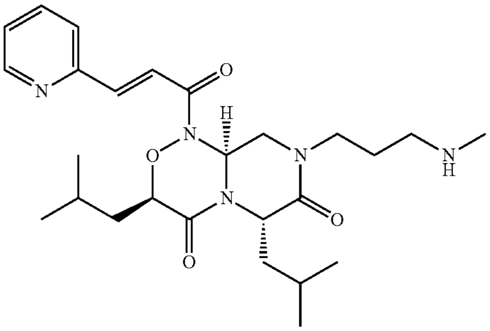 [SMILES: CNCCCN1C[C@@H]2N(C(=O)/C=C/c3ccccn3)O[C@H](CC(C)C)C(=O)N2[C@@H](CC(C)C)C1=O] | 471.65 | 471.32 | 472.3 | A |
| ID-20 | 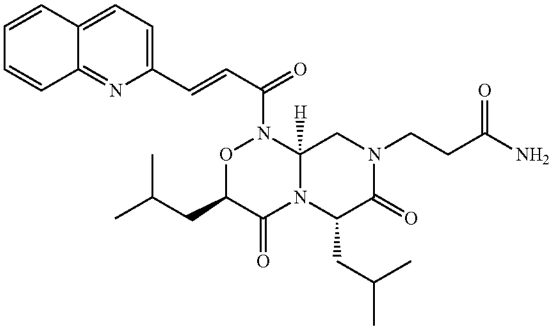 [SMILES: CC(C)C[C@H]1ON(C(=O)/C=C/c2ccc3ccccc3n2)[C@H]2CN(CCC(N)=O)C(=O)[C@H](CC(C)C)N2C1=O] | 535.65 | 535.28 | 536.3 | A |

TABLE 13-4-continued
| | | | | | |
|---|---|---|---|---|---|
| ID-21 | 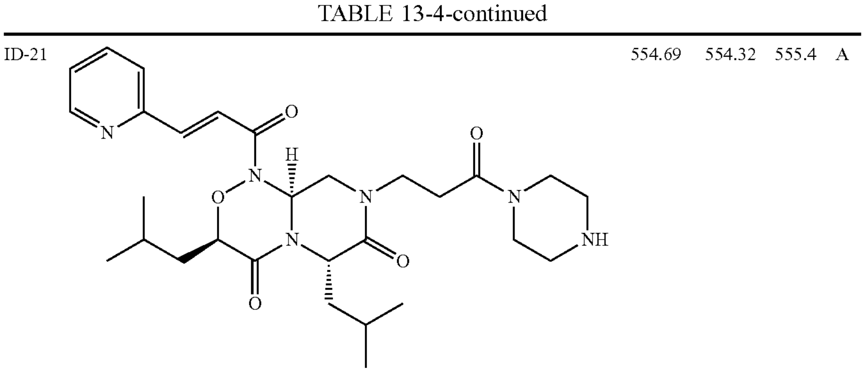 | 554.69 | 554.32 | 555.4 | A |
| ID-22 | 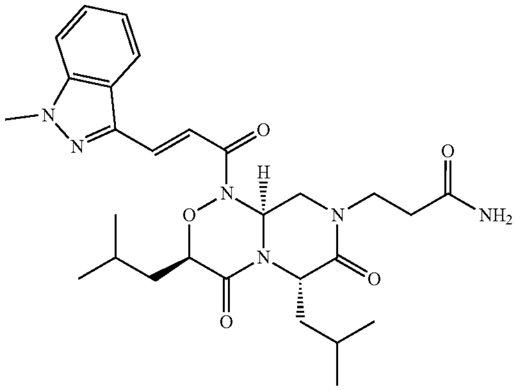 [SMILES: CC(C)C[C@H]1ON(C(=O)/C=C/c2nn(C)c3ccccc23)[C@H]2CN(CCC(N)=O)C(=O)[C@H](CC(C)C)N2C1=O] | 538.65 | 538.29 | 539.4 | A |
| ID-23 | 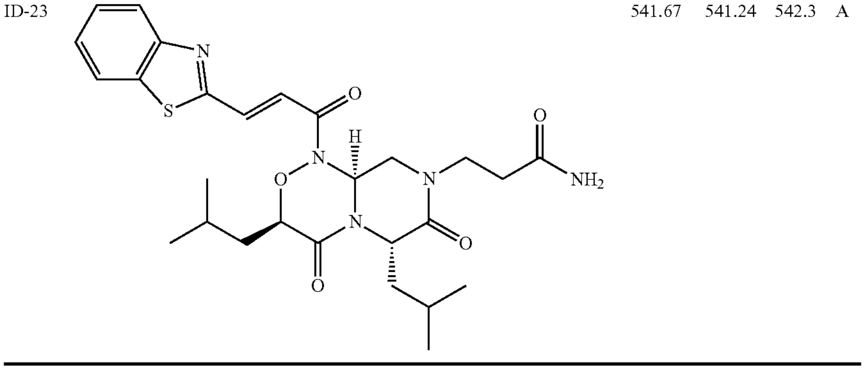 | 541.67 | 541.24 | 542.3 | A |
TABLE 13-5
| | | | | | |
|---|---|---|---|---|---|
| ID-24 | 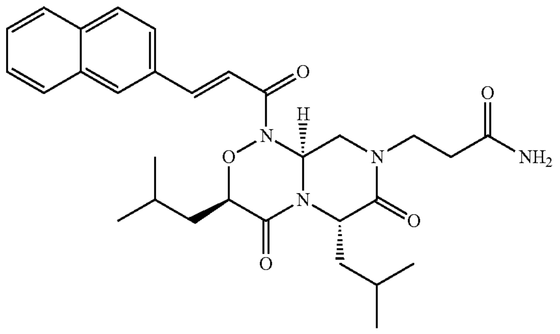 [SMILES: CC(C)C[C@H]1ON(C(=O)/C=C/c2ccc3ccccc3c2)[C@H]2CN(CCC(N)=O)C(=O)[C@H](CC(C)C)N2C1=O] | 534.66 | 534.28 | 535.3 | A |

TABLE 13-5-continued
| | | | | | |
|---|---|---|---|---|---|
| ID-25 | 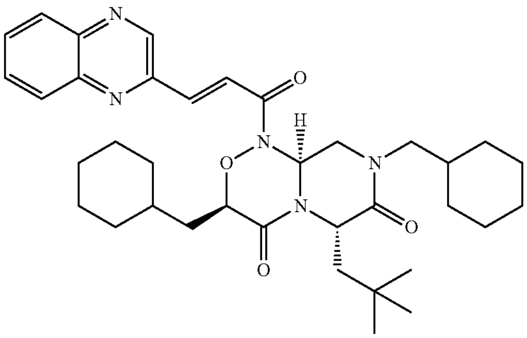 [SMILES: CC(C)(C)C[C@H]1C(=O)N(CC2CCCCC2)C[C@@H]2N(C(=O)/C=C/c3cnc4ccccc4n3)O[C@H](CC3CCCCC3)C(=O)N21] | 615.82 | 615.38 | 616.4 | A |
| ID-26 | 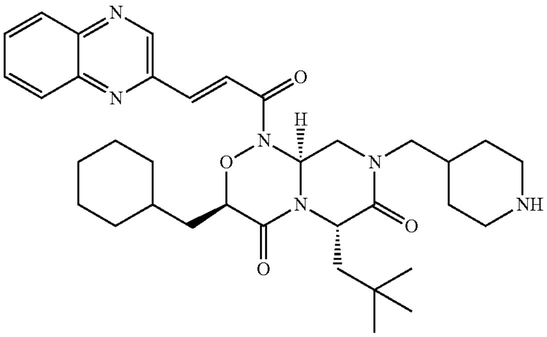 [SMILES: CC(C)(C)C[C@H]1C(=O)N(CC2CCNCC2)C[C@@H]2N(C(=O)/C=C/c3cnc4ccccc4n3)O[C@H](CC3CCCCC3)C(=O)N21] | 616.81 | 616.37 | 617.4 | A |
| ID-27 | 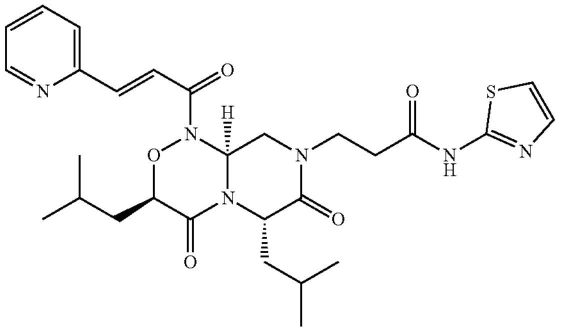 [SMILES: CC(C)C[C@H]1ON(C(=O)/C=C/c2ccccn2)[C@H]2CN(CCC(=O)Nc3nccs3)C(=O)[C@H](CC(C)C)N2C1=O] | 568.69 | 568.25 | 569.3 | A |
| ID-28 | 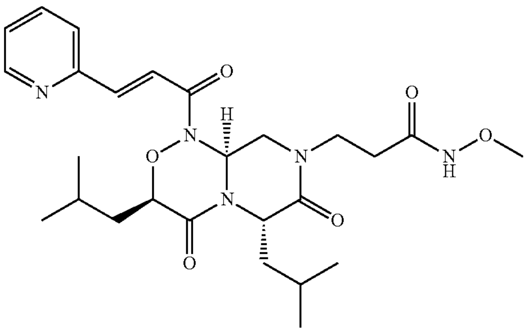 [SMILES: CONC(=O)CCN1C[C@@H]2N(C(=O)/C=C/c3ccccn3)O[C@H](CC(C)C)C(=O)N2[C@@H](CC(C)C)C1=O] | 515.61 | 515.27 | 516.4 | A |

TABLE 13-5-continued
| | | | | | |
|---|---|---|---|---|---|
| ID-29 | 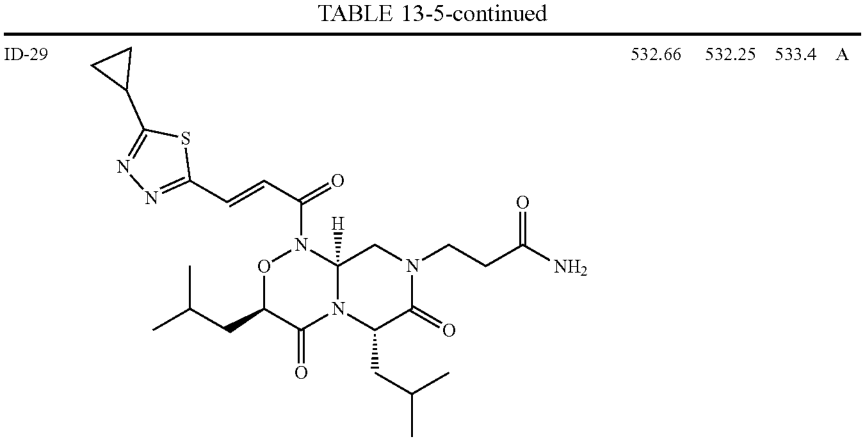 | 532.66 | 532.25 | 533.4 | A |
TABLE 13-6
| | | | | | |
|---|---|---|---|---|---|
| ID-30 | 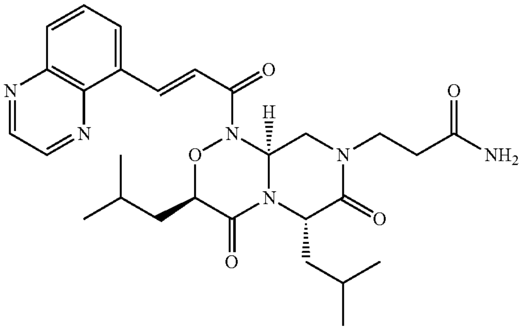 [SMILES: CC(C)C[C@H]1ON(C(=O)/C=C/c2cccc3nccnc23)[C@H]2CN(CCC(N)=O)C(=O)[C@H](CC(C)C)N2C1=O] | 536.63 | 536.27 | 537.4 | A |
| ID-31 | 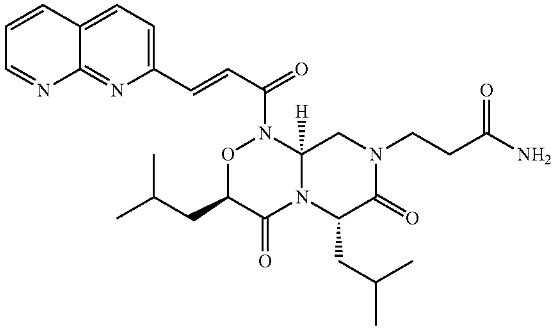 [SMILES: CC(C)C[C@H]1ON(C(=O)/C=C/c2ccc3cccnc3n2)[C@H]2CN(CCC(N)=O)C(=O)[C@H](CC(C)C)N2C1=O] | 536.63 | 536.27 | 537.4 | A |
| ID-32 | 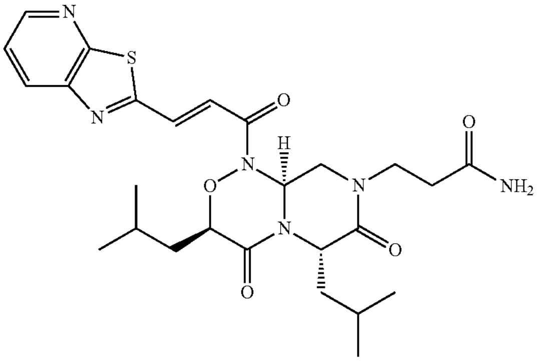 [SMILES: CC(C)C[C@H]1ON(C(=O)/C=C/c2nc3cccnc3s2)[C@H]2CN(CCC(N)=O)C(=O)[C@H](CC(C)C)N2C1=O] | 542.66 | 542.23 | 543.4 | A |

TABLE 13-6-continued
| | | | | | |
|---|---|---|---|---|---|
| ID-33 | 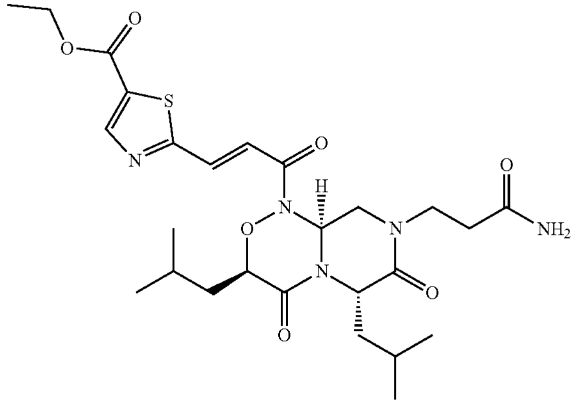 [SMILES: CCOC(=O)c1cnc(/C=C/C(=O)N2O[C@H](CC(C)C)C(=O)N3[C@@H]2CN(CCC(N)=O)C(=O)[C@@H]3CC(C)C)s1] | 563.67 | 563.24 | 564.4 | A |
| ID-34 | 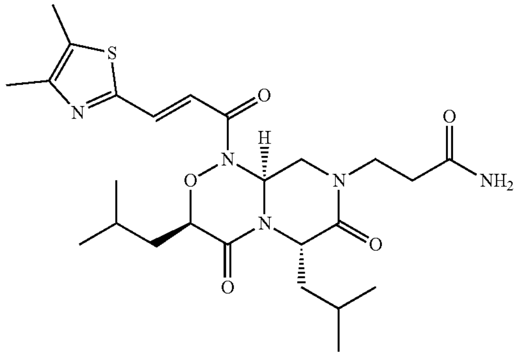 [SMILES: Cc1nc(/C=C/C(=O)N2O[C@H](CC(C)C)C(=O)N3[C@@H]2CN(CCC(N)=O)C(=O)[C@@H]3CC(C)C)sc1C] | 519.66 | 519.25 | 520.4 | A |
| ID-35 | 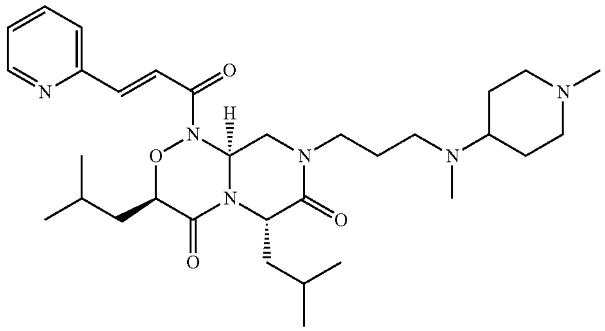 [SMILES: CC(C)C[C@H]1ON(C(=O)/C=C/c2ccccn2)[C@H]2CN(CCCN(C)C3CCN(C)CC3)C(=O)[C@H](CC(C)C)N2C1=O] | 568.81 | 568.41 | 569.5 | A |
TABLE 13-7
| | | | | | |
|---|---|---|---|---|---|
| ID-36 | 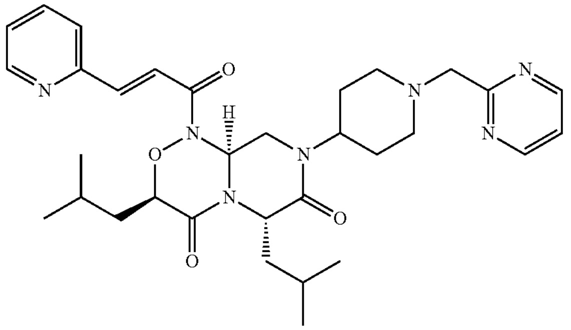 [SMILES: CC(C)C[C@H]1ON(C(=O)/C=C/c2ccccn2)[C@H]2CN(C3CCN(Cc4ncccn4)CC3)C(=O)[C@H](CC(C)C)N2C1=O] | 589.74 | 589.34 | 590.4 | A |

TABLE 13-7-continued
| | | | | | |
|---|---|---|---|---|---|
| ID-37 | 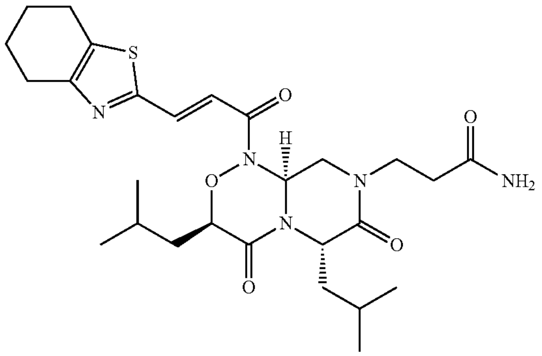 [SMILES: CC(C)C[C@H]1ON(C(=O)/C=C/c2nc3c(s2)CCCC3)[C@H]2CN(CCC(N)=O)C(=O)[C@H](CC(C)C)N2C1=O] | 545.70 | 545.27 | 546.4 | A |
| ID-38 | 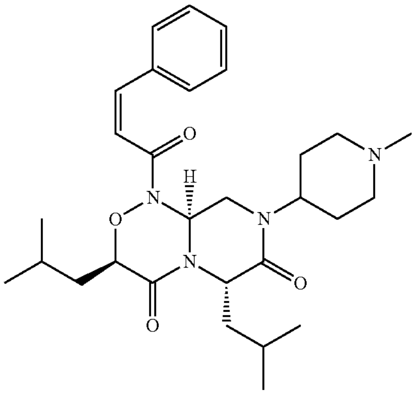 [SMILES: CC(C)C[C@H]1ON(C(=O)/C=C\c2ccccc2)[C@H]2CN(C3CCN(C)CC3)C(=O)[C@H](CC(C)C)N2C1=O] | 510.68 | 510.32 | 511.4 | A |
| ID-39 | 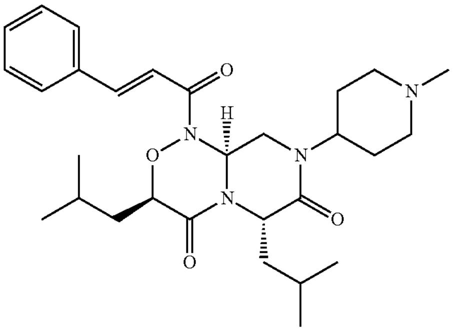 | 510.68 | 510.32 | 511.4 | A |
| ID-40 | 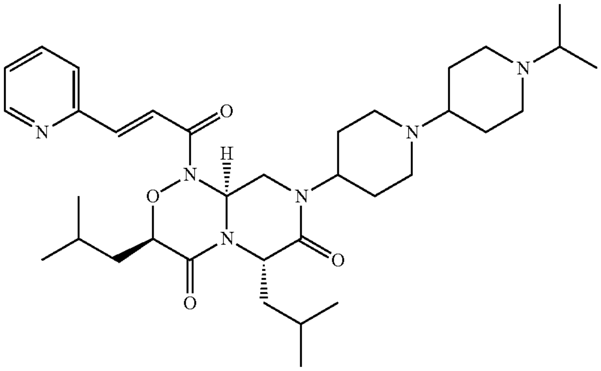 [SMILES: CC(C)C[C@H]1ON(C(=O)/C=C/c2ccccn2)[C@H]2CN(C3CCN(C4CCN(C(C)C)CC4)CC3)C(=O)[C@H](CC(C)C)N2C1=O] | 622.86 | 622.42 | 623.5 | A |

TABLE 13-7-continued
| | | | | | |
|---|---|---|---|---|---|
| ID-41 | 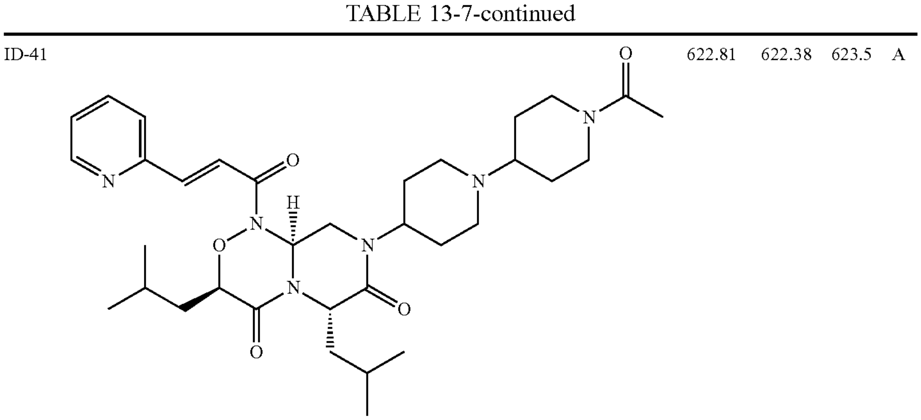 | 622.81 | 622.38 | 623.5 | A |
TABLE 13-8
| | | | | | |
|---|---|---|---|---|---|
| ID-42 | 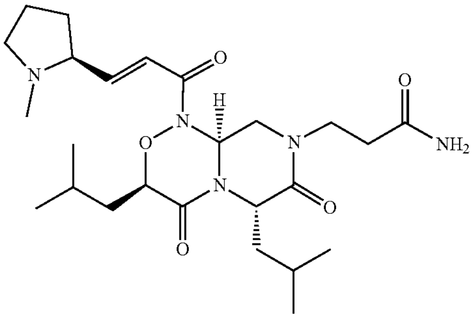 [SMILES: CC(C)C[C@H]1ON(C(=O)/C=C/[C@@H]2CCCN2C)[C@H]2CN(CCC(N)=O)C(=O)[C@H](CC(C)C)N2C1=O] | 491.63 | 491.31 | 492.4 | A |
| ID-43 | 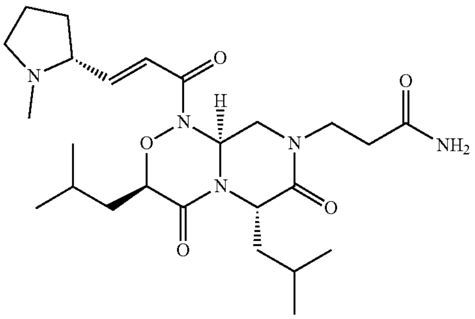 [SMILES: CC(C)C[C@H]1ON(C(=O)/C=C/[C@H]2CCCN2C)[C@H]2CN(CCC(N)=O)C(=O)[C@H](CC(C)C)N2C1=O] | 491.63 | 491.31 | 492.4 | A |
| ID-44 | 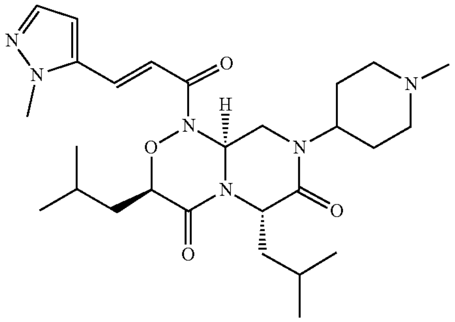 [SMILES: CC(C)C[C@H]1ON(C(=O)/C=C/c2ccnn2C)[C@H]2CN(C3CCN(C)CC3)C(=O)[C@H](CC(C)C)N2C1=O] | 514.67 | 514.33 | 515.4 | A |

TABLE 13-8-continued
| | | | | | |
|---|---|---|---|---|---|
| ID-45 | 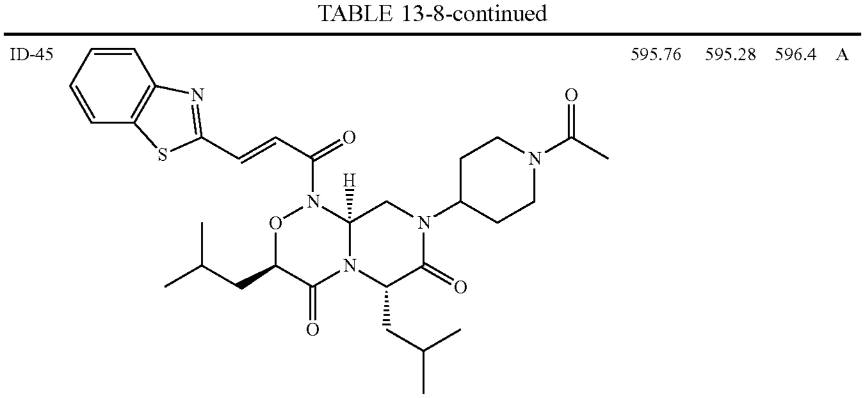 | 595.76 | 595.28 | 596.4 | A |
| ID-46 | 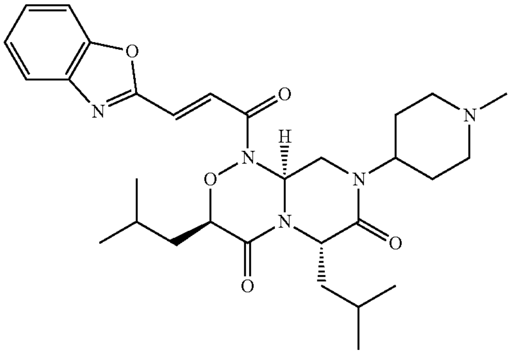 [SMILES: CC(C)C[C@H]1ON(C(=O)/C=C/c2nc3ccccc3o2)[C@H]2CN(C3CCN(C)CC3)C(=O)[C@H](CC(C)C)N2C1=O] | 551.69 | 551.31 | 552.4 | A |
| ID-47 | 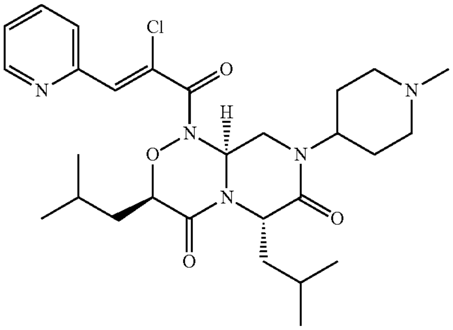 [SMILES: CC(C)C[C@H]1ON(C(=O)/C(Cl)=C/c2ccccn2)[C@H]2CN(C3CCN(C)CC3)C(=O)[C@H](CC(C)C)N2C1=O] | 546.11 | 545.28 | 546.4 | A |
TABLE 13-9
| | | | | | |
|---|---|---|---|---|---|
| ID-48 | 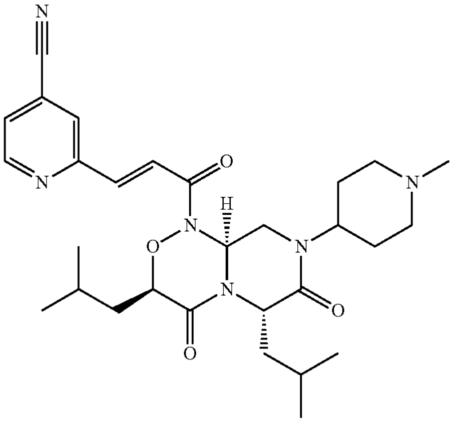 [SMILES: CC(C)C[C@H]1ON(C(=O)/C=C/c2cc(C#N)ccn2)[C@H]2CN(C3CCN(C)CC3)C(=O)[C@H](CC(C)C)N2C1=O] | 536.68 | 536.31 | 537.4 | A |

TABLE 13-9-continued
| | | | | | |
|---|---|---|---|---|---|
| ID-49 | 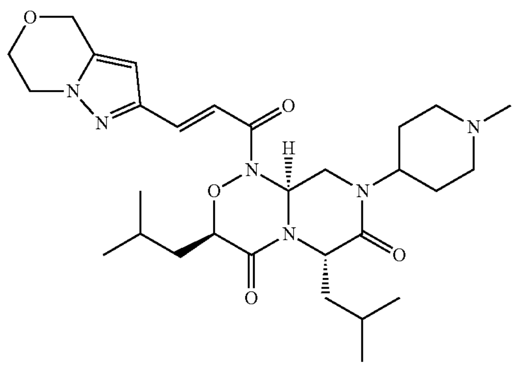 [SMILES: CC(C)C[C@H]1ON(C(=O)/C=C/c2cc3n(n2)CCOC3)[C@H]2CN(C3CCN(C)CC3)C(=O)[C@H](CC(C)C)N2C1=O] | 556.71 | 556.34 | 557.4 | A |
| ID-50 | 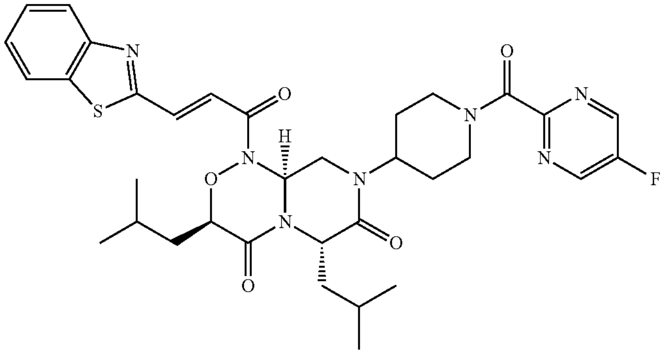 [SMILES: CC(C)C[C@H]1ON(C(=O)/C=C/c2nc3ccccc3s2)[C@H]2CN(C3CCN(C(=O)c4ncc(F)cn4)CC3)C(=O)[C@H](CC(C)C)N2C1=O] | 677.80 | 677.28 | 678.3 | A |
| ID-51 | 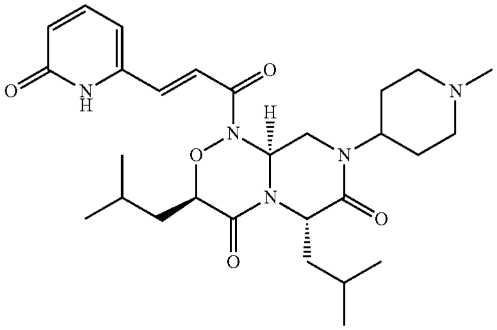 [SMILES: CC(C)C[C@H]1ON(C(=O)/C=C/c2cccc(=O)[nH]2)[C@H]2CN(C3CCN(C)CC3)C(=O)[C@H](CC(C)C)N2C1=O] | 527.67 | 527.31 | 528.4 | A |
| ID-52 | 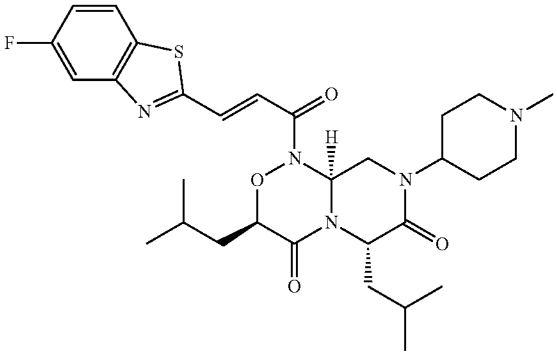 [SMILES: CC(C)C[C@H]1ON(C(=O)/C=C/c2nc3cc(F)ccc3s2)[C@H]2CN(C3CCN(C)CC3)C(=O)[C@H](CC(C)C)N2C1=O] | 585.74 | 585.28 | 586.4 | A |

TABLE 13-9-continued
| | | | | | |
|---|---|---|---|---|---|
| ID-53 | 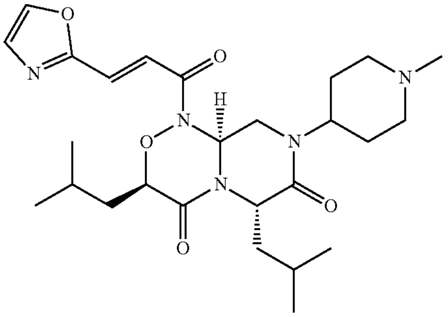 [SMILES: CC(C)C[C@H]1ON(C(=O)/C=C/c2ncco2)[C@H]2CN(C3CCN(C)CC3)C(=O)[C@H](CC(C)C)N2C1=O] | 501.63 | 501.30 | 502.4 | A |
TABLE 13-10
| | | | | | |
|---|---|---|---|---|---|
| ID-54 | 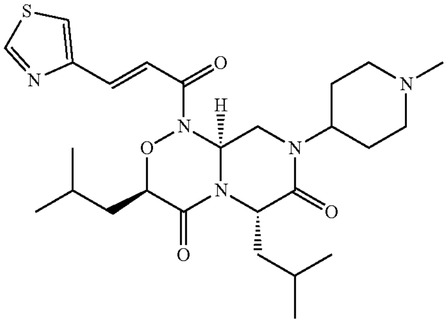 [SMILES: CC(C)C[C@H]1ON(C(=O)/C=C/c2cscn2)[C@H]2CN(C3CCN(C)CC3)C(=O)[C@H](CC(C)C)N2C1=O] | 517.69 | 517.27 | 518.4 | A |
| ID-55 | 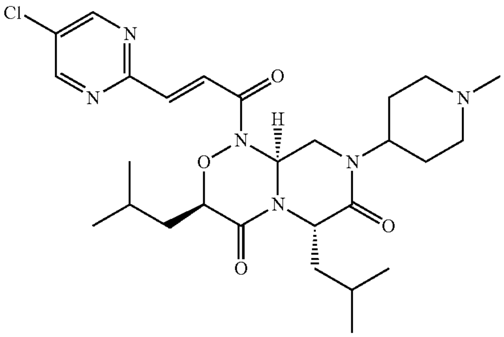 [SMILES: CC(C)C[C@H]1ON(C(=O)/C=C/c2ncc(Cl)cn2)[C@H]2CN(C3CCN(C)CC3)C(=O)[C@H](CC(C)C)N2C1=O] | 547.10 | 546.27 | 547.4 | A |
| ID-56 | 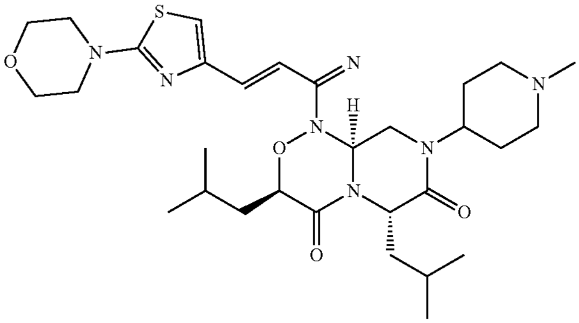 [SMILES: CC(C)C[C@H]1ON(C(=N)/C=C/c2csc(N3CCOCC3)n2)[C@H]2CN(C3CCN(C)CC3)C(=O)[C@H](CC(C)C)N2C1=O] | 602.80 | 602.33 | 603.4 | A |

TABLE 13-10-continued
| | | | | | |
|---|---|---|---|---|---|
| ID-57 | 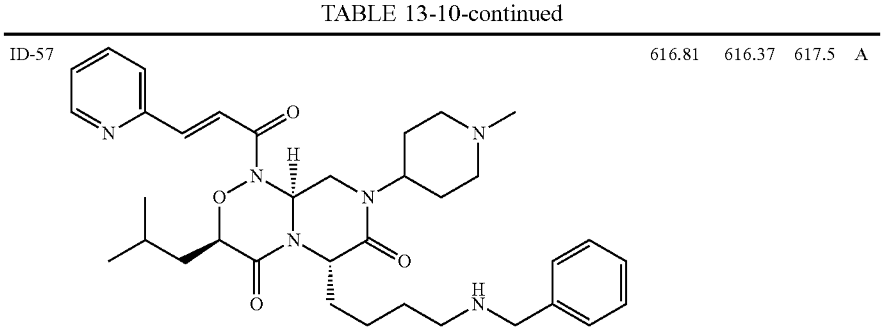 | 616.81 | 616.37 | 617.5 | A |
| ID-58 | 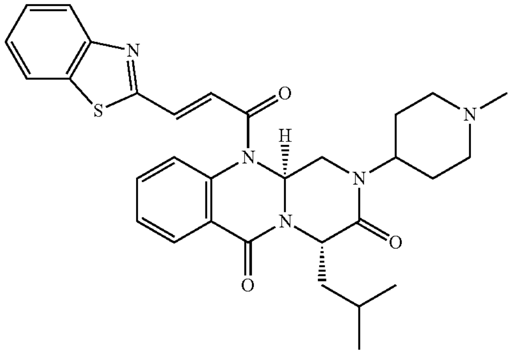 [SMILES: CC(C)C[C@H]1C(=O)N(C2CCN(C)CC2)C[C@@H]2N(C(=O)/C=C/c3nc4ccccc4s3)c3ccccc3C(=O)N21] | 557.71 | 557.25 | 558.3 | A |
TABLE 13-11
| | | | | | |
|---|---|---|---|---|---|
| ID-59 | 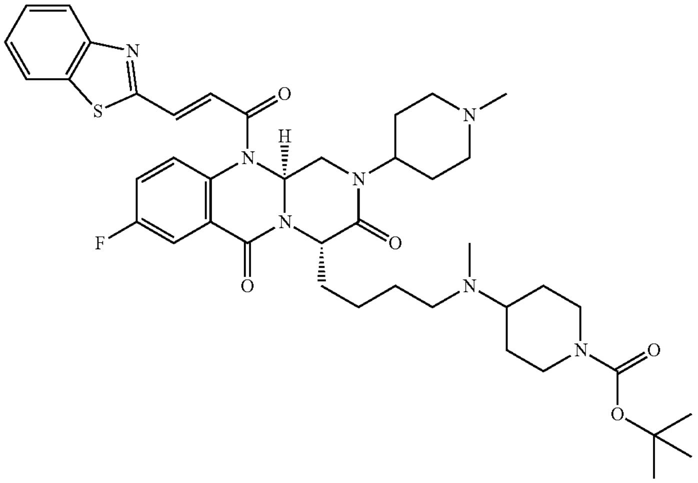 [SMILES: CN1CCC(N2C[C@@H]3N(C(=O)/C=C/c4nc5ccccc5s4)c4ccc(F)cc4C(=O)N3[C@@H](CCCCN(C)C3CCN(C(=O)OC(C)(C)C)CC3)C2=O)CC1] | 788.00 | 787.39 | 788.5 | A |
| ID-60 | 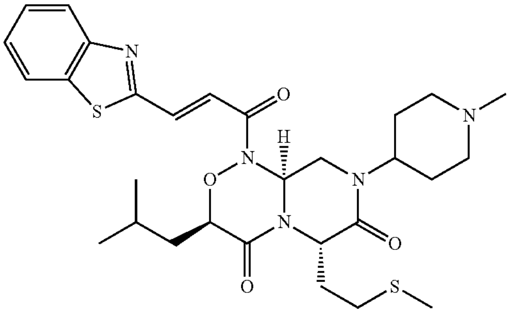 [SMILES: CSCC[C@H]1C(=O)N(C2CCN(C)CC2)C[C@@H]2N(C(=O)/C=C/c3nc4ccccc4s3)O[C@H](CC(C)C)C(=O)N21] | 585.78 | 585.24 | 586.3 | A |

TABLE 13-11-continued
| | | | | | |
|---|---|---|---|---|---|
| ID-61 | 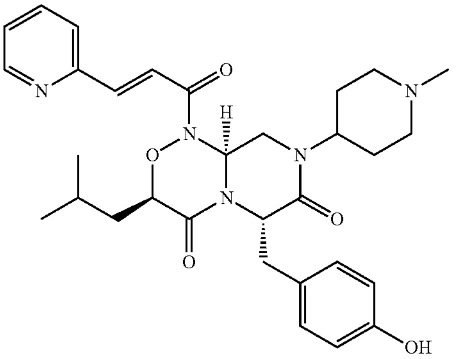 [SMILES: CC(C)C[C@H]1ON(C(=O)/C=C/c2ccccn2)[C@H]2CN(C3CCN(C)CC3)C(=O)[C@H](Cc3ccc(O)cc3)N2C1=O] | 561.68 | 561.30 | 562.3 | A |
| ID-62 | 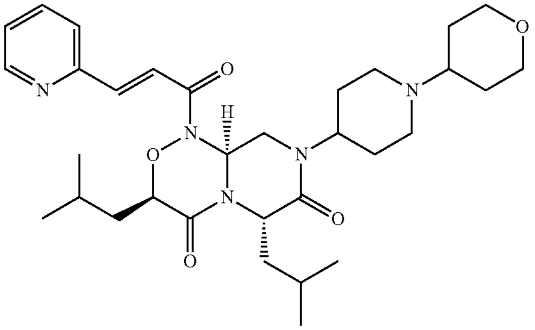 [SMILES: CC(C)C[C@H]1ON(C(=O)/C=C/c2ccccn2)[C@H]2CN(C3CCN(C4CCOCC4)CC3)C(=O)[C@H](CC(C)C)N2C1=O] | 581.76 | 581.36 | 582.4 | A |
| ID-63 | 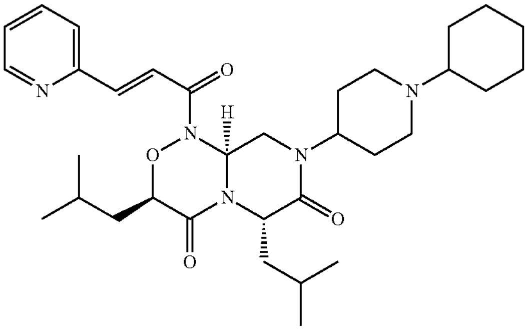 [SMILES: CC(C)C[C@H]1ON(C(=O)/C=C/c2ccccn2)[C@H]2CN(C3CCN(C4CCCCC4)CC3)C(=O)[C@H](CC(C)C)N2C1=O] | 579.79 | 579.38 | 580.4 | A |
| ID-64 | 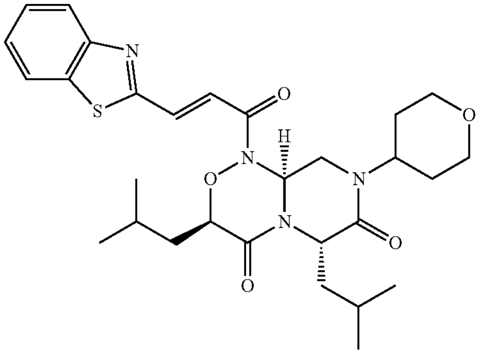 [SMILES: CC(C)C[C@H]1ON(C(=O)/C=C/c2nc3ccccc3s2)[C@H]2CN(C3CCOCC3)C(=O)[C@H](CC(C)C)N2C1=O] | 554.71 | 554.26 | 555.3 | A |

TABLE 13-12
| | | | | | |
|---|---|---|---|---|---|
| ID-65 | 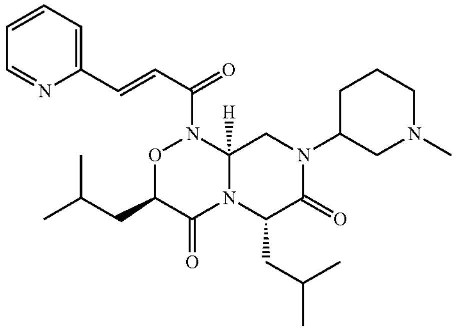 [SMILES: CC(C)C[C@H]1ON(C(=O)/C=C/c2ccccn2)[C@H]2CN(C3CCCN(C)C3)C(=O)[C@H](CC(C)C)N2C1=O] | 511.67 | 511.32 | 512.4 | A |
| ID-66 | 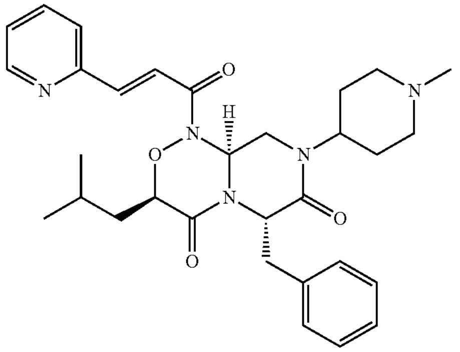 [SMILES: CC(C)C[C@H]1ON(C(=O)/C=C/c2ccccn2)[C@H]2CN(C3CCN(C)CC3)C(=O)[C@H](Cc3ccccc3)N2C1=O] | 545.68 | 545.30 | 546.3 | A |
| ID-67 | 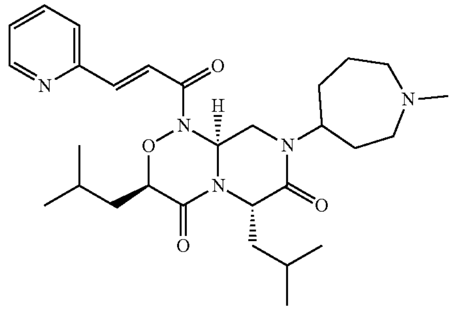 [SMILES: CC(C)C[C@H]1ON(C(=O)/C=C/c2ccccn2)[C@H]2CN(C3CCCN(C)CC3)C(=O)[C@H](CC(C)C)N2C1=O] | 525.69 | 525.33 | 526.4 | A |
| ID-68 | 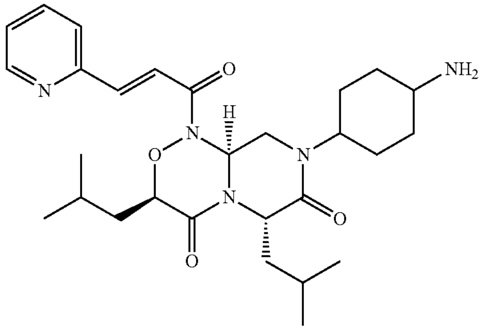 [SMILES: CC(C)C[C@H]1ON(C(=O)/C=C/c2ccccn2)[C@H]2CN(C3CCC(N)CC3)C(=O)[C@H](CC(C)C)N2C1=O] | 511.67 | 511.32 | 512.4 | A |

TABLE 13-12-continued
| | | | | | |
|---|---|---|---|---|---|
| ID-69 | 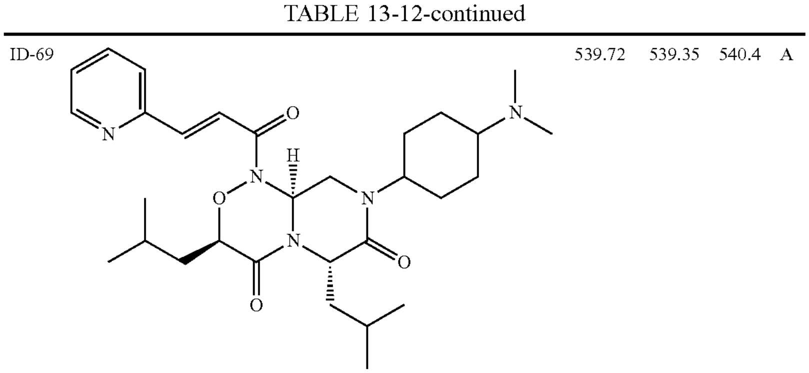 | 539.72 | 539.35 | 540.4 | A |
| ID-70 | 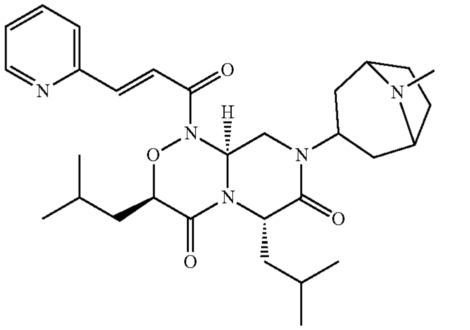 [SMILES: CC(C)C[C@H]1ON(C(=O)/C=C/c2ccccn2)[C@H]2CN(C3CC4CCC(C3)N4C)C(=O)[C@H](CC(C)C)N2C1=O] | 537.71 | 537.33 | 538.4 | A |
TABLE 13-13
| | | | | | |
|---|---|---|---|---|---|
| ID-71 | 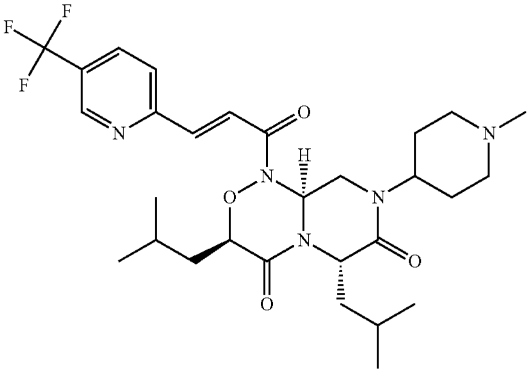 [SMILES: CC(C)C[C@H]1ON(C(=O)/C=C/c2ccc(C(F)(F)F)cn2)[C@H]2CN(C3CCN(C)CC3)C(=O)[C@H](CC(C)C)N2C1=O] | 579.67 | 579.30 | 580.3 | A |
| ID-72 | 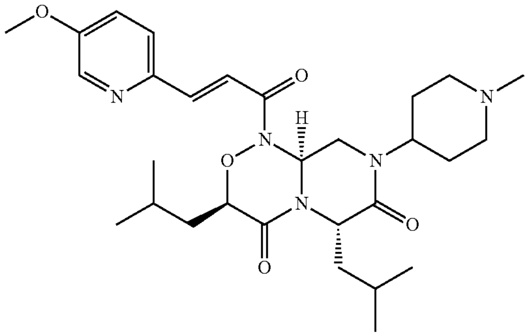 | 541.69 | 541.33 | 542.2 | A |

TABLE 13-13-continued
| | | | | | |
|---|---|---|---|---|---|
| ID-73 | 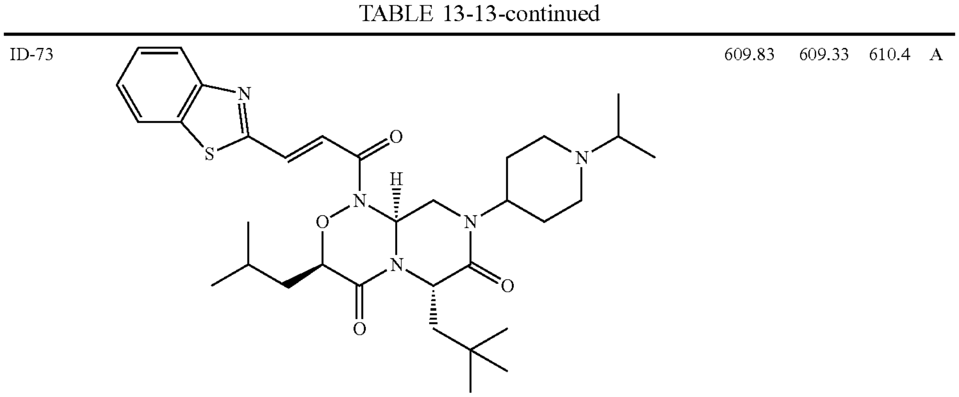 | 609.83 | 609.33 | 610.4 | A |
| ID-74 | 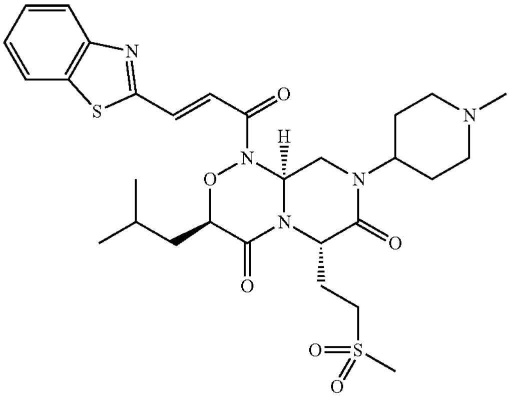 [SMILES: CC(C)C[C@H]1ON(C(=O)/C=C/c2nc3ccccc3s2)[C@H]2CN(C3CCN(C)CC3)C(=O)[C@H](CCS(C)(=O)=O)N2C1=O] | 617.78 | 617.23 | 618.3 | A |
| ID-75 | 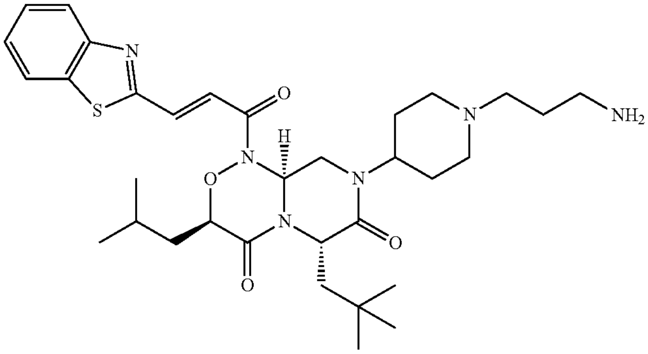 [SMILES: CC(C)C[C@H]1ON(C(=O)/C=C/c2nc3ccccc3s2)[C@H]2CN(C3CCN(CCCN)CC3)C(=O)[C@H](CC(C)(C)C)N2C1=O] | 624.85 | 624.35 | 625.5 | A |
TABLE 13-14
| | | | | | |
|---|---|---|---|---|---|
| ID-76 | 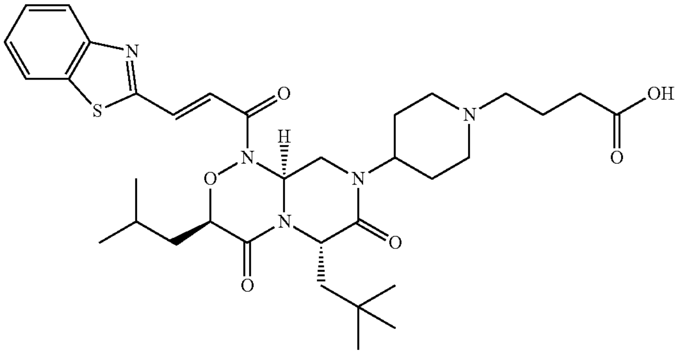 [SMILES: CC(C)C[C@H]1ON(C(=O)/C=C/c2nc3ccccc3s2)[C@H]2CN(C3CCN(CCCC(=O)O)CC3)C(=O)[C@H](CC(C)(C)C)N2C1=O] | 653.84 | 653.32 | 654.4 | A |

TABLE 13-14-continued
| | | | | | |
|---|---|---|---|---|---|
| ID-77 | 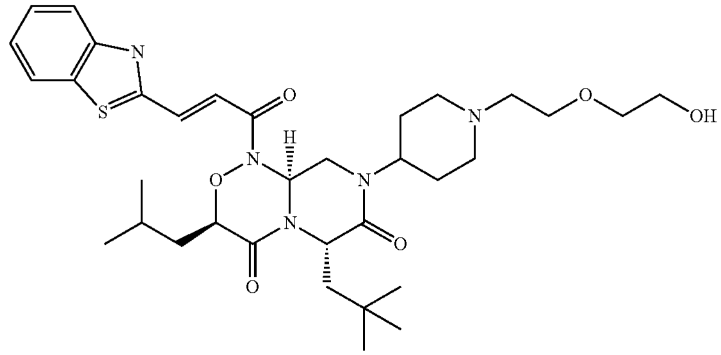 | 655.86 | 655.34 | 656.4 | A |
| ID-78 | 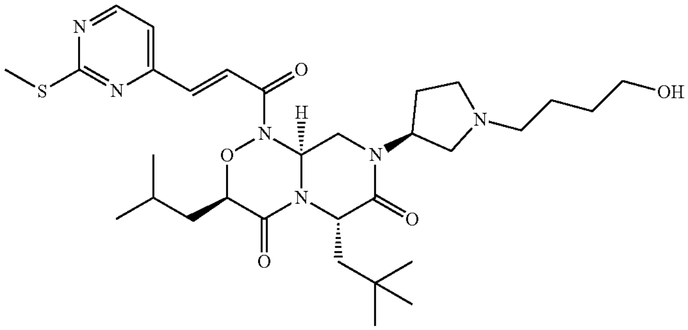 [SMILES: CSc1nccc(/C=C/C(=O)N2O[C@H](CC(C)C)C(=O)N3[C@@H]2CN([C@H]2CCN(CCCCO)C2)C(=O)[C@@H]3CC(C)(C)C)n1] | 616.82 | 616.34 | 617.4 | A |
| ID-79 | 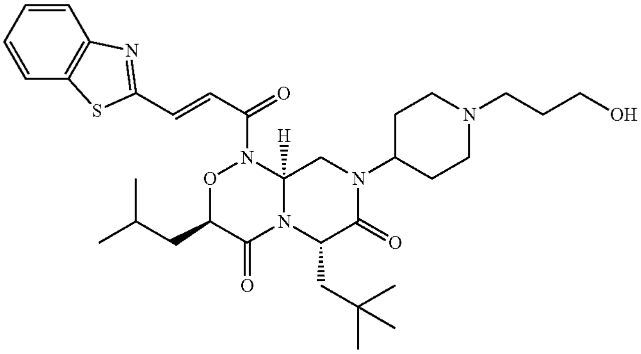 [SMILES: CC(C)C[C@H]1ON(C(=O)/C=C/c2nc3ccccc3s2)[C@H]2CN(C3CCN(CCCO)CC3)C(=O)[C@H](CC(C)(C)C)N2C1=O] | 625.83 | 625.33 | 626.4 | A |
| ID-80 | 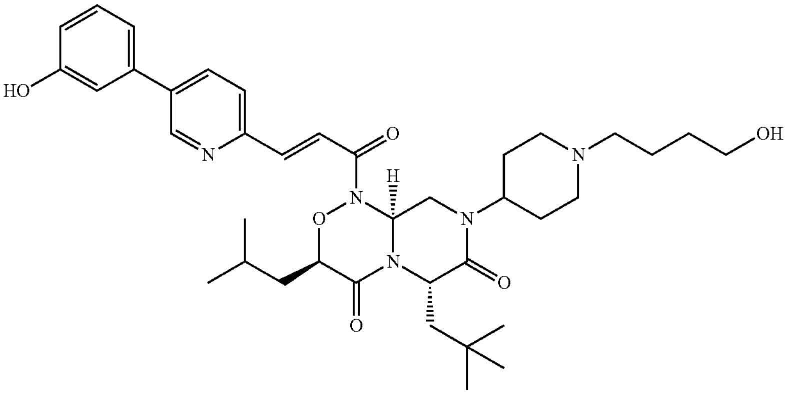 [SMILES: CC(C)C[C@H]1ON(C(=O)/C=C/c2ccc(-c3cccc(O)c3)cn2)[C@H]2CN(C3CCN(CCCCO)CC3)C(=O)[C@H](CC(C)(C)C)N2C1=O] | 675.87 | 675.40 | 676.5 | A |

TABLE 13-14-continued
| | | | | | |
|---|---|---|---|---|---|
| ID-81 | 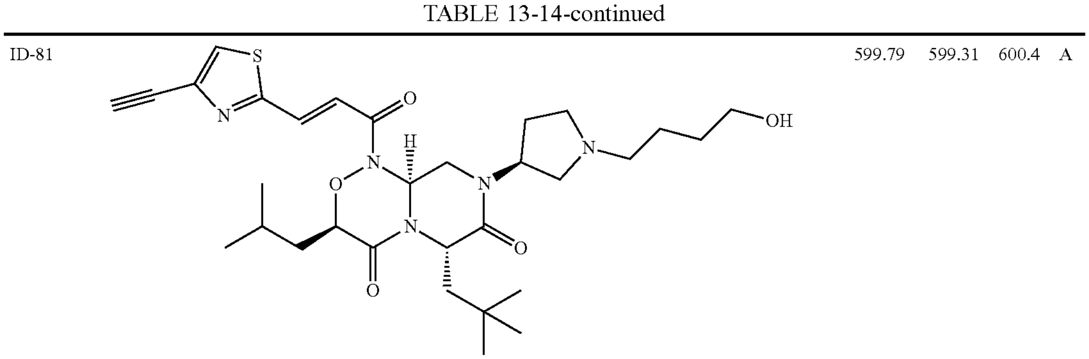 | 599.79 | 599.31 | 600.4 | A |
TABLE 13-15
| | | | | | |
|---|---|---|---|---|---|
| ID-82 | 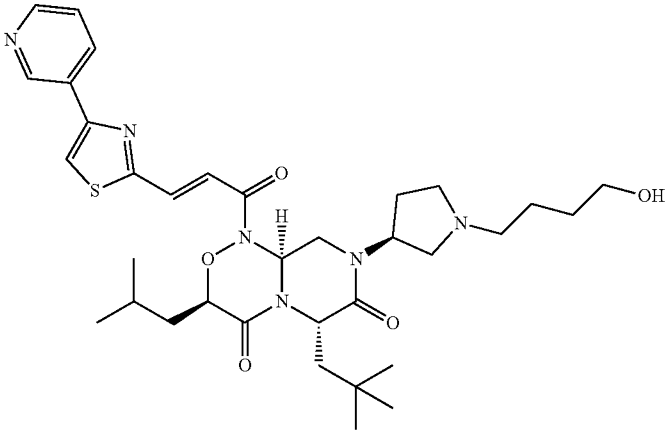 [SMILES: CC(C)C[C@H]1ON(C(=O)/C=C/c2nc(-c3cccnc3)cs2)[C@H]2CN([C@H]3CCN(CCCCO)C3)C(=O)[C@H](CC(C)(C)C)N2C1=O] | 652.86 | 652.34 | 653.4 | A |
| ID-83 | 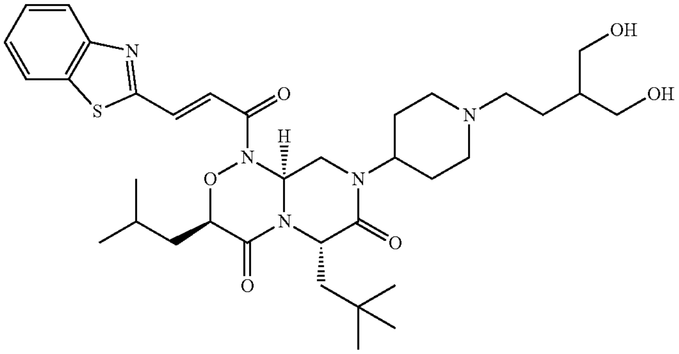 [SMILES: CC(C)C[C@H]1ON(C(=O)/C=C/c2nc3ccccc3s2)[C@H]2CN(C3CCN(CCC(CO)CO)CC3)C(=O)[C@H](CC(C)(C)C)N2C1=O] | 669.88 | 669.36 | 670.3 | A |
| ID-84 | 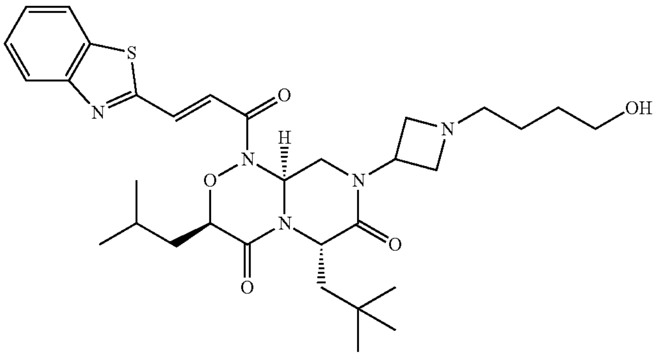 [SMILES: CC(C)C[C@H]1ON(C(=O)/C=C/c2nc3ccccc3s2)[C@H]2CN(C3CN(CCCCO)C3)C(=O)[C@H](CC(C)(C)C)N2C1=O] | 611.80 | 611.31 | 612.4 | B |

TABLE 13-15-continued
| | | | | | |
|---|---|---|---|---|---|
| ID-85 | 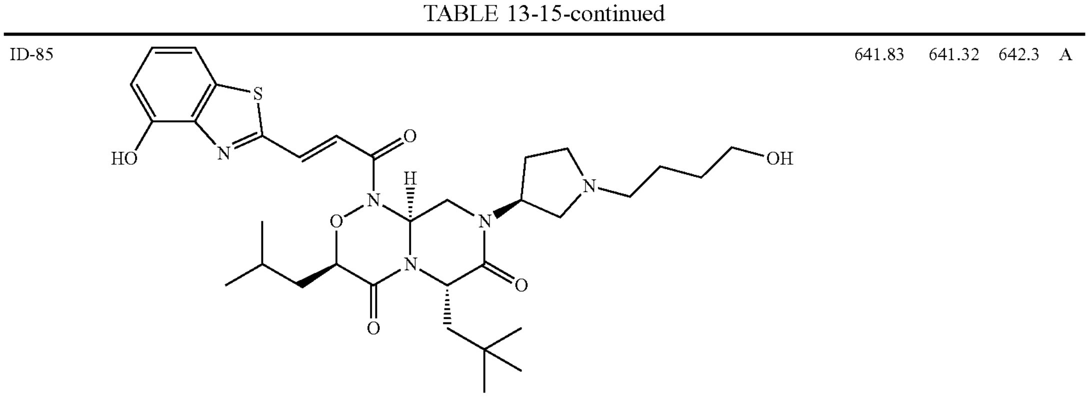 | 641.83 | 641.32 | 642.3 | A |
| ID-86 | 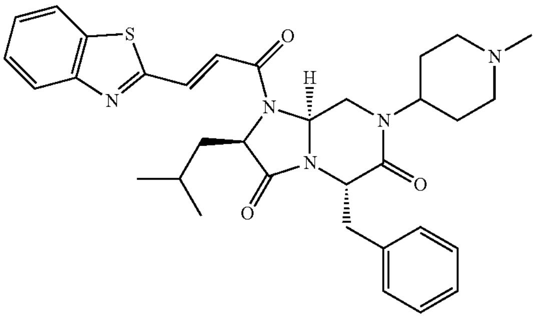 [SMILES: CC(C)C[C@@H]1C(=O)N2[C@H](CN(C3CCN(C)CC3)C(=O)[C@@H]2Cc2ccccc2)N1C(=O)/C=C/c1nc2ccccc2s1] | 585.77 | 585.28 | 586.3 | A |
| ID-87 | 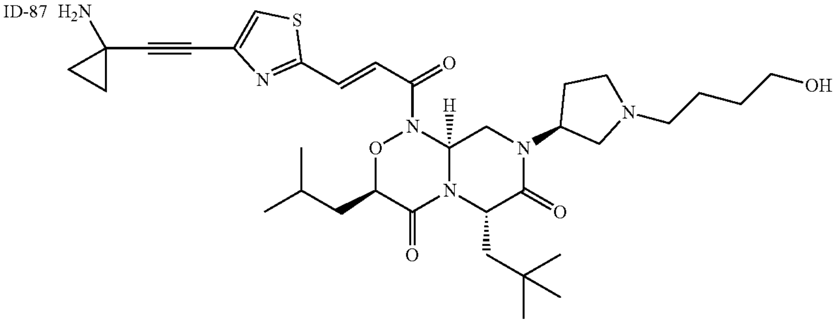 | 654.87 | 654.36 | 655.4 | A |
TABLE 13-16
| | | | | | |
|---|---|---|---|---|---|
| ID-88 | 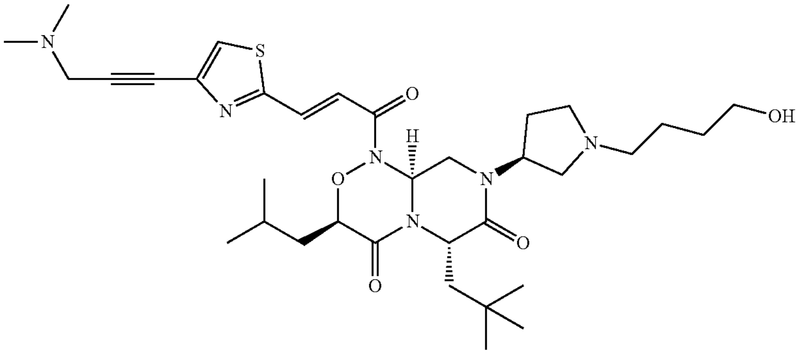 [SMILES: CC(C)C[C@H]1ON(C(=O)/C=C/c2nc(C#CCN(C)C)cs2)[C@H]2CN([C@H]3CCN(CCCCO)C3)C(=O)[C@H](CC(C)(C)C)N2C1=O] | 656.89 | 656.37 | 657.4 | A |

TABLE 13-16-continued
| | | | | | |
|---|---|---|---|---|---|
| ID-89 | 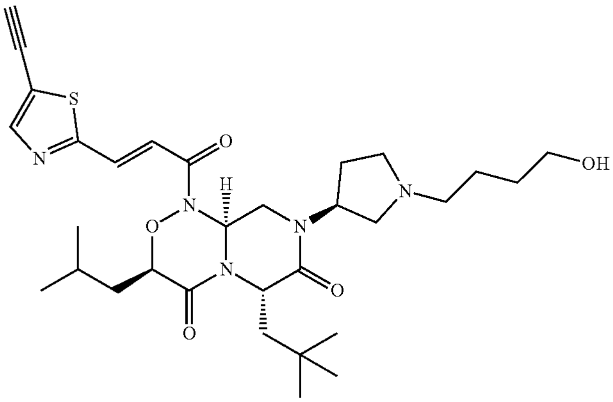 [SMILES: C#Cc1cnc(/C=C/C(=O)N2O[C@H](CC(C)C)C(=O)N3[C@@H]2CN([C@H]2CCN(CCCCO)C2)C(=O)[C@@H]3CC(C)(C)C)s1] | 599.79 | 599.31 | 600.4 | A |
| ID-90 | 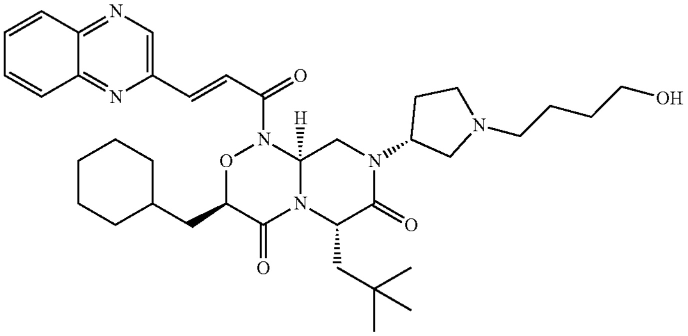 [SMILES: CC(C)(C)C[C@H]1C(=O)N([C@@H]2CCN(CCCCO)C2)C[C@@H]2N(C(=O)/C=C/c3cnc4ccccc4n3)O[C@H](CC3CCCCC3)C(=O)N21] | 660.86 | 660.40 | 661.4 | A |
| ID-91 | 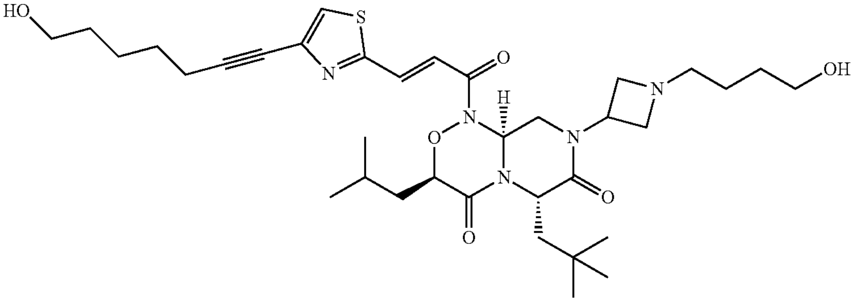 [SMILES: CC(C)C[C@H]1ON(C(=O)/C=C/c2nc(C#CCCCCCO)cs2)[C@H]2CN(C3CN(CCCCO)C3)C(=O)[C@H](CC(C)(C)C)N2C1=O] | 671.90 | 671.37 | 672.4 | A |
| ID-92 | 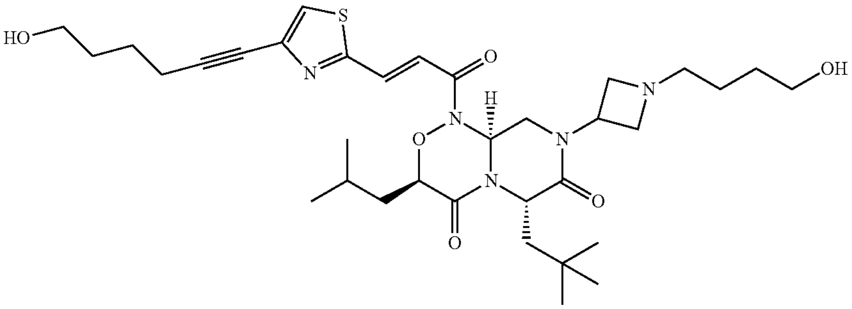 [SMILES: CC(C)C[C@H]1ON(C(=O)/C=C/c2nc(C#CCCCCO)cs2)[C@H]2CN(C3CN(CCCCO)C3)C(=O)[C@H](CC(C)(C)C)N2C1=O] | 657.87 | 657.36 | 658.4 | A |

TABLE 13-17
| | | | | | |
|---|---|---|---|---|---|
| ID-93 | 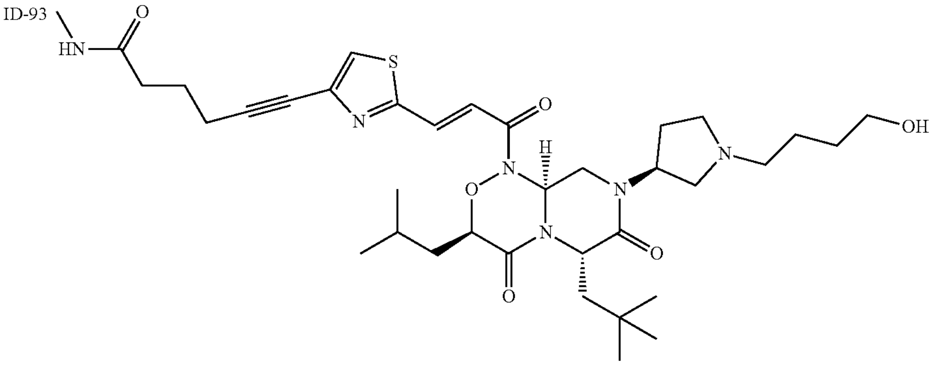 | 698.92 | 698.38 | 699.4 | A |
| ID-94 | 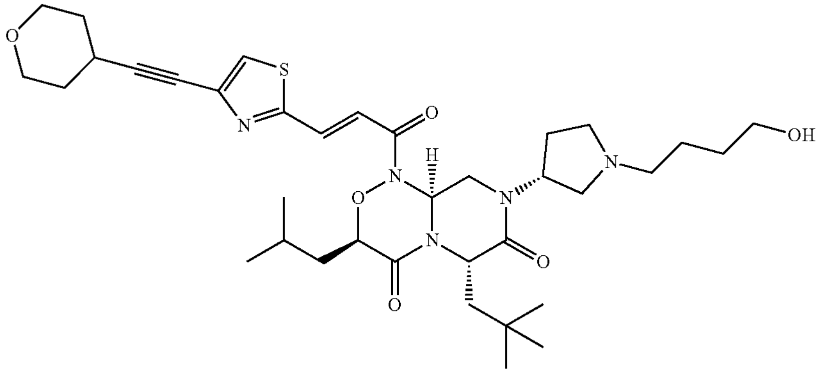 [SMILES: CC(C)C[C@H]1ON(C(=O)/C=C/c2nc(C#CC3CCOCC3)cs2)[C@H]2CN([C@@H]3CCN(CCCCO)C3)C(=O)[C@H](CC(C)(C)C)N2C1=O] | 683.91 | 683.37 | 684.4 | A |
| ID-95 | 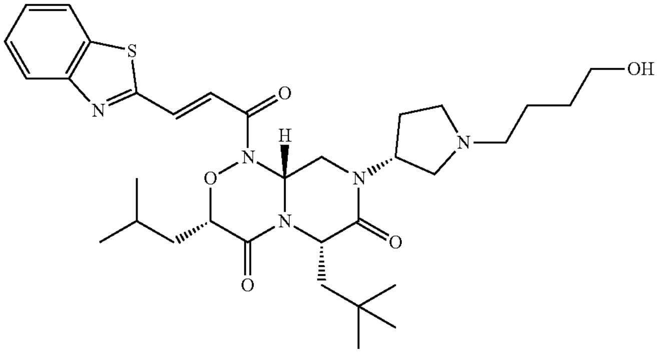 [SMILES: CC(C)C[C@@H]1ON(C(=O)/C=C/c2nc3ccccc3s2)[C@@H]2CN([C@@H]3CCN(CCCCO)C3)C(=O)[C@H](CC(C)(C)C)N2C1=O] | 625.83 | 625.33 | 626.3 | A |
| ID-96 | 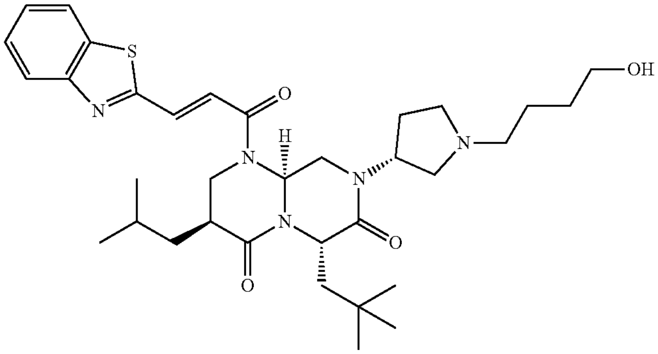 [SMILES: CC(C)C[C@H]1CN(C(=O)/C=C/c2nc3ccccc3s2)[C@H]2CN([C@@H]3CCN(CCCCO)C3)C(=O)[C@H](CC(C)(C)C)N2C1=O] | 623.86 | 623.35 | 624.4 | A |

TABLE 13-17-continued
| | | | | | |
|---|---|---|---|---|---|
| ID-97 | 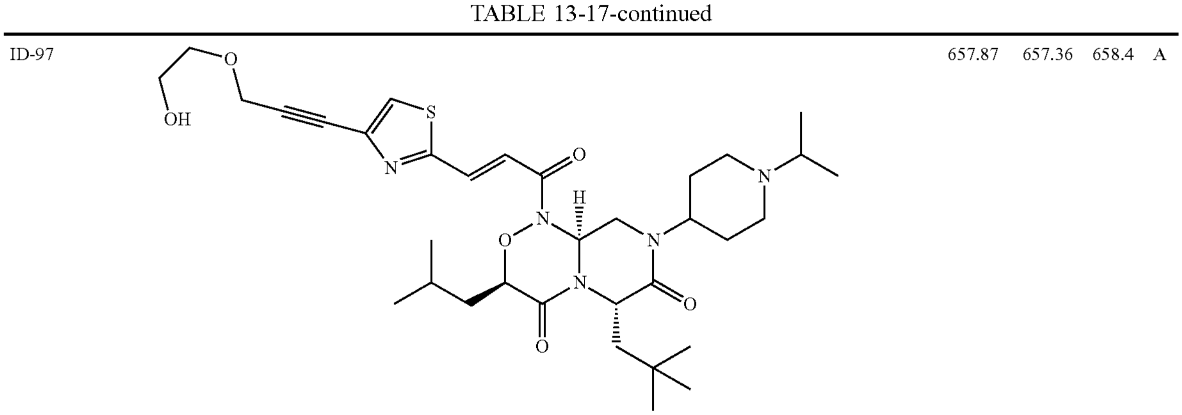 | 657.87 | 657.36 | 658.4 | A |
| ID-98 | 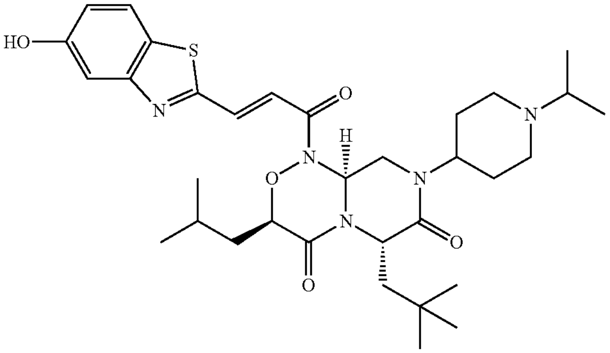 [SMILES: CC(C)C[C@H]1ON(C(=O)/C=C/c2nc3cc(O)ccc3s2)[C@H]2CN(C3CCN(C(C)C)CC3)C(=O)[C@H](CC(C)(C)C)N2C1=O] | 625.83 | 625.33 | 626.4 | A |
TABLE 13-18
| | | | | | |
|---|---|---|---|---|---|
| ID-99 | 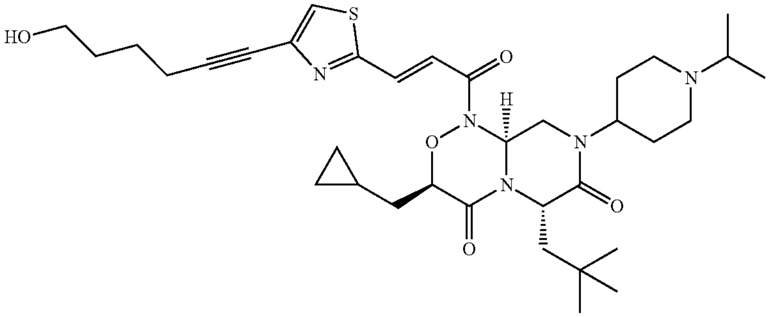 [SMILES: CC(C)N1CCC(N2C[C@@H]3N(C(=O)/C=C/c4nc(C#CCCCCO)cs4)O[C@H](CC4CC4)C(=O)N3[C@@H](CC(C)(C)C)C2=O)CC1] | 653.88 | 653.36 | 654.4 | A |
| ID-100 | 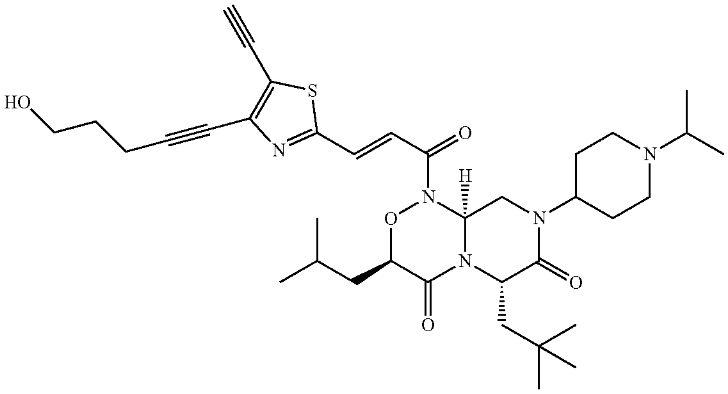 [SMILES: C#Cc1sc(/C=C/C(=O)N2O[C@H](CC(C)C)C(=O)N3[C@@H]2CN(C2CCN(C(C)C)CC2)C(=O)[C@@H]3CC(C)(C)C)nc1C#CCCCO] | 665.89 | 665.36 | 666.3 | A |

TABLE 13-18-continued
| | | | | | |
|---|---|---|---|---|---|
| ID-101 | 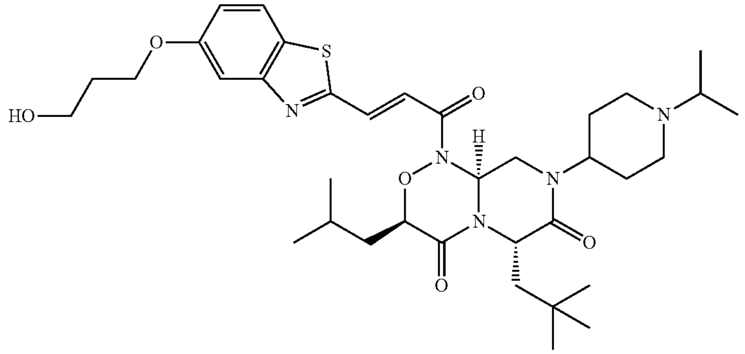 [SMILES: CC(C)C[C@H]1ON(C(=O)/C=C/c2nc3cc(OCCCO)ccc3s2)[C@H]2CN(C3CCN(C(C)C)CC3)C(=O)[C@H](CC(C)(C)C)N2C1=O] | 683.91 | 683.37 | 684.4 | A |
| ID-102 | 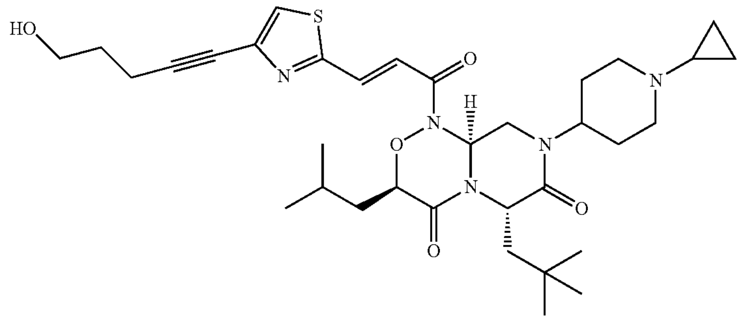 [SMILES: CC(C)C[C@H]1ON(C(=O)/C=C/c2nc(C#CCCCO)cs2)[C@H]2CN(C3CCN(C4CC4)CC3)C(=O)[C@H](CC(C)(C)C)N2C1=O] | 639.86 | 639.35 | 640.4 | A |
| ID-103 | 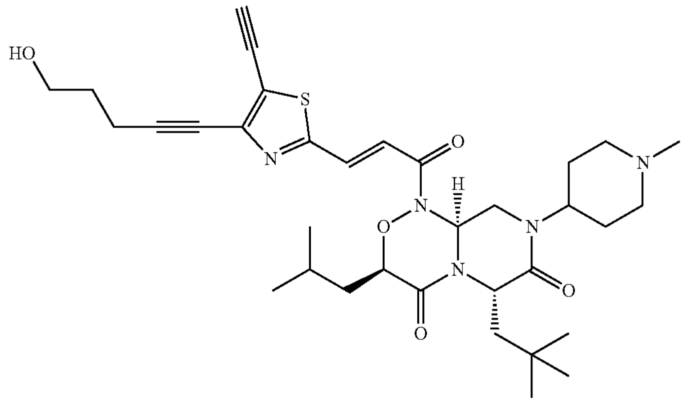 [SMILES: C#Cc1sc(/C=C/C(=O)N2O[C@H](CC(C)C)C(=O)N3[C@@H]2CN(C2CCN(C)CC2)C(=O)[C@@H]3CC(C)(C)C)nc1C#CCCCO] | 637.84 | 637.33 | 638.3 | B |
| ID-104 | 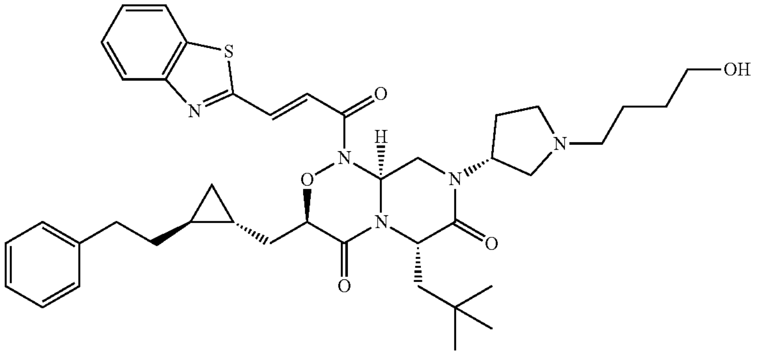 [SMILES: CC(C)(C)C[C@H]1C(=O)N([C@@H]2CCN(CCCCO)C2)C[C@@H]2N(C(=O)/C=C/c3nc4ccccc4s3)O[C@H](C[C@H]3C[C@@H]3CCc3ccccc3)C(=O)N21] | 727.97 | 727.38 | 728.4 | A |

TABLE 13-19

| | | | | | |
|---|---|---|---|---|---|
| ID-105 | 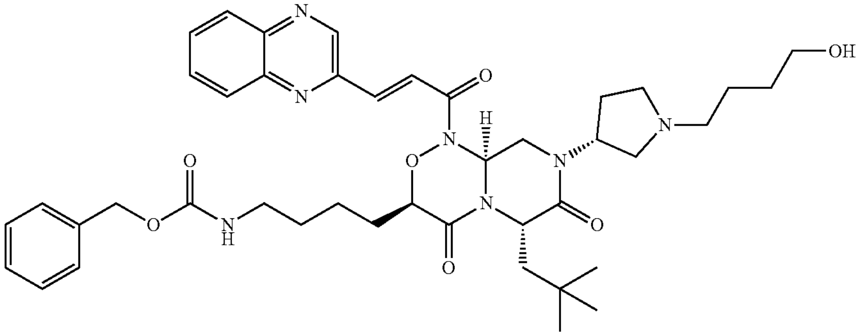 [SMILES: CC(C)(C)C[C@H]1C(=O)N([C@@H]2CCN(CCCCO)C2)C[C@@H]2N(C(=O)/C=C/c3cnc4ccccc4n3)O[C@H](CCCCNC(=O)OCc3ccccc3)C(=O)N21] | 769.94 | 769.42 | 770.4 | B |
| ID-106 | 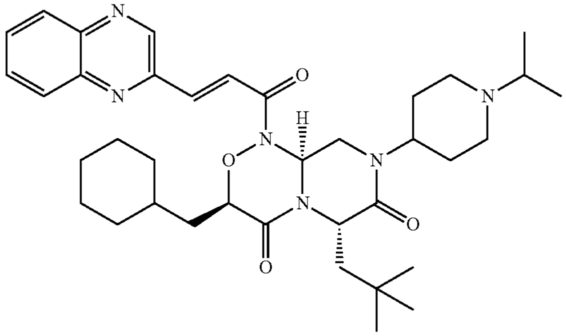 [SMILES: CC(C)N1CCC(N2C[C@@H]3N(C(=O)/C=C/c4cnc5ccccc5n4)O[C@H](CC4CCCCC4)C(=O)N3[C@@H](CC(C)(C)C)C2=O)CC1] | 644.86 | 644.41 | 645.5 | A |
| ID-107 | 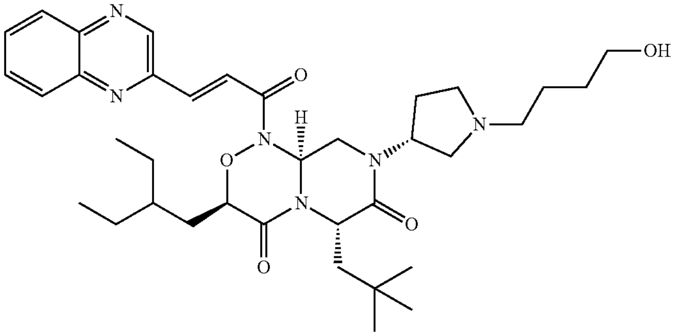 [SMILES: CCC(CC)C[C@H]1ON(C(=O)/C=C/c2cnc3ccccc3n2)[C@H]2CN([C@@H]3CCN(CCCCO)C3)C(=O)[C@H](CC(C)(C)C)N2C1=O] | 648.85 | 648.40 | 649.4 | A |

Chemical names of compounds ID-1 to ID-107 are listed as below:

ID-1

(3R,6S,9aS)-3,6-diisobutyl-8-(1-methylpiperidin-4-yl)-1-((E)-3-(pyridin-2-yl) acryloyl)tetrahydropyrazino[2,1-c][1,2,4]oxadiazine-4,7(3H,6H)-dione

ID-2

(3R,6S,9aS)-1-((E)-3-(benzo[d]thiazol-2-yl)acryloyl)-3,6-diisobutyl-8-(1-methylpiperidin-4-yl)tetrahydropyrazino[2,1-c][1,2,4]oxadiazine-4,7(3H,6H)-dione

ID-3

2-((E)-3-((3R,6S,9aS)-3,6-diisobutyl-8-(1-methylpiperidin-4-yl)-4,7-dioxohexahydropyrazino[2,1-c][1,2,4]oxadiazin-1(6H)-yl)-3-oxoprop-1-en-1-yl)thiazole-4-carbonitrile

ID-4

(3R,6S,9aS)-1-((E)-3-(benzo[d]thiazol-2-yl)acryloyl)-8-(1-(4-hydroxybutyl) piperidin-4-yl)-3-isobutyl-6-neopentyltetrahydropyrazino[2,1-c][1,2,4]oxadiazine-4,7 (3H,6H)-dione

ID-5

(3R,6S,9aS)-1-((E)-3-(benzo[d]thiazol-2-yl)acryloyl)-8-((S)-1-(4-hydroxybutyl)pyrrolidin-3-yl)-3-isobutyl-6-neopentyltetrahydropyrazino[2,1-c][1,2,4]oxadiazine-4,7(3H,6H)-dione

ID-6

(3R,6S,9aS)-1-((E)-3-(benzo[d]thiazol-2-yl)acryloyl)-8-((R)-1-(4-hydroxybutyl)pyrrolidin-3-yl)-3-isobutyl-6-neopentyltetrahydropyrazino[2,1-c][1,2,4]oxadiazine-4,7(3H,6H)-dione

ID-7

(3R,6S,9aS)-1-((E)-3-(5-hydroxybenzo[d]thiazol-2-yl)acryloyl)-8-((S)-1-(4-hydroxybutyl)pyrrolidin-3-yl)-3-isobutyl-6-neopentyltetrahydropyrazino[2,1-c][1,2,4]oxadiazine-4,7(3H,6H)-dione

ID-8

(3R,6S,9aS)-1-((E)-3-(5-hydroxybenzo[d]thiazol-2-yl)acryloyl)-8-(1-(4-hydroxybutyl)azetidin-3-yl)-3-isobutyl-6-neopentyltetrahydropyrazino[2,1-c][1,2,4]oxadiazine-4,7(3H,6H)-dione

ID-9

(3R,6S,9aS)-8-((S)-1-(4-hydroxybutyl)pyrrolidin-3-yl)-1-((E)-3-(4-(6-hydroxyhex-1-yn-1-yl)thiazol-2-yl)acryloyl)-3-isobutyl-6-neopentyltetrahydropyrazino[2,1-c][1,2,4]oxadiazine-4,7(3H,6H)-dione ID-10
(3R,6S,9aS)-1-((E)-3-(4-(5-hydroxypent-1-yn-1-yl)thiazol-2-yl)acryloyl)-3-isobutyl-8-(1-isopropylpiperidin-4-yl)-6-neopentyltetrahydropyrazino[2,1-c][1,2,4]oxadiazine-4,7(3H,6H)-dione
ID-11
(3R,6S,9aS)-8-((R)-1-(4-hydroxybutyl)pyrrolidin-3-yl)-1-((E)-3-(4-(6-hydroxyhex-1-yn-1-yl)thiazol-2-yl)acryloyl)-3-isobutyl-6-neopentyltetrahydropyrazino[2,1-c][1,2,4]oxadiazine-4,7(3H,6H)-dione
ID-12
(3R,6S,9aS)-1-((E)-3-(5-hydroxybenzo[d]thiazol-2-yl)acryloyl)-8-((R)-1-(4-hydroxybutyl)pyrrolidin-3-yl)-3-isobutyl-6-neopentyltetrahydropyrazino[2,1-c][1,2,4]oxadiazine-4,7(3H,6H)-dione
ID-13
(3R,6S,9aS)-8-((R)-1-(4-hydroxybutyl)pyrrolidin-3-yl)-1-((E)-3-(4-(7-hydroxyhept-1-yn-1-yl)thiazol-2-yl)acryloyl)-3-isobutyl-6-neopentyltetrahydropyrazino[2,1-c][1,2,4]oxadiazine-4,7(3H,6H)-dione
ID-14
3-((3R,6S,9aS)-3,6-diisobutyl-4,7-dioxo-1-((E)-3-(pyridin-2-yl)acryloyl)hexahydropyrazino[2,1-c][1,2,4]oxadiazin-8 (1H)-yl)propanamide
ID-15
(3R,6S,9aS)-8-(1-benzoylpiperidin-4-yl)-3,6-diisobutyl-1-((E)-3-(pyridin-2-yl)acryloyl)tetrahydropyrazino[2,1-c][1,2,4]oxadiazine-4,7(3H,6H)-dione
ID-16
(3R,6S,9aS)-3,6-diisobutyl-8-(piperidin-4-yl)-1-((E)-3-(pyridin-2-yl)acryloyl)tetrahydropyrazino[2,1-c][1,2,4]oxadiazine-4,7(3H,6H)-dione
ID-17
3-((3R,6S,9aS)-3,6-diisobutyl-4,7-dioxo-1-((E)-3-(thiazol-2-yl)acryloyl)hexahydropyrazino[2,1-c][1,2,4]oxadiazin-8(1H)-yl)propanamide
ID-18
3-((3R,6S,9aS)-3,6-diisobutyl-4,7-dioxo-1-((E)-3-(pyridin-2-yl)acryloyl)hexahydropyrazino[2,1-c][1,2,4]oxadiazin-8 (1H)-yl)—N-methylpropanamide
ID-19
(3R,6S,9aS)-3,6-diisobutyl-8-(3-(methylamino)propyl)-1-((E)-3-(pyridin-2-yl)acryloyl)hexahydropyrazino[2,1-c][1,2,4]oxadiazin-4(3H)-one
ID-20
3-((3R,6S,9aS)-3,6-diisobutyl-4,7-dioxo-1-((E)-3-(quinolin-2-yl)acryloyl)hexahydropyrazino[2,1-c][1,2,4]oxadiazin-8 (1H)-yl)propanamide
ID-21
(3R,6S,9aS)-3,6-diisobutyl-8-(3-oxo-3-(piperazin-1-yl)propyl)-1-((E)-3-(pyridin-2-yl)acryloyl)tetrahydropyrazino[2,1-c][1,2,4]oxadiazine-4,7 (3H, 6H)-dione
ID-22
3-((3R,6S,9aS)-3,6-diisobutyl-1-((E)-3-(1-methyl-1H-indazol-3-yl)acryloyl)-4,7-dioxohexahydropyrazino[2,1-c][1,2,4]oxadiazin-8(1H)-yl)propanamide
ID-23
3-((3R,6S,9aS)-1-((E)-3-(benzo[d]thiazol-2-yl)acryloyl)-3,6-diisobutyl-4,7-dioxohexahydropyrazino[2,1-c][1,2,4]oxadiazin-8(1H)-yl)propanamide
ID-24
3-((3R,6S,9aS)-3,6-diisobutyl-1-((E)-3-(naphthalen-2-yl)acryloyl)-4,7-dioxohexahydropyrazino[2,1-c][1,2,4]oxadiazin-8(1H)-yl)propanamide
ID-25
(3R,6S,9aS)-3,8-bis(cyclohexylmethyl)-6-neopentyl-1-((E)-3-(quinoxalin-2-yl)acryloyl)tetrahydropyrazino[2,1-c][1,2,4]oxadiazine-4,7(3H,6H)-dione
ID-26
(3R,6S,9aS)-3-(cyclohexylmethyl)-6-neopentyl-8-(piperidin-4-ylmethyl)-1-((E)-3-(quinoxalin-2-yl)acryloyl)tetrahydropyrazino[2,1-c][1,2,4]oxadiazine-4,7(3H,6H)-dione
ID-27
3-((3R,6S,9aS)-3,6-diisobutyl-4,7-dioxo-1-((E)-3-(pyridin-2-yl)acryloyl)hexahydropyrazino[2,1-c][1,2,4]oxadiazin-8 (1H)-yl)—N-(thiazol-2-yl)propanamide
ID-28
3-((3R,6S,9aS)-3,6-diisobutyl-4,7-dioxo-1-((E)-3-(pyridin-2-yl)acryloyl)hexahydropyrazino[2,1-c][1,2,4]oxadiazin-8(1H)-yl)—N-methoxypropanamide
ID-29
3-((3R,6S,9aS)-1-((E)-3-(5-cyclopropyl-1,3,4-thiadiazol-2-yl)acryloyl)-3,6-diisobutyl-4,7-dioxohexahydropyrazino[2,1-c][1,2,4]oxadiazin-8(1H)-yl)propanamide
ID-30
3-((3R,6S,9aS)-3,6-diisobutyl-4,7-dioxo-1-((E)-3-(quinoxalin-5-yl)acryloyl)hexahydropyrazino[2,1-c][1,2,4]oxadiazin-8 (1H)-yl)propanamide
ID-31
3-((3R,6S,9aS)-1-((E)-3-(1,8-naphthyridin-2-yl)acryloyl)-3,6-diisobutyl-4,7-dioxohexahydropyrazino[2,1-c][1,2,4]oxadiazin-8(1H)-yl)propanamide
ID-32
3-((3R,6S,9aS)-3,6-diisobutyl-4,7-dioxo-1-((E)-3-(thiazolo[5,4-b]pyridin-2-yl)acryloyl)hexahydropyrazino[2,1-c][1,2,4]oxadiazin-8(1H)-yl)propanamide
ID-33
ethyl 2-((E)-3-((3R,6S,9aS)-8-(3-amino-3-oxopropyl)-3,6-diisobutyl-4,7-dioxohexahydropyrazino[2,1-c][1,2,4]oxadiazin-1(6H)-yl)-3-oxoprop-1-en-1-yl)thiazole-5-carboxylate
ID-34
3-((3R,6S,9aS)-1-((E)-3-(4,5-dimethylthiazol-2-yl)acryloyl)-3,6-diisobutyl-4,7-dioxohexahydropyrazino[2,1-c][1,2,4]oxadiazin-8(1H)-yl)propanamide
ID-35
(3R,6S,9aS)-3,6-diisobutyl-8-(3-(methyl(1-methylpiperidin-4-yl)amino)propyl)-1-((E)-3-(pyridin-2-yl)acryloyl)hexahydropyrazino[2,1-c][1,2,4]oxadiazin-4(3H)-one
ID-36
(3R,6S,9aS)-3,6-diisobutyl-1-((E)-3-(pyridin-2-yl)acryloyl)-8-(1-(pyrimidin-2-ylmethyl)piperidin-4-yl)tetrahydropyrazino[2,1-c][1,2,4]oxadiazine-4,7(3H,6H)-dione
ID-37
3-((3R,6S,9aS)-3,6-diisobutyl-4,7-dioxo-1-((E)-3-(4,5,6,7-tetrahydrobenzo[d]thiazol-2-yl)acryloyl)hexahydropyrazino[2,1-c][1,2,4]oxadiazin-8 (1H)-yl)propanamide
ID-38
(3R,6S,9aS)-3,6-diisobutyl-8-(1-methylpiperidin-4-yl)-1-((Z)-3-phenylacryloyl)tetrahydropyrazino[2,1-c][1,2,4]oxadiazine-4,7 (3H, 6H)-dione
ID-39
(3R,6S,9aS)-1-cinnamoyl-3,6-diisobutyl-8-(1-methylpiperidin-4-yl)tetrahydropyrazino[2,1-c][1,2,4]oxadiazine-4,7 (3H, 6H)-dione
ID-40
(3R,6S,9aS)-3,6-diisobutyl-8-(1'-isopropyl-[1,4'-bipiperidin]-4-yl)-1-((E)-3-(pyridin-2-yl)acryloyl)tetrahydropyrazino[2,1-c][1,2,4]oxadiazine-4,7(3H,6H)-dione ID-41
(3R,6S,9aS)-8-(1'-acetyl-[1,4'-bipiperidin]-4-yl)-3,6-diisobutyl-1-((E)-3-(pyridin-2-yl)acryloyl)tetrahydropyrazino[2,1-c][1,2,4]oxadiazine-4,7(3H,6H)-dione ID-42
3-((3R,6S,9aS)-3,6-diisobutyl-1-((E)-3-((S)-1-methylpyrrolidin-2-yl)acryloyl)-4,7-dioxohexahydropyrazino[2,1-c][1,2,4]oxadiazin-8(1H)-yl)propanamide ID-43
3-((3R,6S,9aS)-3,6-diisobutyl-1-((E)-3-((R)-1-methylpyrrolidin-2-yl)acryloyl)-4,7-dioxohexahydropyrazino[2,1-c][1,2,4]oxadiazin-8 (1H)-yl)propanamide ID-44
(3R,6S,9aS)-3,6-diisobutyl-1-((E)-3-(1-methyl-1H-pyrazol-5-yl)acryloyl)-8-(1-methylpiperidin-4-yl)tetrahydropyrazino[2,1-c][1,2,4]oxadiazine-4,7(3H,6H)-dione ID-45
(3R,6S,9aS)-8-(1-acetylpiperidin-4-yl)-1-((E)-3-(benzo[d]thiazol-2-yl)acryloyl)-3,6-diisobutyltetrahydropyrazino[2,1-c][1,2,4]oxadiazine-4,7(3H,6H)-dione ID-46
(3R,6S,9aS)-1-((E)-3-(benzo[d]oxazol-2-yl) acryloyl)-3,6-diisobutyl-8-(1-methylpiperidin-4-yl)tetrahydropyrazino[2,1-c][1,2,4]oxadiazine-4,7(3H,6H)-dione ID-47
(3R,6S,9aS)-1-((Z)-2-chloro-3-(pyridin-2-yl)acryloyl)-3,6-diisobutyl-8-(1-methylpiperidin-4-yl)tetrahydropyrazino[2,1-c][1,2,4]oxadiazine-4,7(3H,6H)-dione ID-48
2-((E)-3-((3R,6S,9aS)-3,6-diisobutyl-8-(1-methylpiperidin-4-yl)-4,7-dioxohexahydropyrazino[2,1-c][1,2,4]oxadiazin-1(6H)-yl)-3-oxoprop-1-en-1-yl)isonicotinonitrile ID-49
(3R,6S,9aS)-1-((E)-3-(6,7-dihydro-4H-pyrazolo[5,1-c][1,4]oxazin-2-yl)acryloyl)-3,6-diisobutyl-8-(1-methylpiperidin-4-yl)tetrahydropyrazino[2,1-c][1,2,4]oxadiazine-4,7(3H, 6H)-dione ID-50
(3R,6S,9aS)-1-((E)-3-(benzo[d]thiazol-2-yl)acryloyl)-8-(1-(5-fluoropyrimidine-2-carbonyl)piperidin-4-yl)-3,6-diisobutyltetrahydropyrazino[2,1-c][1,2,4]oxadiazine-4,7(3H,6H)-dione ID-51
(3R,6S,9aS)-3,6-diisobutyl-8-(1-methylpiperidin-4-yl)-1-((E)-3-(6-oxo-1,6-dihydropyridin-2-yl)acryloyl)tetrahydropyrazino[2,1-c][1,2,4]oxadiazine-4,7(3H,6H)-dione ID-52
(3R,6S,9aS)-1-((E)-3-(5-fluorobenzo[d]thiazol-2-yl)acryloyl)-3,6-diisobutyl-8-(1-methylpiperidin-4-yl)tetrahydropyrazino[2,1-c][1,2,4.]oxadiazine-4,7(3H,6H)-dione ID-53
(3R,6S,9aS)-3,6-diisobutyl-8-(1-methylpiperidin-4-yl)-1-((E)-3-(oxazol-2-yl)acryloyl)tetrahydropyrazino[2,1-c][1,2,4]oxadiazine-4,7(3H,6H)-dione ID-54
(3R,6S,9aS)-3,6-diisobutyl-8-(1-methylpiperidin-4-yl)-1-((E)-3-(thiazol-4-yl)acryloyl)tetrahydropyrazino[2,1-c][1,2,4]oxadiazine-4,7(3H,6H)-dione ID-55
(3R,6S,9aS)-1-((E)-3-(5-chloropyrimidin-2-yl)acryloyl)-3,6-diisobutyl-8-(1-methylpiperidin-4-yl)tetrahydropyrazino[2,1-c][1,2,4]oxadiazine-4,7(3H,6H)-dione ID-56
(3R,6S,9aS)-3,6-diisobutyl-8-(1-methylpiperidin-4-yl)-1-((E)-3-(2-morpholinothiazol-4-yl)acryloyl)tetrahydropyrazino[2,1-c][1,2,4]oxadiazine-4,7 (3H, 6H)-dione ID-57
(3R,6S,9aS)-6-(4-(benzylamino)butyl)-3-isobutyl-8-(1-methylpiperidin-4-yl)-1-((E)-3-(pyridin-2-yl)acryloyl)tetrahydropyrazino[2,1-c][1,2,4]oxadiazine-4,7(3H,6H)-dione ID-58
(4S,11aS)-11-((E)-3-(benzo[d]thiazol-2-yl)acryloyl)-4-isobutyl-2-(1-methylpiperidin-4-yl)-1,2,11,11a-tetrahydro-6H-pyrazino[2,1-b]quinazoline-3,6(4H)-dione ID-59
tert-butyl 4-((4-((4S,11aS)-11-((E)-3-(benzo[d]thiazol-2-yl)acryloyl)-8-fluoro-2-(1-methylpiperidin-4-yl)-3,6-dioxo-1,3,4,6,11,11a-hexahydro-2H-pyrazino[2,1-b]quinazolin-4-yl)butyl)(methyl)amino)piperidine-1-carboxylate ID-60
(3R,6S,9aS)-1-((E)-3-(benzo[d]thiazol-2-yl)acryloyl)-3-isobutyl-8-(1-methylpiperidin-4-yl)-6-(2-(methylthio)ethyl)tetrahydropyrazino[2,1-c][1,2,4]oxadiazine-4,7(3H,6H)-dione ID-61
(3R,6S,9aS)-6-(4-hydroxybenzyl)-3-isobutyl-8-(1-methylpiperidin-4-yl)-1-((E)-3-(pyridin-2-yl)acryloyl)tetrahydropyrazino[2,1-c][1,2,4]oxadiazine-4,7(3H,6H)-dione ID-62
(3R,6S,9aS)-3,6-diisobutyl-1-((E)-3-(pyridin-2-yl)acryloyl)-8-(1-(tetrahydro-2H-pyran-4-yl)piperidin-4-yl)tetrahydropyrazino[2,1-c][1,2,4]oxadiazine-4,7(3H,6H)-dione ID-63
(3R,6S,9aS)-8-(1-cyclohexylpiperidin-4-yl)-3,6-diisobutyl-1-((E)-3-(pyridin-2-yl)acryloyl)tetrahydropyrazino[2,1-c][1,2,4]oxadiazine-4,7(3H,6H)-dione ID-64
(3R,6S,9aS)-1-((E)-3-(benzo[d]thiazol-2-yl)acryloyl)-3,6-diisobutyl-8-(tetrahydro-2H-pyran-4-yl)tetrahydropyrazino[2,1-c][1,2,4]oxadiazine-4,7(3H,6H)-dione ID-65
(3R,6S,9aS)-3,6-diisobutyl-8-(1-methylpiperidin-3-yl)-1-((E)-3-(pyridin-2-yl)acryloyl)tetrahydropyrazino[2,1-c][1,2,4]oxadiazine-4,7(3H,6H)-dione ID-66
(3R,6S,9aS)-6-benzyl-3-isobutyl-8-(1-methylpiperidin-4-yl)-1-((E)-3-(pyridin-2-yl)acryloyl)tetrahydropyrazino[2,1-c][1,2,4]oxadiazine-4,7(3H,6H)-dione ID-67
(3R,6S,9aS)-3,6-diisobutyl-8-(1-methylazepan-4-yl)-1-((E)-3-(pyridin-2-yl)acryloyl)tetrahydropyrazino[2,1-c][1,2,4]oxadiazine-4,7(3H,6H)-dione ID-68
(3R,6S,9aS)-8-(4-aminocyclohexyl)-3,6-diisobutyl-1-((E)-3-(pyridin-2-yl)acryloyl)tetrahydropyrazino[2,1-c][1,2,4]oxadiazine-4,7(3H,6H)-dione ID-69
(3R,6S,9aS)-8-(4-(dimethylamino)cyclohexyl)-3,6-diisobutyl-1-((E)-3-(pyridin-2-yl)acryloyl)tetrahydropyrazino[2,1-c][1,2,4]oxadiazine-4,7(3H,6H)-dione ID-70
(3R,6S,9aS)-3,6-diisobutyl-8-(8-methyl-8-azabicyclo[3.2.1]octan-3-yl)-1-((E)-3-(pyridin-2-yl)acryloyl)tetrahydropyrazino[2,1-c][1,2,4]oxadiazine-4,7(3H,6H)-dione ID-71
(3R,6S,9aS)-3,6-diisobutyl-8-(1-methylpiperidin-4-yl)-1-((E)-3-(5-(trifluoromethyl)pyridin-2-yl)acryloyl)tetrahydropyrazino[2,1-c][1,2,4]oxadiazine-4,7(3H,6H)-dione ID-72
(3R,6S,9aS)-3,6-diisobutyl-1-((E)-3-(5-methoxypyridin-2-yl)acryloyl)-8-(1-methylpiperidin-4-yl)tetrahydropyrazino[2,1-c][1,2,4]oxadiazine-4,7(3H,6H)-dione ID-73
(3R,6S,9aS)-1-((E)-3-(benzo[d]thiazol-2-yl)acryloyl)-3-isobutyl-8-(1-isopropylpiperidin-4-yl)-6-neopentyltetrahydropyrazino[2,1-c][1,2,4]oxadiazine-4,7(3H,6H)-dione ID-74
(3R,6S,9aS)-1-((E)-3-(benzo[d]thiazol-2-yl)acryloyl)-3-isobutyl-8-(1-methylpiperidin-4-yl)-6-(2-(methylsulfonyl)ethyl)tetrahydropyrazino[2,1-c][1,2,4]oxadiazine-4,7(3H,6H)-dione ID-75
(3R,6S,9aS)-8-(1-(3-aminopropyl)piperidin-4-yl)-1-((E)-3-(benzo[d]thiazol-2-yl)acryloyl)-3-isobutyl-6-neopentyltetrahydropyrazino[2,1-c][1,2,4]oxadiazine-4,7(3H,6H)-dione ID-76
4-(4-((3R,6S,9aS)-1-((E)-3-(benzo[d]thiazol-2-yl)acryloyl)-3-isobutyl-6-neopentyl-4,7-dioxohexahydropyrazino[2,1-c][1,2,4]oxadiazin-8 (1H)-yl)piperidin-1-yl)butanoic acid ID-77
(3R,6S,9aS)-1-((E)-3-(benzo[d]thiazol-2-yl)acryloyl)-8-(1-(2-(2-hydroxyethoxy)ethyl)piperidin-4-yl)-3-isobutyl-6-neopentyltetrahydropyrazino[2,1-c][1,2,4]oxadiazine-4,7(3H,6H)-dione ID-78
(3R,6S,9aS)-8-((S)-1-(4-hydroxybutyl)pyrrolidin-3-yl)-3-isobutyl-1-((E)-3-(2-(methylthio)pyrimidin-4-yl)acryloyl)-6-neopentyltetrahydropyrazino[2,1-c][1,2,4]oxadiazine-4,7(3H,6H)-dione ID-79
(3R,6S,9aS)-1-((E)-3-(benzo[d]thiazol-2-yl)acryloyl)-8-(1-(3-hydroxypropyl)piperidin-4-yl)-3-isobutyl-6-neopentyltetrahydropyrazino[2,1-c][1,2,4]oxadiazine-4,7(3H,6H)-dione ID-80
(3R,6S,9aS)-8-(1-(4-hydroxybutyl)piperidin-4-yl)-1-((E)-3-(5-(3-hydroxyphenyl)pyridin-2-yl)acryloyl)-3-isobutyl-6-neopentyltetrahydropyrazino[2,1-c][1,2,4]oxadiazine-4,7(3H,6H)-dione ID-81
(3R,6S,9aS)-1-((E)-3-(4-ethynylthiazol-2-yl)acryloyl)-8-((S)-1-(4-hydroxybutyl)pyrrolidin-3-yl)-3-isobutyl-6-neopentyltetrahydropyrazino[2,1-c][1,2,4]oxadiazine-4,7(3H,6H)-dione ID-82
(3R,6S,9aS)-8-((S)-1-(4-hydroxybutyl)pyrrolidin-3-yl)-3-isobutyl-6-neopentyl-1-((E)-3-(4-(pyridin-3-yl)thiazol-2-yl)acryloyl)tetrahydropyrazino[2,1-c][1,2,4]oxadiazine-4,7 (3H, 6H)-dione ID-83
(3R,6S,9aS)-1-((E)-3-(benzo[d]thiazol-2-yl)acryloyl)-8-(1-(4-hydroxy-3-(hydroxymethyl)butyl)piperidin-4-yl)-3-isobutyl-6-neopentyltetrahydropyrazino[2,1-c][1,2,4]oxadiazine-4,7(3H,6H)-dione ID-84
(3R,6S,9aS)-1-((E)-3-(benzo[d]thiazol-2-yl)acryloyl)-8-(1-(4-hydroxybutyl)azetidin-3-yl)-3-isobutyl-6-neopentyltetrahydropyrazino[2,1-c][1,2,4]oxadiazine-4,7(3H,6H)-dione ID-85
(3R,6S,9aS)-1-((E)-3-(4-hydroxybenzo[d]thiazol-2-yl)acryloyl)-8-((S)-1-(4-hydroxybutyl)pyrrolidin-3-yl)-3-isobutyl-6-neopentyltetrahydropyrazino[2,1-c][1,2,4]oxadiazine-4,7(3H,6H)-dione ID-86
(2R,5S,8aR)-1-((E)-3-(benzo[d]thiazol-2-yl)acryloyl)-5-benzyl-2-isobutyl-7-(1-methylpiperidin-4-yl)tetrahydroimidazo[1,2-a]pyrazine-3,6(2H,5H)-dione ID-87
(3R,6S,9aS)-1-((E)-3-(4-((1-aminocyclopropyl)ethynyl)thiazol-2-yl)acryloyl)-8-((S)-1-(4-hydroxybutyl)pyrrolidin-3-yl)-3-isobutyl-6-neopentyltetrahydropyrazino[2,1-c][1,2,4]oxadiazine-4,7(3H,6H)-dione ID-88
(3R,6S,9aS)-1-((E)-3-(4-(3-(dimethylamino)prop-1-yn-1-yl)thiazol-2-yl)acryloyl)-8-((S)-1-(4-hydroxybutyl)pyrrolidin-3-yl)-3-isobutyl-6-neopentyltetrahydropyrazino[2,1-c][1,2,4]oxadiazine-4,7(3H,6H)-dione ID-89
(3R,6S,9aS)-1-((E)-3-(5-ethynylthiazol-2-yl)acryloyl)-8-((S)-1-(4-hydroxybutyl)pyrrolidin-3-yl)-3-isobutyl-6-neopentyltetrahydropyrazino[2,1-c][1,2,4]oxadiazine-4,7(3H,6H)-dione ID-90
(3R,6S,9aS)-3-(cyclohexylmethyl)-8-((R)-1-(4-hydroxybutyl)pyrrolidin-3-yl)-6-neopentyl-1-((E)-3-(quinoxalin-2-yl)acryloyl)tetrahydropyrazino[2,1-c][1,2,4]oxadiazine-4,7(3H,6H)-dione ID-91
(3R,6S,9aS)-8-(1-(4-hydroxybutyl)azetidin-3-yl)-1-((E)-3-(4-(7-hydroxyhept-1-yn-1-yl)thiazol-2-yl)acryloyl)-3-isobutyl-6-neopentyltetrahydropyrazino[2,1-c][1,2,4]oxadiazine-4,7(3H,6H)-dione ID-92
(3R,6S,9aS)-8-(1-(4-hydroxybutyl)azetidin-3-yl)-1-((E)-3-(4-(6-hydroxyhex-1-yn-1-yl)thiazol-2-yl)acryloyl)-3-isobutyl-6-neopentyltetrahydropyrazino[2,1-c][1,2,4]oxadiazine-4,7(3H,6H)-dione ID-93
6-(2-((E)-3-((3R,6S,9aS)-8-((S)-1-(4-hydroxybutyl)pyrrolidin-3-yl)-3-isobutyl-6-neopentyl-4,7-dioxohexahydropyrazino[2,1-c][1,2,4]oxadiazin-1(6H)-yl)-3-oxoprop-1-en-1-yl)thiazol-4-yl)—N-methylhex-5-ynamide ID-94
(3R,6S,9aS)-8-((R)-1-(4-hydroxybutyl)pyrrolidin-3-yl)-3-isobutyl-6-neopentyl-1-((E)-3-(4-((tetrahydro-2H-pyran-4-yl)ethynyl)thiazol-2-yl)acryloyl)tetrahydropyrazino[2,1-c][1,2,4]oxadiazine-4,7-(3H,6H)-dione ID-95
(3S,6S,9aR)-1-((E)-3-(benzo[d]thiazol-2-yl)acryloyl)-8-((R)-1-(4-hydroxybutyl)pyrrolidin-3-yl)-3-isobutyl-6-neopentyltetrahydropyrazino[2,1-c][1,2,4]oxadiazine-4,7(3H,6H)-dione ID-96
(3S,6S,9aR)-1-((E)-3-(benzo[d]thiazol-2-yl)acryloyl)-8-((R)-1-(4-hydroxybutyl)pyrrolidin-3-yl)-3-isobutyl-6-neopentylhexahydro-4H-pyrazino[1,2-a]pyrimidine-4,7(6H)-dione ID-97
(3R,6S,9aS)-1-((E)-3-(4-(3-(2-hydroxyethoxy)prop-1-yn-1-yl)thiazol-2-yl)acryloyl)-3-isobutyl-8-(1-isopropylpiperidin-4-yl)-6-neopentyltetrahydropyrazino[2,1-c][1,2,4]oxadiazine-4,7 (3H, 6H)-dione ID-98
(3R,6S,9aS)-1-((E)-3-(5-hydroxybenzo[d]thiazol-2-yl)acryloyl)-3-isobutyl-8-(1-isopropylpiperidin-4-yl)-6-neopentyltetrahydropyrazino[2,1-c][1,2,4]oxadiazine-4,7(3H,6H)-dione
ID-99
(3R,6S,9aS)-3-(cyclopropylmethyl)-1-((E)-3-(4-(6-hydroxyhex-1-yn-1-yl)thiazol-2-yl)acryloyl)-8-(1-isopropylpiperidin-4-yl)-6-neopentyltetrahydropyrazino[2,1-c][1,2,4]oxadiazine-4,7(3H,6H)-dione
ID-100
(3R,6S,9aS)-1-((E)-3-(5-ethynyl-4-(5-hydroxypent-1-yn-1-yl)thiazol-2-yl)acryloyl)-3-isobutyl-8-(1-isopropylpiperidin-4-yl)-6-neopentyltetrahydropyrazino[2,1-c][1,2,4]oxadiazine-4,7(3H,6H)-dione
ID-101
(3R,6S,9aS)-1-((E)-3-(5-(3-hydroxypropoxy)benzo[d]thiazol-2-yl)acryloyl)-3-isobutyl-8-(1-isopropylpiperidin-4-yl)-6-neopentyltetrahydropyrazino[2,1-c][1,2,4]oxadiazine-4,7(3H,6H)-dione
ID-102
(3R,6S,9aS)-8-(1-cyclopropylpiperidin-4-yl)-1-((E)-3-(4-(5-hydroxypent-1-yn-1-yl)thiazol-2-yl)acryloyl)-3-isobutyl-6-neopentyltetrahydropyrazino[2,1-c][1,2,4]oxadiazine-4,7(3H,6H)-dione
ID-103
(3R,6S,9aS)-1-((E)-3-(5-ethynyl-4-(5-hydroxypent-1-yn-1-yl)thiazol-2-yl)acryloyl)-3-isobutyl-8-(1-methylpiperidin-4-yl)-6-neopentyltetrahydropyrazino[2,1-c][1,2,4]oxadiazine-4,7 (3H, 6H)-dione
ID-104
(3R,6S,9aS)-1-((E)-3-(benzo[d]thiazol-2-yl)acryloyl)-8-((R)-1-(4-hydroxybutyl)pyrrolidin-3-yl)-6-neopentyl-3-(((1R,2S)-2-phenethylcyclopropyl)methyl)tetrahydropyrazino[2,1-c][1,2,4]oxadiazine-4,7(3H,6H)-dione
ID-105
benzyl (4-((3R,6S,9aS)-8-((R)-1-(4-hydroxybutyl)pyrrolidin-3-yl)-6-neopentyl-4,7-dioxo-1-((E)-3-(quinoxalin-2-yl)acryloyl)octahydropyrazino[2,1-c][1,2,4]oxadiazin-3-yl)butyl)carbamate
ID-106
(3R,6S,9aS)-3-(cyclohexylmethyl)-8-(1-isopropylpiperidin-4-yl)-6-neopentyl-1-((E)-3-(quinoxalin-2-yl)acryloyl)tetrahydropyrazino[2,1-c][1,2,4]oxadiazine-4,7(3H,6H)-dione
ID-107
(3R,6S,9aS)-3-(2-ethylbutyl)-8-((R)-1-(4-hydroxybutyl)pyrrolidin-3-yl)-6-neopentyl-1-((E)-3-(quinoxalin-2-yl)acryloyl)tetrahydropyrazino[2,1-c][1,2,4]oxadiazine-4,7(3H,6H)-dione

Experimental Example: MTS Assay on Panc-1 (Human Pancreas Carcinoma Cell Line)

(Materials and Methods)

1. Cell
   - cell line name: PANC-1
   - derived from: human pancreas glandular cancer
   - purchased from: ATCC
   - product code: CRL-1469
2. Cell Culture 2.1 Reagent for Cell Culture D-MEM (High Glucose) with L-Glutamine and Phenol Red (Wako, Cat. No.: 044-29765)

Fetal Bovine Serum (FBS; Life Technologies, Cat. No.: 26140-079) penicillin-streptomycin solution (×100) (Wako, Cat. No.: 168-23191)

10×D-PBS (-) (Wako, Cat. No.: 048-29805)

0.25 w/v % Trypsin-1 mmol/l EDTA·4Na Solution with Phenol Red (Wako, Cat. No.: 201-16945)

2.2 Culture Conditions

Respective cells were cultured under the following conditions. Where necessary, they were passaged.

proliferation medium: D-MEM+10% FBS culture environment: 37° C., 5% $CO_2$ seeding density: $5.0\times10^5$ cells/25 $cm^2$ 2.3 Measurement Sample solvent control substance: DMSO (HYBRI-MAX®, Sigma-Aldrich Corp.)

test substance: Example compound (ID-1-ID-13)

A DMSO solution of the test substance was prepared by serially diluting (common ratio 2) each test substance with DMSO.

2.4 Measurement and Analysis

A solvent control substance sample and a test substance sample were exposed to a human pancreatic cancer-derived cell line (PANC-1), and the survival rate of the cell 6 days later was measured by the MTS method. The measurement was performed 3 times and the average thereof was adopted. The survival rate of the cell in each test substance sample was calculated by the following formula 1 with the value at exposure of the solvent control substance sample as 100% survival rate.

$$\text{survival rate (\%)} = 100\times\text{absorbance of each test substance sample/absorbance of solvent control substance sample} \quad \text{formula 1}$$

Normalized values calculated by the following formula 2 from the absorbances of each sample at 492 nm and 630 nm and the absorbances of the blank were used as the absorbances in the above-mentioned formula 1.

$$\text{normalized value } (ABS492\text{ nm}-630\text{ nm}) = (ABSsa\ 492\text{ nm}-ABSsa\ 630\text{ nm})-(ABSbl\ 492\text{ nm}-ABSbl\ 630\text{ nm})$$

*ABSsa* 492: absorbance of each sample at wavelength 492 nm

*ABSsa* 630: absorbance of each sample at wavelength 630 nm

*ABSbl* 492: absorbance of blank corresponding to each sample at wavelength 492 nm

*ABSbl* 630: absorbance of blank corresponding to each sample at wavelength 630 nm The analysis was performed by using nplr package on R (The R Foundation for Statistical Computing) and estimating the logistic regression curve (4-parameter).

The results are shown in Table 14.

TABLE 14

| Compound | $IC_{50}$ | Growth inhibition (%) | | | | | | | |
|---|---|---|---|---|---|---|---|---|---|
| ID | (µM) | 0.15625 µM | 0.3125 µM | 0.625 µM | 1 µM | 1.25 µM | 2.5 µM | 10 µM | 30 µM |
| ID-1 | 4.1 | | | | | | | | |
| ID-2 | 0.27 | | | | | | | | |
| ID-3 | 0.34 | | | | | | | | |
| ID-4 | 0.21 | | | | | | | | |
| ID-5 | 0.18 | | | | | | | | |
| ID-6 | 0.13 | | | | | | | | |
| ID-7 | 0.070 | | | | | | | | |
| ID-8 | 0.063 | | | | | | | | |
| ID-9 | 0.099 | | | | | | | | |
| ID-10 | 0.048 | | | | | | | | |
| ID-11 | 0.14 | | | | | | | | |
| ID-12 | 0.060 | | | | | | | | |
| ID-13 | 0.14 | | | | | | | | |
| ID-14 | 17.8 | | | | | | | | |
| ID-15 | 5.8 | | | | | | | | 99.9 |
| ID-16 | 4.7 | | | | | | | | 100.2 |
| ID-17 | 11.4 | | | | | | | | 100.0 |
| ID-18 | 15.9 | | | | | | | | 96.4 |
| ID-19 | 10.2 | | | | | | | | 99.7 |
| ID-20 | 2.4 | | | | | | | | 100.1 |
| ID-21 | 19.8 | | | | | | | | 99.5 |
| ID-22 | 15.6 | | | | | | | | 95.4 |
| ID-23 | 0.77 | | | | | | | | 102.4 |
| ID-24 | 15.8 | | | | | | | | 101.8 |
| ID-25 | | | | 4.7 | 6.0 | | | | 98.5 |
| ID-26 | | | | 4.2 | 96.1 | | | | |
| ID-27 | 8.6 | | | | | | | | 99.3 |
| ID-28 | 16.2 | | | | | | | | 96.2 |
| ID-29 | 2.3 | | | | | | | 100.7 | |
| ID-30 | | | | | | | | 58.4 | |
| ID-31 | 2.7 | | | | | | | 99.3 | |
| ID-32 | 0.62 | | | | | | | 100.9 | |
| ID-33 | 1.1 | | | | | | | 99.9 | |
| ID-34 | 2.6 | | | | | | | 95.5 | |
| ID-35 | 5.0 | | | | | | | 99.0 | |
| ID-36 | | | | | | | | 76.0 | |
| ID-37 | 4.7 | | | | | | | 95.8 | |
| ID-38 | 8.0 | | | | | | | 82.6 | |
| ID-39 | 8.9 | | | | | | | 80.8 | |
| ID-40 | 4.0 | | | | | | | 102.2 | |
| ID-41 | 6.3 | | | | | | | 98.5 | |
| ID-42 | | | | | | | | 65.3 | |
| ID-43 | 9.4 | | | | | | | 78.5 | |
| ID-44 | | | | | | | | 94.7 | |
| ID-45 | 0.81 | | | | | | | 101.3 | |
| ID-46 | 1.4 | | | | | | | 99.1 | |
| ID-47 | 10.0 | | | | | | | 66.6 | |
| ID-48 | 0.58 | | | | | | | 100.4 | |
| ID-49 | | | | | | | | 74.9 | |
| ID-50 | 0.59 | | | | | | | 100.7 | |
| ID-51 | | | | | | | | 47.5 | |
| ID-52 | 0.48 | | | | | | | 100.6 | |
| ID-53 | 1.2 | | | | | | | 100.0 | |
| ID-54 | | | | | | | | 57.0 | |
| ID-55 | 0.46 | | | | | | | 99.8 | |
| ID-56 | | | | | | | | 95.3 | |
| ID-57 | 1.0 | | | | | | | 100.6 | |
| ID-58 | 0.56 | | | | 78.4 | | | | |
| ID-59 | 0.55 | | | | 98.8 | | | | |
| ID-60 | 0.27 | | | | | | | 93.7 | |
| ID-61 | 7.3 | | | | | | | | |
| ID-62 | 3.4 | | | | | | | | |
| ID-63 | 1.4 | | | | | | | | |
| ID-64 | 0.88 | | | | | | | | |
| ID-65 | 4.7 | | | | | | | 96.5 | |
| ID-66 | 5.2 | | | | | | | 96.7 | |
| ID-67 | 3.3 | | | | | | | 100.0 | |
| ID-68 | 2.8 | | | | | | | | |
| ID-69 | 2.8 | | | | | | | | |
| ID-70 | 2.5 | | | | | | | | |
| ID-71 | | | | | | | 97.3 | | |
| ID-72 | | | | | | | 37.0 | | |
| ID-73 | 0.14 | | 88.1 | | | | | | |
| ID-74 | | | 38.7 | | | | | | |

TABLE 14-continued

| Compound | $IC_{50}$ | Growth inhibition (%) | | | | | | | |
|---|---|---|---|---|---|---|---|---|---|
| ID | (μM) | 0.15625 μM | 0.3125 μM | 0.625 μM | 1 μM | 1.25 μM | 2.5 μM | 10 μM | 30 μM |
| ID-75 | 0.39 | | 19.9 | | | | | | |
| ID-76 | 1.6 | | | | | | | | |
| ID-77 | | | 55.2 | | | | | | |
| ID-78 | | | 41.5 | | | | | | |
| ID-79 | | | 72.2 | | | | | | |
| ID-80 | | | | 63.2 | | | | | |
| ID-81 | | | 69.6 | | | | | | |
| ID-82 | | | 48.6 | | | | | | |
| ID-83 | | | 46.5 | | | | | | |
| ID-84 | 0.11 | | 88.9 | | | | | | |
| ID-85 | 0.11 | 58.9 | | | | | | | |
| ID-86 | | | | | | 50.0 | | | |
| ID-87 | | | 54.5 | | | | | | |
| ID-88 | | | 38.0 | | | | | | |
| ID-89 | 0.18 | | 100.0 | | | | | | |
| ID-90 | 0.21 | | 66.0 | | 99.0 | | | | |
| ID-91 | 0.12 | | | | | | | | |
| ID-92 | 0.12 | | | | | | | | |
| ID-93 | | 37.4 | | | | | | | |
| ID-94 | | 42.3 | | | | | | | |
| ID-95 | 1.4 | | | | | | | | |
| ID-96 | | | −1.7 | | | | | 101.3 | |
| ID-97 | 0.15 | 51.0 | | | | | | | |
| ID-98 | | 61.7 | | | | | | | |
| ID-99 | | 61.1 | | | | | | | |
| ID-100 | | 99.8 | | | | | | | |
| ID-101 | | 65.6 | | | | | | | |
| ID-102 | | 36.9 | | | | | | | |
| ID-103 | | | 99.6 | | | | | | |
| ID-104 | | | 30.1 | | | | | | |
| ID-105 | | | | | | | | | 98.3 |
| ID-106 | | | 29.8 | | 100.7 | | | | |
| ID-107 | 0.20 | | 94.3 | | 98.5 | | | | |

INDUSTRIAL APPLICABILITY

The compound of the present invention inhibits cancer cell proliferation, and thus can be used for treating diseases such as cancer.

Although only some exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention.

This application is based on U.S. provisional patent application No. 63/052,587 (filing date: Jul. 16, 2020) filed in US, the contents of which are incorporated in full herein.

The invention claimed is:

1. A compound represented by the following formula (I):

(I)

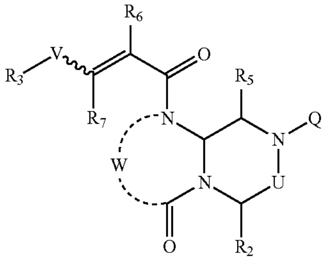

wherein

Q is a hydrogen atom or is represented by any of the following formulas (II-1) to (II-8):

II-1

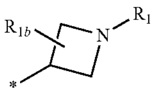

II-2

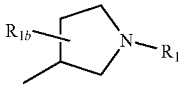

II-3

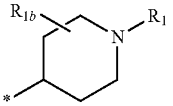

II-4

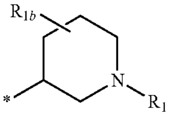

II-5

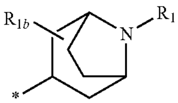

II-6

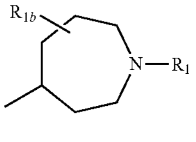

-continued

II-7

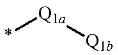

II-8

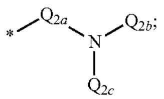

$R_1$ is a hydrogen atom, optionally substituted alkyl, optionally substituted cycloalkyl, optionally substituted heterocycloalkyl, optionally substituted aryl, optionally substituted heteroaryl, optionally substituted arylalkyl, optionally substituted heteroarylalkyl, optionally substituted cycloalkylalkyl, optionally substituted heterocycloalkylalkyl, or —(CO)—$R_{1a}$;

$R_{1a}$ is optionally substituted alkyl, optionally substituted alkoxy, optionally substituted aryl, or optionally substituted heteroaryl;

$R_{1b}$ is a hydrogen atom, or 1 to 3 same or different alkyls;

$Q_{1a}$ is a single bond, optionally substituted alkylene;

$Q_{1b}$ is a hydrogen atom, hydroxy, halogen, cyano, -$Q_{1c}$, —$COQ_{1c}$, —$CONQ_{1c}Q_{1d}$, $CONQ_{1c}$-$OQ_{1d}$, —$NQ_{1c}Q_{1d}$, or —$OQ_{1c}$;

$Q_{1c}$ is a hydrogen atom, optionally substituted alkyl, optionally substituted cycloalkyl, optionally substituted heterocycloalkyl, optionally substituted aryl, optionally substituted heteroaryl;

$Q_{1d}$ is a hydrogen atom or optionally substituted alkyl;

$Q_{2a}$ is optionally substituted cycloalkylene;

$Q_{2b}$ and $Q_{2c}$ are the same or different and each is a hydrogen atom or optionally substituted alkyl;

U is —CO— or —$CH_2$—;

$R_2$ is a hydrogen atom, optionally substituted alkyl, optionally substituted alkenyl, optionally substituted alkynyl, optionally substituted arylalkyl, optionally substituted heteroarylalkyl, optionally substituted cycloalkylalkyl, or —X—$N(R_{2a})(R_{2b})$;

X is an alkylene group;

$R_{2a}$ and $R_{2b}$ are the same or different and each is a hydrogen atom, optionally substituted alkyl, optionally substituted cycloalkyl, optionally substituted heterocycloalkyl, optionally substituted aryl, optionally substituted heteroaryl, optionally substituted arylalkyl, optionally substituted heteroarylalkyl, or optionally substituted cycloalkylalkyl;

V is an optionally substituted aryl ring, an optionally substituted heteroaryl ring, an optionally substituted partially saturated heteroaryl ring, or an optionally substituted heterocycloalkyl ring;

$R_3$ is a hydrogen atom, hydroxy, halogen, cyano, optionally substituted alkyl, optionally substituted cycloalkyl, optionally substituted heterocycloalkyl, optionally substituted aryl, optionally substituted heteroaryl, —C≡C—$R_{3a}$ or —$COOR_{3b}$;

$R_{3a}$ is a hydrogen atom, optionally substituted alkyl, optionally substituted cycloalkyl, optionally substituted heterocycloalkyl, or optionally substituted heteroaryl, $R_{3b}$ is a hydrogen atom or optionally substituted alkyl,

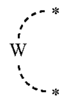

is represented by any of the following formulas (III-1) to (III-4):

(III-1)

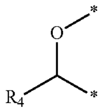

(III-2)

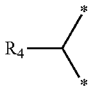

(III-3)

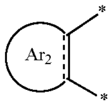

(III-4)

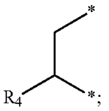

$R_4$ is a hydrogen atom, optionally substituted alkyl, optionally substituted alkenyl, optionally substituted alkynyl, optionally substituted arylalkyl, optionally substituted heteroarylalkyl, optionally substituted cycloalkylalkyl, or optionally substituted heterocycloalkylalkyl, and $Ar_2$ is an optionally substituted aryl ring or an optionally substituted heteroaryl ring; and $R_5$ is a hydrogen atom, or optionally substituted alkyl; and $R_6$ and $R_7$ are the same or different and each is a hydrogen atom or halogen, or a pharmaceutically acceptable salt thereof.

2. The compound according to claim 1, wherein the compound is represented by the following formula (I-a):

(I-a)

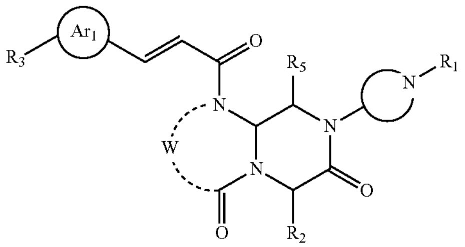

wherein $R_1$ is a hydrogen atom, optionally substituted alkyl, optionally substituted cycloalkyl, optionally substituted heterocycloalkyl, optionally substituted aryl, optionally substituted heteroaryl, optionally substituted arylalkyl, optionally substituted heteroarylalkyl, optionally substituted cycloalkylalkyl, optionally substituted heterocycloalkylalkyl, or —(CO)—$R_{1a}$;

$R_{1a}$ is optionally substituted alkyl, optionally substituted alkoxy, optionally substituted aryl, or optionally substituted heteroaryl;

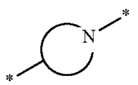

is represented by any of the following formulas (II-1-a) to (II-6-a):

II-1-a

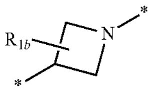

II-2-a

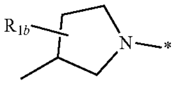

II-3-a

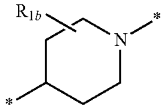

II-4-a

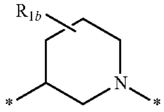

II-5-a

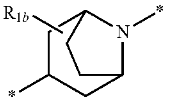

II-6-a

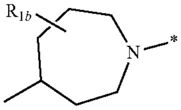

$R_{1b}$ is a hydrogen atom, or 1 to 3 same or different alkyls;

$R_2$ is a hydrogen atom, optionally substituted alkyl, optionally substituted alkenyl, optionally substituted alkynyl, optionally substituted arylalkyl, optionally substituted heteroarylalkyl, optionally substituted cycloalkylalkyl, or —X—N($R_{2a}$)($R_{2b}$);

X is an alkylene group;

$R_{2a}$ and $R_{2b}$ are the same or different and each is a hydrogen atom, optionally substituted alkyl, optionally substituted cycloalkyl, optionally substituted heterocycloalkyl, optionally substituted aryl, optionally substituted heteroaryl, optionally substituted arylalkyl, optionally substituted heteroarylalkyl, or optionally substituted cycloalkylalkyl;

$Ar_1$ is an optionally substituted aryl ring or an optionally substituted heteroaryl ring;

$R_3$ is a hydrogen atom, hydroxy, halogen, cyano, optionally substituted alkyl, optionally substituted cycloalkyl, optionally substituted heterocycloalkyl, optionally substituted aryl, optionally substituted heteroaryl, —C≡C—$R_{3a}$ or —COO$R_{3b}$;

$R_{3a}$ is a hydrogen atom, optionally substituted alkyl, optionally substituted cycloalkyl, optionally substituted heterocycloalkyl, or optionally substituted heteroaryl, $R_{3b}$ is a hydrogen atom or optionally substituted alkyl,

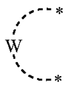

is represented by any of the following formulas (III-1) to (III-3):

(III-1)

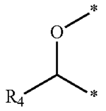

(III-2)

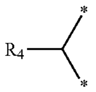

(III-3)

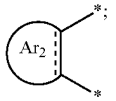

$R_4$ is a hydrogen atom, optionally substituted alkyl, optionally substituted alkenyl, optionally substituted alkynyl, optionally substituted arylalkyl, optionally substituted heteroarylalkyl, optionally substituted cycloalkylalkyl, or optionally substituted heterocycloalkylalkyl, and $Ar_2$ is an optionally substituted aryl ring or an optionally substituted heteroaryl ring; and $R_5$ is a hydrogen atom, or optionally substituted alkyl, or a pharmaceutically acceptable salt thereof.

3. The compound according to claim 1, wherein the compound is represented by the following formula (IV):

(IV)

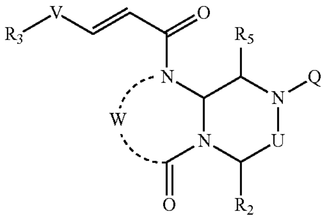

wherein each symbol is as defined in claim 1, or a pharmaceutically acceptable salt thereof.

4. The compound according to claim 1, wherein the compound is represented by the following formula (IV-a):

(IV-a)

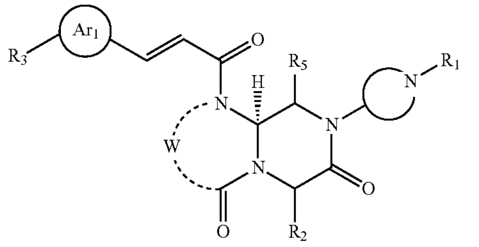

wherein each symbol is as defined in claim 2, or a pharmaceutically acceptable salt thereof.

5. The compound according to claim 1, wherein Q is represented by any of the following formulas (VI-1) to (VI-3):

(VI-1)

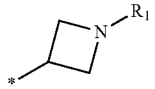

(VI-2)

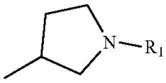

(VI-3)

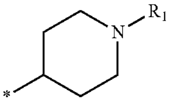

wherein each symbol is as defined in claim 1, or a pharmaceutically acceptable salt thereof.

6. The compound according to claim 1, wherein Q is represented by the following formulas (II-7):

II-7

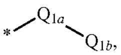

and $Q_{1a}$ is an alkylene and $Q_{1b}$ is —CONH-$Q_{1c}$, -$Q_{1d}$, —CO-$Q_{1a}$, —N($Q_{1c}$)-$Q_{1d}$, wherein $Q_{1c}$ is a hydrogen atom or an alkyl and $Q_{1d}$ is a hydrogen atom or heterocycloalkyl optionally substituted by alkyl, or a pharmaceutically acceptable salt thereof.

7. The compound according to claim 2, wherein

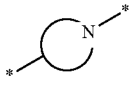

is represented by any of the following formulas (VI-1-a) to (VI-3-a):

(VI-1-a)

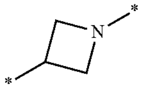

-continued (VI-2-a)

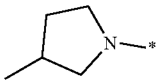

(VI-3-a)

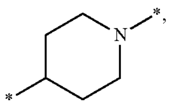

or a pharmaceutically acceptable salt thereof.

8. The compound according to claim 2, wherein $Ar_1$ is an optionally substituted pyridine ring, an optionally substituted thiazole ring, an optionally substituted benzothiazole ring, or an optionally substituted quinoxaline ring, or a pharmaceutically acceptable salt thereof.

9. The compound according to claim 8, wherein

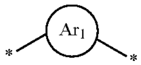

is represented by the following formula (VII-1-a), (VII-2-a), or (VII-3-a):

(VII-1-a)

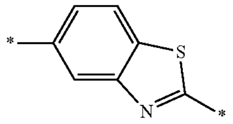

(VII-2-a)

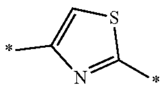

(VII-3-a)

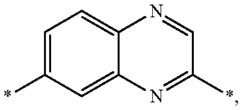

or a pharmaceutically acceptable salt thereof.

10. The compound according to claim 1, wherein $R_1$ is a hydrogen atom, optionally substituted alkyl, optionally substituted cycloalkyl, optionally substituted heterocycloalkyl, optionally substituted heteroarylalkyl, optionally substituted cycloalkylalkyl, or —(CO)—$R_{1a}$;

$R_{1a}$ is optionally substituted alkyl, optionally substituted alkoxy, optionally substituted aryl, or optionally substituted heteroaryl;

$R_{1b}$ is a hydrogen atom;

$R_2$ is optionally substituted alkyl, or optionally substituted arylalkyl;

$R_{3a}$ is a hydrogen atom, optionally substituted alkyl, optionally substituted cycloalkyl, optionally substituted heterocycloalkyl, or optionally substituted heteroaryl, $R_4$ is optionally substituted alkyl, $Ar_2$ is an optionally substituted aryl ring, and $R_5$ is a hydrogen atom, or a pharmaceutically acceptable salt thereof.

11. The compound according to claim 1, wherein

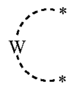

is represented by the following formula (V):

(V)

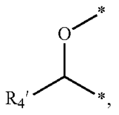

and $R_4$' is optionally substituted alkyl or optionally substituted cycloalkyl, or a pharmaceutically acceptable salt thereof.

12. The compound according to claim 11, wherein
$R_4$' is an alkyl group,
or a pharmaceutically acceptable salt thereof.

13. The compound according to claim 11, wherein $R_4$' is an isobutyl group, or a pharmaceutically acceptable salt thereof.

14. The compound according to claim 1, wherein $R_2$ is alkyl optionally substituted by alkylthio or alkylsulfonyl, or arylalkyl, or a pharmaceutically acceptable salt thereof.

15. The compound according to claim 14, wherein $R_2$ is isobutyl, neopentyl, sec-butyl, or benzyl, or a pharmaceutically acceptable salt thereof.

16. The compound according to claim 1, wherein $R_1$ is alkyl or alkyl substituted by 1 or 2 hydroxys, or a pharmaceutically acceptable salt thereof.

17. The compound according to claim 1, wherein $R_3$ is a hydrogen atom, hydroxy, or $—C≡C—R_{3a}$; and $R_{3a}$ is alkyl substituted by hydroxy, or a pharmaceutically acceptable salt thereof.

18. A pharmaceutical composition comprising a compound according to claim 1 or a pharmaceutically acceptable salt thereof, and optionally a pharmaceutically acceptable carrier or diluent.

* * * * *